US006800434B2

(12) United States Patent
Saksena et al.

(10) Patent No.: US 6,800,434 B2
(45) Date of Patent: Oct. 5, 2004

(54) PEPTIDES AS NS3-SERINE PROTEASE INHIBITORS OF HEPATITIS C VIRUS

(75) Inventors: Anil K. Saksena, Upper Montclair, NJ (US); Viyyoor Moopil Girijavallabhan, Parsippany, NJ (US); Raymond G. Lovey, West Caldwell, NJ (US); Edwin Jao, Warren, NJ (US); Frank Bennett, Piscataway, NJ (US); Jinping L. McCormick, Edison, NJ (US); Haiyan Wang, Cranbury, NJ (US); Russell E. Pike, Stanhope, NJ (US); Stephane L. Bogen, Somerset, NJ (US); Yi-Tsung Liu, Morris Township, NJ (US); Ashok Arasappan, Bridgewater, NJ (US); Tejal Parekh, Mountain View, CA (US); Patrick A. Pinto, Morris Plains, NJ (US); F. George Njoroge, Warren, NJ (US); Ashit K. Ganguly, Upper Montclair, NJ (US); Terence K. Brunck, Santa Fe, NM (US); Scott Jeffrey Kemp, San Diego, CA (US); Odile Esther Levy, San Diego, CA (US); Marguerita Lim-Wilby, La Jolla, CA (US)

(73) Assignees: Schering Corporation, Kenilworth, NJ (US); Dendreon Corporation, Seattle, WA (US)

(*) Notice: Subject to any disclaimer, the term of this patent is extended or adjusted under 35 U.S.C. 154(b) by 0 days.

(21) Appl. No.: 09/909,062

(22) Filed: Jul. 19, 2001

(65) Prior Publication Data

US 2003/0036501 A1 Feb. 20, 2003

Related U.S. Application Data

(60) Provisional application No. 60/220,109, filed on Jul. 21, 2000.

(51) Int. Cl.[7] .............................................. A61K 38/00
(52) U.S. Cl. ................................ 435/5; 435/6; 435/23; 514/9; 514/17; 514/18; 514/160; 424/85.4; 530/324; 530/325; 530/326; 530/327; 530/328; 530/329
(58) Field of Search ...................... 435/5, 6, 23; 514/9, 514/17, 18, 160, 16; 424/85.4; 530/324–329, 332

(56) References Cited

U.S. PATENT DOCUMENTS

| 5,488,067 A | 1/1996 | Hanson |
| 5,514,694 A | 5/1996 | Powers et al. |
| 6,265,380 B1 * | 7/2001 | Tung et al. .................. 514/17 |

FOREIGN PATENT DOCUMENTS

| CA | 2362911 A1 | 9/2000 |
| EP | 381 216 | 8/1990 |
| FR | 2778406 | 11/1999 |
| WO | WO 89/04669 | 6/1989 |
| WO | WO 98/17679 | 4/1998 |
| WO | WO 98 17679 | 4/1998 |
| WO | WO 98/22496 | 5/1998 |
| WO | WO 99 07734 | 2/1999 |
| WO | WO 99/07734 | 2/1999 |
| WO | WO 99 64442 | 12/1999 |
| WO | WO 00/09543 | 2/2000 |
| WO | WO 00/09558 | 2/2000 |
| WO | WO 00/52032 | 9/2000 |
| WO | WO 01/40262 A1 | 6/2001 |
| WO | WO 01/74768 A2 | 10/2001 |

OTHER PUBLICATIONS

STN Registry No. 207001–88–5. Reference to Tung et al. including citation of STN No. 207001–88–5 found therein.*
Pizzi, (1994) *Proc. Natl. Acad. Sci(USA)* 91:888–892.
Failla (1996) *folding & Design* 1:35–42.
Kollykhalov (1994) *J. Virol.* 68:7525–7533.
Komoda (1994) *J. Virol.* 68:7351–7357.
Landro (1997) *Biochem* 36:9340–9348.
Ingallinella (1998) *Biochem* 37:8906–8914.
Llinas–Brunet (1998) *Bioorg. Med. Chem. Lett*, 8:1713–1718.
Martin (1998) *Biochem* 37:11459–11468.
Dimasi (1997) *J. Virol.* 71:7461–7469.
Martin (1997) *Protein Eng.* 10:607–614.
Elzouki (1997) *J. Hepat.* 27:42–48.
*Bio World Today* 9(217): 4 (Nov. 10, 1998).
Berenguer (1998) *Proc. Assoc. Am. Physicians* 110(2): 98–112.
Hoofnagle (1997) *New England Journal Med.* 336:347.
Zhang (199) *Analytical Biochemistry* 270:268–275.
Sali (1998) *Biochemistry* 3392–3401.
Barlos (1991) *Int. J. Pept. Protein Res* 513–520.
Holmberg (1979) *Acta Chem. Scand.*, B33:410–412.
Agrawal(1999) *Hepatology* Supplement to Vol 30 "Development and Characterization of Hepatitis C Virus Serine Protease Cell–based Trans–Cleavage Assay".
Hughes (1992) *Org. Reactions* 42:335.
Heck (1989) *Org. Reactions* 27:345–390.

(List continued on next page.)

Primary Examiner—Christopher R. Tate
Assistant Examiner—Maury Audet
(74) Attorney, Agent, or Firm—Palaiyur S. Kalyanaraman; Lerner, David, Littenberg, Krumholz & Mentlik, LLP

(57) ABSTRACT

The present invention discloses novel peptide compounds which have HCV protease inhibitory activity as well as methods for preparing such compounds. In another embodiment, the invention discloses pharmaceutical compositions comprising such peptides as well as methods of using them to treat disorders associated with the HCV protease.

1 Claim, No Drawings

OTHER PUBLICATIONS

Han, (2000) *Bioorganic & Medicinal Chemistry Letters 10* "α–Ketoamides, α–Ketoesters and α–Kiketones as HCV NS3 Protease Inhibitors" pp. 711–713.

Marchetti(1999)*Synlett*, vol. S1, "Synthesis of Two Novel Cyclic Biphenyl Ether Analogs of an Inhibitor of HCV NS3 Protease", pp 1000–1002.

Llinas–Brunet, "Studies on the C–terminal of hexapeptide inhibitors of the hepatitis C virus serine protease", *Bioorg. Med. Chem. Lett*, (1998) vol. 8, (19), pp. 2719–2724.

Bennett, J.M., "The identification of alpha–ketoamides as potent inhibitors of hepatitis c virus NS3–4A proteinase", *Bioorganic & Medicinal Chemistry Letters*, 2001, vol. 11 (3), pp. 355–357.

Han, Wei., "alpha.–Keto amides., alpha–keto esters, and alpha.–diketones as HCV NS3 protease inhibitors", *Bioorganic & Medicinal Chemistry Letters*, 2000, vol. 10(8), pp. 711–713.

Narjes, Frank, "alpha.–Ketoacids Are Potent Slow Binding Inhibitors of the Hepatitis C Virus NS3 Protease", *Biochemistry*, 2000, vol. 39(7) pp. 1849–1861.

* cited by examiner

PEPTIDES AS NS3-SERINE PROTEASE INHIBITORS OF HEPATITIS C VIRUS

The present application claims benefit of U.S. Provisional Patent Application No. 60/220,109, filed Jul. 21, 2000, the disclosure of which is hereby incorporated by reference herein.

FIELD OF INVENTION

The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention specifically discloses novel peptide compounds as inhibitors of the HCV NS3/NS4a serine protease.

BACKGROUND OF THE INVENTION

Hepatitis C virus (HCV) is a (+)-sense single-stranded RNA virus that has been implicated as the major causative agent in non-A, non-B hepatitis (NANBH), particularly in blood-associated NANBH (BB-NANBH)(see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliary cirrhosis.

Recently, an HCV protease necessary for polypeptide processing and viral replication has been identified, cloned and expressed; (see, e.g., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e. trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) *Proc. Natl. Acad. Sci (USA)* 91 :888–892, Failla et al. (1996) *Folding & Design* 1:35–42. The NS3/NS4a cleavage site is also more tolerant of mutagenesis than the other sites. See, e.g., Kollykhalov et al. (1994) *J. Virol.* 68:7525–7533. It has also been found that acidic residues in the region upstream of the cleavage site are required for efficient cleavage. See, e.g., Komoda et al. (1994) *J. Virol.* 68:7351–7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) *Biochem.* 36:9340–9348, Ingallinella et al. (1998) *Biochem.* 37:8906–8914, Llinàs-Brunet et al. (1998) *Bioorg. Med. Chem. Lett.* 8:1713–1718), inhibitors based on the 70-amino acid polypeptide eglin c (Martin et al. (1998) *Biochem.* 37:11459–11468, inhibitors affinity selected from human pancreatic secretory trypsin inhibitor (hPSTI-C3) and minibody repertoires (MBip) (Dimasi et al. (1997) *J. Virol.* 71:7461–7469), $cV_HE2$ (a "camelized" variable domain antibody fragment) (Martin et al.(1997) *Protein Eng.* 10:607–614), and α1-antichymotrypsin (ACT) (Elzouki et al.) (1997) *J. Hepat.* 27:42–28). A ribozyme designed to selectively destroy hepatitis C virus RNA has recently been disclosed (see, *BioWorld Today* 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche A G); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10–30%, whereas those with localized unresectable hepatocellular carcinoma have a five-year survival rate of less than 1%.

Reference is made to A. Marchetti et al, *Synlett, S1*, 1000–1002 (1999) describing the synthesis of bicylic analogs of an inhibitor of HCV NS3 protease. A compound disclosed therein has the formula:

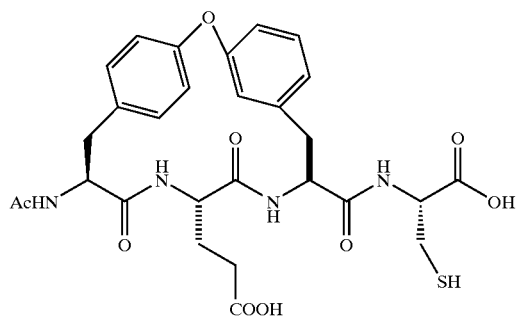

Reference is also made to WO 00/09558 (Assignee: Boehringer Ingelheim Limited; Published Feb. 24, 2000) which discloses peptide derivatives of the formula:

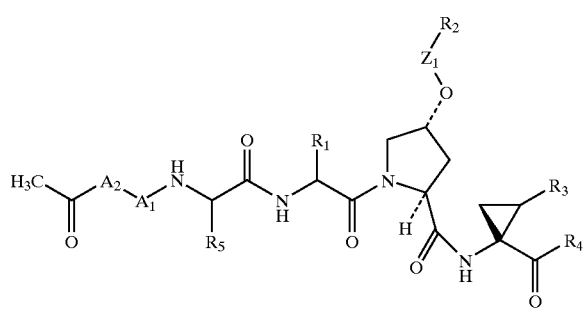

where the various elements are defined therein. An illustrative compound of that series is:

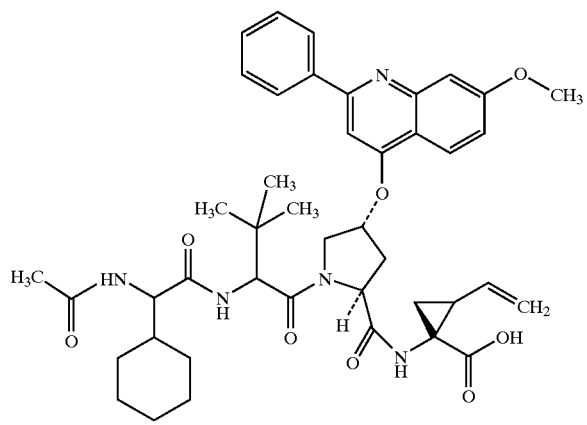

Reference is also made to WO 00/09543 (Assignee: Boehringer Ingelheim Limited; Published Feb. 24, 2000) which discloses peptide derivatives of the formula:

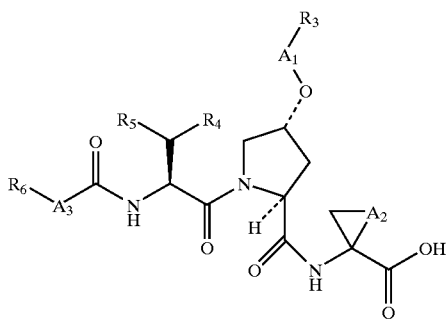

where the various elements are defined therein. An illustrative compound of that series is:

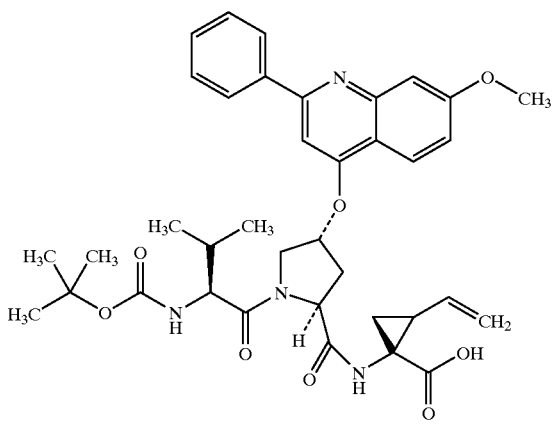

Current therapies for hepatitis C include interferon-α ($INF_\alpha$) and combination therapy with ribavirin and interferon. See, e.g., Beremguer et al. (1998) *Proc. Assoc. Am. Physicians* 110(2):98–112. These therapies suffer from a low sustained response rate and frequent side effects. See, e.g. Hoofnagle et al. (1997) *N. Engl. J. Med.* 336:347. Currently, no vaccine is available for HCV infection.

Pending and copending U.S. patent application Serial No. 60/220,110, filed Jul. 21, 2000, Serial No. 60/220,107, filed Jul. 21, 2000, Serial No. 60/220,108, filed Jul. 21, 2000, Serial No. 60/220,101, filed Jul. 21, 2000, Serial No. 60/254, 869, filed Dec. 12, 2000, Serial No. 60/194,607, filed Apr. 5, 2000, and Serial No. 60/198,204, filed Apr. 19, 2000 disclose various types of peptides as NS-3 serine protease inhibitors of hepatitis C virus.

There is a need for new treatments and therapies for HCV infection. It is, therefore, an object of this invention to provide compounds useful in the treatment or prevention or amelioration of one or more symptoms of hepatitis C.

It is a further object herein to provide methods of treatment or prevention or amelioration of one or more symptoms of hepatitis C.

A still further object of the present invention is to provide methods for modulating the activity of serine proteases, particularly the HCV NS3/NS4a serine protease, using the compounds provided herein.

Another object herein is to provide methods of modulating the processing of the HCV polypeptide using the compounds provided herein.

SUMMARY OF THE INVENTION

In its many embodiments, the present invention provides a novel class of inhibitors of the HCV protease, pharmaceutical compositions containing one or more of the compounds, methods of preparing pharmaceutical formulations comprising one or more such compounds, and methods of treatment, prevention or amelioration or one or more of the symptoms of hepatitis C. Also provided are methods of modulating the interaction of an HCV polypeptide with HCV protease. Among the compounds provided herein, compounds that inhibit HCV NS3/NS4a serine protease activity are preferred. The presently disclosed compounds generally contain about four or more amino acid residues and less than about twelve amino acid residues. Specifically, the present application discloses peptide compounds, defined further below.

In its first embodiment, the present invention provides a compound of Formula I:

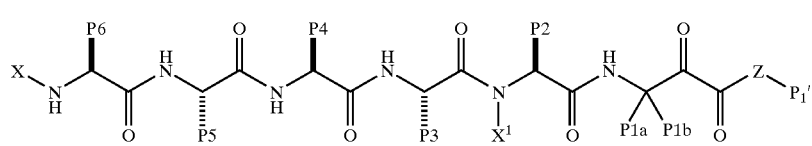

Formula I or a pharmaceutically acceptable salt, solvate or derivative thereof, wherein:

Z is O, NH or $NR^{12}$;

X is alkylsulfonyl, heterocyclylsulfonyl, heterocyclylalkylsulfonyl, arylsulfonyl, heteroarylsulfonyl, alkylcarbonyl, heterocyclylcarbonyl, heterocyclylalkylcarbonyl, arylcarbonyl, heteroarylcarbonyl, alkoxycarbonyl, heterocyclyloxycarbonyl, aryloxycarbonyl, heteroaryloxycarbonyl, alkyaminocarbonyl, heterocyclylaminocarbonyl, arylaminocarbonyl, or heteroarylaminocarbonyl moiety, with the proviso that X may be additionally optionally substituted with $R^{12}$ or $R^{13}$;

$X^1$ is H; $C_1$–$C_4$ straight chain alkyl; $C_1$–$C_4$ branched alkyl or; $CH_2$-aryl (substituted or unsubstituted);

$R^{12}$ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl moiety, with the proviso that $R^{12}$ may be additionally optionally substituted with $R^{13}$.

$R^{13}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro moiety, with the proviso that the alkyl, alkoxy, and aryl may be additionally optionally substituted with moieties independently selected from $R^{13}$.

P1a, P1b, P2, P3, P4, P5, and P6 are independently:

H; C1–C10 straight or branched chain alkyl; C2–C10 straight or branched chain alkenyl;

C3–C8 cycloalkyl, C3–C8 heterocyclic; (cycloalkyl)alkyl or (heterocyclyl)alkyl, wherein said cycloalkyl is made up of 3 to 8 carbon atoms, and zero to 6 oxygen, nitrogen, sulfur, or phosphorus atoms, and said alkyl is of 1 to 6 carbon atoms;

aryl, heteroaryl, arylalkyl, or heteroarylalkyl, wherein said alkyl is of 1 to 6 carbon atoms;

wherein all aforesaid alkyl, alkenyl, cycloalkyl, heterocyclyl; (cycloalkyl)alkyl and (heterocyclyl)alkyl moieties may be optionally substituted with $R^{13}$. Additionally, the atoms of P1a and P1b may be joined to each other in such a fashion to form a spirocyclic or spiroheterocyclic ring, with said spirocyclic or spiroheterocyclic ring containing zero to 6 oxygen, nitrogen, sulfur, or phosphorus atoms, and may be optionally substituted with $R^{13}$.

P1' is H, alkyl, alkenyl, alkynyl, cycloalkyl, cycloalkyl-alkyl, heterocyclyl, heterocyclyl-alkyl, aryl, aryl-alkyl, heteroaryl, or heteroaryl-alkyl; with the proviso that said P1' may be additionally optionally substituted with $R^{13}$.

Among the above-stated definitions for X, R12, R13, P1a, P1b, P2, P3, P4, P5, and P1', the preferred groups for the various moieties are as follows:

Preferred moieties for X are:

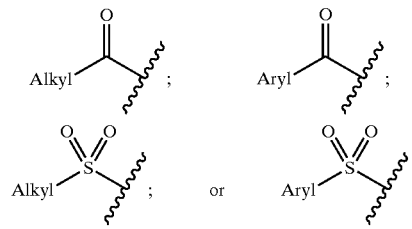

wherein Alkyl is C1 to C4 straight or branched chain, and wherein Aryl is phenyl or substituted phenyl.

Preferred moieties for P6 are:

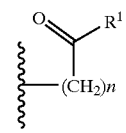

with n being 1–4.

Preferred moieties for P5 are:

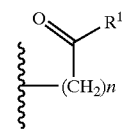

with n being 1–4; additionally, P6 and P5 may be the same or different.

Preferred moieties for $R^1$ are OH, O-t-Bu, $OR^3$, $NHR^3$, NH-phenyl or NH-trityl.

Preferred moieties for $R^3$ are H, $C_1$ to $C_4$ straight or branched chain alkyl P3 and P4 may be the same or different and preferred moieties for P3 and P4 are:

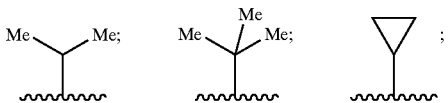

-continued
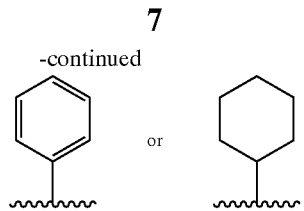
Preferred moieties for P2 are:
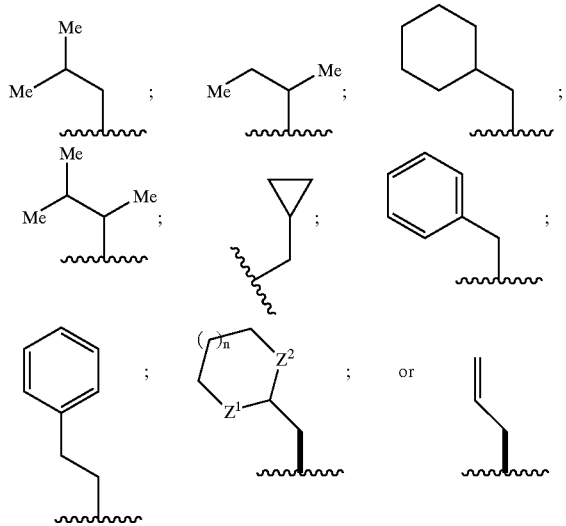
wherein n=0, 1, 2 or 3;
Preferred moieties for P1a and P1b are:
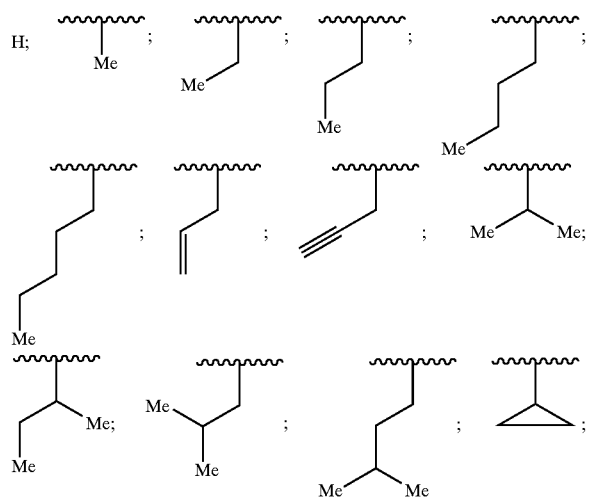
-continued
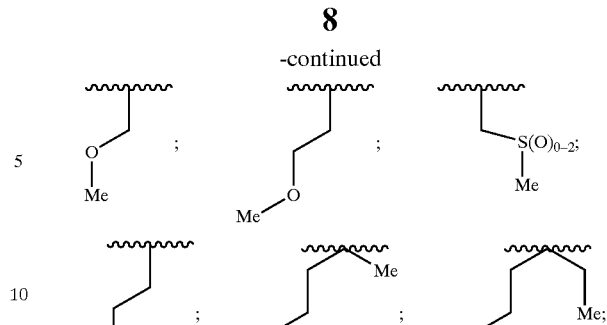
Preferred moieties for P1' are:
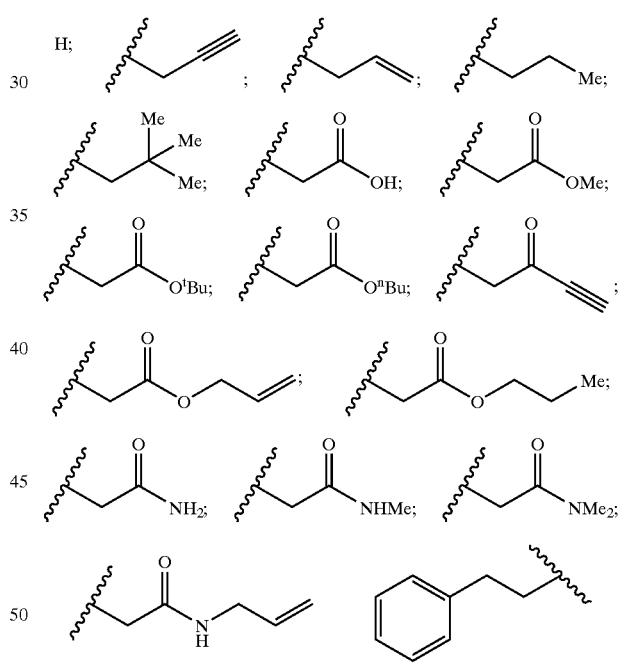
In another embodiment, the present invention provides a compound of Formula II:
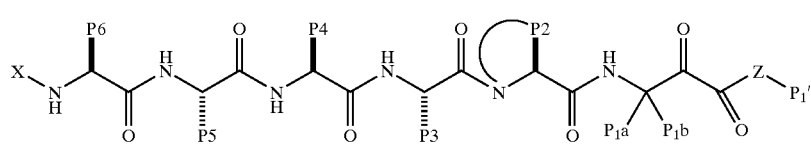
Formula II wherein X, P6, P5, P4, P3, P2, P1a, P1b and P1' are as defined above. Z is O, NH or NR$^{12}$ where R$^{12}$ has been defined before. In Formula II, P2, when connected with the N atom adjacent to C atom it is attached to, forms a cyclic ring, with the proviso that said cyclic ring does not contain a carbonyl group as part of the cyclic ring structure. The cyclic ring moiety comprised of P2, the carbon atom to which P2 is attached, and the nitrogen atom adjacent to that carbon atom is noted above as:

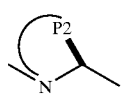

which may denote a five-membered ring or a six-membered ring structure. Preferred representatives for that cyclic ring structure are selected from the following:

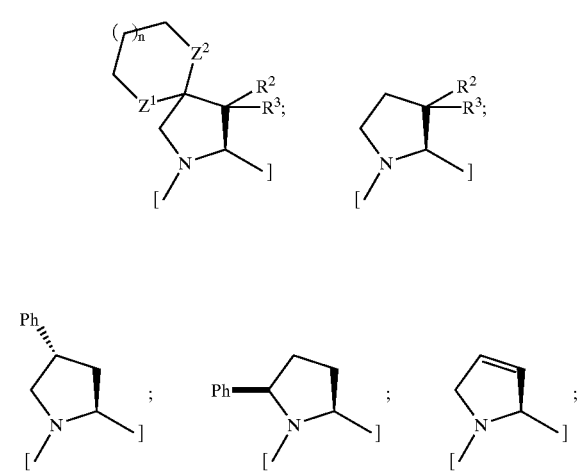

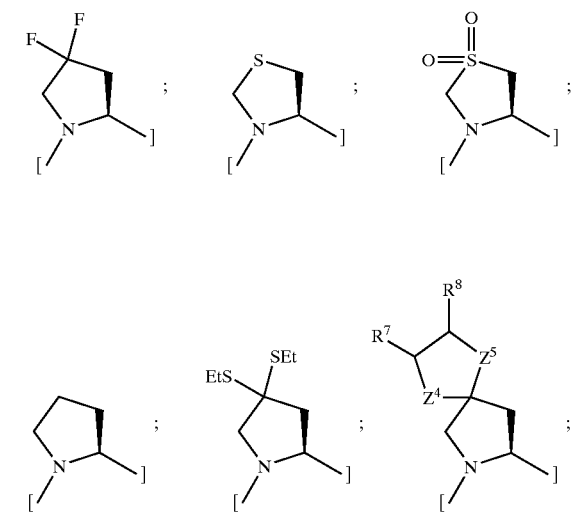

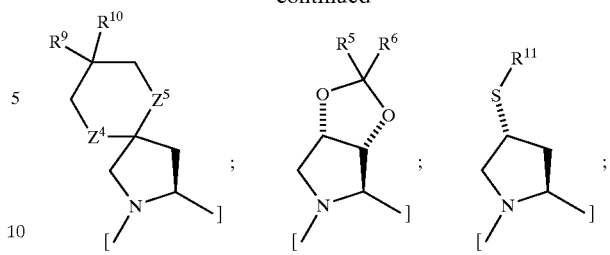

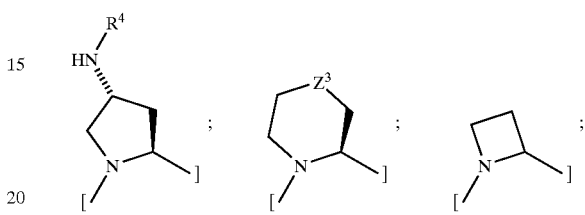

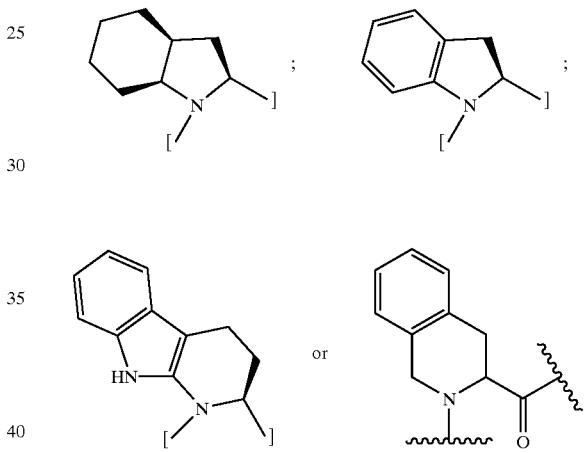

wherein:

R$^2$ and R$^3$ may be the same or different and are selected from H; C$_1$–C$_6$ straight chain alkyl; C$_1$–C$_6$ branched alkyl or cycloalkyl;

R$^4$ is CO-Alkyl (alkyl being C1–C6 straight chain or branched or cycloalkyl); CO-aryl; COO-alkyl or COO-aryl;

R$^5$ and R$^6$ may be the same or different and are selected from H; C$_1$–C$_3$ straight chain alkyl; or C$_1$–C$_3$ branched alkyl;

R$^7$ and R$^8$ may be the same or different and are selected from H; C$_1$–C$_3$ straight chain alkyl; C$_1$–C$_3$ branched alkyl or CH$_2$OH;

R$^9$ and R$^{10}$ may be the same or different and are selected from H; C$_1$–C$_3$ straight chain alkyl; C$_1$–C$_3$ branched alkyl; COOMe; COOH or CH$_2$OH;

R$^{11}$ is C$_1$–C$_6$ straight chain alkyl; C$_1$–C$_6$ branched alkyl; cyclocalkyl; or CH$_2$-aryl (substituted or unsubstituted);

Z$^1$ and Z$^2$ may be the same or different and are selected from S; O; or CH$_2$;

Z$^3$ is CH$_2$; S, SO$_2$; NH or NR$^4$;

Z$^4$ and Z$^5$ may be the same or different and are selected from S, O or CH$_2$.

In yet another embodiment, the present invention discloses compounds of Formula III:

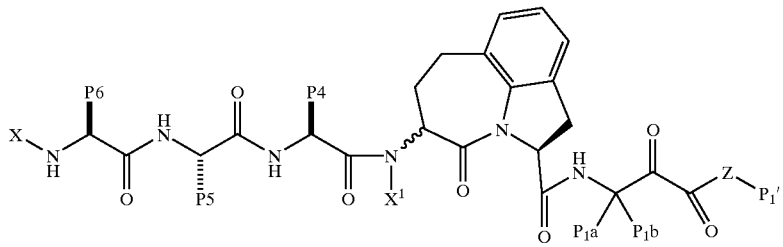

Formula III where the various elements are as defined above.

Unless defined otherwise, all technical and scientific terms used herein have the same meaning as is commonly understood by one of skill in the art to which this invention belongs. Thus, for example, the term alkyl (including the alkyl portions of alkoxy) refers to a monovalent group derived from a straight or branched chain saturated hydrocarbon by the removal of a single atom having from 1 to 8 carbon atoms, preferably from 1 to 6;

aryl—represents a carbocyclic group having from 6 to 14 carbon atoms and having at least one benzenoid ring, with all available substitutable aromatic carbon atoms of the carbocyclic group being intended as possible points of attachment. Preferred aryl groups include phenyl, 1-naphthyl, 2-naphthyl and indanyl, and especially phenyl and substituted phenyl;

aralkyl—represents a moiety containing an aryl group linked vial a lower alkyl;

alkylaryl—represents a moiety containing a lower alkyl linked via an aryl group;

cycloalkyl—represents a saturated carbocyclic ring having from 3 to 8 carbon atoms, preferably 5 or 6, optionally substituted.

heterocyclic—represents, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6- or 7-membered and may or may not have double bonds that lack delocalized pi electrons, which ring structure has from 2 to 8, preferably from 3 to 6 carbon atoms, e.g., 2- or 3-piperidinyl, 2- or 3-piperazinyl, 2- or 3-morpholinyl, or 2- or 3-thiomorpholinyl;

halogen—represents fluorine, chlorine, bromine and iodine;

heteroaryl—represents a cyclic organic group having at least one O, S and/or N atom interrupting a carbocyclic ring structure and having a sufficient number of delocalized pi electrons to provide aromatic character, with the aromatic heterocyclyl group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 4-imidazolyl, 2-, 4- or 5-pyrimidinyl, 2-pyrazinyl, or 3- or 4-pyridazinyl, etc. Preferred heteroaryl groups are 2-, 3- and 4-pyridyl; such heteroaryl groups may also be optionally substituted.

Also included in the invention are tautomers, rotamers, enantiomers and other optical isomers of compounds of Formula I, Formula II and Formula III, as well as pharmaceutically acceptable salts, solvates and derivatives thereof.

A further feature of the invention is pharmaceutical compositions containing as active ingredient a compound of Formula I, Formula II or Formula III (or its salt, solvate or isomers) together with a pharmaceutically acceptable carrier or excipient.

The invention also provides methods for preparing compounds of Formulas I, II and III, as well as methods for treating diseases such as, for example, HCV and related disorders. The methods for treating comprise administering to a patient suffering from said disease or diseases a therapeutically effective amount of a compound of Formula I, II or III, or pharmaceutical compositions comprising a compound of Formula I, II or III.

Also disclosed is the use of a compound of Formulas I, II or III for the manufacture of a medicament for treating HCV and related disorders.

DETAILED DESCRIPTION OF PREFERRED EMBODIMENTS

In one embodiment, the present invention discloses compounds of Formula I as inhibitors of HCV protease, especially the HCV NS3/NS4a serine protease, or a pharmaceutically acceptable derivative thereof, where the various definitions are given above.

In another embodiment, the present invention discloses compounds of Formula II as inhibitors of HCV protease, especially the HCV NS3/NS4a serine protease, or a pharmaceutically acceptable derivative thereof, where the various definitions are given above.

In another embodiment, the present invention discloses compounds of Formula III as inhibitors of HCV protease, especially the HCV NS3/NS4a serine protease, or a pharmaceutically acceptable derivative thereof, where the various definitions are given above.

Representative compounds of the invention which exhibit excellent HCV protease inhibitory activity are listed below in Table 1 along with their activity (ranges of $K_i^*$ values in nanomolar, nM).

TABLE 1

Compounds and HCV protease continuous assay results

| Compound from Example No. | $K_i^*$ Range |
|---|---|
| 1 | b |
| 2 | b |

TABLE 1-continued

Compounds and HCV protease continuous assay results

| Compound from Example No. | Ki* Range |
|---|---|
| 3 | c |
| 4 | b |
| 5 | b |
| 6 | c |
| 7 | c |
| 8 | b |
| 9 | b |
| 10 | c |
| 11 | c |
| 12 | b |
| 13 | c |
| 14 | b |
| 15 | b |
| 16 | c |
| 17 | c |
| 18 | c |
| 19 | c |
| 20 | c |
| 21 | c |
| 22 | c |
| 23 | c |
| 24 | c |
| 25 | a |
| 26 | b |
| 27 | a |
| 28 | c |
| 29 | c |
| 30 | c |
| 31 | b |
| 32 | b |
| 33 | b |
| 34 | c |
| 35 | c |
| 36 | a |
| 37 | b |
| 38 | a |
| 39 | a |
| 40 | a |
| 41 | c |
| 42 | a |
| 43 | a |
| 44 | a |
| 45 | a |
| 46 | c |
| 47 | c |
| 48 | b |
| 49 | a |
| 50 | c |
| 51 | b |
| 52 | b |
| 53 | b |
| 54 | b |
| 55 | a |
| 56 | b |
| 57 | b |
| 58 | c |
| 59 | b |
| 60 | b |
| 61 | a |
| 62 | a |
| 63 | a |
| 64 | b |
| 65 | b |
| 66 | b |
| 67 | b |
| 68 | c |
| 69 | c |
| 70 | c |
| 71 | b |
| 72 | b |
| 73 | c |
| 74 | c |
| 75 | c |
| 76 | c |
| 77 | c |
| 78 | b |
| 79 | a |
| 80 | a |
| 81 | a |
| 82 | a |
| 83 | a |
| 84 | a |
| 85 | a |
| 86 | a |
| 87 | a |
| 88 | b |

Category a=1–100 nM; Category b=101–999 nM; Category c=1000–10,000.

Some of the types of the inventive compounds and methods of synthesizing the various types of the inventive compounds of both Formula I and Formula II are listed below, then schematically described, followed by the illustrative Examples.

(81)

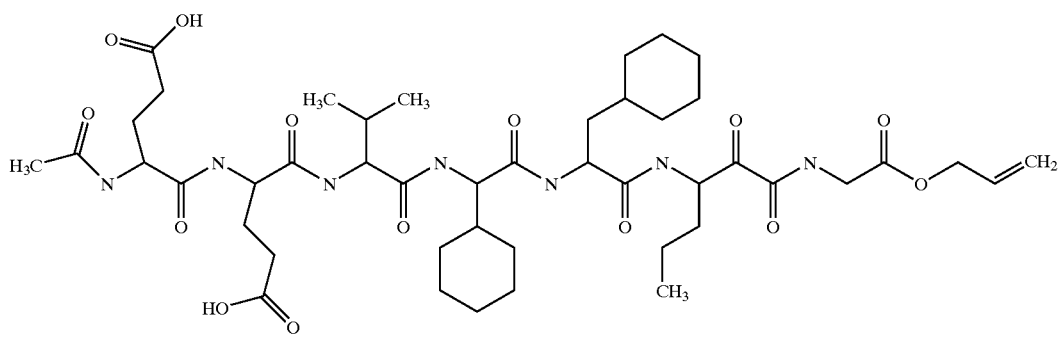

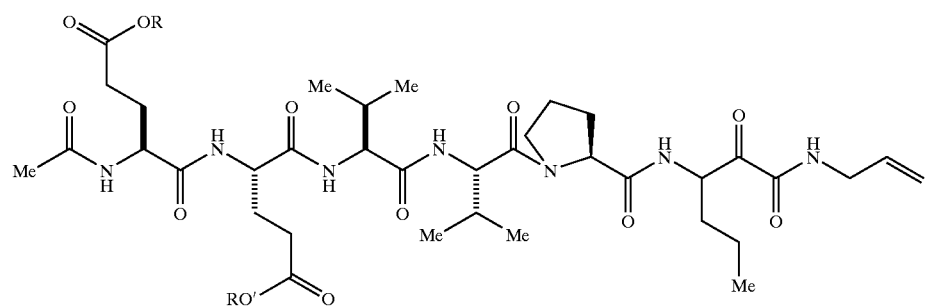
(4) R = H
(5) R = ᵗBu
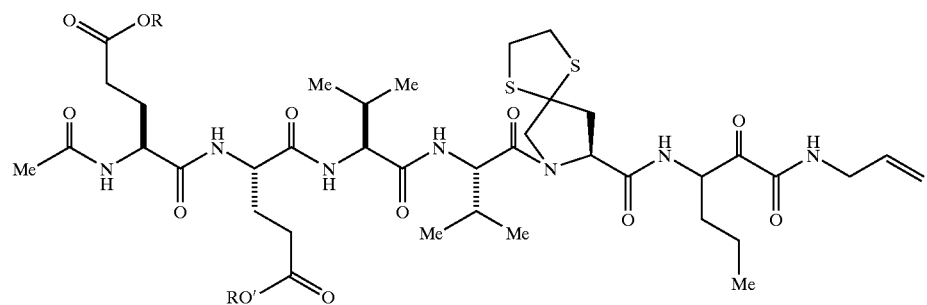
(43) R = R' = ᵗBu
(44) R = H, R' = ᵗBu
(45) R = R' = H
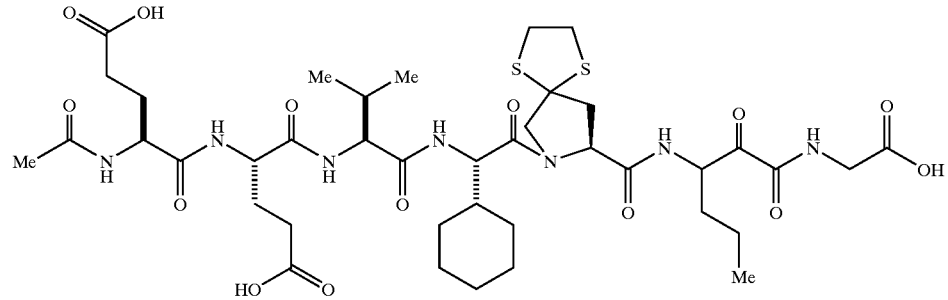
(86)
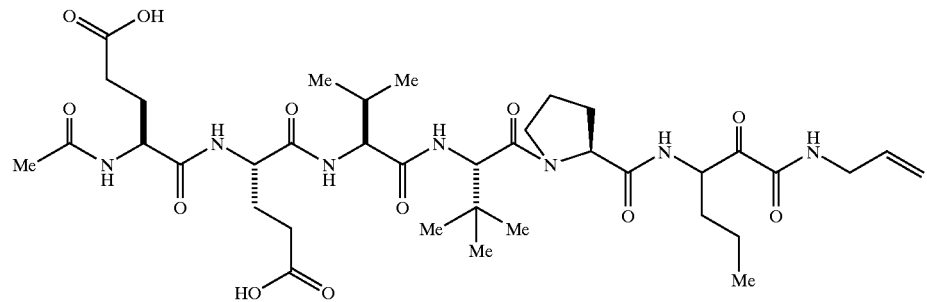
(49)

-continued
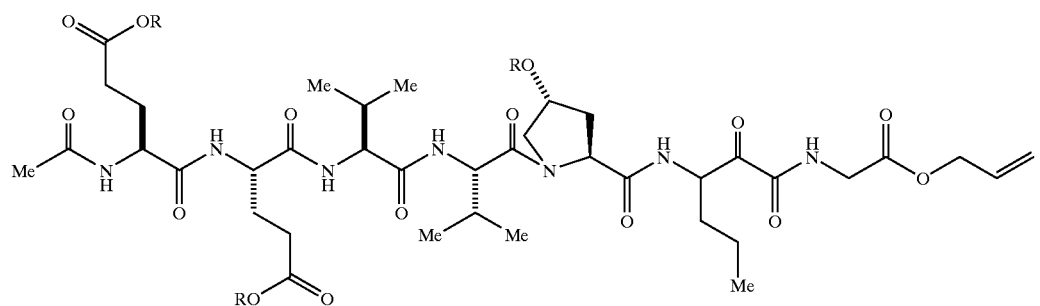
(40) R = ⁱBu
(42) R = H
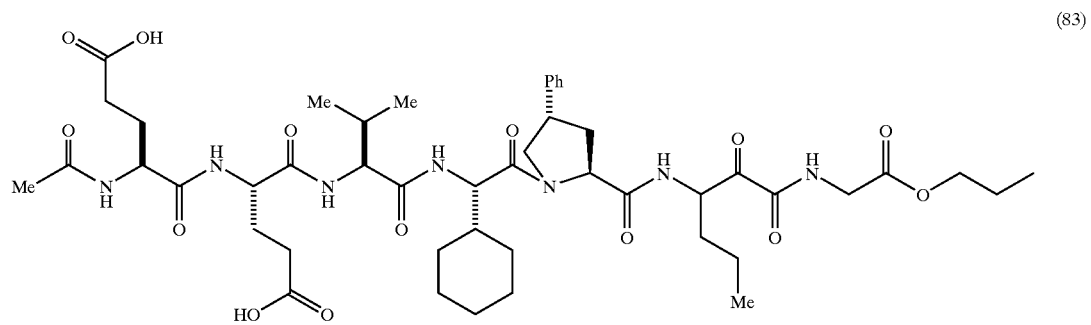
(83)
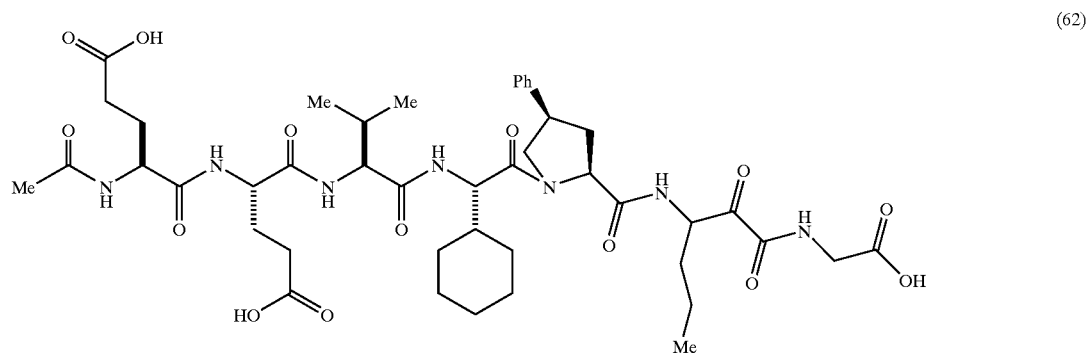
(62)
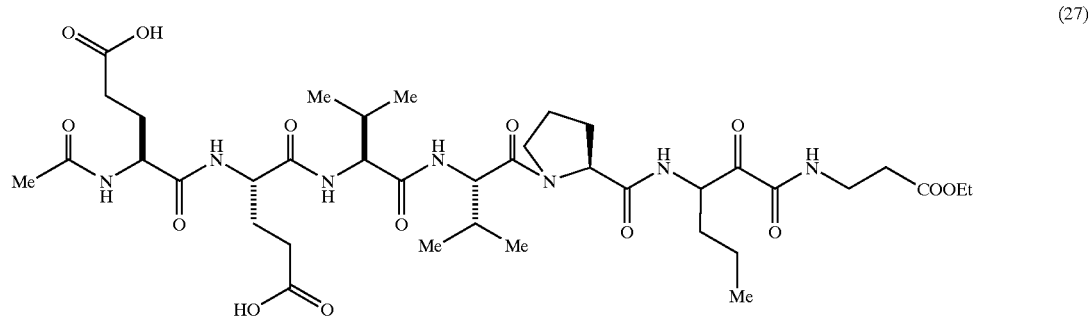
(27)

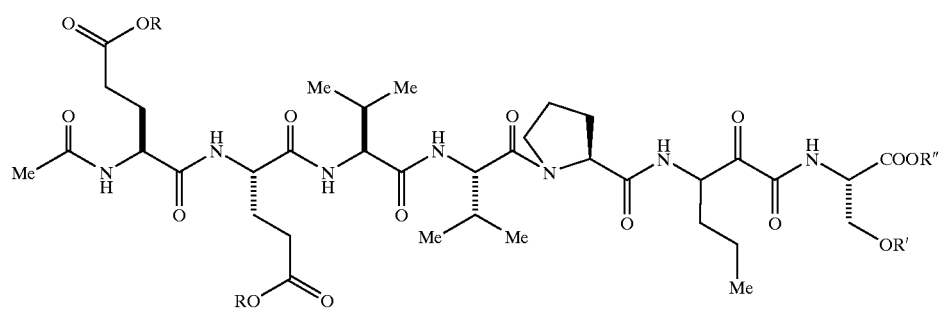
(31) R = R' = ᵗBu,
R″ = H
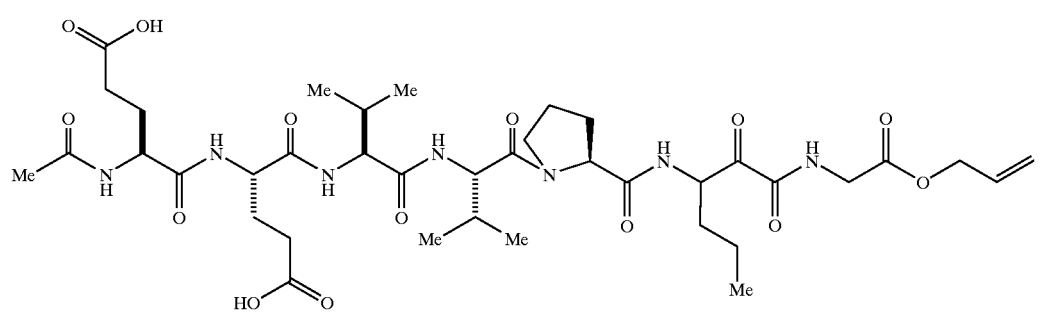
(39)
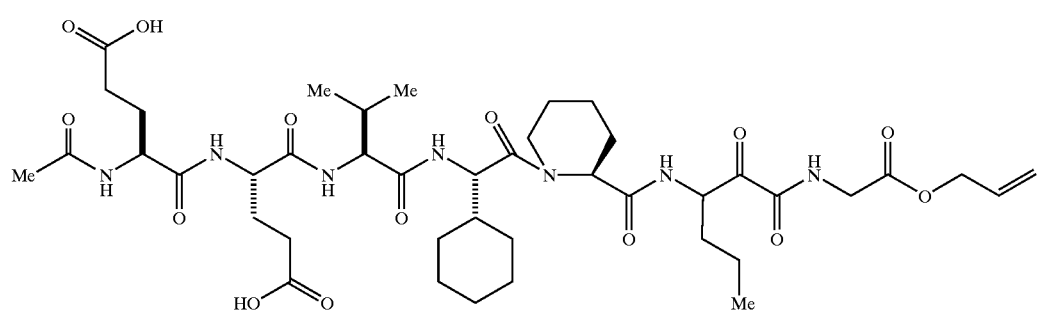
(79)
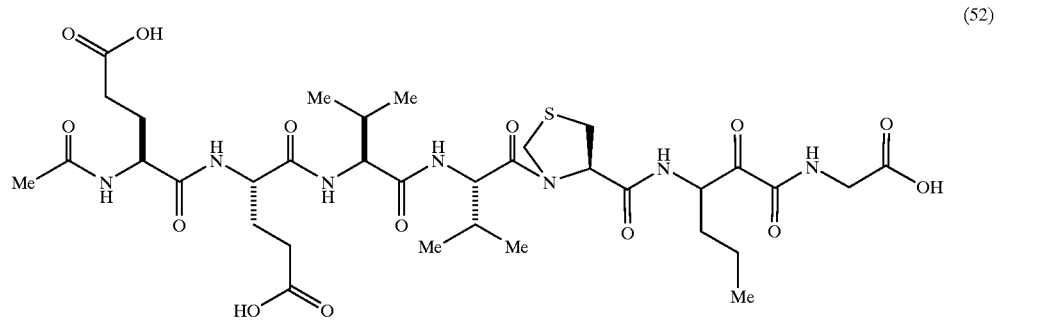
(52)
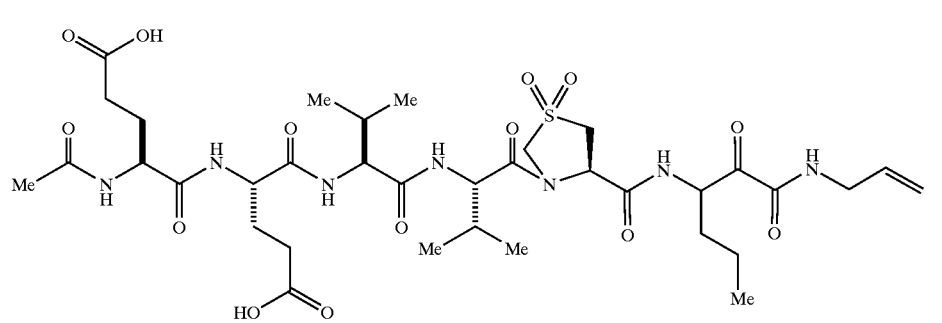
(53)

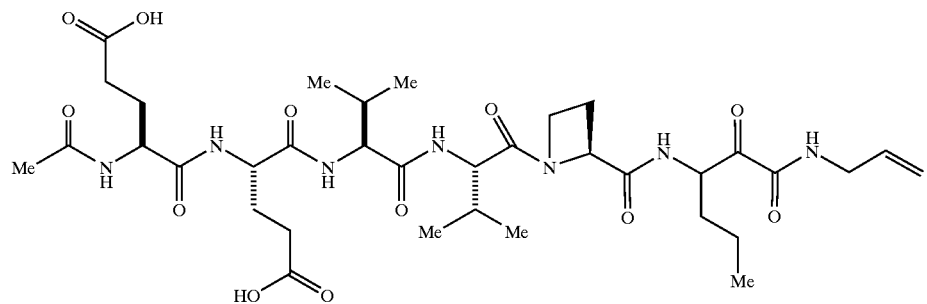
(33)
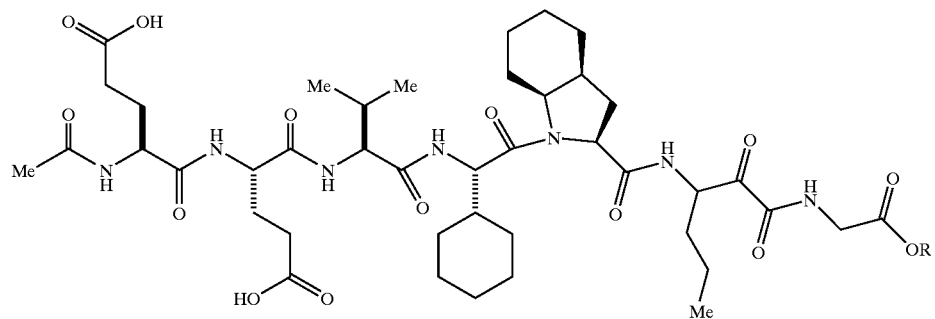
(60) R = H
(61) R = Allyl
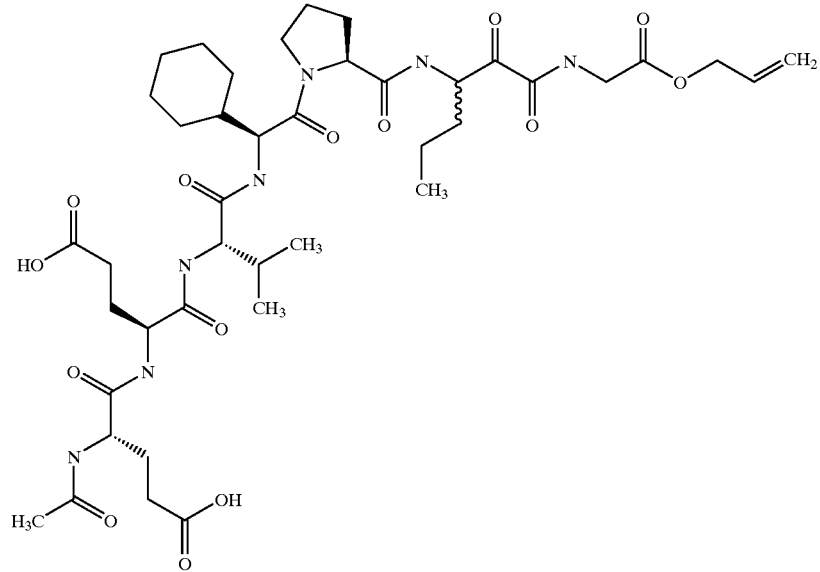
(55)

-continued (11)

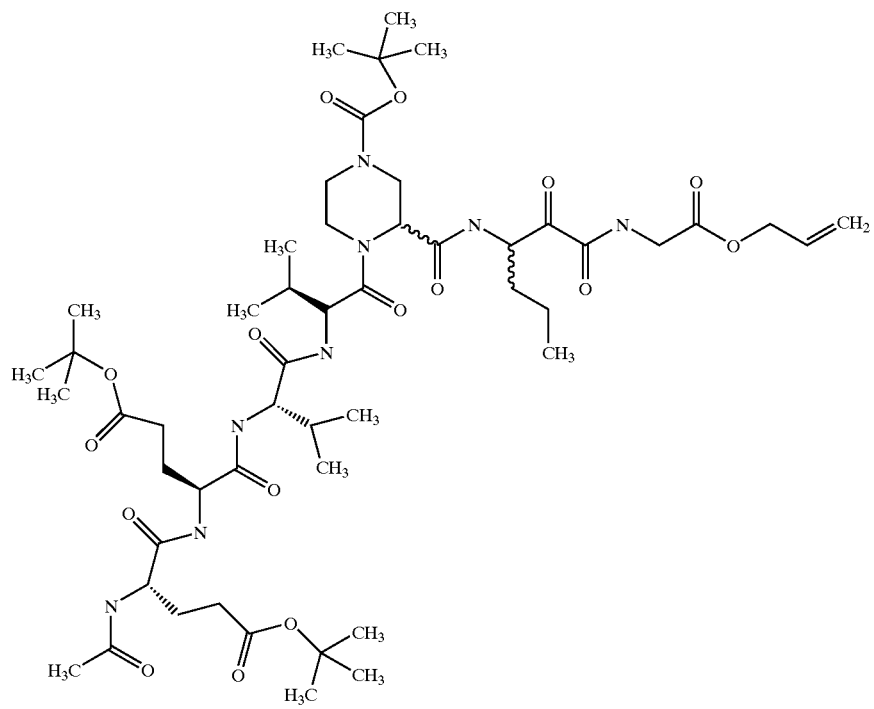

Depending upon their structure, the compounds of the invention may form pharmaceutically acceptable salts with organic or inorganic acids, or organic or inorganic bases. Examples of suitable acids for such salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. For formation of salts with bases, suitable bases are, for example, NaOH, KOH, $NH_4OH$, tetraalkylammonium hydroxide, and the like.

In another embodiment, this invention provides pharmaceutical compositions comprising the inventive peptides as an active ingredient. The pharmaceutical compositions generally additionally comprise a pharmaceutically acceptable carrier diluent, excipient or carrier (collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally, intravenously or subcutaneously.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the pharmaceutical compositions disclosed above for treatment of diseases such as, for example, hepatitis C and the like. The method comprises administering a therapeutically effective amount of the inventive pharmaceutical composition to a patient having such a disease or diseases and in need of such a treatment.

In yet another embodiment, the compounds of the invention may be used for the treatment of HCV in humans in monotherapy mode or in a combination therapy mode such as, for example, in combination with antiviral agents such as, for example, ribavirin and/or interferon such as, for example, α-interferon and the like.

As stated earlier, the invention includes tautomers, rotamers, enantiomers and other stereoisomers of the compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. Representative illustrative procedures are outlined in the following reaction schemes. It is to be understood that while the following illustrative schemes describe the preparation of a few representative inventive compounds, suitable substitution of any of both the natural and unnatural amino acids will result in the formation of the desired compounds based on such substitution. Such variations are contemplated to be within the scope of the invention.

Abbreviations which are used in the descriptions of the schemes, preparations and the examples that follow are:

THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCl: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
DCC: Dicyclohexylcarbodiimide
HOBt: Hydroxybezotriazole
HATU: O-(7-Azabenzotriazol-1-yl)-N,N,N',N'-tetramethyluronium hexafluorophosphate
TEMPO: 2,2,6,6-tetramethyl-1-piperidinyloxy free radical
TBTU: 2-(1H-Benzotriazole-1-yl)-1,1,3,3,-tetramethyluronium tetrafluoroborate
PAM: 4-Hydroxymethylphenylacetamidomethyl
DTT: Dithiothreitol
Hünigs base (DIPEA or DIEA): Diisopropylethyl amine
DCM: Dichloromethane
MeOH: Methanol
EtOH: Ethanol
Et₂O: Diethyl ether
PyBrOP: Bromo-tris-pyrrolidinophosphonium hexafluorophosphate
Trt: Trityl
PMB: Para-methoxybenzyl
Bzl=Bn: Benzyl
Boc: tert-Butyloxycarbonyl
Cbz: Benzyloxycarbonyl
Cp: Cylcopentyidienyl
Ts: p-toluenesulfonyl
Me: Methyl General Preparative Schemes:

The following schemes describe the methods of synthesis of intermediate building blocks:

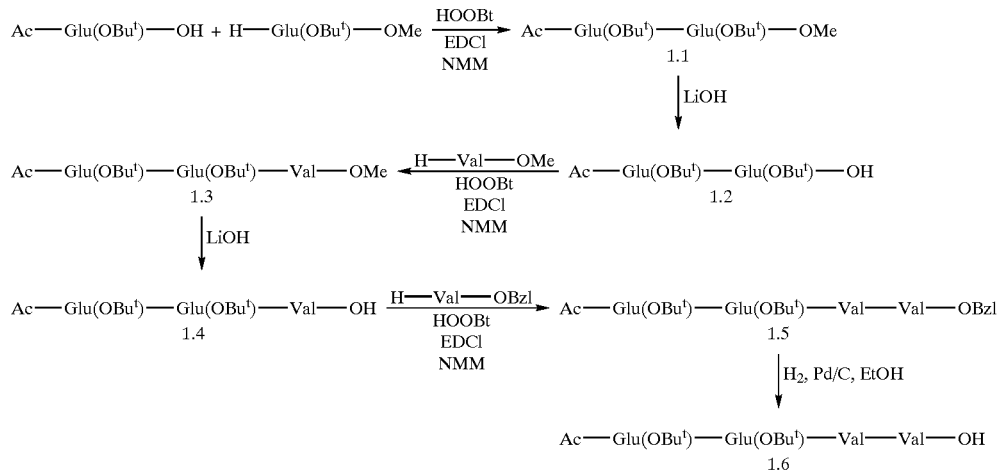

SCHEME 1

SCHEME 2
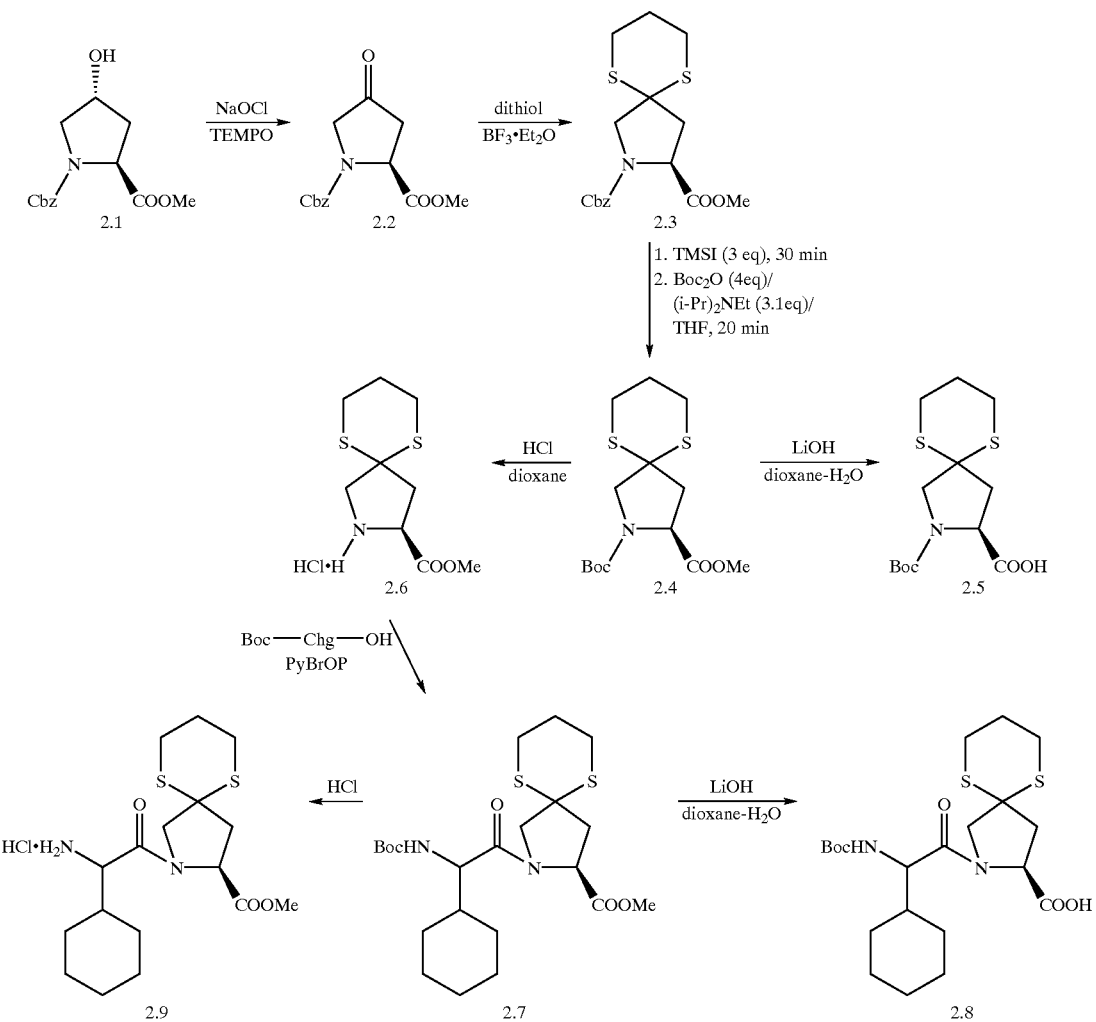
SCHEME 3
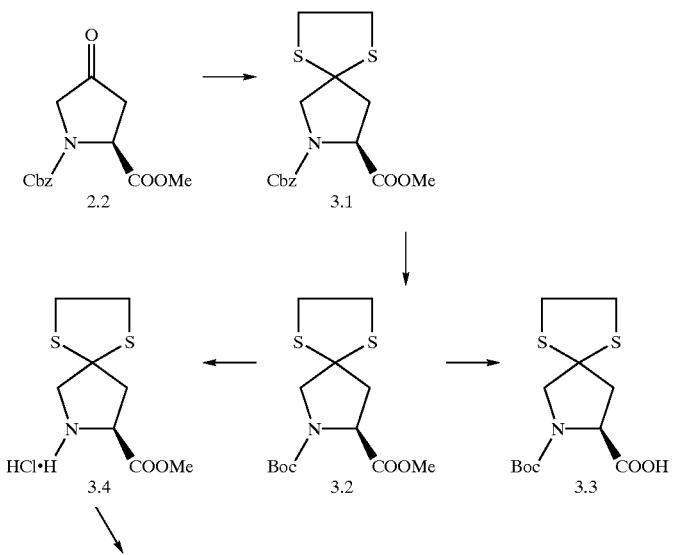

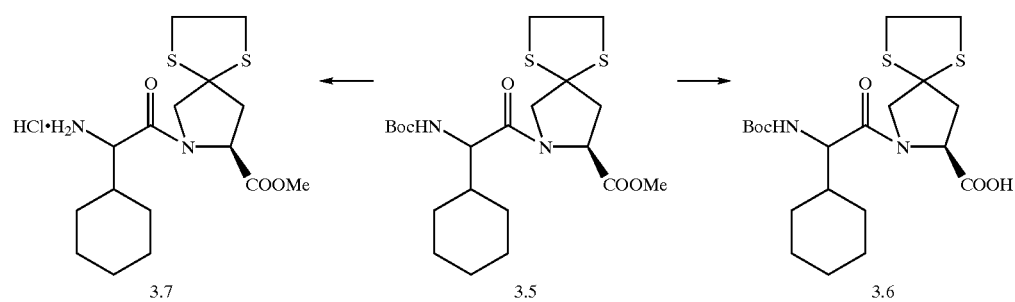
SCHEME 4
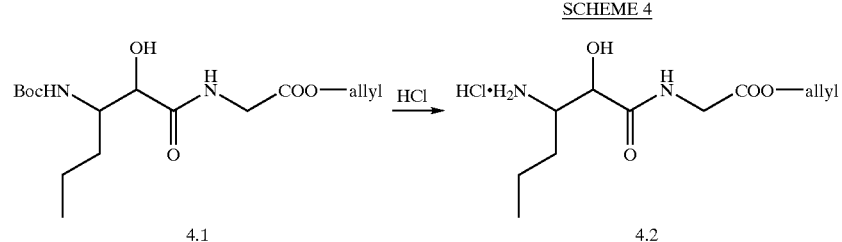
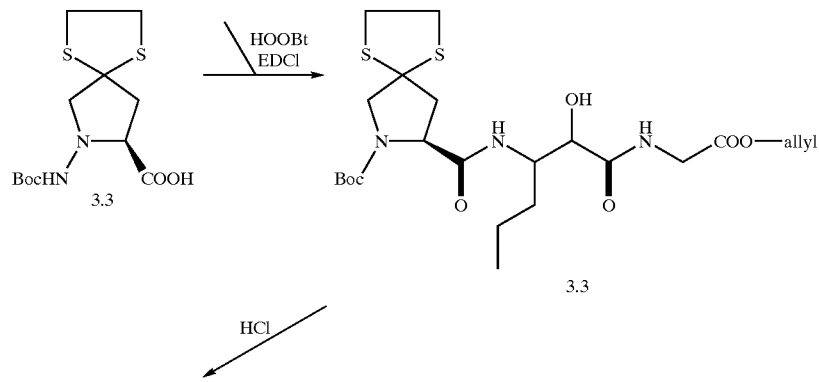
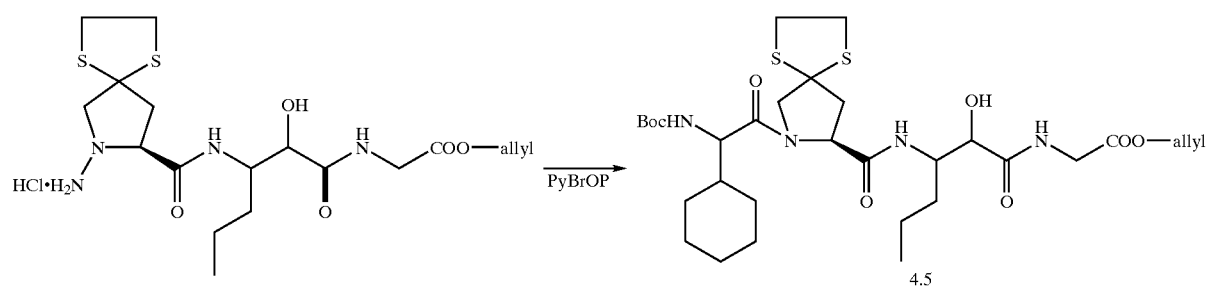

-continued
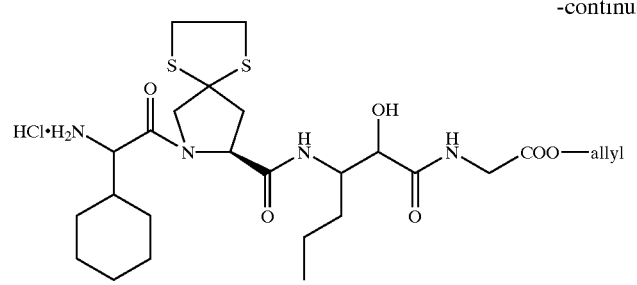
4.6
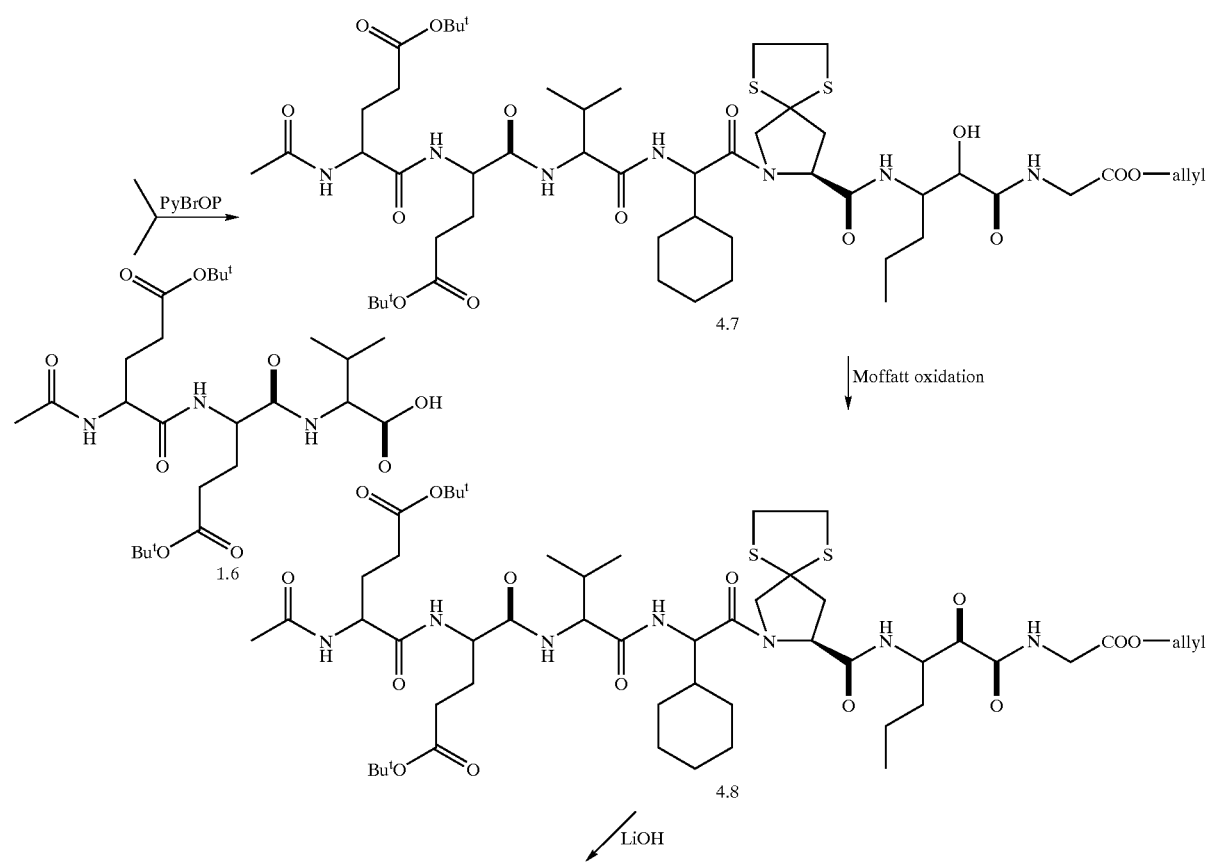
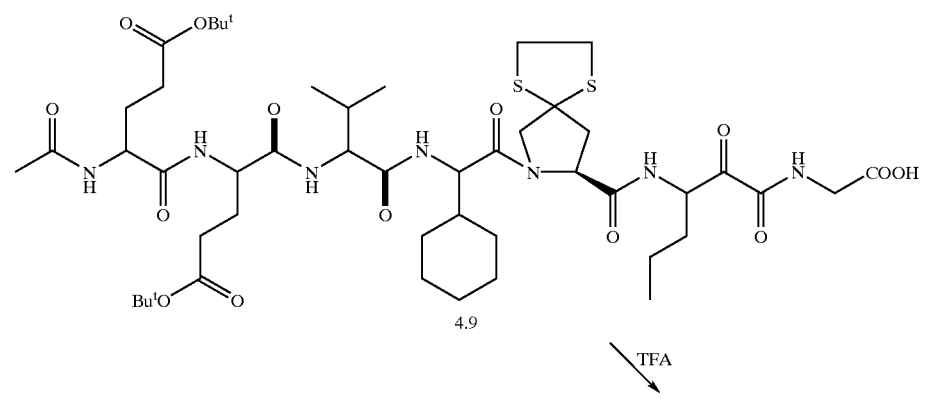
4.9

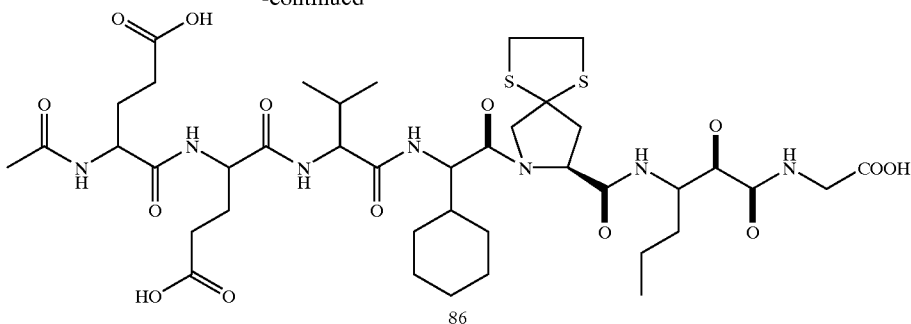

86

Preparation of Intermediates:

The procedures to modify an amino acid with N-Boc, N-Cbz, COOBzl, COOBu$^t$, Obzl, Obu$^t$, COOMe, both putting them on or taking them off in the presence of each other in various combinations, are generally well known to those skilled in the art. Any modifications from the known procedures are noted herein.

Commercially Available Intermediates:

The following amino acids, used as P2 units in the preparation of the various inventive compounds, are commercially available, and were converted to their N-Boc derivatives with di-tert-butyidicarbonate, using known procedures.

Aldrich Chemical Co.

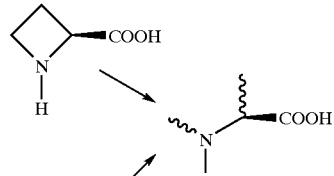

Tyger Scientific Inc.,
Monmouth Junction, New Jersey

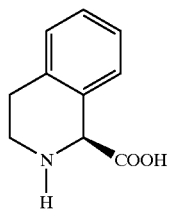

The following N-Boc-amino acids, used as P2 units, are commercially available.

Bachem Biosciences, Inc.

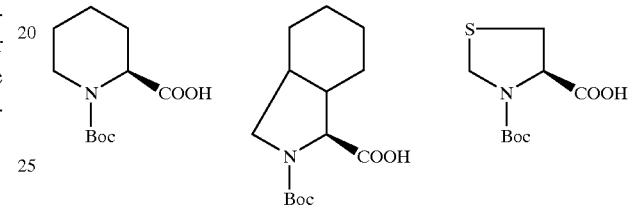

Neosystems,
Princeton, New Jersey

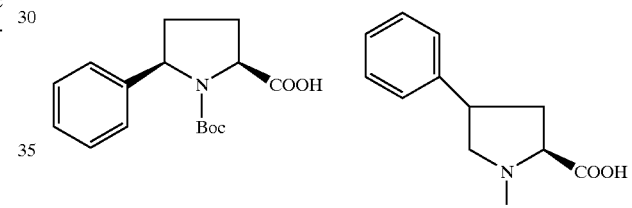

The following N-Boc-amino acid, used as P2 unit, is commercially available. After coupling the carboxylic acid, the Fmoc is removed by known treatment with piperidine before subsequent coupling.

RSP Amino Acid Analogues, Inc.
Worchester, Massachusetts

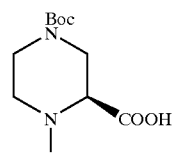

Certain intermediates which were not commercially available were synthesized, as needed, by following the procedures given below:

1.

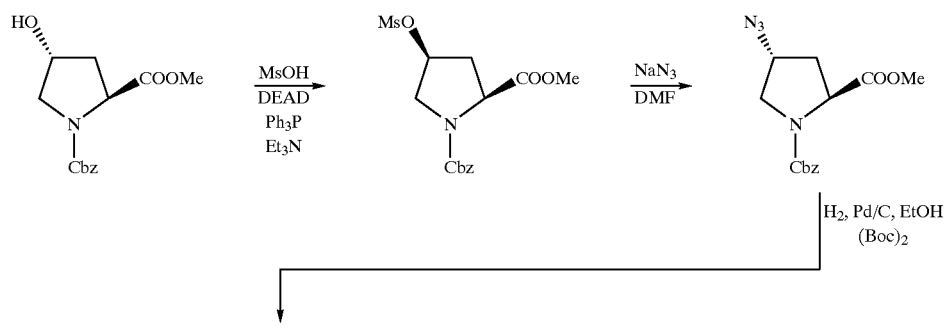

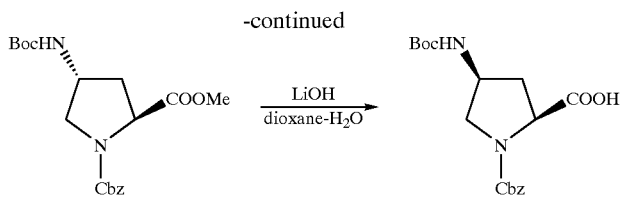

A. Mesylate:

A mixture of triphenylphosphine (8.7 g), toluene (200 mL), and methanesulfonic acid (2.07 mL) was stirred at 15° C. while slowly adding diethylazidodicarboxylate (7.18 g) to maintain the temperature below 35° C. The mixture was cooled to 20° C., and the N-Boc amino acid (7.4 g, Bachem Biosciences, Inc.), and $Et_3N$ (1.45 mL) were added, and then the mixture was stirred at 70° C. for 5 hr. The mixture was cooled to 5° C., the organic supernate decanted, and solvent was removed from it in vacuo. The residue was stirred with $Et_2O$ (200 mL) until a precipitate deposits, the mixture was filtered, and the ethereal solution was chromatographed on silica gel (5:95 to 20:80 EtOAc-$Et_2O$) to obtain the product (9.3 g), which was carried into the next step.

B. Azide

Sodium azide (1.98 g) was added to a solution of the product of the step above (9.3 g) in DMF (100 mL), and the mixture stirred at 70° C. for 8 hr. The mixture was cooled, and poured into 5% aqueous $NaHCO_3$, and extracted with EtOAc. The organic layer was washed with brine, then dried over anhydrous $MgSO_4$. The mixture was filtered, and the filtrate evaporated in vacuo, to obtain the product (6.2 g), which was carried into the next step.

C. N-Cbz(4-N-Boc)-PrO-OMe

A solution of the product of the step above (0.6 g) in dioxane (40 mL) was treated with di-tert-butyidicarbonate (0.8 g), 10% Pd-C (0.03g), and hydrogen at one atmosphere for 18 hr. The mixture was filtered, the filtrate evaporated in vacuo, and the residue chromatographed on silica gel (1:1 to 2:1 $Et_2O$-hexane) to obtain the product.

D. N-Cbz(4-N-Boc)-PrO-OH was prepared using known ester hydrolysis using LiOH.

2. Sulfones by Oxidation:

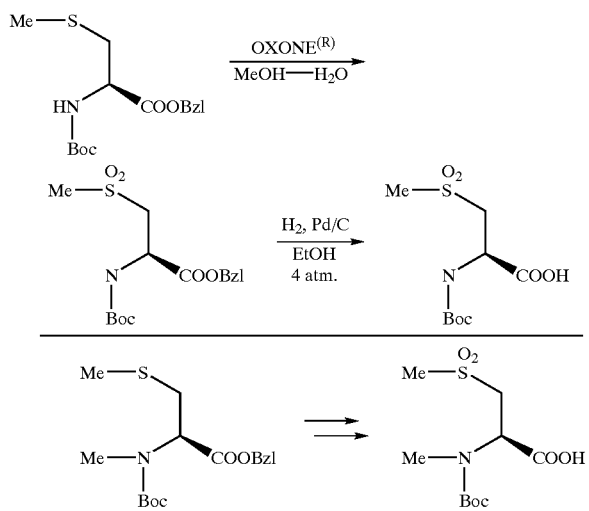

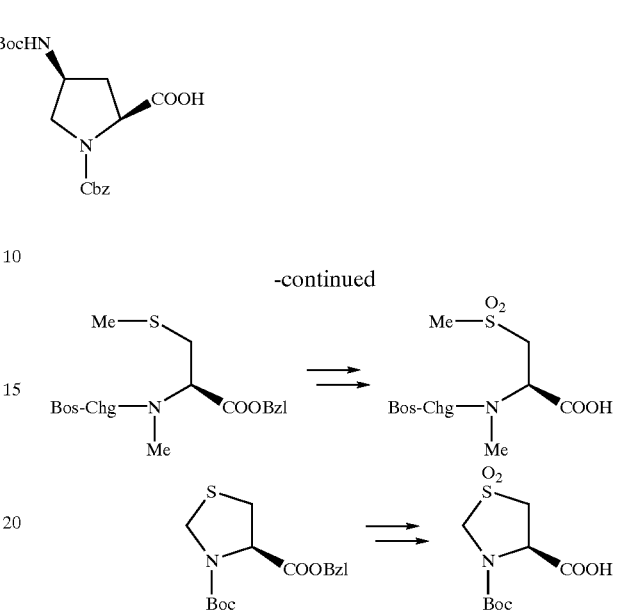

These were prepared by following the procedure of U. Larsson, et al., Acta Chem. Scan., (1994), 48(6), 517–525. A solution of oxone$^{(R)}$ (20.2 g, from Aldrich Chemical Co.) in water (110 mL) was added slowly to a 0° C. solution of the sulfide (7.2 g, from Bachem Biosciences, Inc.) in MeOH (100 mL). The cold bath was removed and the mixture stirred for 4 hr. The mixture was concentrated to ½ volume on a rotary evaporator, cold water (100 mL) added, extracted with EtOAc, the extract washed with brine, and then it was dried over anhydrous $MgSO_4$. The mixture was filtered, and the filtrate evaporated in vacuo, to obtain the product as a white solid (7.7 g). A portion was crystallized from (i-Pr)$_2$O to obtain an analytical sample, $[\alpha]_D$+8.6 (c 0.8, $CHCl_3$). Using the same procedure, the other sulfides shown were oxidized to sulfones to lead to the subject targets.

PREPARATIVE EXAMPLE 1

Preparation of Ac-Glu(OBu$^t$)-Glu(OBu$^t$)-Val-Val-OH (1.6) (Scheme 1):

Step A Compound (1.1).

To a mixture of Ac-Glu(OBzl)-OH (2.0 g), H-Glu(OBzl)-OMe.HCl (2.0 g), HOOBt (1.35 g), N-methylmorpholine (0.87 mL), and dimethylformamide (70 mL) at −20° C. was added EDCl (2.50 g) and stirred for 48 hr. The reaction mixture was poured into 5% aqueous $KH_2PO_4$ (500 mL) and extracted with ethyl acetate (2×150 mL). The combined organic layer was washed with cold 5% aqueous $K_2CO_3$, then 5% aqueous $KH_2PO_4$, then brine, and dried over anhydrous $MgSO_4$. The mixture was filtered and evaporated under vacuum. The residue was triturated with hexane (200 mL), and filtered to leave the title compound (3.4 g, 96% yield), TLC (EtOAc) Rf=0.7.

Step B Compound (1.2)

A solution of Compound (1.1) from Step A (3.4 g), MeOH (125 mL), and 1 M aqueous LiOH (7.25 mL) was stirred at room temperature for 18 hr. The mixture was concentrated, treated with cold 0.5 N HCl (250 mL), and extracted with ethyl acetate (2×150 mL). The combined organic layer was washed with cold water, then brine. The mixture was evaporated under vacuum, triturated with $Et_2O$-hexane, and filtered to leave the title compound (2.8 g, 85% yield).

Step C Compound (1.3)

In essentially the same manner as in Step A, but substituting proportional amounts of compound (1.2) the product of Step B for Ac-Glu(OBzl)-OH, and H-Val-OMe.HCl for H-Glu(OBzl)-Ome, the title compound was prepared (80% yield).

Step D Compound (1.4)

In essentially the same manner as in Step B, but substituting a proportional amount of compound (1.3) the product of Step C for compound (1.1) the product of Step A, the title compound was prepared (41% yield); $C_{25}H_{43}N_3O_9$ (529.64), mass spec. (FAB) M+1=530.3; $[\alpha]_D$ −24.6 (c=0.7, MeOH).

Step E Compound (1.5)

In essentially the same manner as in Step A, but substituting proportional amounts of compound (1.4), the product of Step D for Ac-Glu(OBzl)-OH, and H-Val-OBzl.HCl for H-Glu(OBzl)-Ome, the title compound was prepared (86% yield), $C_{37}H_{58}N_4O_{10}$ (718.90) mass spec. (FAB) M+1=719.3.

Step F Compound (1.6)

A mixture of compound (1.5) the product of Step E (2.6 g), 10% Pd/C (0.2 g), and EtOH-dioxane (1:1, 240 mL) was stirred under 1 atm. $H_2$ for 18 hr. The mixture was filtered and evaporated to dryness under vacuum to afford the title compound (2.1 g, 93% yield), $C_{30}H_{52}N_4O_{10}$ (628.77) mass spec. (FAB) M+1=629.5.

PREPARATIVE EXAMPLE 2

Step A Compound (2.2)

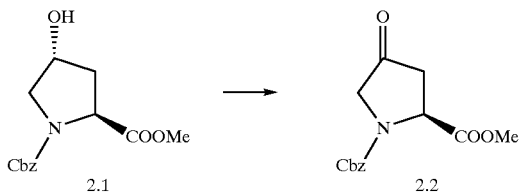

In a pot were combined N-Cbz-hydroxyproline methyl ester (available from Bachem Biosciences, Incorporated, King of Prussia, Pa.), compound (2.1) (3.0 g), toluene (30 mL), and ethyl acetate (30 mL). The mixture was stirred vigorously, and then a solution of NaBr/water (1.28 g /5 mL) was added. To this was added 2,2,6,6-tetramethyl-1-piperidinyloxy free radical (TEMPO, 17 mg, from Aldrich Chemicals, Milwaukee, Wis.). The stirred mixture was cooled to 5° C. and then was added a prepared solution of oxidant [commercially available bleach, Clorox® (18 mL), $NaHCO_3$ (2.75 g) and water to make up 40 mL] dropwise over 0.5 hr. To this was added 2-propanol (0.2 mL). The organic layer was separated, and the aqueous layer extracted with ethyl acetate. The organic extracts were combined, washed with 2% sodium thiosulfate, then saturated brine. The organic solution was dried over anhydrous $MgSO_4$, filtered, and evaporated the filtrate under vacuum to leave a pale yellow gum suitable for subsequent reactions (2.9 g, 97% yield), $C_{14}H_{15}NO_5$ (277.28), mass spec. (FAB) M+1=278.1.

Step B Compound (2.3).

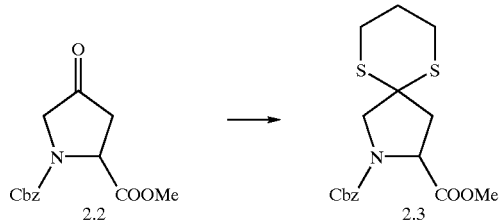

Compound (2.2) from Step A above (7.8 g) was dissolved in dichloromethane (100 mL), and cooled to 15° C. To this mixture was first added 1,3-propanedithiol (3.1 mL), followed by freshly distilled boron trifluoride etherate (3.7 mL). The mixture was stirred at room temperature for 18 h. While stirring vigorously, a solution of $K_2CO_3$/water (2 g/30 mL) was carefully added, followed by saturated $NaHCO_3$ (10 mL). The organic layer was separated from the aqueous layer (pH ~7.4), washed with water (10 mL), then brine. The organic solution was dried over anhydrous $MgSO_4$, filtered, and evaporated under vacuum. The residue was chromatographed on silica gel, eluting with toluene, then a with a gradient of hexane-$Et_2O$ (2:3 to 0:1) to afford a brown oil (7.0 g, 68% yield), $C_{17}H_{21}NO_4S_2$ (367.48), mass spec. (FAB) M+1=368.1.

Step C Compound (2.4)

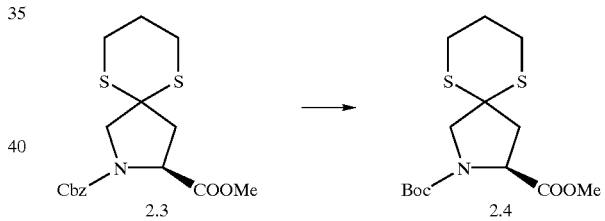

A solution of compound (2.3) from Step B above (45 g) in acetonitrile (800 mL) at 20° C. was treated with freshly distilled iodotrimethylsilane (53 mL) at once. The reaction was stirred for 30 min., then poured into a freshly prepared solution of di-t-butyldicarbonate (107 g), ethyl ether (150 mL), and diisopropylethylamine (66.5 mL). The mixture stirred for 30 min. more then was washed with hexane (2×500 mL). Ethyl acetate (1000 mL) was added to the lower acetonitrile layer, and then the layer was washed with 10% aqueous $KH_2PO_4$ (2×700 mL), and brine. The filtrate was evaporated under vacuum in a 25° C. water bath, taken up in fresh ethyl acetate (1000 mL), and washed successively with 0.1 N HCl, 0.1 N NaOH, 10% aqueous $KH_2PO_4$, and brine. The organic solution was dried over anhydrous $MgSO_4$, filtered, and evaporated under vacuum. The residue (66 g) was chromatographed on silica gel (2 kg), eluting with hexane (2 L), then $Et_2O$/hexane (55:45, 2 L), then $Et_2O$ (2 L) to afford an orange gum which slowly crystallized on standing (28 g, 69% yield), $C_{14}H_{23}NO_4S_2$ (333.46), mass spec. (FAB) M+1=334.1.

Step D Compound (2.5)

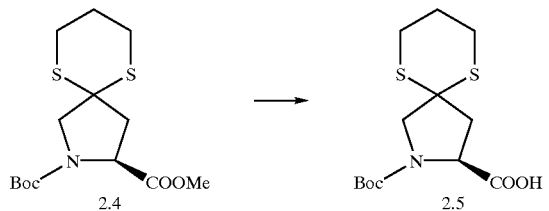

A solution of compound (2.4) from Step C above (11 g) in dioxane (150 mL) at 20° C. was treated with 1N aqueous LiOH (47 mL) and stirred for 30 h. The mixture was concentrated under vacuum in a 30° C. water bath to half volume. The remainder was diluted with water (300 mL), extracted with $Et_2O$ (2×200 mL). The aqueous layer was acidified to pH ~4 with 12 N HCl (3–4 mL), extracted with ethyl acetate, and washed with brine. The organic solution was dried over anhydrous $MgSO_4$, filtered, and evaporated under vacuum to leave the title compound (8.1 g, 78%), $C_{13}H_{21}NO_4S_2$ (319.44), mass spec. (FAB) M+1=320.1.

Step E Compound (2.6).

To a solution of compound (2.4) from Step C above (1 g) in dioxane (5 mL), was added 4 N HCl-dioxane solution (50 mL). The mixture was stirred vigorously for 1 hr. The mixture was evaporated under vacuum in a 25° C. water bath. The residue was triturated with $Et_2O$, and filtered to leave the title compound (0.76 g, 93% yield), $C_9H_{15}NO_2S_2$·HCl (269.81), mass spec. (FAB) M+1=234.0.

Step F Compound (2.7).

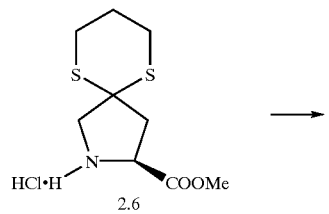

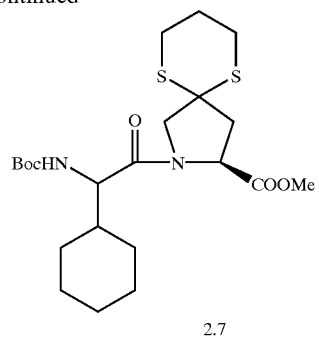

A mixture of compound (2.6) from Step E above (1.12 g), N-Boc-cyclohexylglycine (1.0 g, from Sigma Chemicals, St. Louis, Mo.), dimethylformamide (20 mL), and PyBrOP coupling reagent (2.1 g) was cooled to 5° C. To this was added diisopropylethylamine (DIEA or DIPEA, 2.8 mL). The mixture was stirred cold for 1 min., then stirred at room temperature for 6 hr. The reaction mixture was poured into cold 5% aqueous $H_3PO_4$ (150 mL) and extracted with ethyl acetate (2×150 mL). The combined organic layer was washed with cold 5% aqueous $K_2CO_3$, then 5% aqueous $KH_2PO_4$, then brine. The organic solution was dried over anhydrous $MgSO_4$, filtered, and evaporated under vacuum. The residue was chromatographed on silica gel, eluting with EtOAc-$CH_2Cl_2$ to afford a white solid (0.8 g, 50% yield), $C_{22}H_{36}N_2O_5S_2$ (472.66), mass spec. (FAB) M+1=473.2.

Step G Compound (2.8).

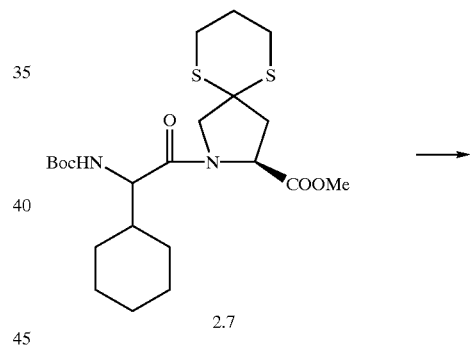

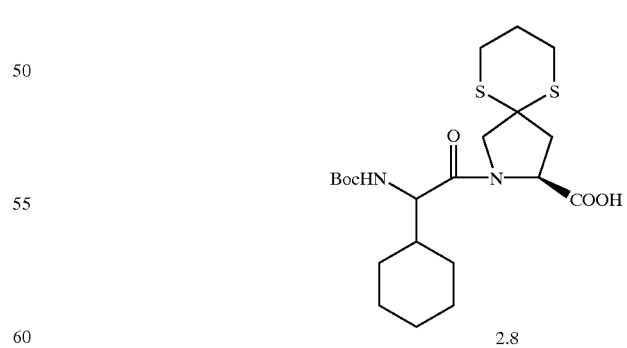

Following essentially the same procedure of Step D above, but substituting compound (2.7) (0.8 g) as starting material, compound (2.8) (0.7 g) was obtained $C_{21}H_{34}N_2O_5S_2$ (458.64), mass spec. (FAB) M+1=459.2.

Step H Compound (2.9).

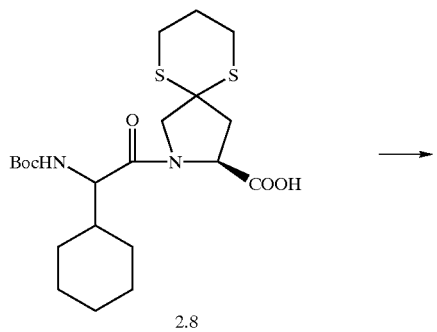

2.8

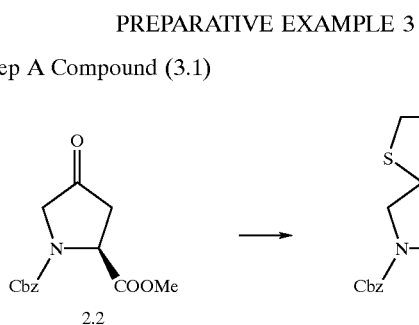

2.9

Following essentially the same procedure of Step E above, but substituting compound (2.8) as starting material, compound (2.9) was obtained. $C_{17}H_{28}N_2O_3S_2 \cdot HCl$ (409.01), mass spec. (FAB) M+1=373.2.

PREPARATIVE EXAMPLE 3

Step A Compound (3.1)

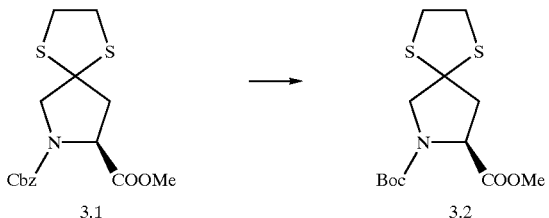

Following essentially the same procedure of Preparative Example 2, Step B, substituting ethane dithiol for propane dithiol, compound (3.1) was obtained.

Step B Compound (3.2).

Following essentially the same procedure of Preparative Example 2, Step C, substituting compound (3.1) for compound (2.3), the product compound (3.2) was obtained.

Step C Compound (3.3)

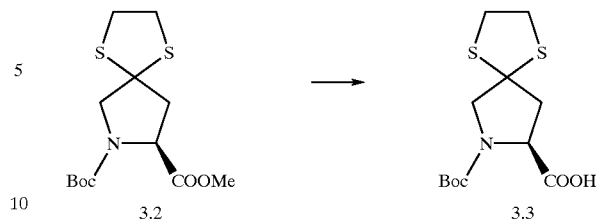

Following essentially the same procedure of Preparative Example 2, Step D, substituting compound (3.2) for compound (2.4) the product compound (3.3) was obtained.

Step D Compound (3.4)

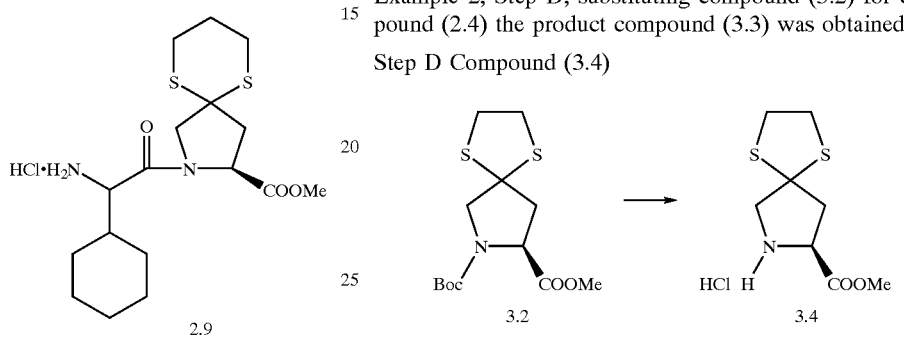

Following essentially the same procedure of Preparative Example 2, Step E, substituting compound (3.2) for compound (2.4) the product compound (3.4) was obtained.

Step E Compound (3.5)

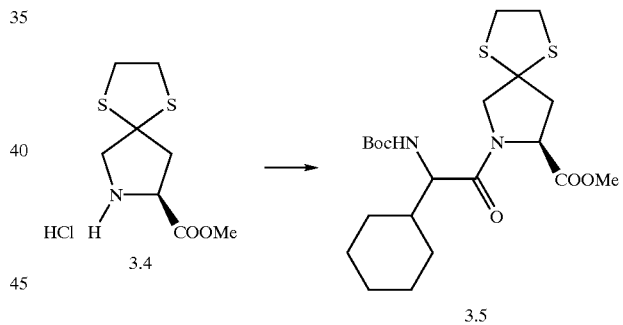

Following essentially the same procedure of Preparative Example 2, Step F, substituting compound (3.4) for compound (2.6) the product compound (3.5) was obtained.

Step F Compound (3.6)

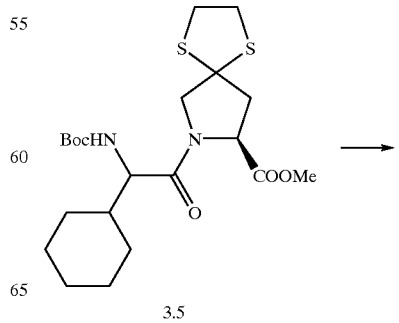

3.5

-continued

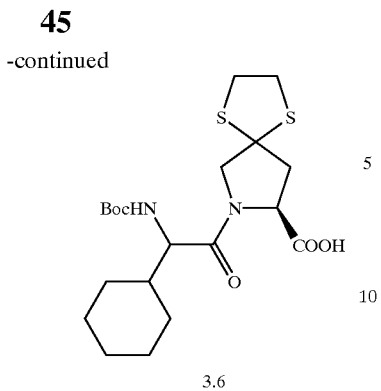

3.6

Following essentially the same procedure of Preparative Example 2, Step G, substituting compound (3.5) for compound (2.7) the product compound (3.6) was obtained. Step G Compound (3.7)

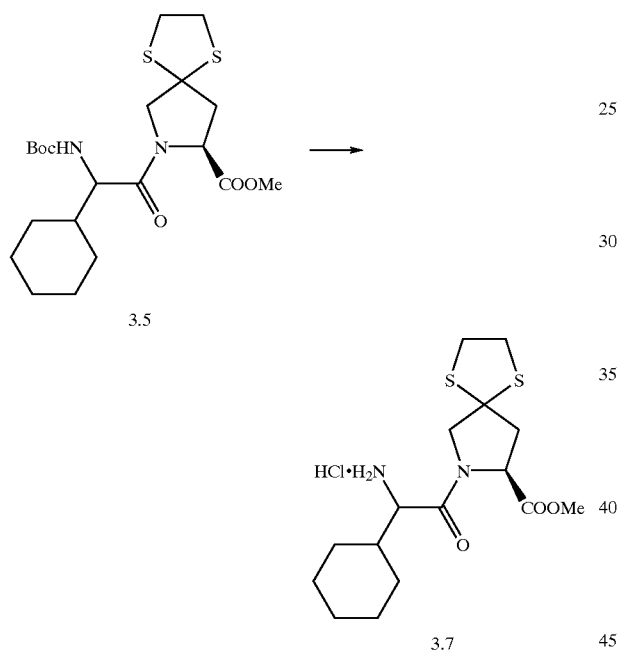

Following essentially the same procedure of Preparative Example 2, Step H, substituting compound (3.5) for compound (2.7) the product compound (3.7) was obtained.

PREPARATIVE EXAMPLE 4

Step A Compound (4.1)

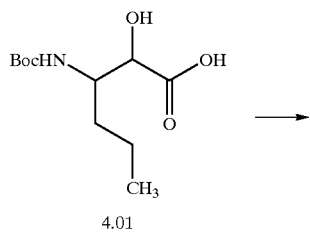

-continued

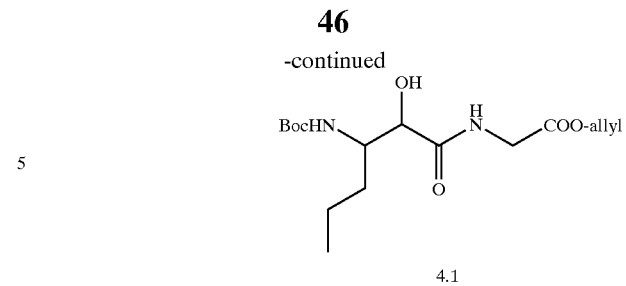

4.1

To a stirred solution of compound (4.01) (3.00 g, 12.0 mmol) prepared according to S. L. Harbeson et al., *J. Med. Chem.* 37 (18), 2918–2929 (1994), in DMF (15 mL) and CH$_2$Cl$_2$ (15 mL) at −20° C. was added HOOBt (1.97 g, 12.0 mmol), N-methyl morpholine (4.0 mL, 36.0 mmol) and EDCl (2.79 g, 14.5 mmol). The reaction mixture stirred for 10 minutes, followed by the addition of HCl.H$_2$N-Gly-Oallyl (2.56 g, 13.0 mmol). The resulting solution was stirred at −20° C. for 2 hrs, then kept in the refrigerator overnight. The solution was concentrated to dryness, then diluted with EtOAc (150 mL). The EtOAc solution was then washed twice with saturated NaHCO3, H2O, 5% H$_3$PO$_4$, and brine, dried over Na$_2$SO$_4$, filtered and concentrated to dryness to give the product (4.1). LRMS m/z MH$^+$=345.2.

Step B Compound (4.2)

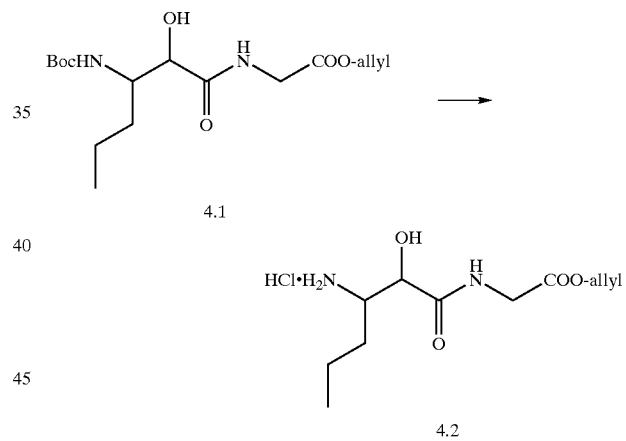

Following essentially the same procedure of Preparative Example 2, Step E, but substituting compound (4.1) from Step A above, as the starting material, compound (4.2) was obtained C$_{11}$H$_{20}$N$_2$O$_4$.HCl (280.75).

Step C Compound (4.3)

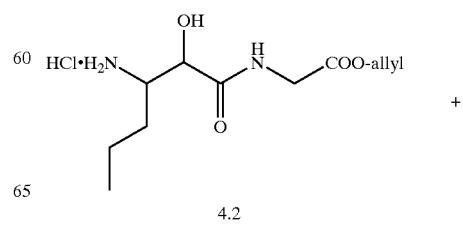

+

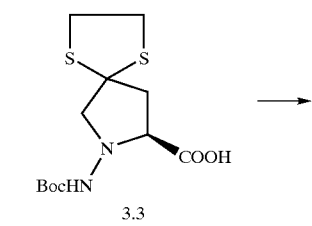

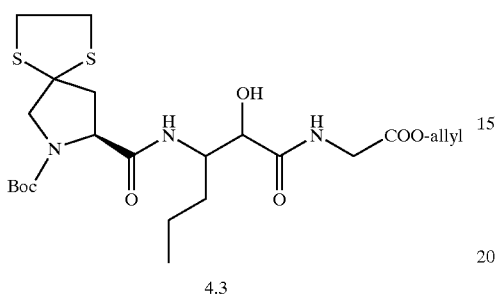

Following essentially the same procedure of Preparative Example 1, Step A, reacting compound (4.2) from Step B above, with compound (3.3) from Preparative example 3, Step C, compound (4.3) was obtained. $C_{28}H_{37}N_3O_7S_2$ (531.69).

Step D Compound (4.4).

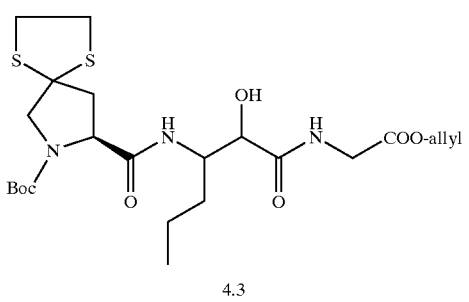

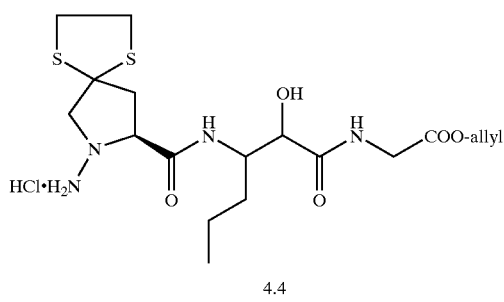

Following essentially the same procedure of Preparative Example 2, Step E, but substituting compound (4.3) from Step C above, as starting material, compound (4.4) was obtained. $C_{18}H_{30}N_4O_5S_2 \cdot HCl$ (483.05).

Step E Compound (4.5)

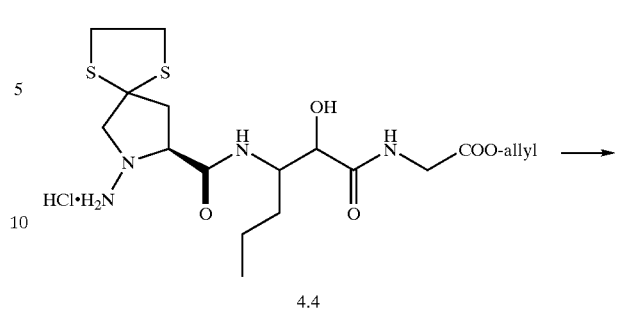

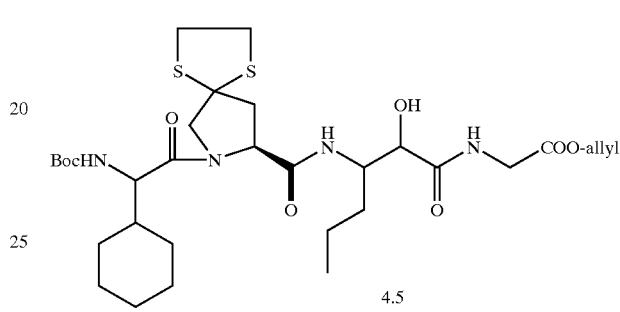

Following essentially the same procedure of Preparative Example 1, Step A, reacting compound (4.4) from Step D above, with N-Boc-cyclohexylglycine, compound (4.5) was obtained. $C_{31}H_{50}N_4O_8S_2$ (670.88).

Step F Compound (4.6).

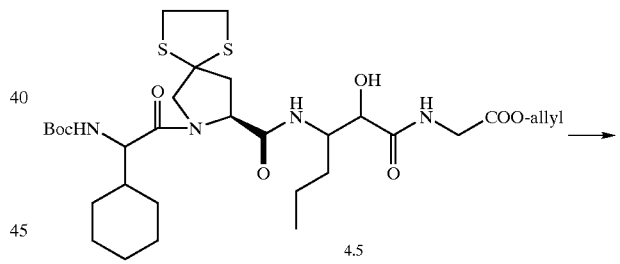

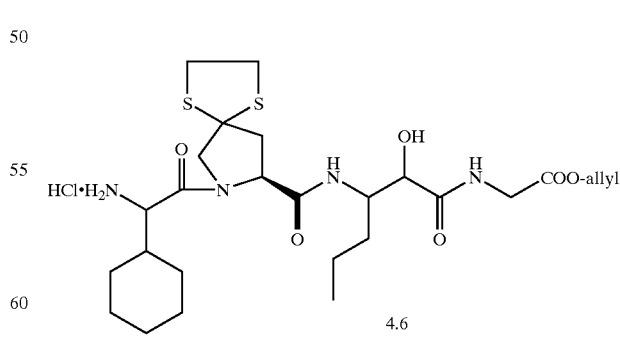

Following essentially the same procedure of Preparative Example 2, Step E, but substituting compound (4.5) from Step E above, as start ing material, compound (4.6) was obtained. $C_{26}H_{42}N_4O_6S_2 \cdot HCl$ (607.23).

Step G Compound (4.7).
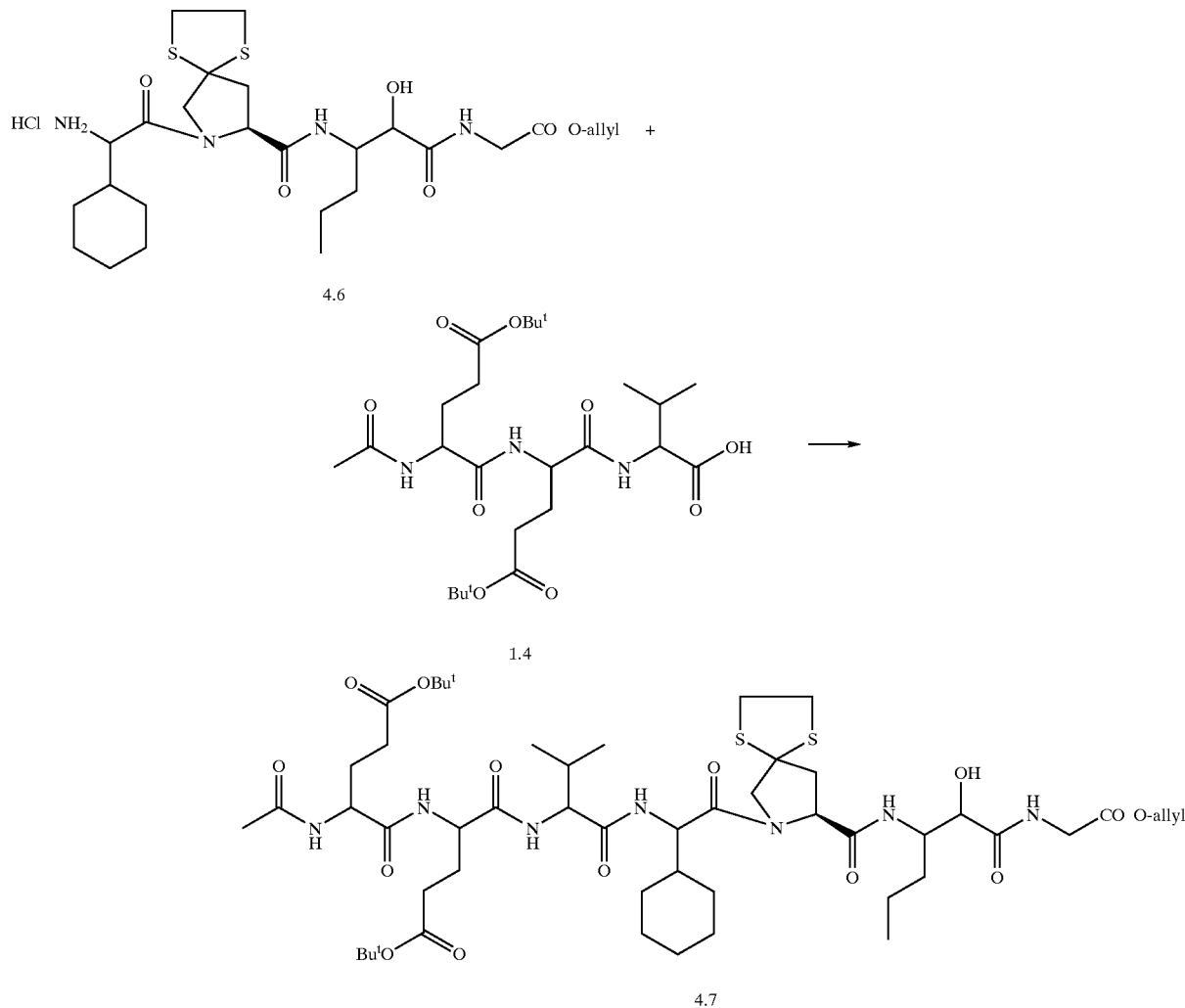
Following essentially the same procedure of Preparative Example 1, Step A, reacting compound (4.6) from Step F above, with compound (1.4) from Preparative example 1, Step D, compound (4.7) was obtained. $C_{51}H_{83}N_7O_{14}S_2$ (1082.38).
Step H Compound (4.8).
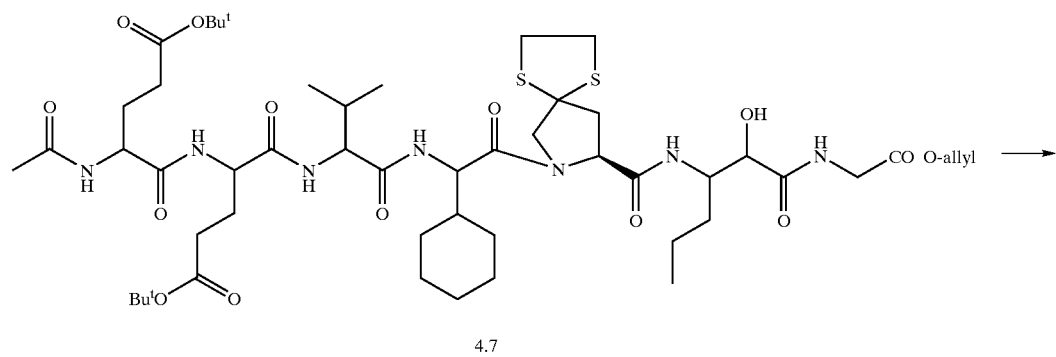

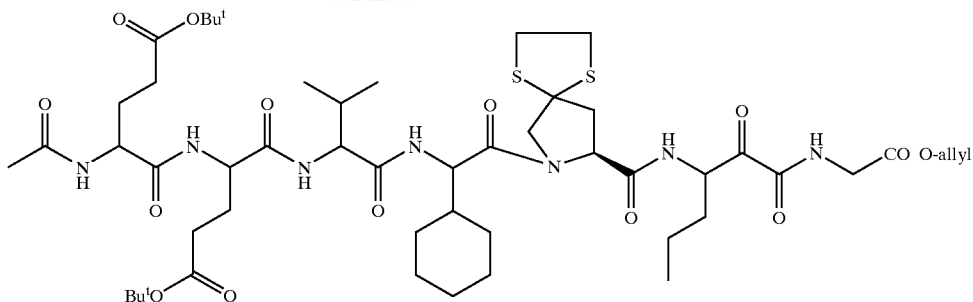

4.8

A mixture of compound (4.7) from Step G above (0.47 g), dichloromethane (20 mL), methyl sulfoxide (0.9 mL), and 2,2-dichloroacetic acid (0.142 mL) was stirred at 5° C. To this was added a solution of 1 M dicyclohexylcarbodiimide in $CH_2Cl_2$ (9.6 mL), and the resulting mixture was stirred cold for 5 min., at room temperature for 3 h. A solution of oxalic acid (0.35 g) in methanol (3 mL) was added to destroy excess oxidant, stirred for 15 min., and then filtered to remove the precipitated urea. The filtrate was diluted with excess ethyl acetate, and washed with cold 0.1 N NaOH, then cold 0.2 N $H_3PO_4$, then brine. The organic solution was dried over anhydrous $MgSO_4$, filtered, and evaporated under vacuum. The residue was chromatographed on silica gel, eluting with a gradient of $MeOH-CH_2Cl_2$ (1:99 to 5:95) to obtain the title compound (4.8) (0.25 g, 53% yield) $C_{51}H_{81}N_7O_{14}S_2$ (1080.36), mass spec. (FAB) M+1=1080.6.

Step I Compound (4.9).

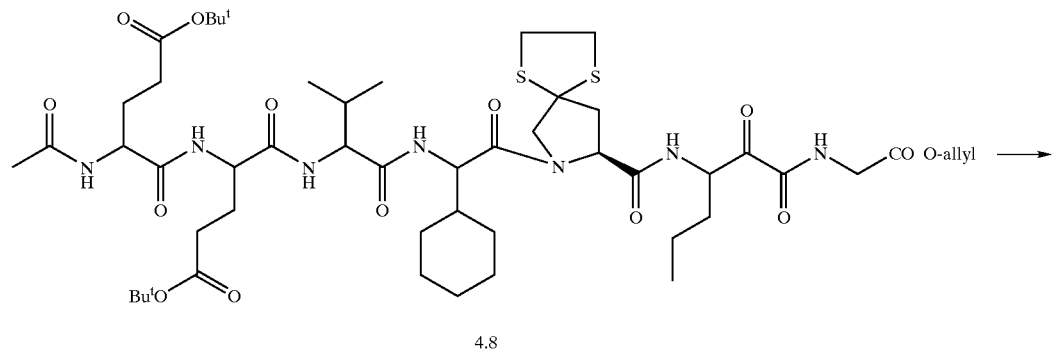

4.8

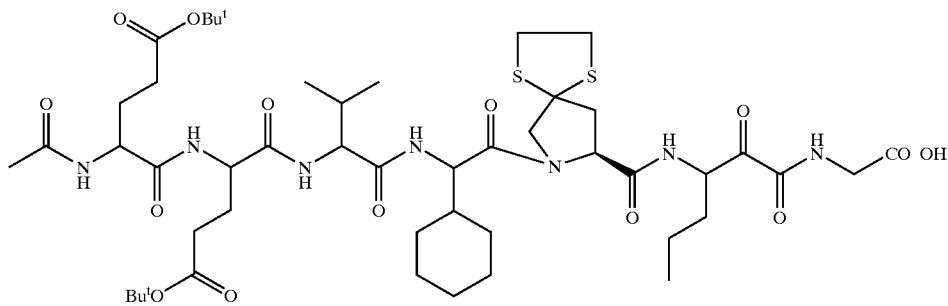

4.9

Following essentially the same procedure of Preparative Example 2, Step D, but substituting compound (4.8) from Step H above, as the starting material, compound (4.9) was obtained $C_{48}H_{73}N_7O_{14}S_2$ (1036.26), mass spec. (FAB) M+1=1036.6.

Step J Compound (86).

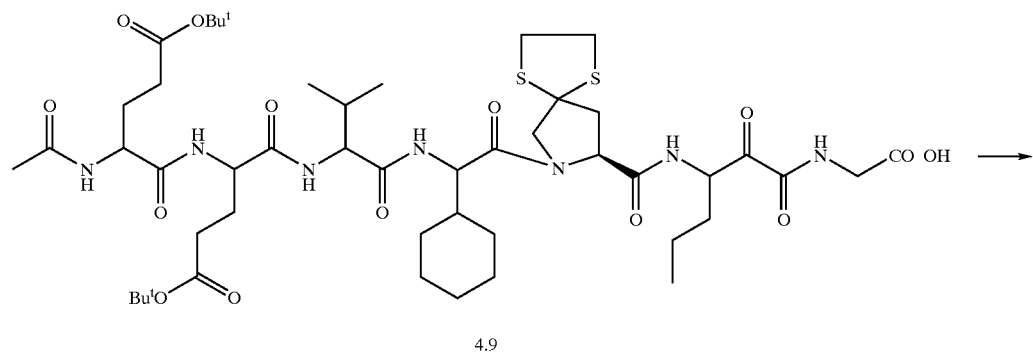

4.9

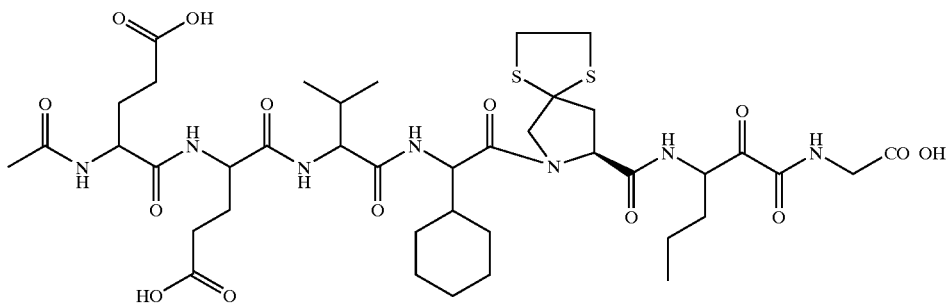

86

Compound (4.9) from Step I above (0.10 g) was treated with a solution of anhydrous trifluoroacetic acid-dichloromethane (1:1, 10 mL) for 2 h. The solution was diluted with xylene (50 mL) and evaporated under vacuum. The residue was triturated with $Et_2O$, and filtered to leave the title compound (86) (0.04 g), $C_{40}H_{61}N_7O_{14}S_2$ (928.08), mass spec. (FAB) M+1=928.4.

EXAMPLES

Using the procedures of Preparative Example 1, Step A, and Preparative Example 2, Step F, for couplings; Preparative Example 1, Step B, Preparative Example 1, Step F, Preparative Example 2, Step D, and Preparative Example 4, Step J for ester deprotection; Preparative Example 2, Step E, and Preparative Example 4, Step J, for amine deprotection; and Preparative Example 4, Step H, for oxidation of hydroxyamides to ketoamides—together with the α-amino acids of the above examples or those commercially available or those described in the literature, in the necessary various combinations, the following compounds in Table 2 were prepared:

TABLE 2
| Compound from Example No. | STRUCTURE | Molecular Weight |
|---|---|---|
| 1 | 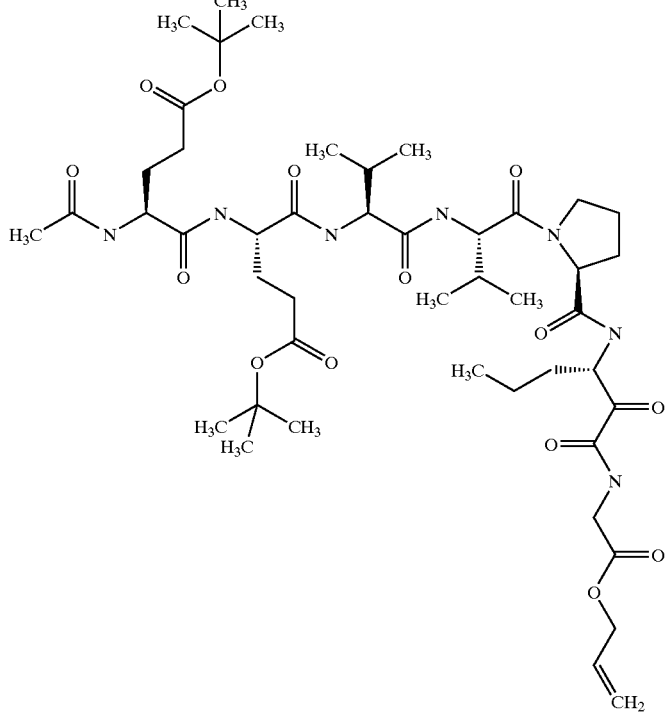 | 950.149 |
| 2 | 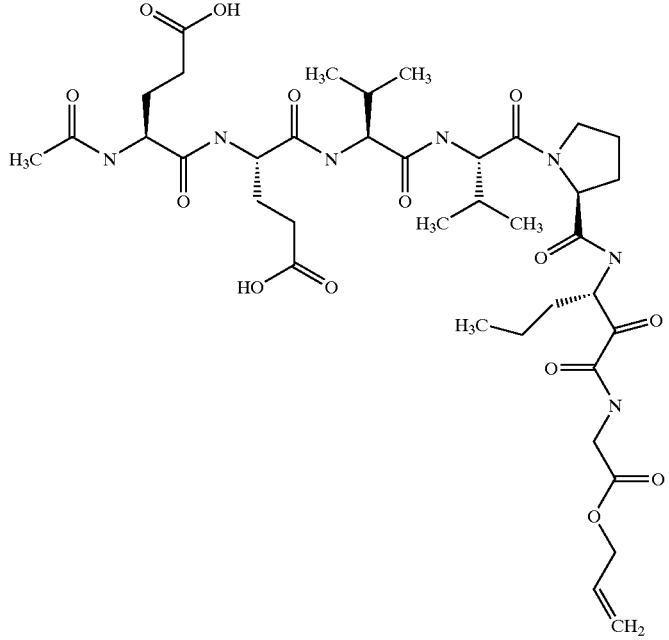 | 837.932 |

TABLE 2-continued

| Compound from Example No. | STRUCTURE | Molecular Weight |
|---|---|---|
| 3 | 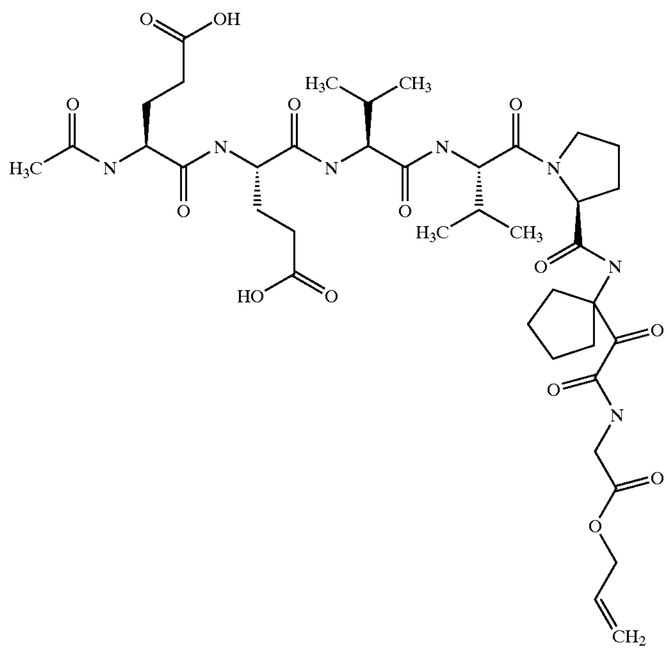 | 849.944 |
| 4 | 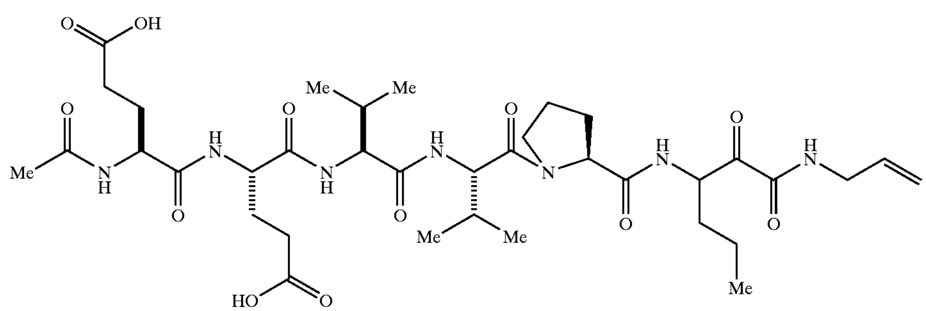 | 779.895 |
| 5 | 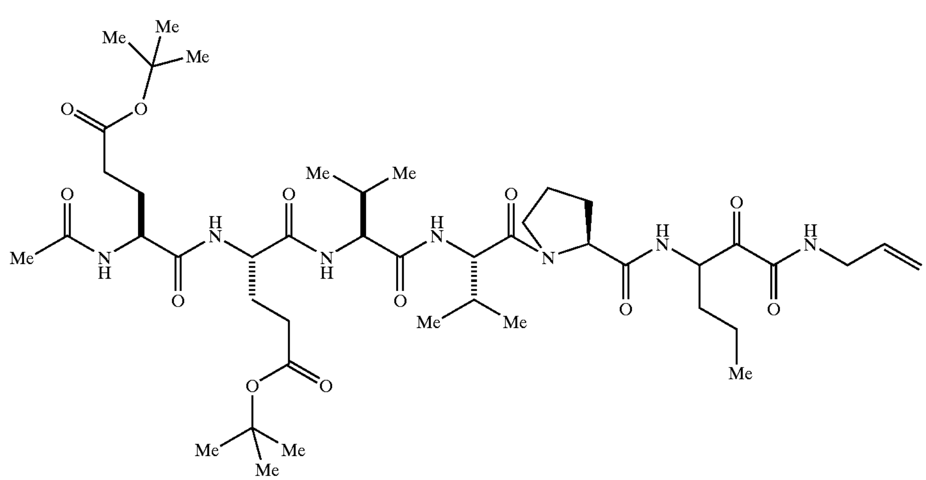 | 892.112 |

TABLE 2-continued
| Compound from Example No. | STRUCTURE | Molecular Weight |
|---|---|---|
| 6 | 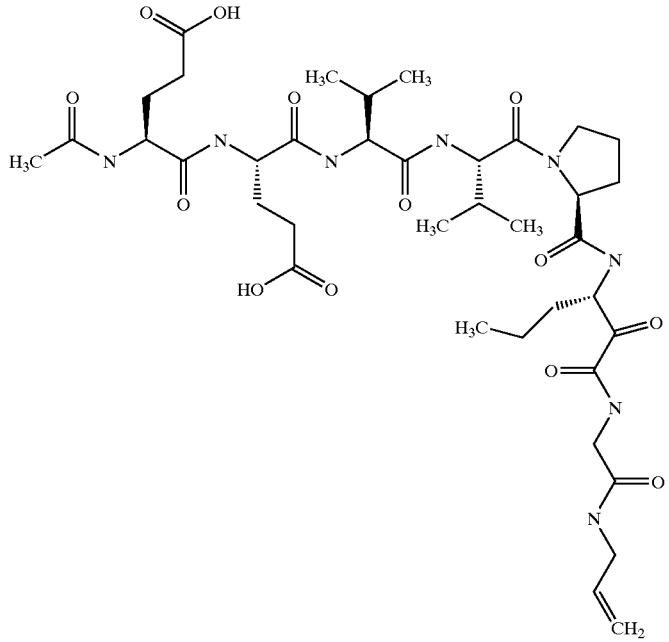 | 836.948 |
| 7 | 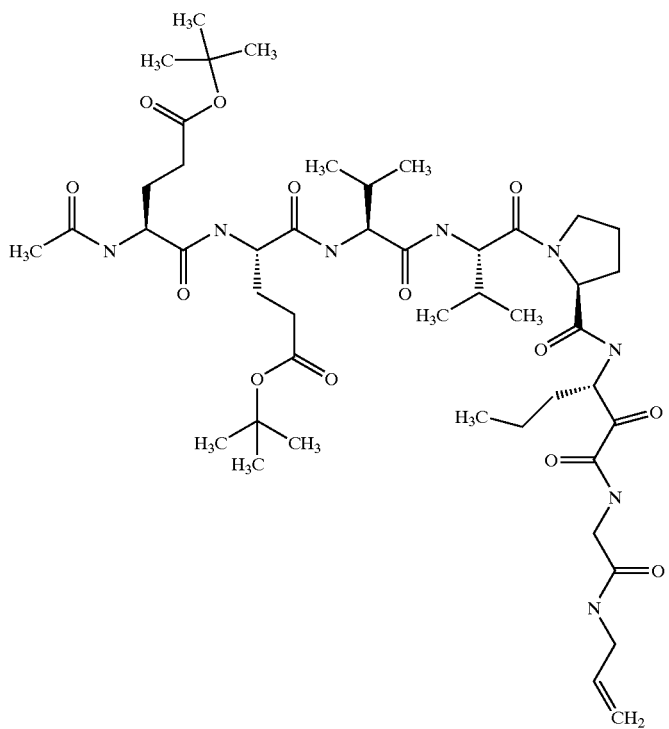 | 949.164 |

TABLE 2-continued

| Compound from Example No. | STRUCTURE | Molecular Weight |
|---|---|---|
| 8 | 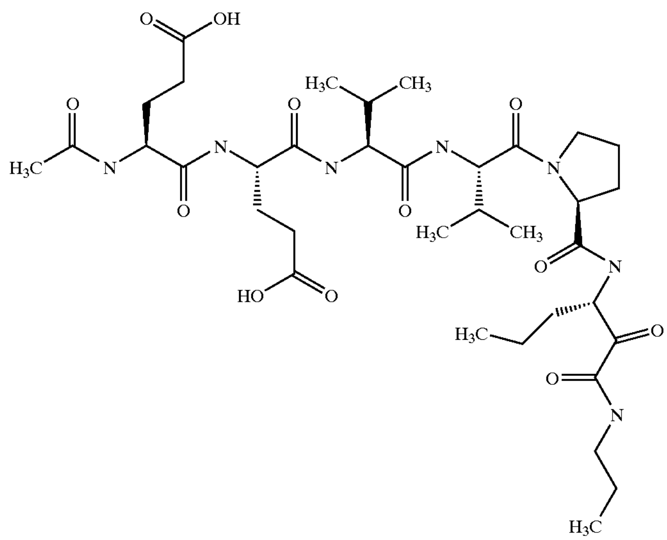 | 781.911 |
| 9 | 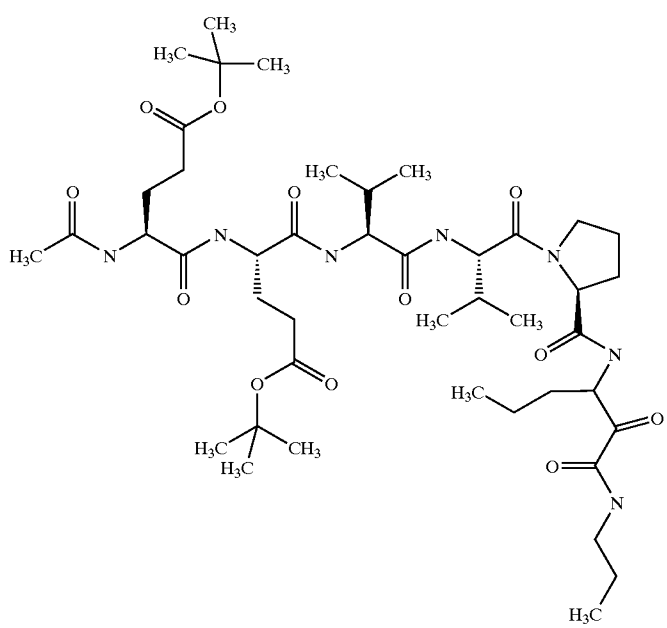 | 894.128 |

TABLE 2-continued

| Compound from Example No. | STRUCTURE | Molecular Weight |
|---|---|---|
| 10 | 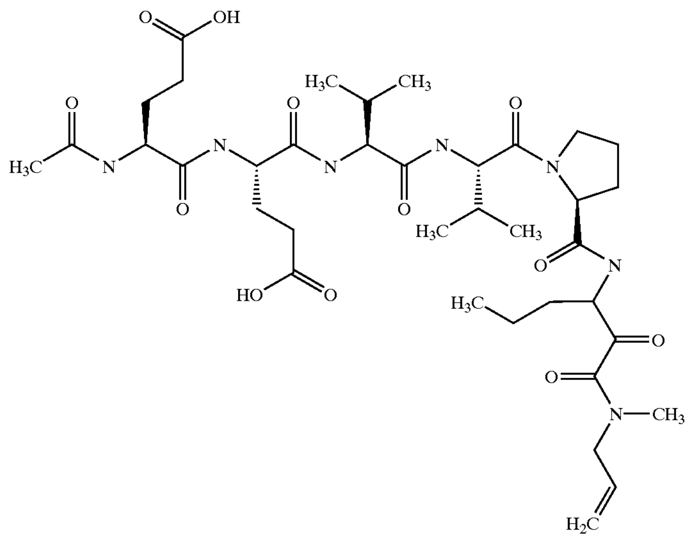 | 793.922 |
| 11 | 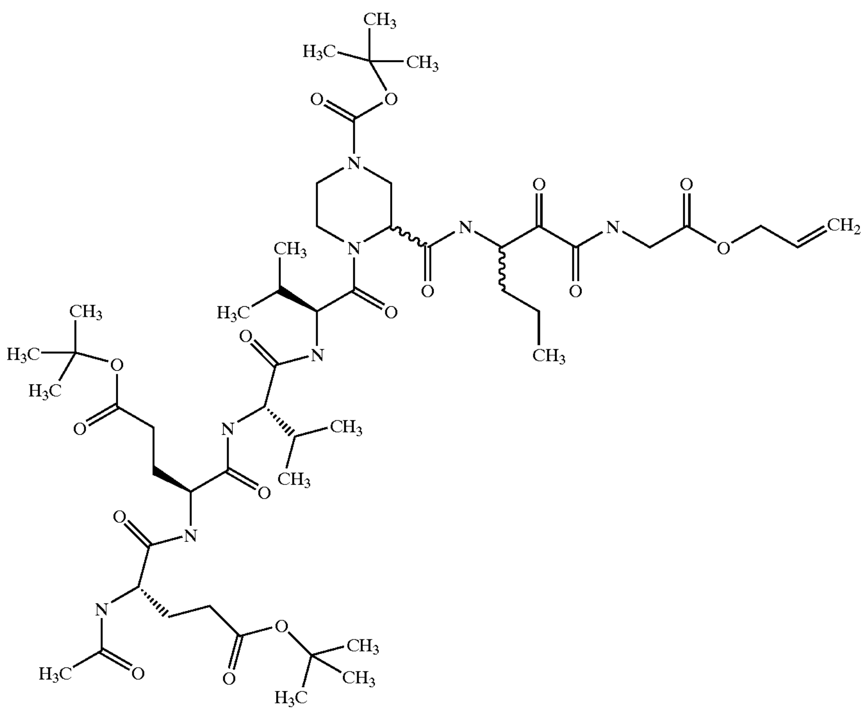 | 1065.28 |
| 12 | 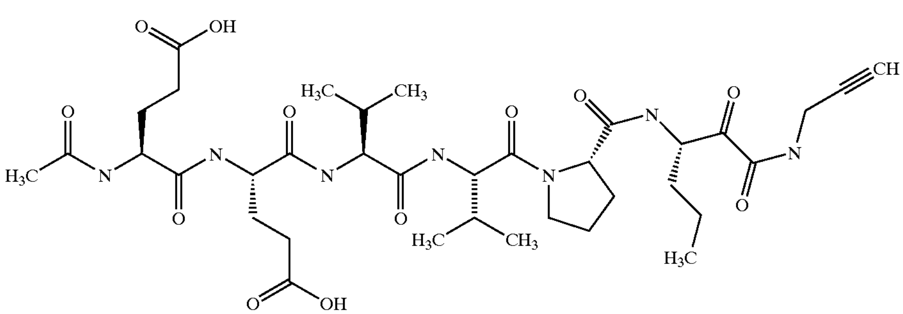 | 777.879 |

TABLE 2-continued
| Compound from Example No. | STRUCTURE | Molecular Weight |
|---|---|---|
| 13 | 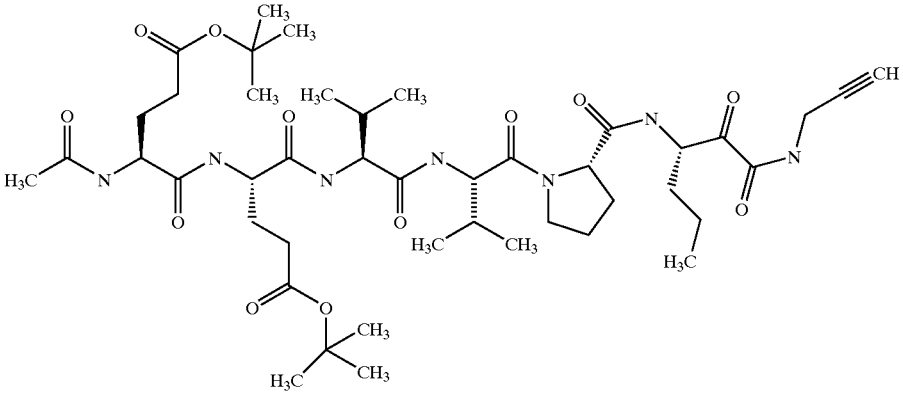 | 890.096 |
| 14 | 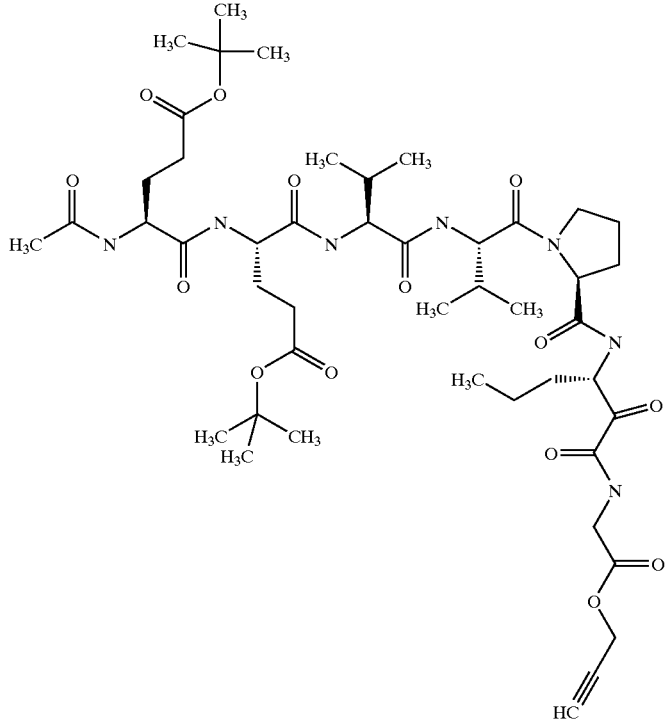 | 948.133 |

TABLE 2-continued
| Compound from Example No. | STRUCTURE | Molecular Weight |
|---|---|---|
| 15 | 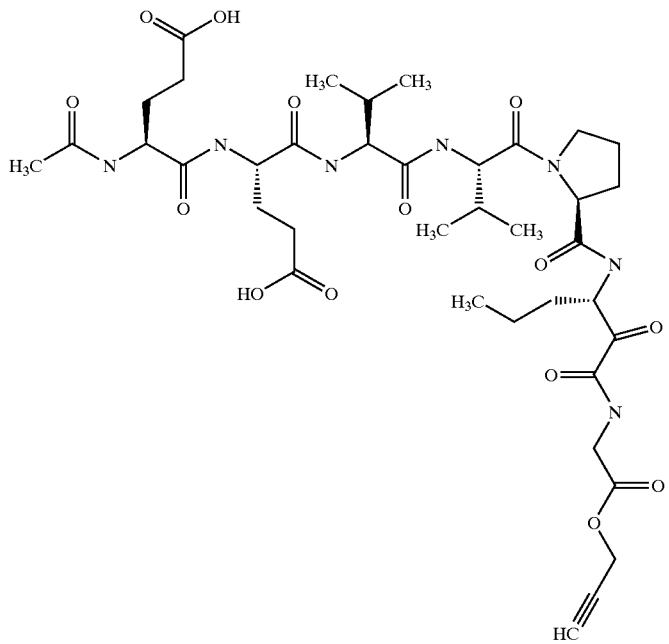 | 835.916 |
| 16 | 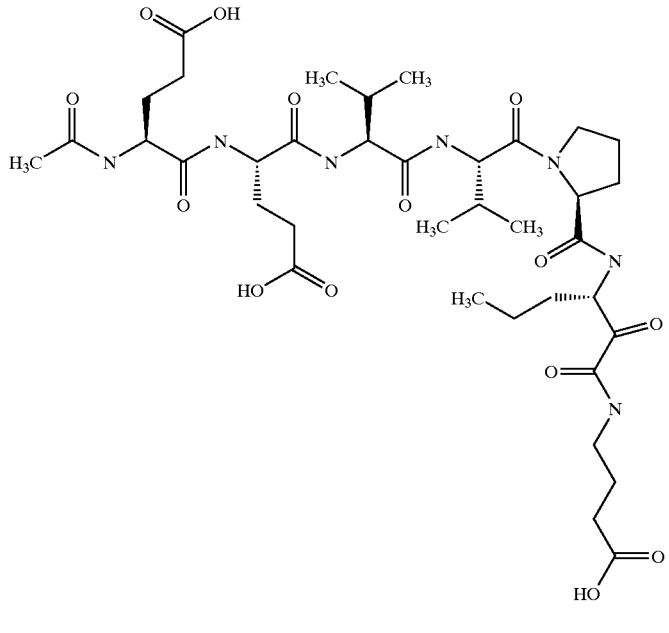 | 825.921 |

TABLE 2-continued
| Compound from Example No. | STRUCTURE | Molecular Weight |
|---|---|---|
| 17 | 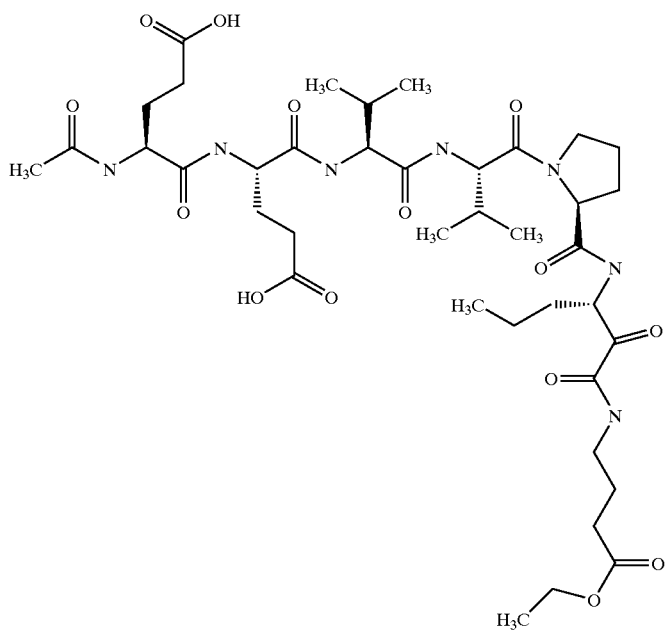 | 853.975 |
| 18 | 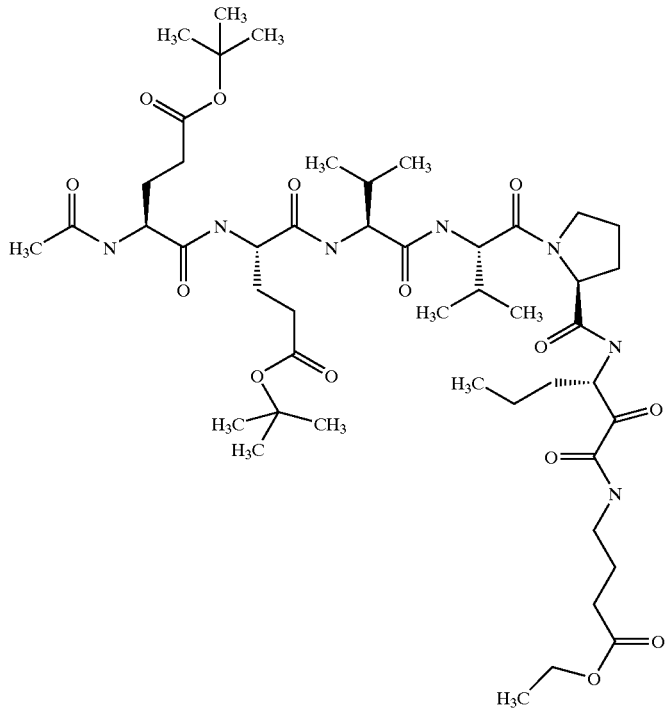 | 966.192 |

TABLE 2-continued
| Compound from Example No. | STRUCTURE | Molecular Weight |
|---|---|---|
| 19 | 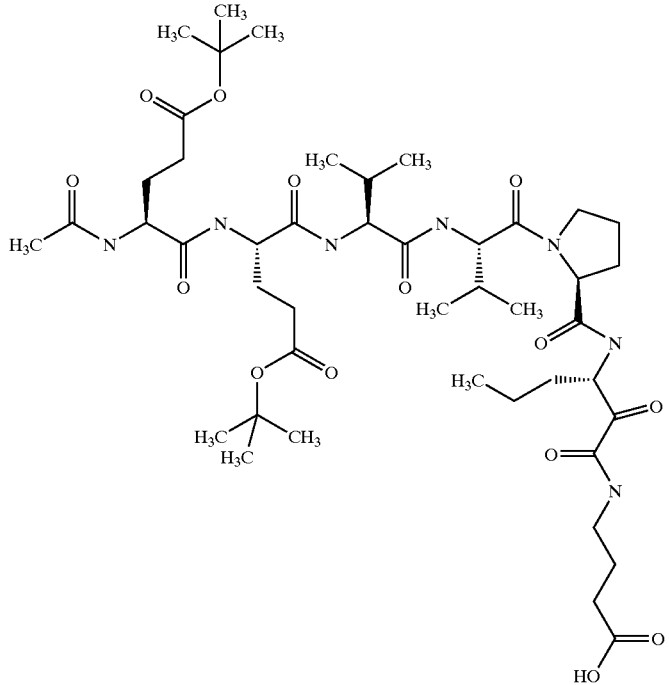 | 938.138 |
| 20 | 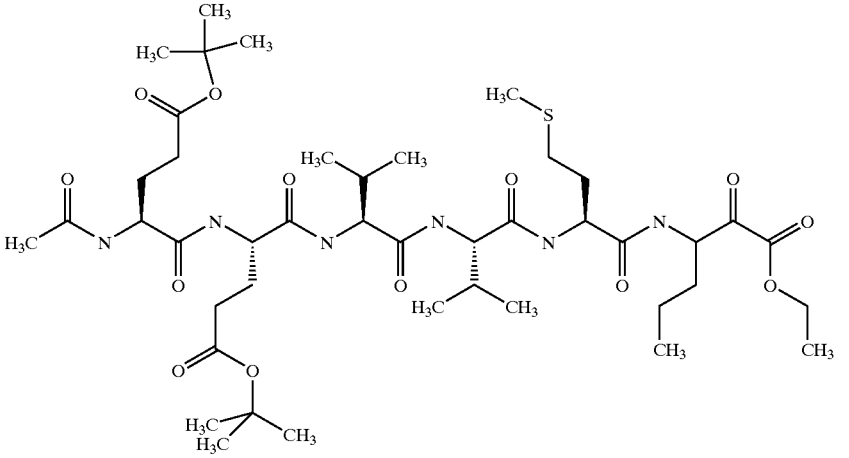 | 915.166 |

TABLE 2-continued
| Compound from Example No. | STRUCTURE | Molecular Weight |
|---|---|---|
| 21 | 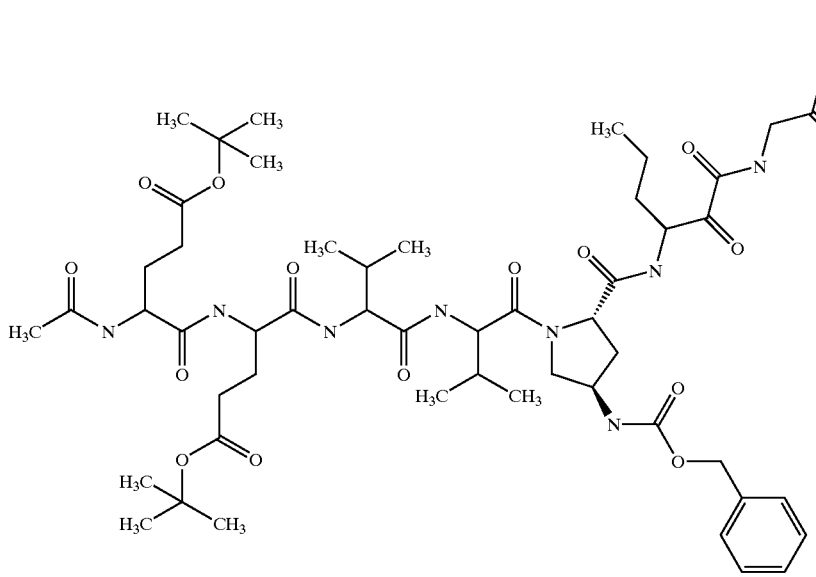 | 889.408 |
| 22 | 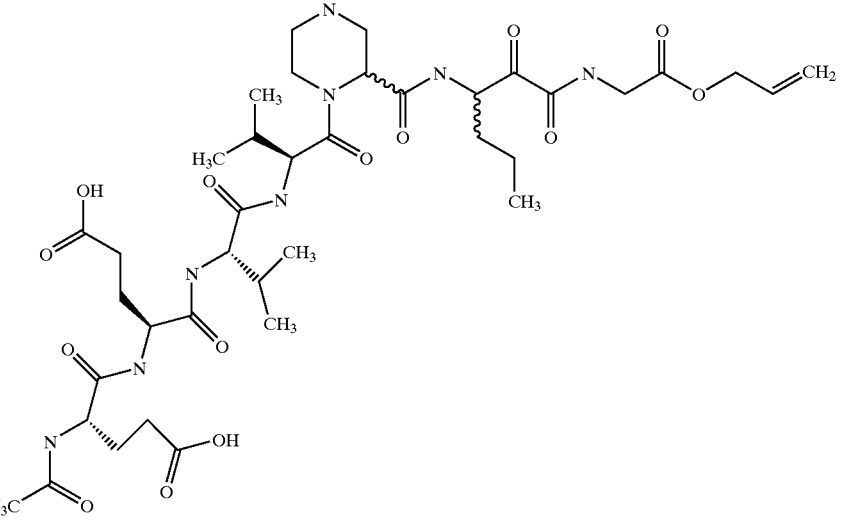 | 1099.30 |

TABLE 2-continued
| Compound from Example No. | STRUCTURE | Molecular Weight |
|---|---|---|
| 23 | 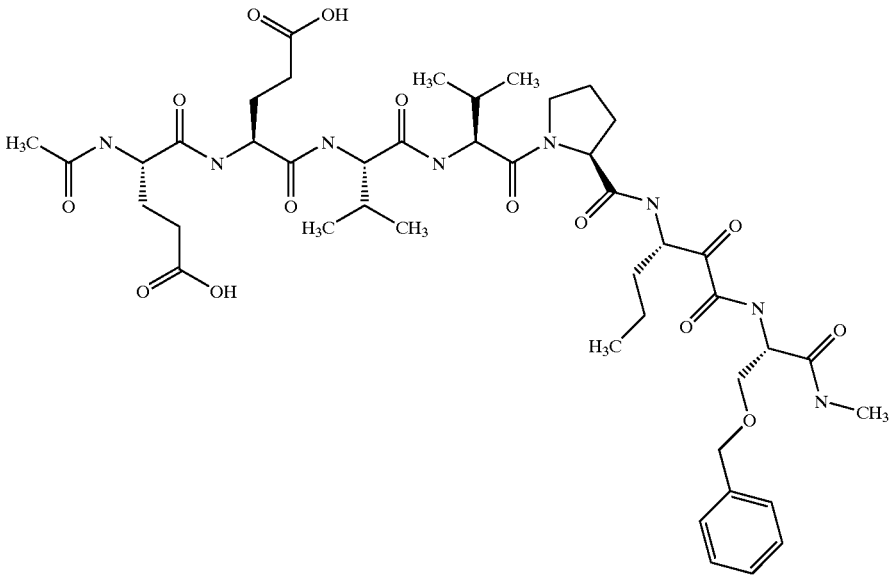 | 931.062 |
| 24 | 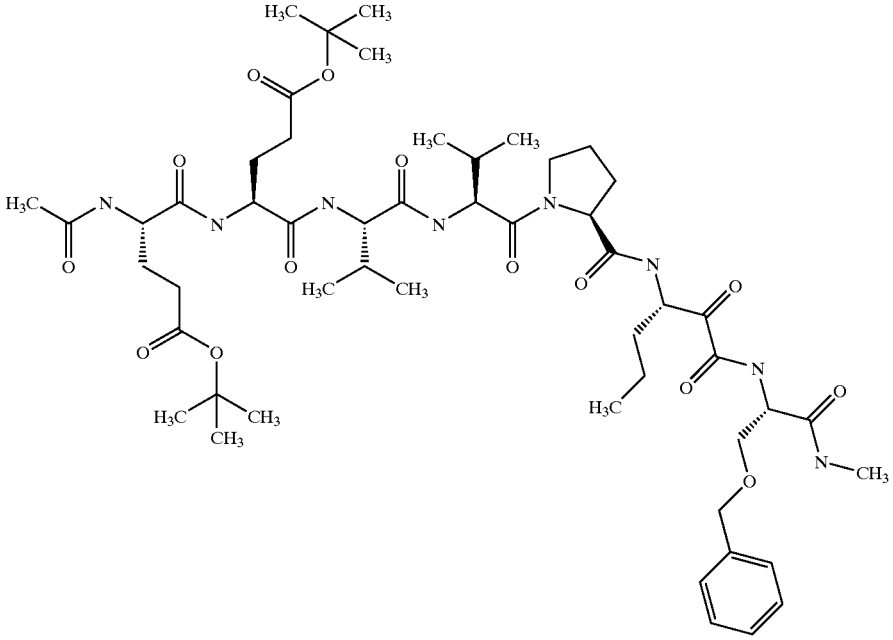 | 1043.28 |

TABLE 2-continued
| Compound from Example No. | STRUCTURE | Molecular Weight |
|---|---|---|
| 25 | 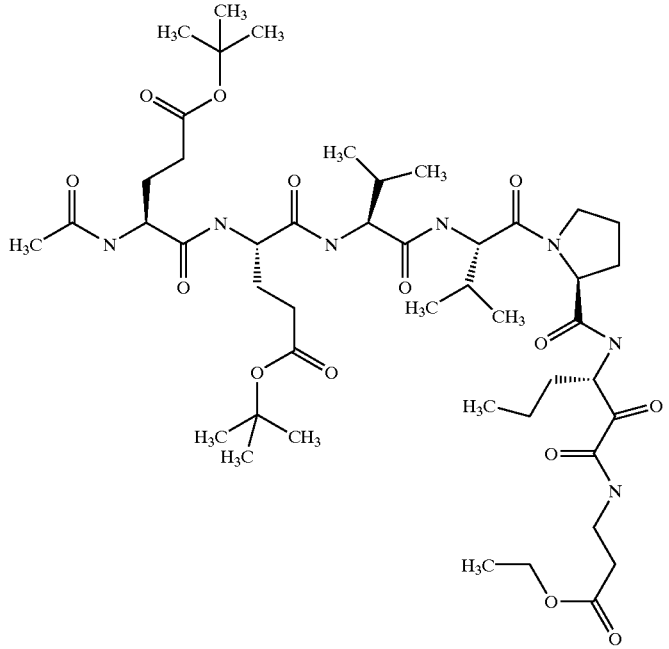 | 952.165 |
| 26 | 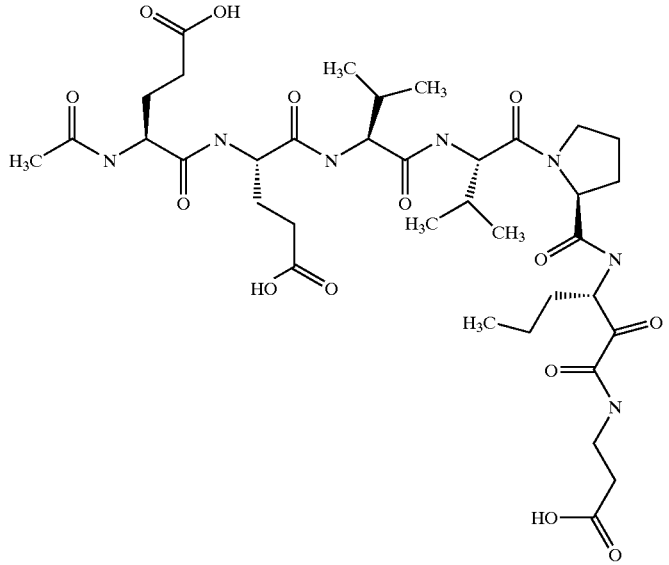 | 811.894 |

TABLE 2-continued
| Compound from Example No. | STRUCTURE | Molecular Weight |
|---|---|---|
| 27 | 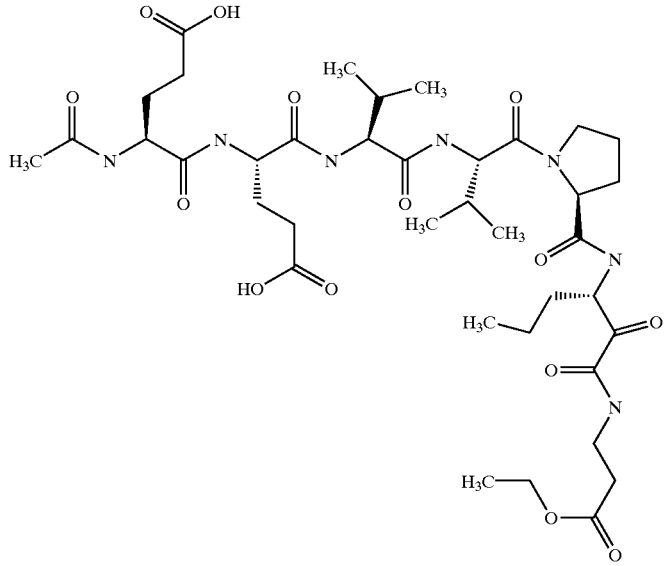 | 839.948 |
| 28 | 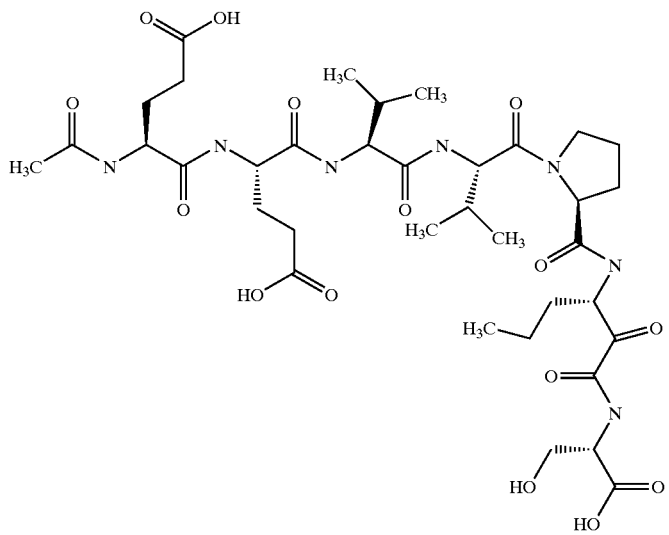 | 827.894 |

TABLE 2-continued

| Compound from Example No. | STRUCTURE | Molecular Weight |
|---|---|---|
| 29 | 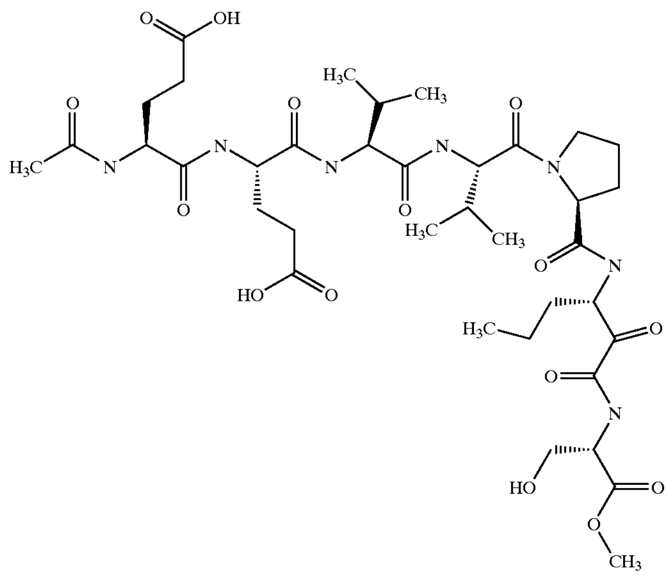 | 841.921 |
| 30 | 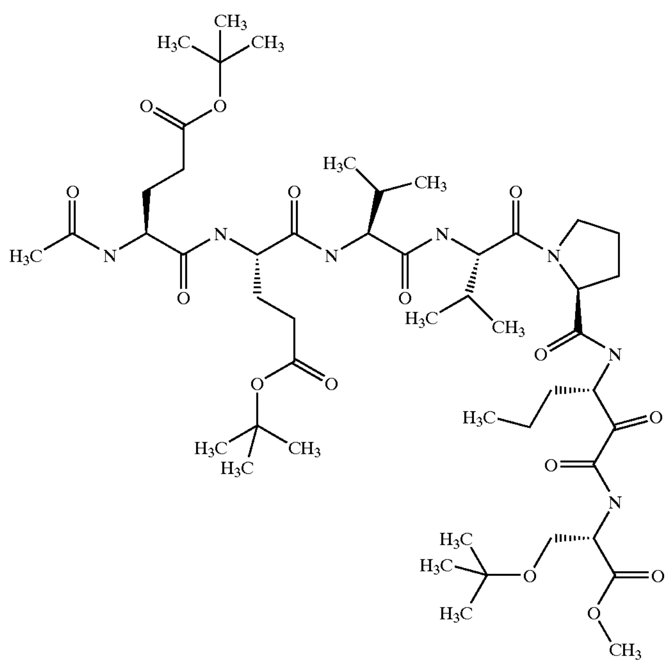 | 1010.25 |

TABLE 2-continued
| Compound from Example No. | STRUCTURE | Molecular Weight |
|---|---|---|
| 31 | 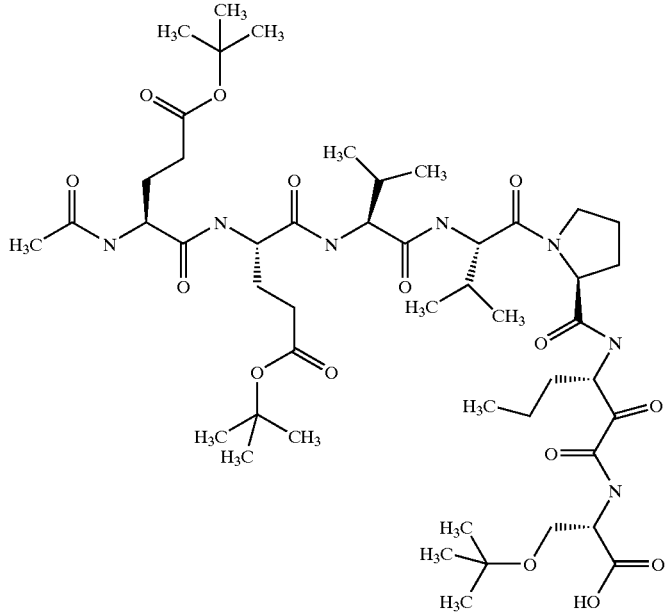 | 996.219 |
| 32 | 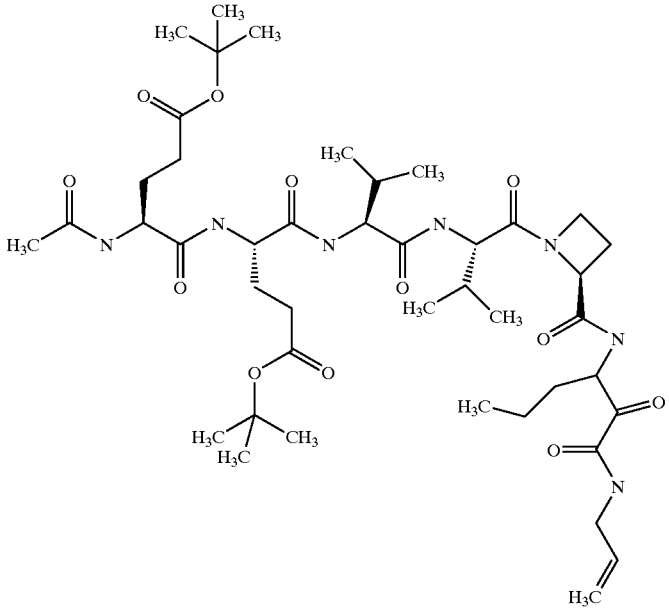 | 878.085 |

TABLE 2-continued

| Compound from Example No. | STRUCTURE | Molecular Weight |
|---|---|---|
| 33 | 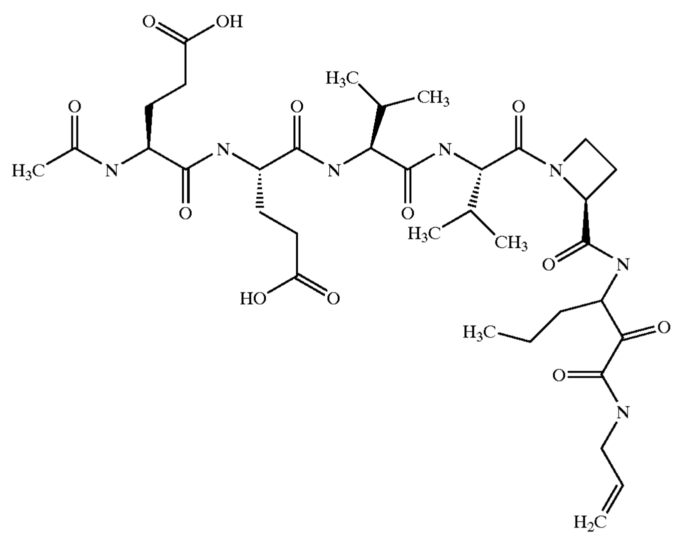 | 765.868 |
| 34 | 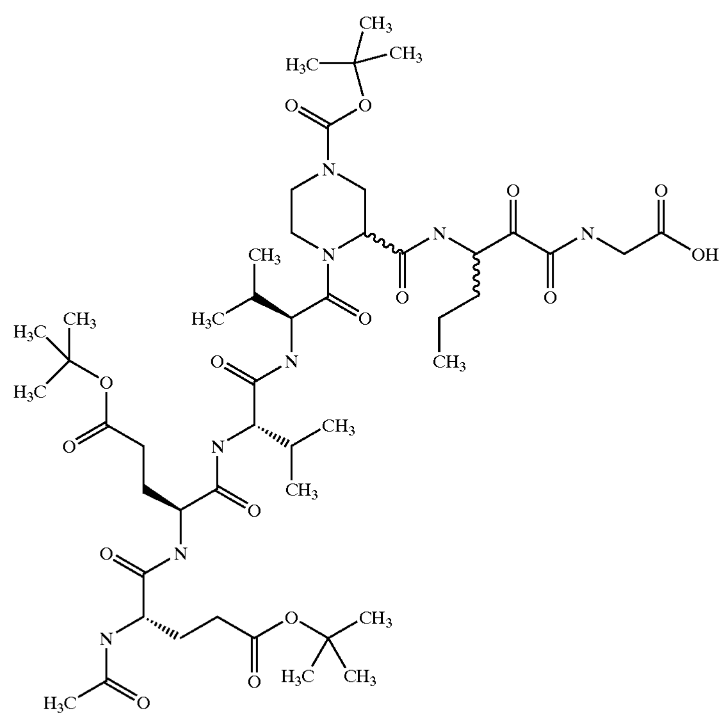 | 1025.22 |

TABLE 2-continued

| Compound from Example No. | STRUCTURE | Molecular Weight |
|---|---|---|
| 35 | 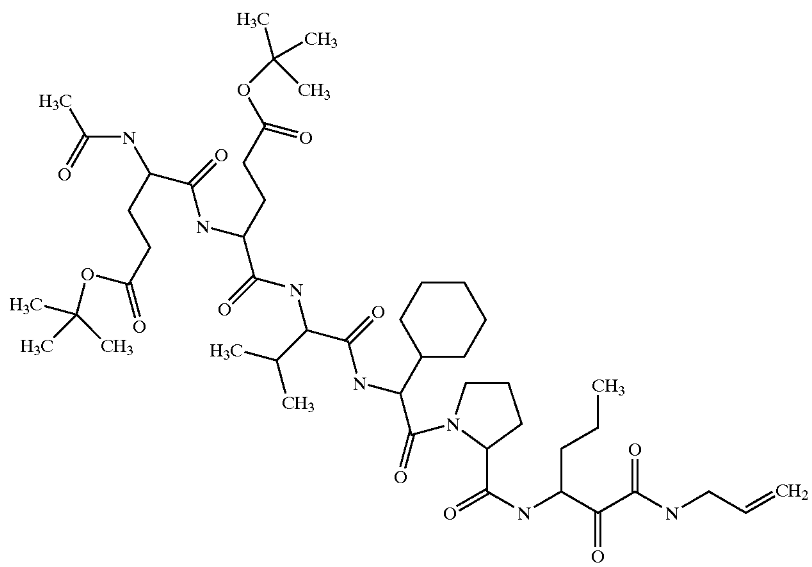 | 932.177 |
| 36 | 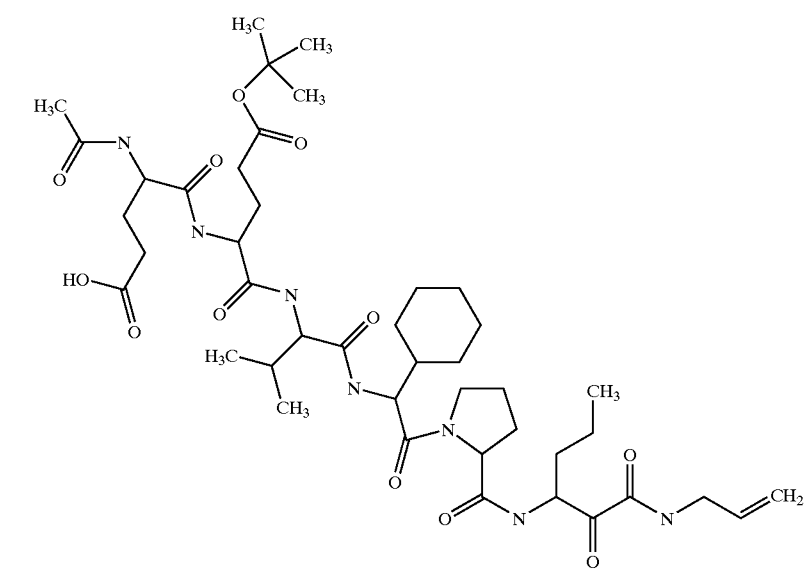 | 876.069 |

TABLE 2-continued
| Compound from Example No. | STRUCTURE | Molecular Weight |
|---|---|---|
| 37 | 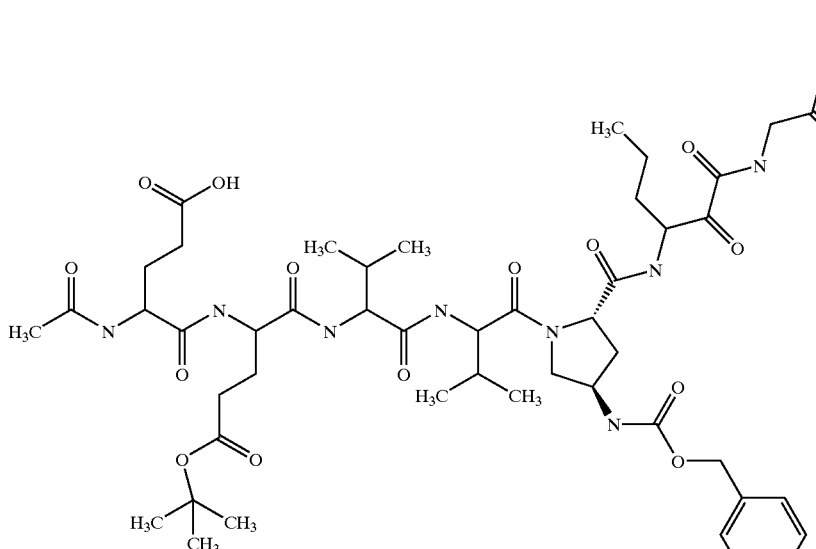 | 1043.19 |
| 38 | 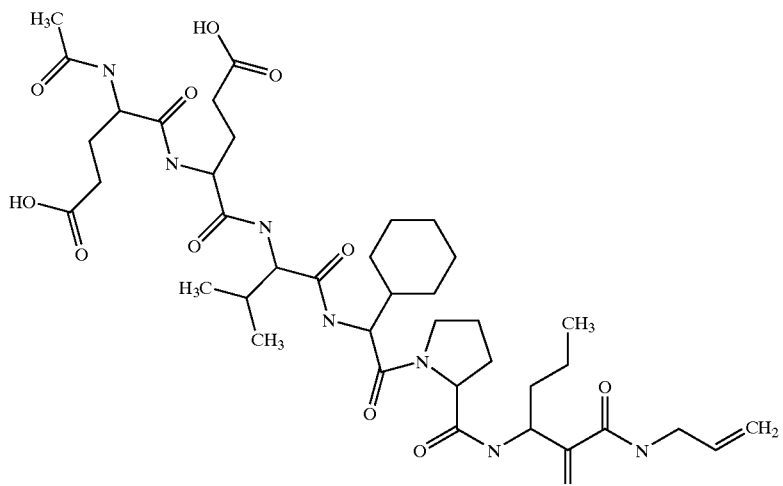 | 819.961 |

TABLE 2-continued
| Compound from Example No. | STRUCTURE | Molecular Weight |
|---|---|---|
| 39 | 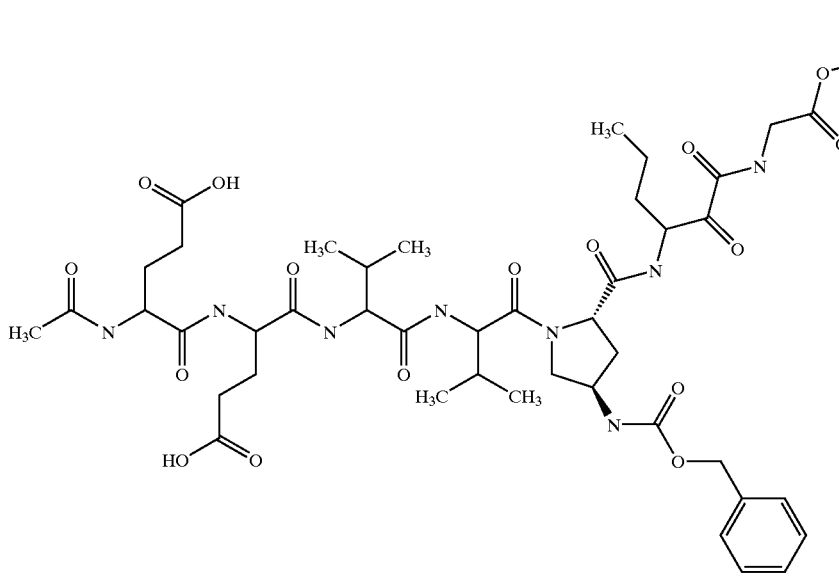 | 987.083 |
| 40 | 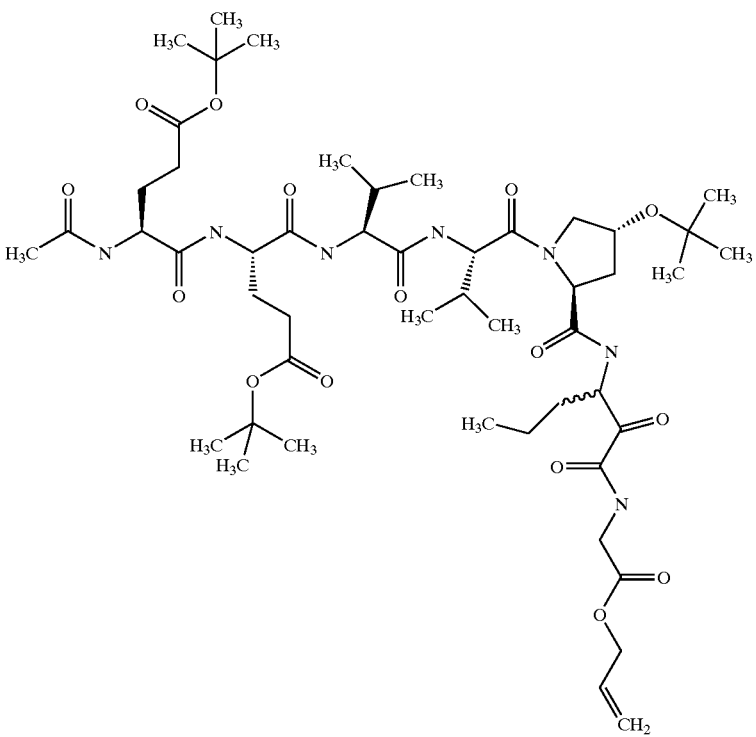 | 1022.26 |

TABLE 2-continued
| Compound from Example No. | STRUCTURE | Molecular Weight |
|---|---|---|
| 41 | 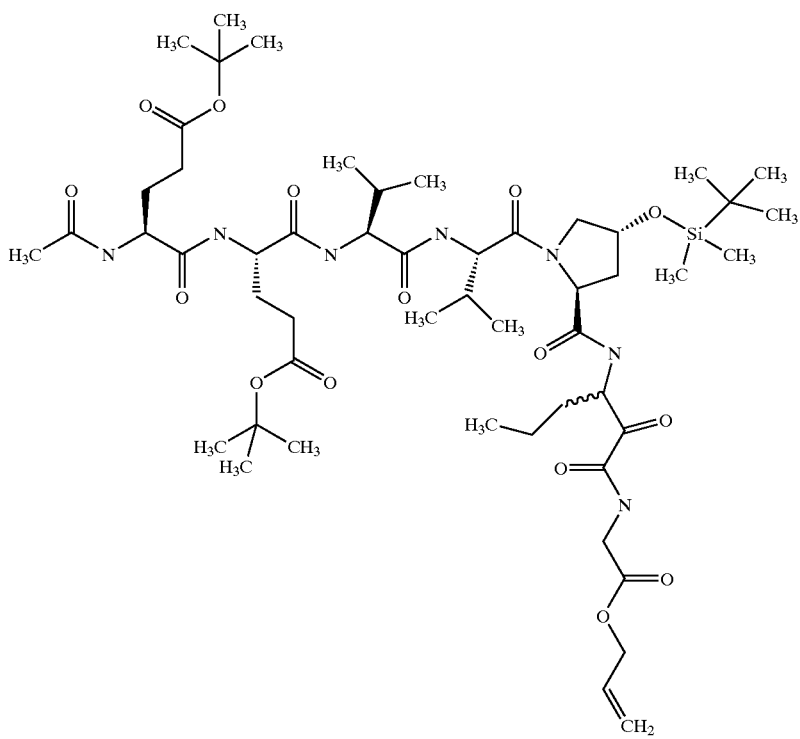 | 1080.41 |
| 42 | 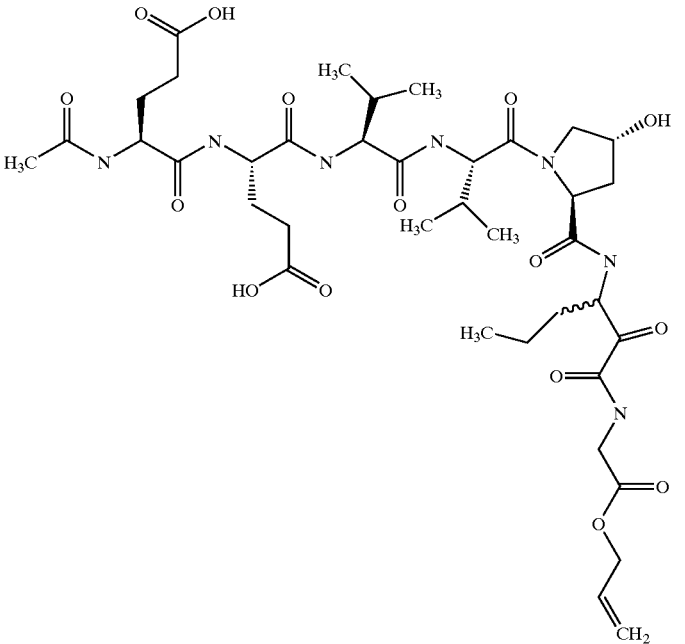 | 853.932 |

TABLE 2-continued
| Compound from Example No. | STRUCTURE | Molecular Weight |
|---|---|---|
| 43 | 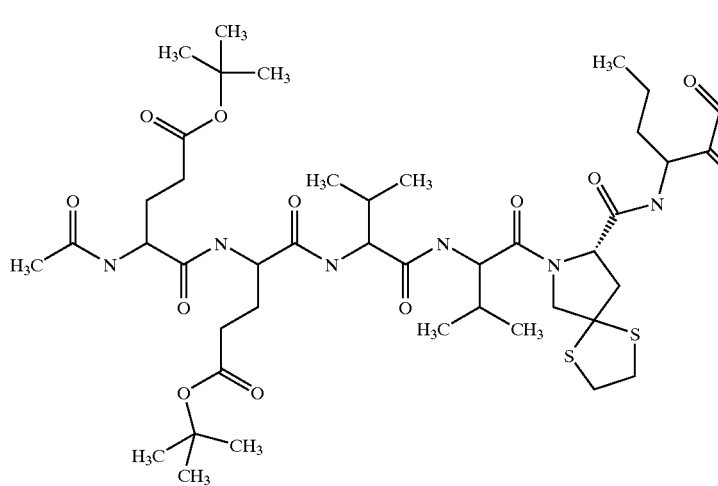 | 982.278 |
| 44 | 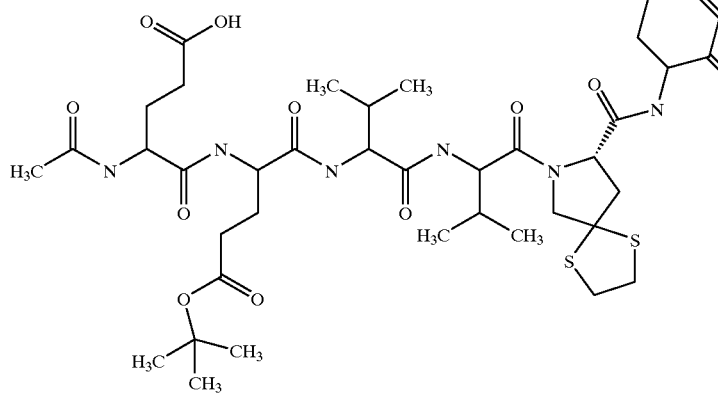 | 926.170 |
| 45 | 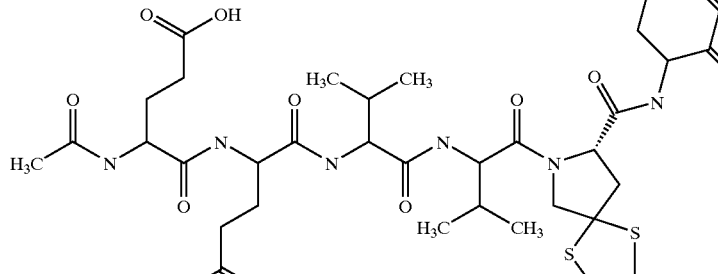 | 870.062 |

TABLE 2-continued
| Compound from Example No. | STRUCTURE | Molecular Weight |
|---|---|---|
| 46 | 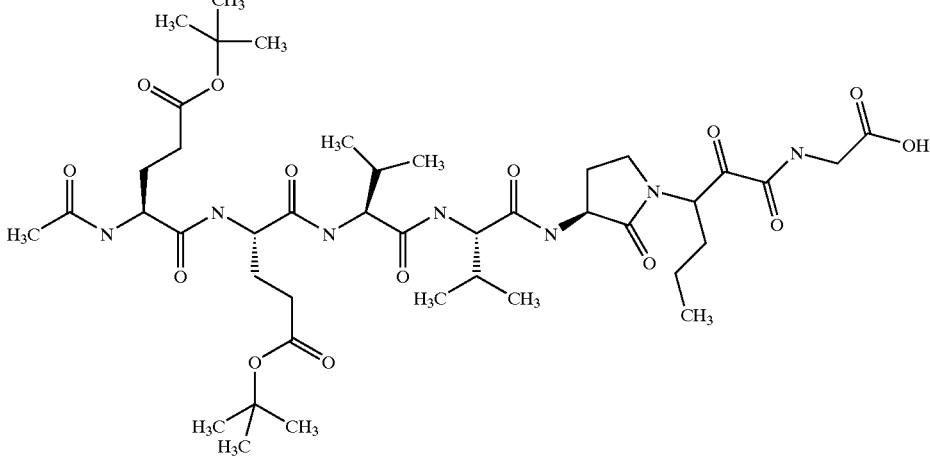 | 896.057 |
| 47 | 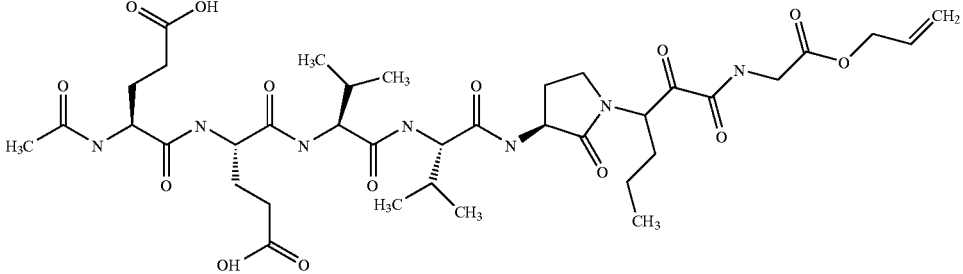 | 823.905 |
| 48 | 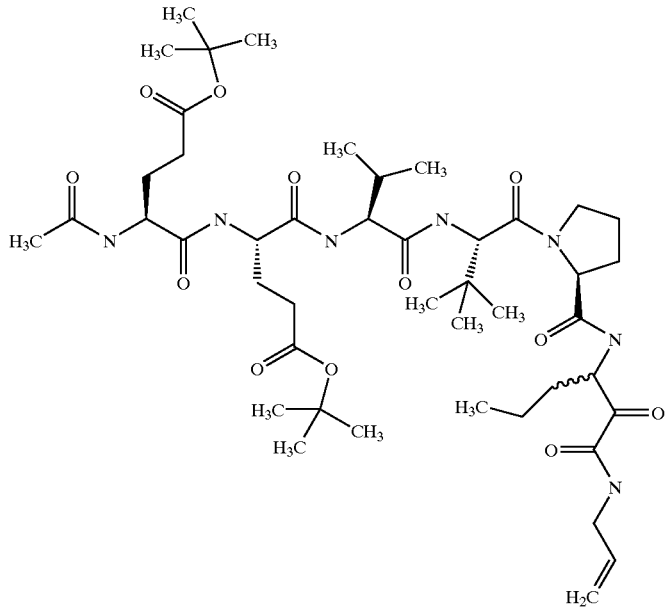 | 906.139 |

TABLE 2-continued
| Compound from Example No. | STRUCTURE | Molecular Weight |
|---|---|---|
| 49 | 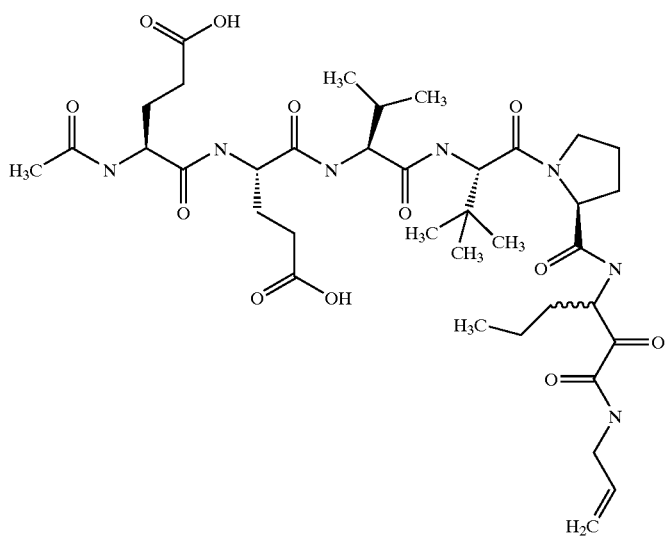 | 793.922 |
| 50 | 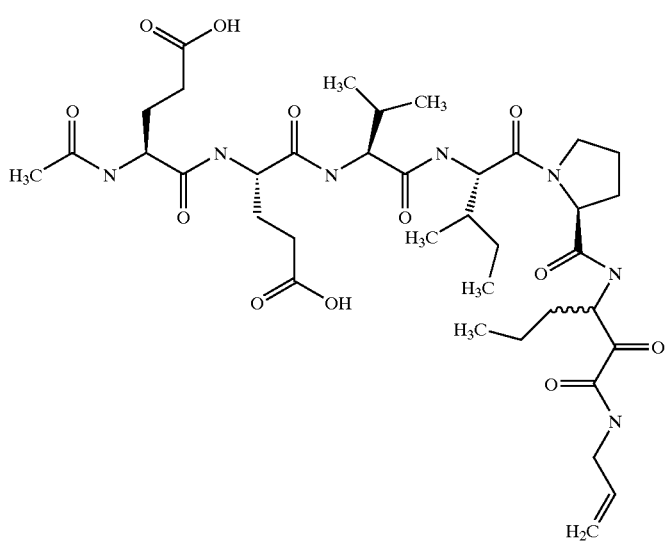 | 793.922 |

TABLE 2-continued

| Compound from Example No. | STRUCTURE | Molecular Weight |
|---|---|---|
| 51 | 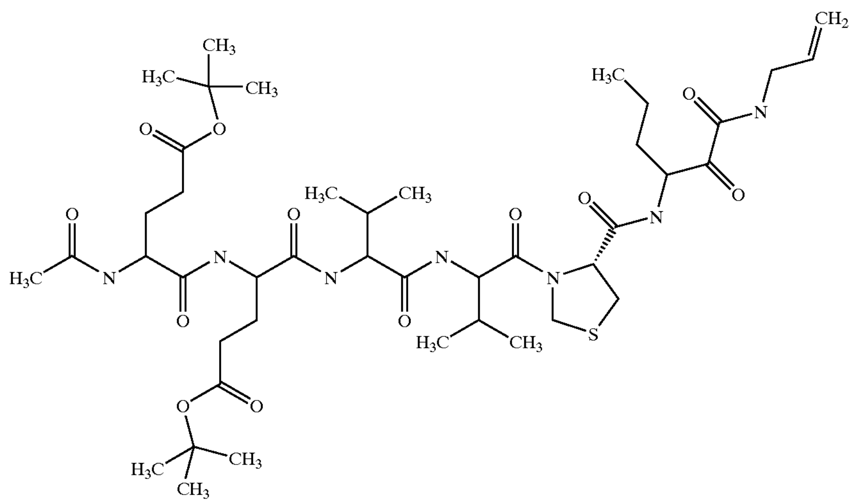 | 910.149 |
| 52 | 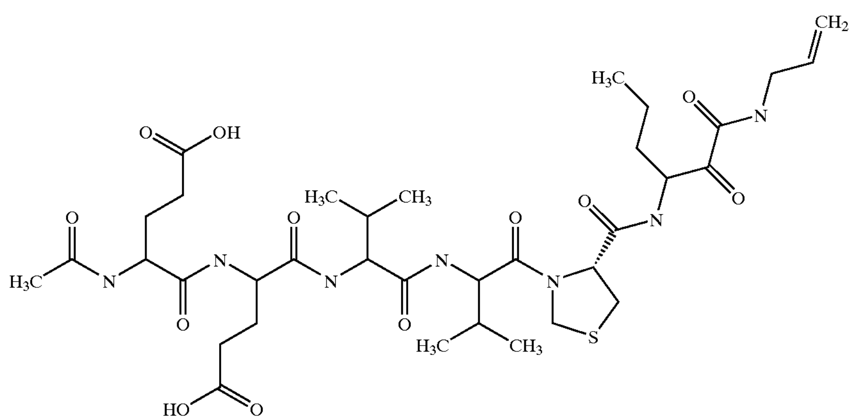 | 797.932 |
| 53 | 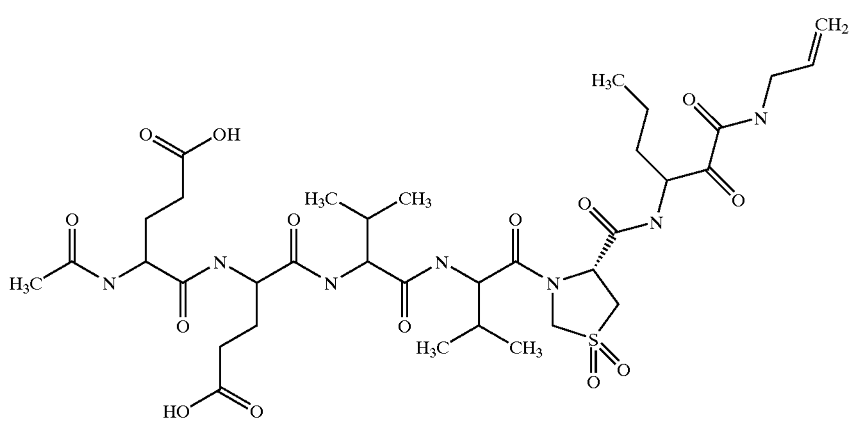 | 829.931 |

//
TABLE 2-continued
| Compound from Example No. | STRUCTURE | Molecular Weight |
|---|---|---|
| 54 | 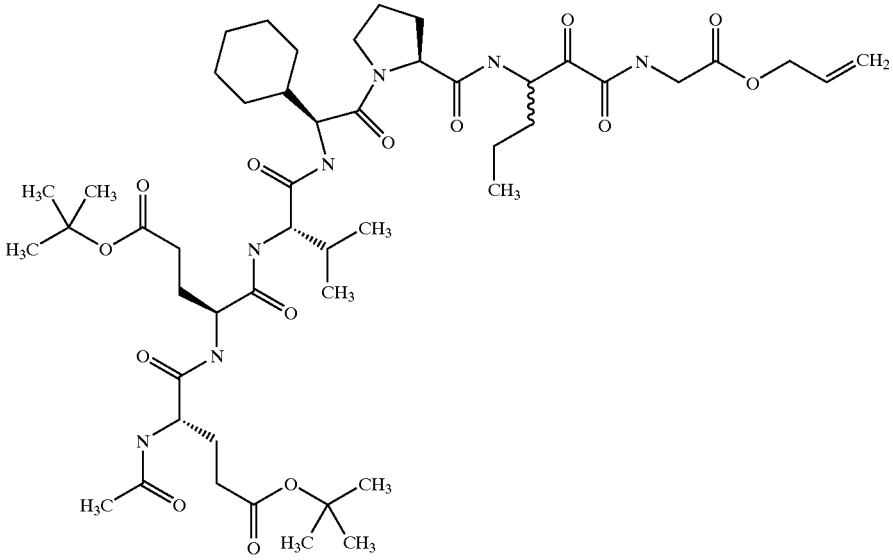 | 990.214 |
| 55 | 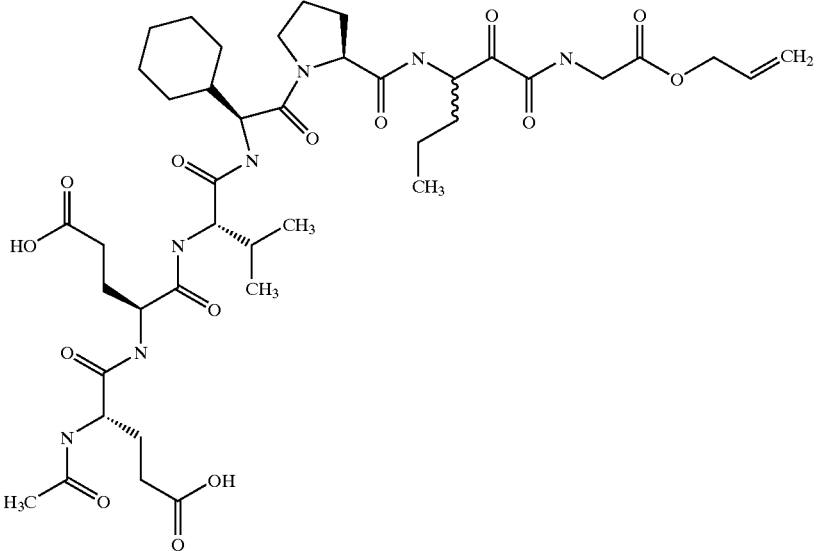 | 877.998 |

TABLE 2-continued
| Compound from Example No. | STRUCTURE | Molecular Weight |
|---|---|---|
| 56 | 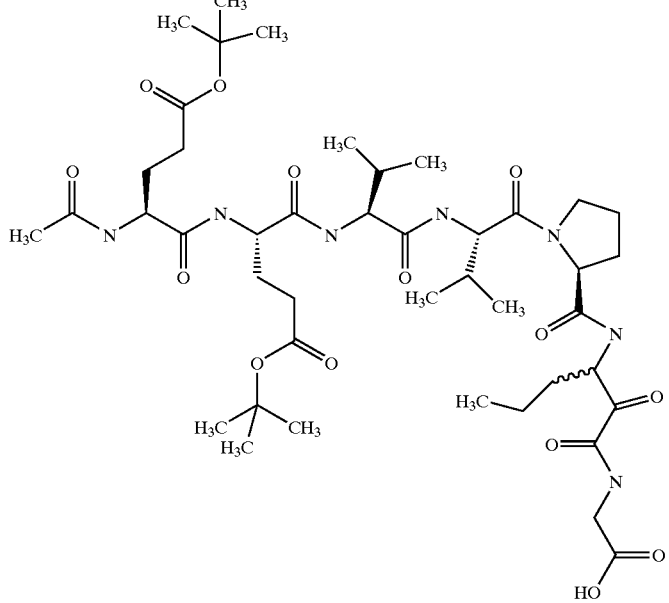 | 910.084 |
| 57 | 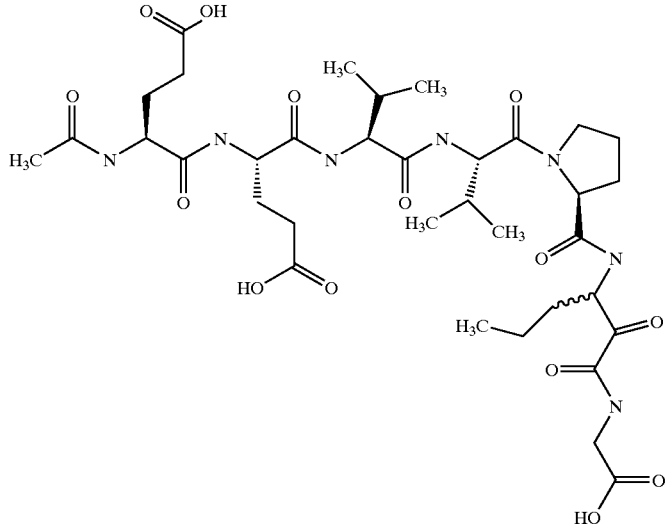 | 797.867 |

TABLE 2-continued
| Compound from Example No. | STRUCTURE | Molecular Weight |
|---|---|---|
| 58 | 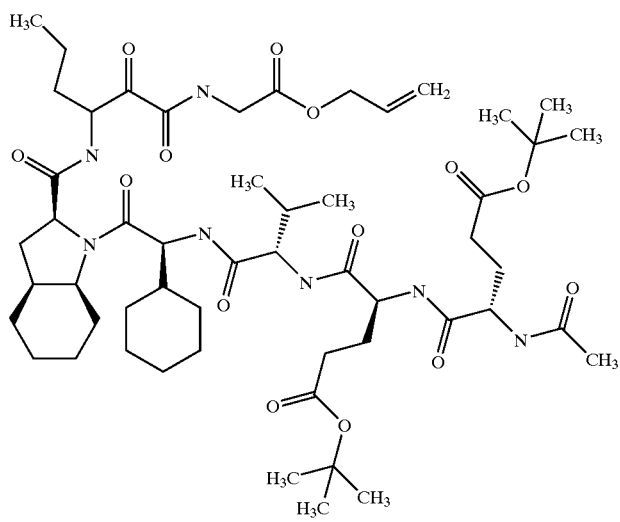 | 1044.31 |
| 59 | 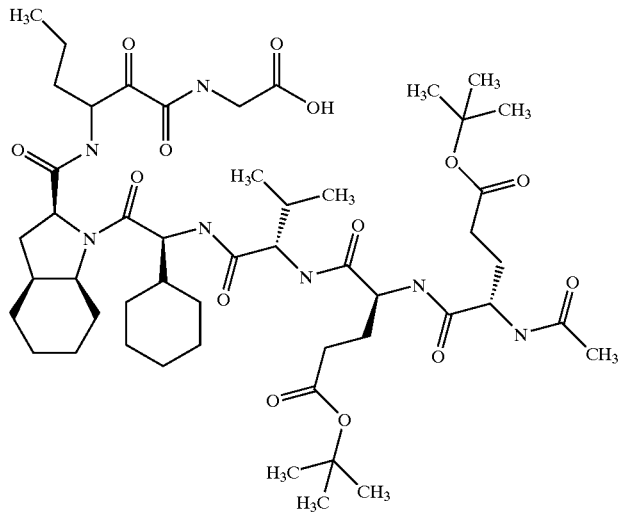 | 1004.24 |
| 60 | 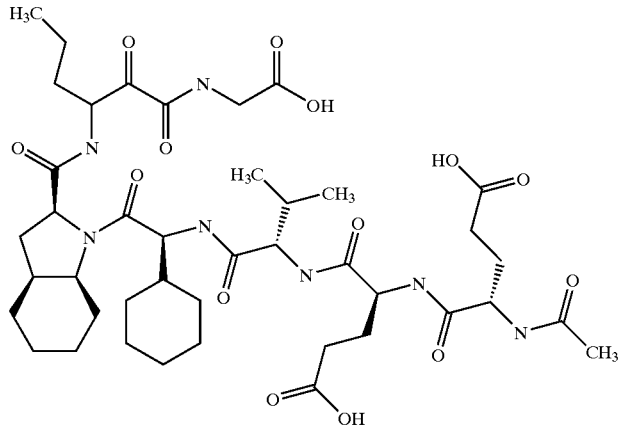 | 892.025 |

TABLE 2-continued

| Compound from Example No. | STRUCTURE | Molecular Weight |
|---|---|---|
| 61 | 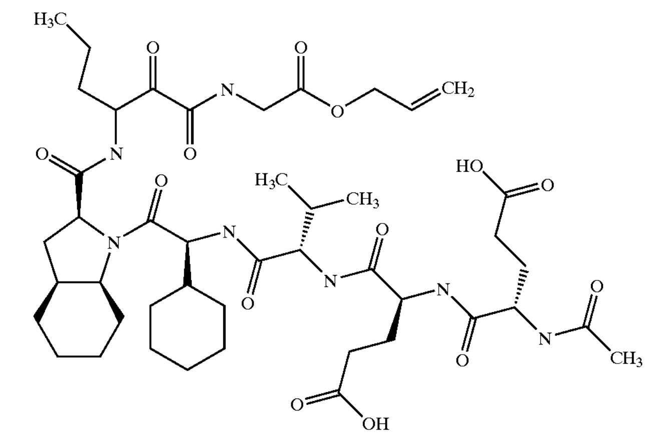 | 932.09 |
| 62 | 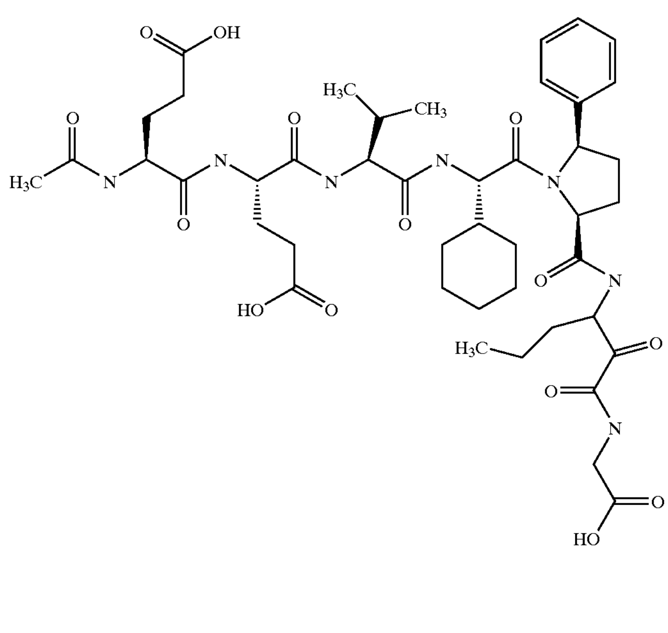 | 914.031 |

TABLE 2-continued

| Compound from Example No. | STRUCTURE | Molecular Weight |
|---|---|---|
| 63 | 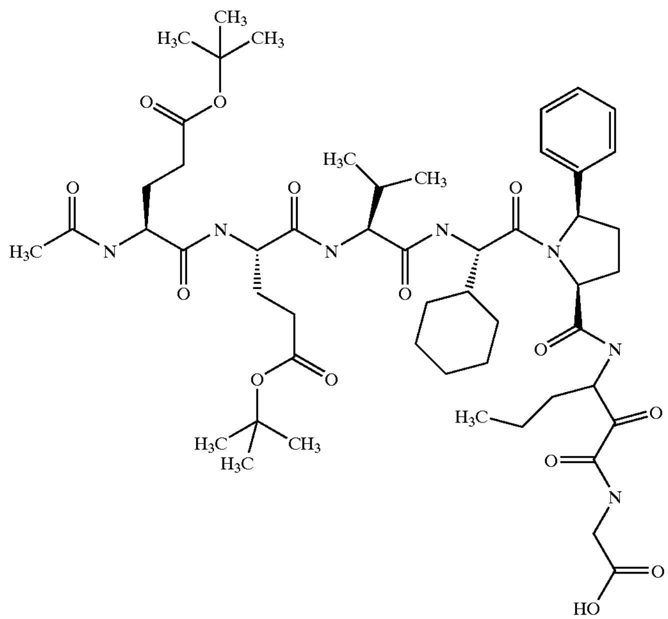 | 1026.25 |
| 64 | 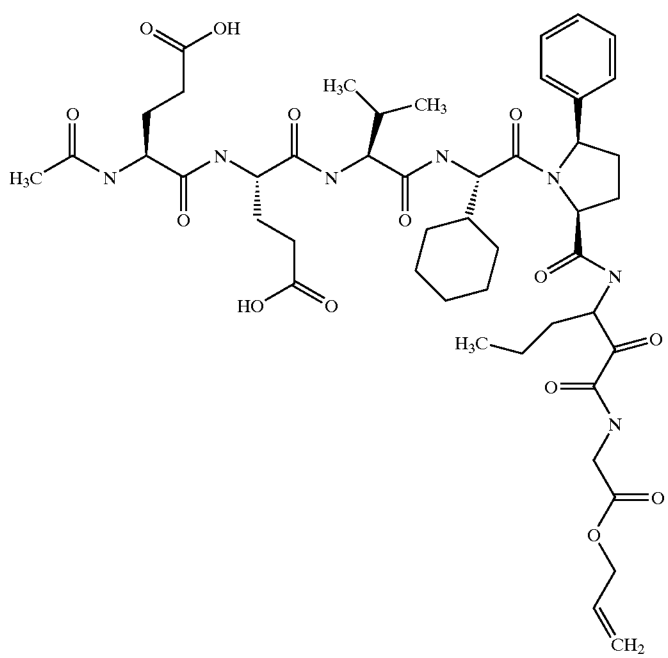 | 954.097 |

TABLE 2-continued

| Compound from Example No. | STRUCTURE | Molecular Weight |
|---|---|---|
| 65 | 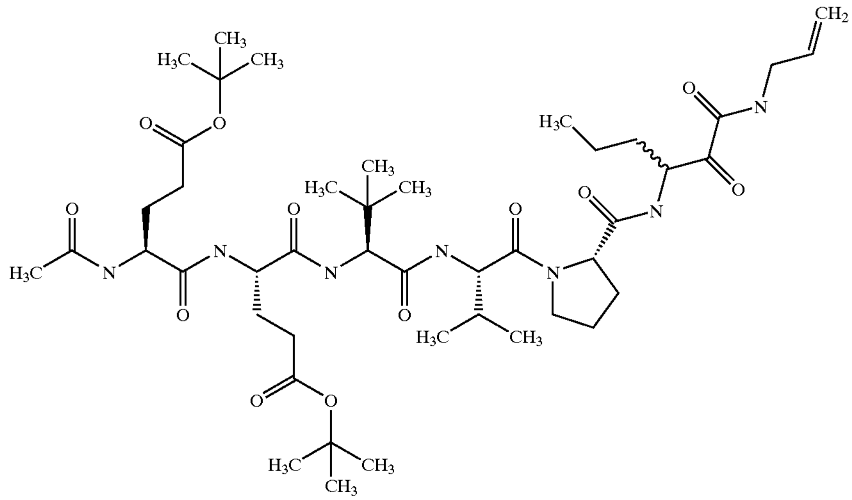 | 906.139 |
| 66 | 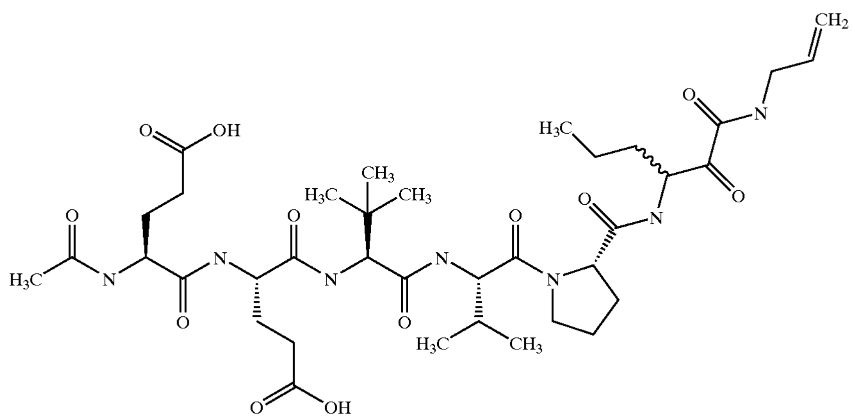 | 793.922 |
| 67 | 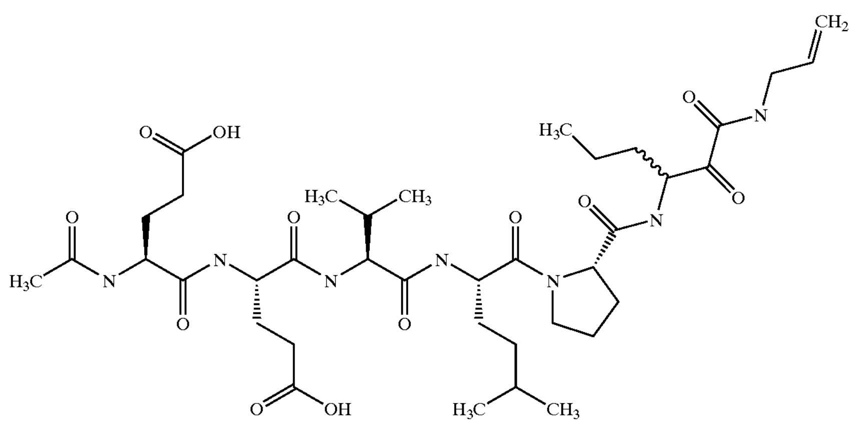 | 807.950 |

TABLE 2-continued
| Compound from Example No. | STRUCTURE | Molecular Weight |
|---|---|---|
| 68 | 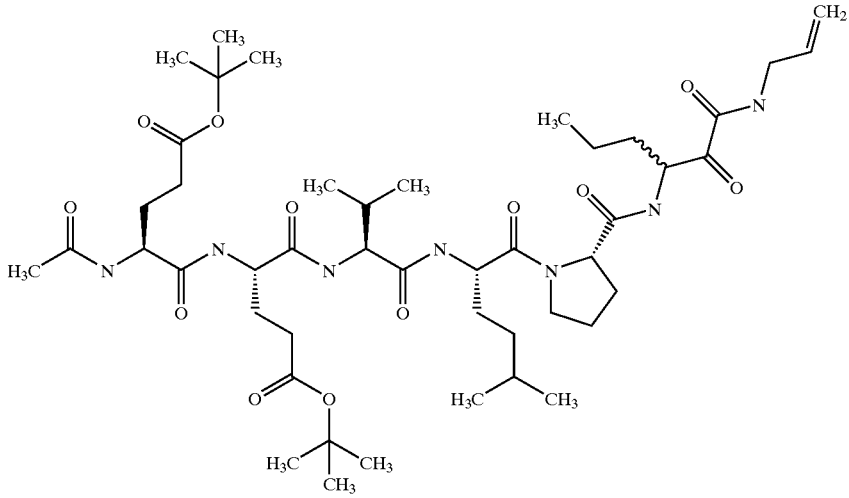 | 920.166 |
| 69 | 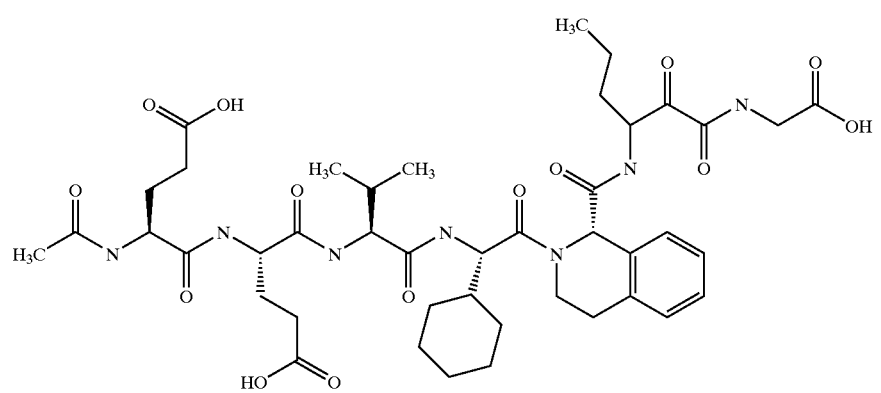 | 900.004 |
| 70 | 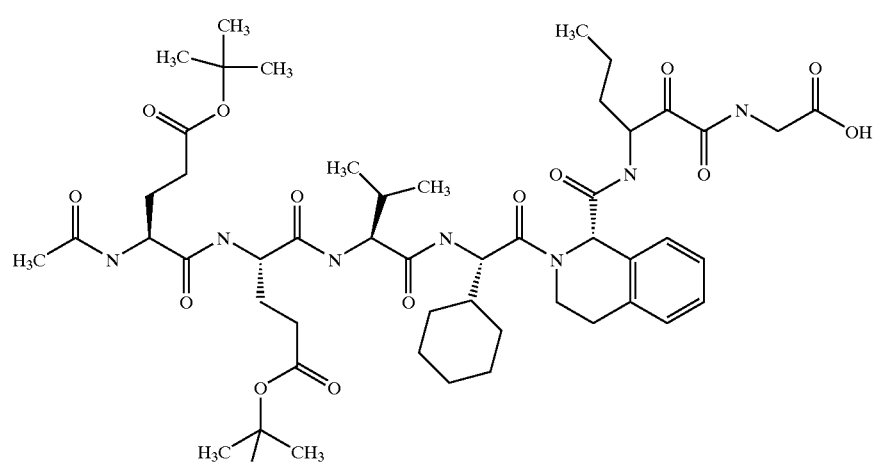 | 1012.22 |

TABLE 2-continued

| Compound from Example No. | STRUCTURE | Molecular Weight |
|---|---|---|
| 71 | 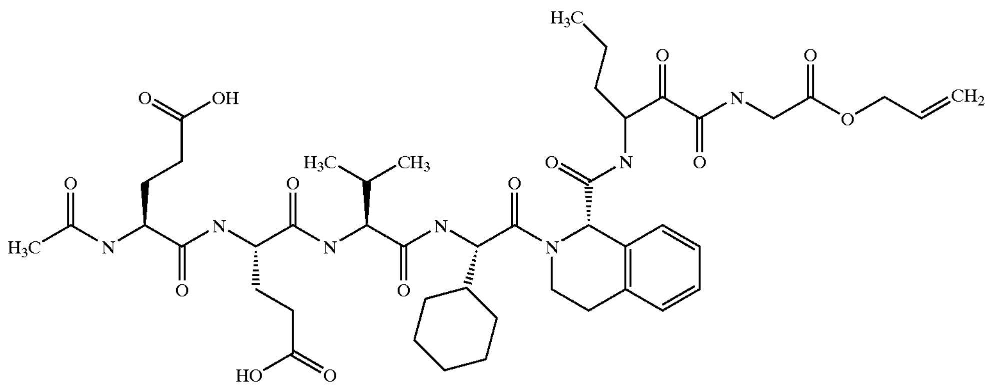 | 940.069 |
| 72 | 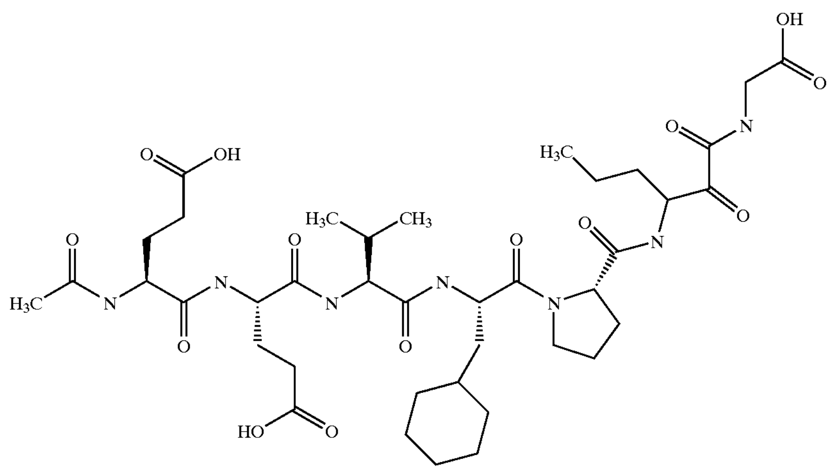 | 851.960 |
| 73 | 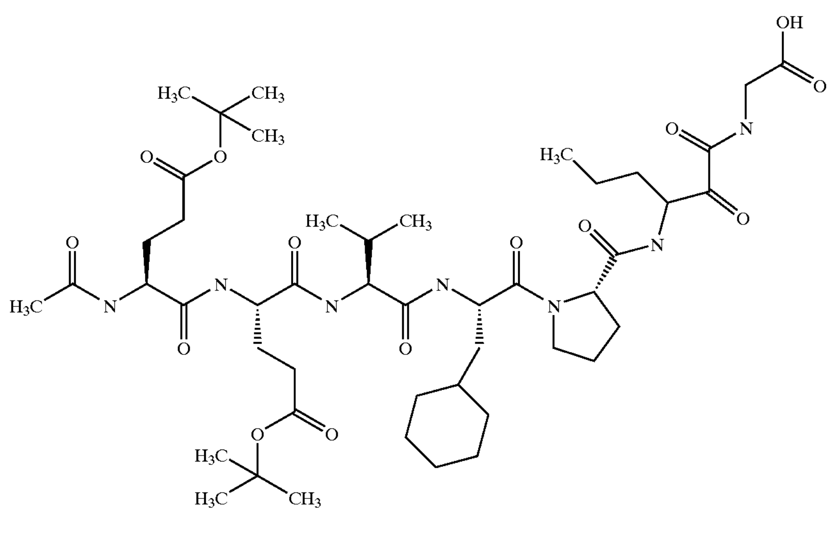 | 964.176 |

TABLE 2-continued
| Compound from Example No. | STRUCTURE | Molecular Weight |
|---|---|---|
| 74 | 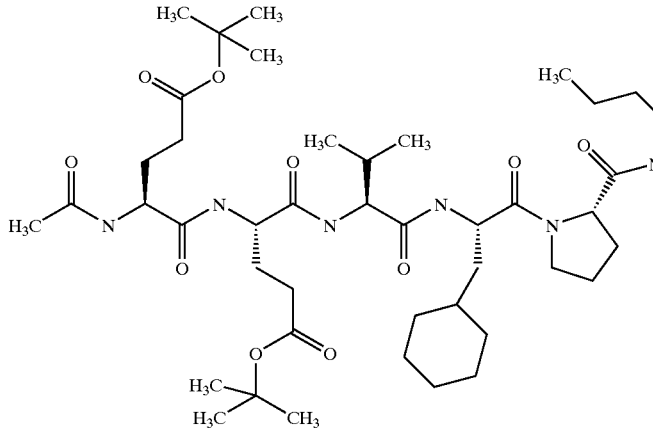 | 1004.24 |
| 75 | 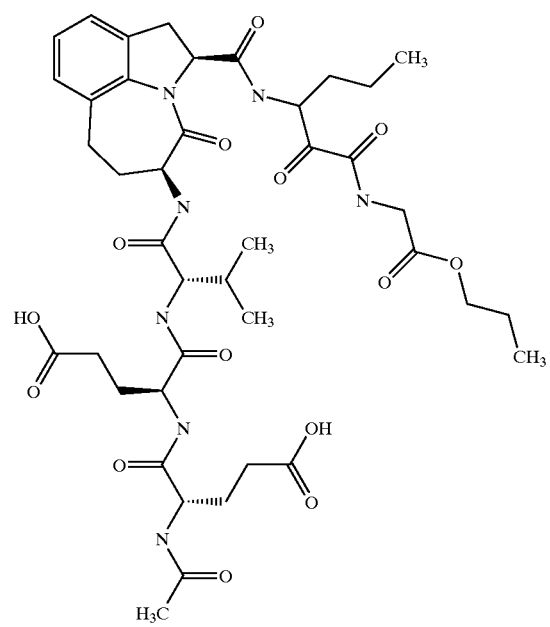 | 871.950 |

TABLE 2-continued
| Compound from Example No. | STRUCTURE | Molecular Weight |
|---|---|---|
| 76 | 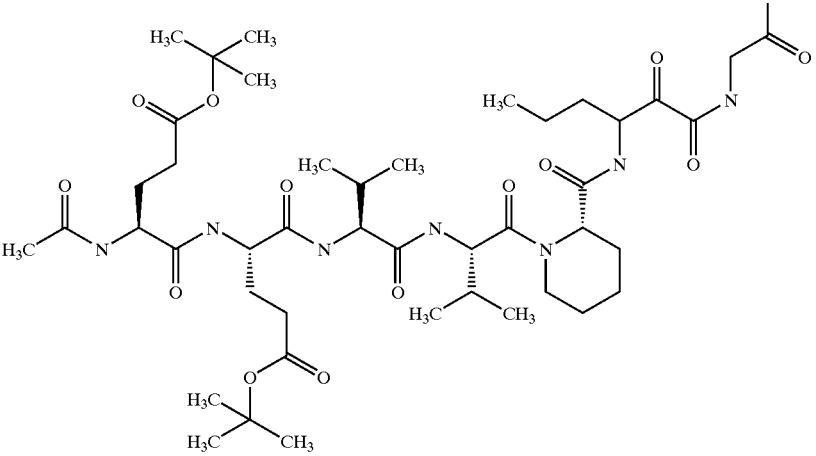 | 966.192 |
| 77 | 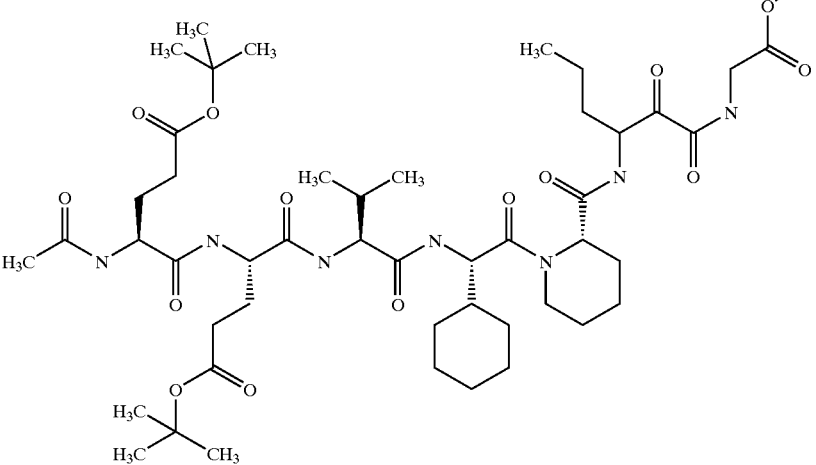 | 1006.26 |

| Compound from Example No. | STRUCTURE | Molecular Weight |
|---|---|---|
| 78 | 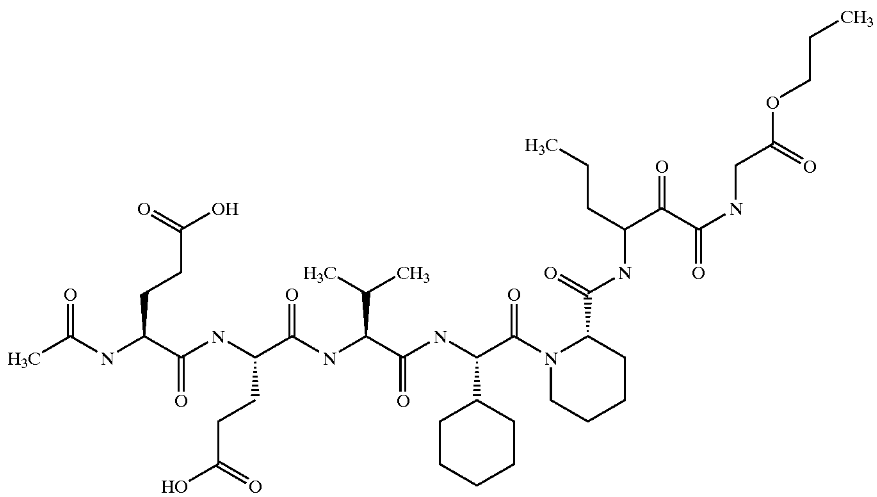 | 894.041 |
| 79 | 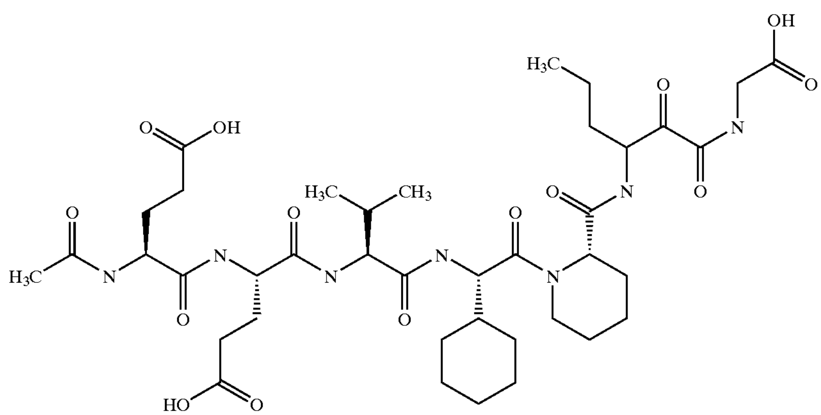 | 851.960 |
| 80 | 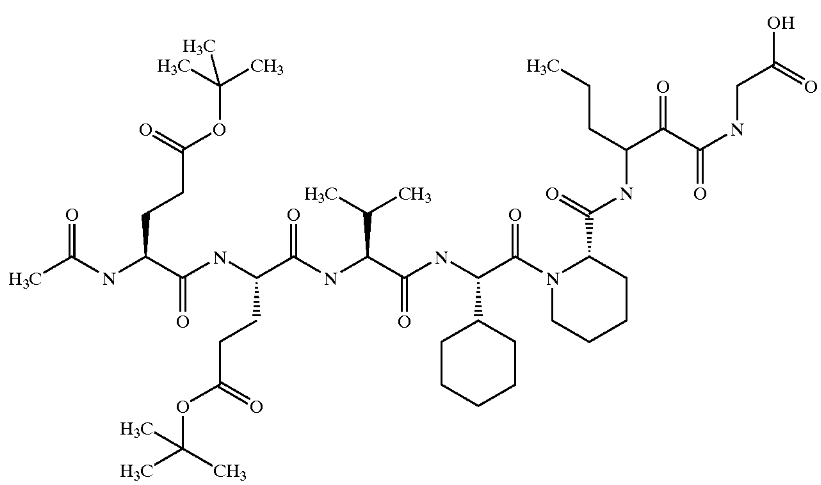 | 964.176 |

TABLE 2-continued

| Compound from Example No. | STRUCTURE | Molecular Weight |
|---|---|---|
| 81 | 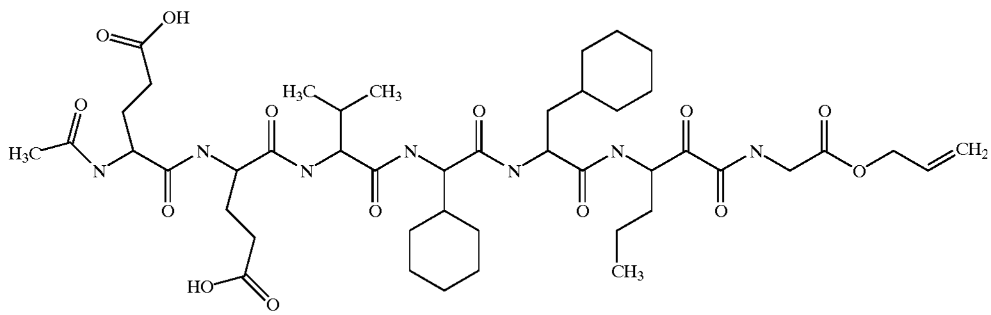 | 934.106 |
| 82 | 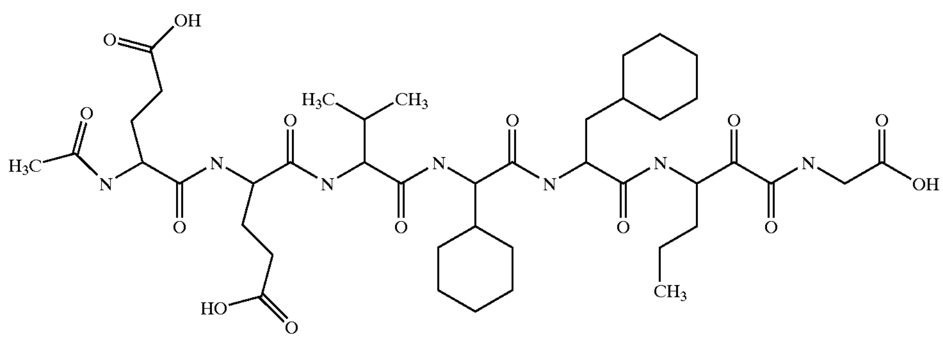 | 894.04 |
| 83 | 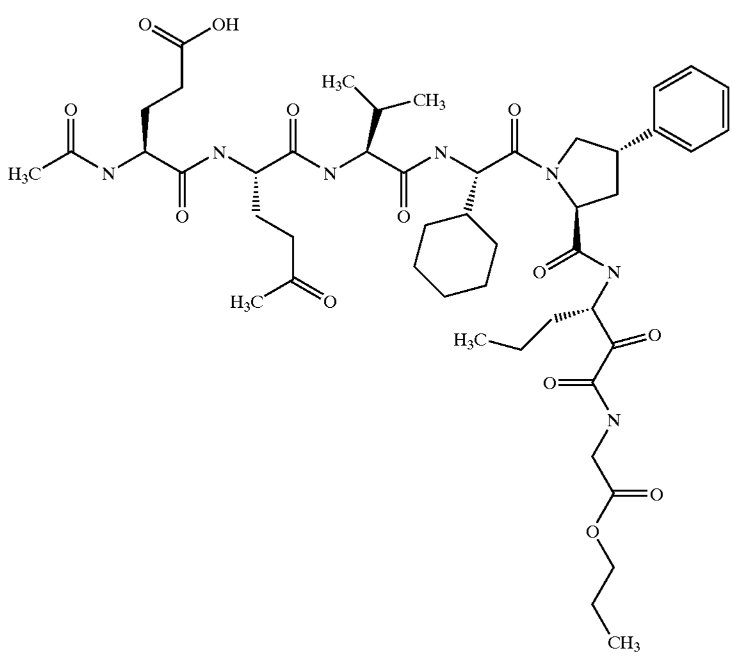 | 956.112 |

TABLE 2-continued
| Compound from Example No. | STRUCTURE | Molecular Weight |
|---|---|---|
| 84 | 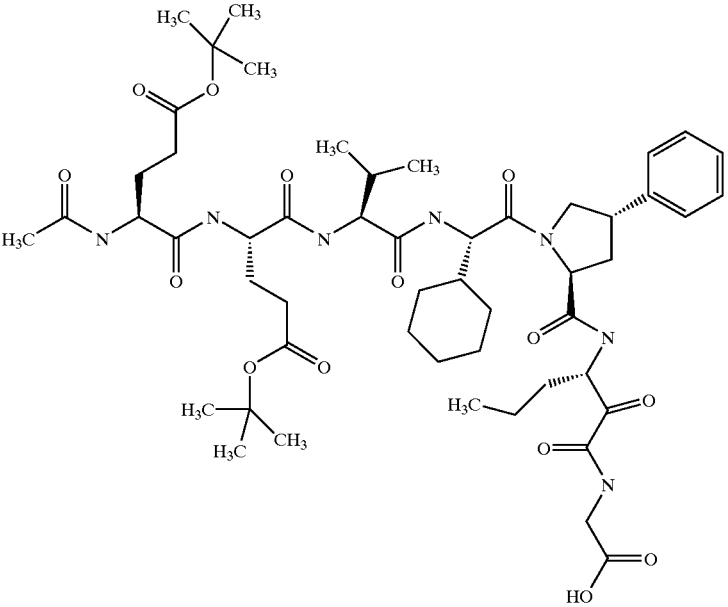 | 1026.25 |
| 85 | 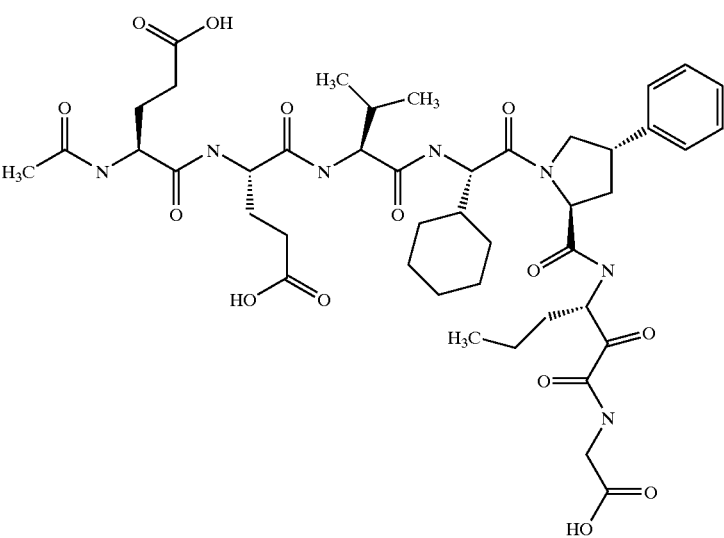 | 914.031 |

TABLE 2-continued

| Compound from Example No. | STRUCTURE | Molecular Weight |
|---|---|---|
| 86 | 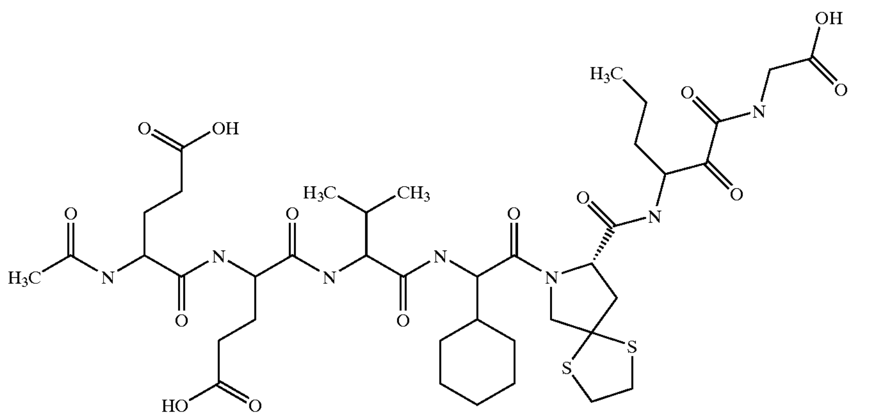 | 928.099 |
| 87 | 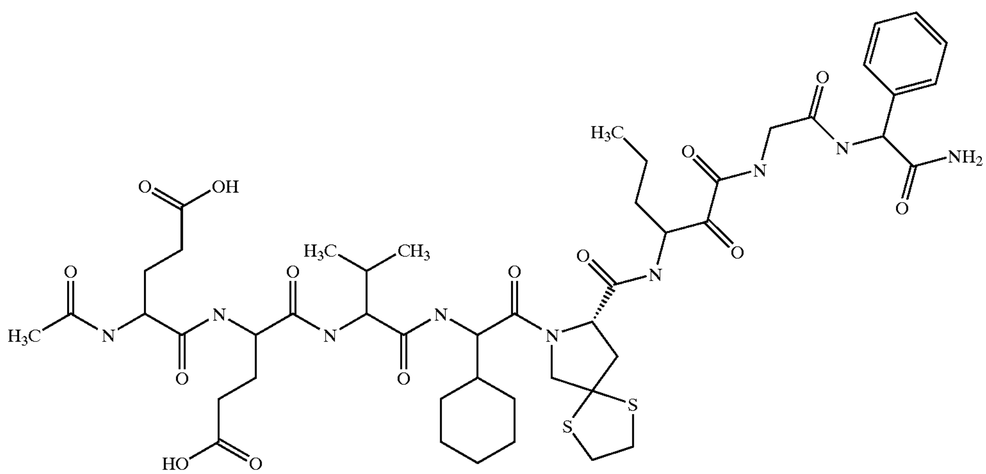 | 1060.27 |
| 88 | 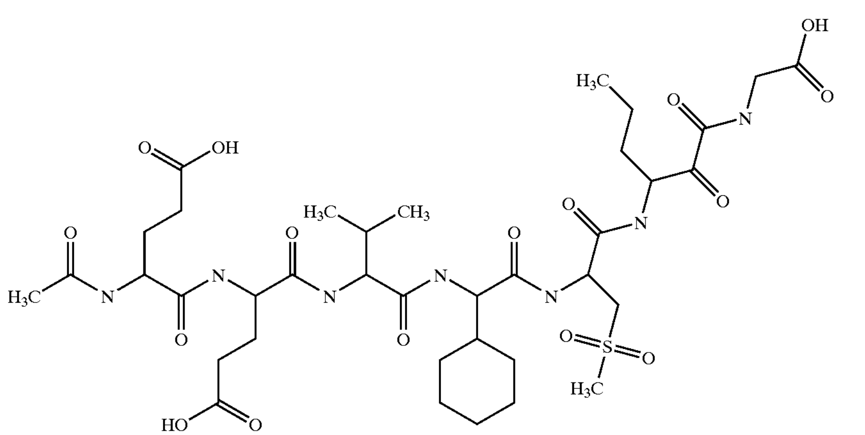 | 889.984 |

Additional compounds were prepared by the following procedures and examples. The compounds are listed in Tables immediately following the examples. The structures of many of the so-prepared compounds and their activity are given in the attached Table 3.

General Procedure for Preparation of The Compounds of Table 3:

Solid-phase synthesis is useful for the production of small amounts of certain compounds of the present invention. As with the conventional solid-phase synthesis of peptides, reactors for the solid-phase synthesis of peptidyl argininals are comprised of a reactor vessel with at least one surface permeable to solvent and dissolved reagents, but not permeable to synthesis resin of the selected mesh size. Such reactors include glass solid phase reaction vessels with a sintered glass frit, polypropylene tubes or columns with frits, or reactor Kans™ made by Irori Inc., San Diego Calif. The type of reactor chosen depends on volume of solid-phase resin needed, and different reactor types might be used at different stages of a synthesis.

General Procedure for the Synthesis of 4-alkylprolines (Intermediates Used in the Synthesis (Steps 1–4 Below):

Step 1
tert-Butyl N-α-t-butoxycarbonyl-L-pyroglutamate

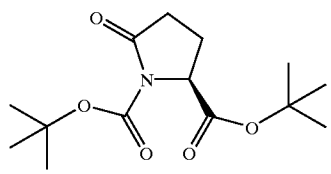

To a solution of L-pyroglutamic acid (100 g, 775 mmol) in tert-butyl acetate (1.3 L) was added 70% aqueous perchloric acid (25 mL). After stirring for 18 hours in a 3-liter round bottom flask sealed with a rubber septum, the reaction mixture was poured carefully into saturated aqueous sodium bicarbonate (800 mL) and extracted with ethyl acetate (1 L, then 300 mL). The combined organic layers were dried (sodium sulfate), filtered and concentrated to provide tert-Butyl L-pyroglutamate (100.5 g, 70% mass recovery). The tert-butyl L-pyroglutamate was dissolved in acetonitrile (1.5 L) with 4-dimethylaminopyridine (6.0 g, 49.1 mmol) and cooled to 0° C. A solution of di-tert-butyl-dicarbonate (154 g, 705 mmol) in acetonitrile (150 mL) was added over 30 min and after an additional 30 min the cooling bath was removed. After stirring at room temperature for 48 hours, the reaction mixture was concentrated. The residue was dissolved in ether (1 L) and hexanes (1 L), then washed with saturated aqueous sodium bicarbonate (2×100 mL) and saturated aqueous sodium chloride. The solution was dried (sodium sulfate), filtered and concentrated to give a yellow oil (140 g). The residue was purified by recrystallization from hexanes (800 ml) and ethyl acetate (25 mL), and the mother liquor was recrystallized from hexanes (300 mL) and ethyl acetate (10 mL) to give two crops of the title compound (122 g, 428 mmol, 55%) as a white solid. NMR data was consistent with previously reported material: R. A. August et al, *J. Chem. Soc., Perkin Trans.* 1 (1996) 507–514.

Step 2
tert-Butyl N-α-t-butoxycarbonyl-4-alkyl-L-pyroglutamate

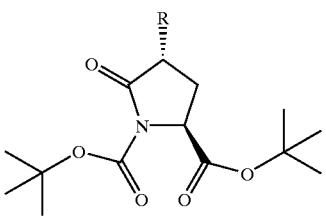

To a solution of the compound of Step 1 (1.15 g, 4.0 mmol) in tetrahydrofuran (20 mL) stirring at −78° C., was added a 1 M solution of lithium hexamethyldisilazide in tetrahydrofuran (4.4 mL, 4.4 mmol) dropwise over 5 min. After 40 min, alkylbromide (4.8 mmol) in tetrahydrofuran (5 mL) was added. After 2 h at −78° C., the cooling bath was removed and saturated aqueous ammonium chloride (20 mL) was added. The solution was stirred for 20 minutes, then extracted with 50% ether/ethyl acetate (3×70 mL). The combined organic layers were washed with brine (30 mL), dried (sodium sulfate), filtered, and concentrated. The resulting residues were purified by flash chromatography and/or recrystallization to afford the title compounds.

| Compound | Alkylbromide | Yield (%) |
|---|---|---|
| R = Bn | benzyl bromide | 63 |
| R = PMB | p-methoxybenzyl bromide | 57 |
| R = allyl | allyl bromide | 22 |
| R = CH2CO2Bn | benzyl a-bromoacetate | 51 |

Step 3
4-alkyl-proline

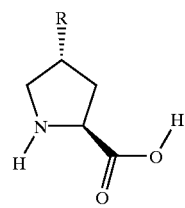

(Modification of known procedure: C. Pedregal et al, *Tetrahedron Letters* 35 (13) (1994) 35(13) 2053–2056.) To a solution of tert-butyl N-tert-butoxycarbonyl-4-alkylpyroglutamate (2.0 mmol) in tetrahydrofuran (5 mL) stirring at −78° C., was added a 1 M solution of lithium triethylborohydride in tetrahydrofuran (2.4 mL, 2.4 mmol) dropwise over 5 min. After 30 min, the cooling bath was removed and saturated aqueous sodium bicarbonate (5 mL) was added. The reaction mixture was immersed in an ice/water bath and 30% aqueous hydrogen peroxide (10 drops) was added. The solution was stirred for 20 minutes at 0° C., then the reaction mixture was concentrated in vacuo to remove the tetrahydrofuran. The aqueous solution was diluted with water (10 mL) and extracted with dichloromethane (3×40 mL). The organic layers were dried (sodium sulfate), filtered and concentrated. The residue was dissolved in dichloromethane (20 mL) and triethylsilane (310 μL, 2.0 mmol), then cooled to −78° C. and boron trifluoride etherate (270 μL, 2.13 mmol) was added dropwise. Stirring was continued for 30 min, at which time additional triethylsilane (310 μL, 2.0 mmol) and boron trifluoride etherate (270 μL, 2.13 mmol) were added. After stirring at −78° C. for an additional 2 h, the cooling bath was removed and saturated aqueous sodium bicarbonate (4 mL) was added. After 5 min the mixture was extracted with dichloromethane (3×40 mL). The organic layers were dried (sodium sulfate), filtered and concentrated. The residue was dissolved in dichloromethane (5 mL) and trifluoroacetic (5 mL) and stirred at ambient temperature for 5 h. The solution was concentrated and then dried under high vacuum to afford the title compound.

| Compound | Yield (%) |
|---|---|
| R = Bn | 72 |
| R = PMB | 76 |
| R = allyl | 65 |
| R = CH2CO2Bn | 34 |

Step 4

N-α-t-butoxycarbonyl-4-alkyl-proline

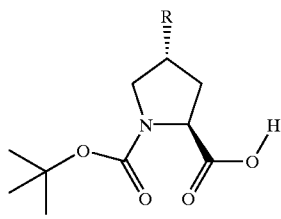

To a solution of 4-alkylproline trifluoroacetate salt (1.5 mmol) in dioxane (7 mL), acetonitrile (12 mL) and diisopropylethylamine (700 μL, 4 mmol) was added di-tert-butyl-dicarbonate (475 mg, 2.18 mmol) in acetonitrile (5 mL). After stirring for 12 h at room temperature the solution was concentrated in vacuo, dissolved in saturated aqueous sodium bicarbonate(50 mL) and washed with ether (3×40 mL). The aqueous layer was acidified to pH 3 with citric acid, then extracted with dichloromethane (3×40 mL). The combined organic layers were dried (sodium sulfate), filtered and concentrated to afford the title compounds, which where pure enough to be used without further purification.

| Compound | Yield (%) |
|---|---|
| R = Bn | 59 |
| R = PMB | 69 |
| R = allyl | 58 |
| R = CH2CO2Bn | 67 |

Synthesis of Other Intermediates:

4-methylsulfinyl-2S-fluorenylmethyloxycarboaminobutyric Acid (Fmoc-Met(O2)-OH:

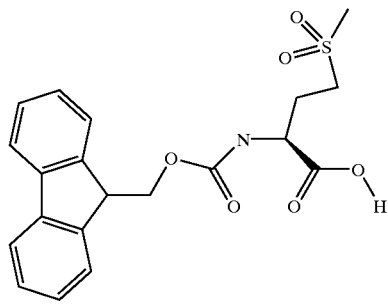

To a solution of N-α-fluorenylmethyloxycarbonyl-methionine (3.72 g, 10 mmol) in chloroform (225 mL) at 0° C., was added 56–87% m-chloroperbenzoic acid (20–31 mmol) in portions over 10 min. The cold bath was removed and the reaction was stirred for 18 h. The solid (4.09 g) was collected by filtration (filtrate was discarded), dissolved in hot methanol (90 mL), allowed to cool, then filtered and concentrated. The crude product was recrystallized from ethyl acetate and hexanes to yield the title compound (2.577 g, 6.39 mmol, 64%).

N-α-fluorenylmethyloxycarbonyl-3-methylsulfinylalanine (Fmoc-Cys(O2,Me)-OH:

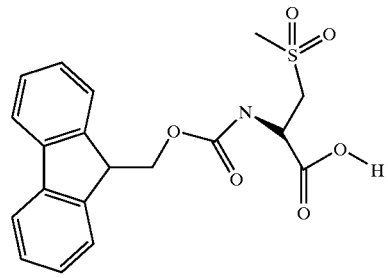

To a solution of N-α-fluorenylmethyloxycarbonyl-S-methylcysteine (893 mg, 2.5 mmol) in chloroform (50 mL) at 0° C., was added 56–87% m-chloroperbenzoic acid (1.555 g, 5.0–7.8 mmol, ≧2 eq) in portions over 10 min. The cold bath was removed and the reaction was stirred for 18 h. The solid was collected by filtration (filtrate was discarded), dried in vacuo, dissolved in hot ethyl acetate (150 mL), filtered and concentrated. The solid was dissolved in a minimal amount of hot methanol, then crystallized by the addition of isopropyl ether, followed by 10% ethyl acetate in hexanes. The solid (658.6 mg) was collected and recrystallized again to give the title compound (520 mg, 1.335 mmol, 53%).

Synthesis of N-tert-butoxycarbonyl-trans-4-(N-fluorenylmethyloxycarbonyl amino)-L-proline (Boc-Pro(4t-NHFmoc): (Steps 1–3 Below):

Step 1

N-tert-butoxycarbonyl-cis-4-chloro-L-proline Benzyl Ester

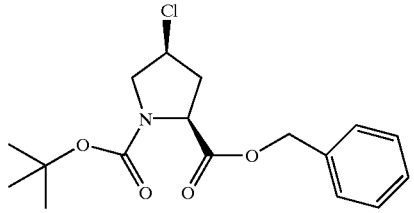

A mixture of N-α-t-butoxycarbonyl-trans-4-hydroxyproline (8.79 g, 38 mmol), potassium carbonate (13.0 g, 94 mmol), benzyl bromide (4.5 ml, 38 mmol) and dimethylformamide (150 mL) was stirred for 18 h. Addition of ethyl acetate (100 mL) was followed by filtration. The white cloudy filtrate was clarified by the addition of 1M HCl (100 mL). The layers were separated and the aqueous layer was extracted with additional ethyl acetate (2×100 mL). The combined organic layers were washed with water (2×50 mL), dried (sodium sulfate), filtered and concentrated. Toluene was added to the crude benzyl ester, and the solution was filtered and reconcentrated. Dichloromethane (70 mL) and carbon tetrachloride (70 mL) was added, followed by triphenylphosphine (21.11 g, 80 mmol). The reaction mixture was stirred for 10 h, quenched with ethanol (7 mL) and stirred for 5 more h. The solution was concentrated to approx. 100 ml, then dichloromethane (40 mL) was added, followed by the addition of ether (200 mL) while stirring. The solution was cooled for 4 h, filtered and concentrated to give a yellow-brown oil which was purified by flash chromatography using ether/hexane/dichloromethane 2:2:1 to give the title compound (9.13 g, 26.9 mmol, 71%) as a white solid.

Step 2

N-α-t-butoxycarbonyl-trans-4-azido-L-proline Benzyl Ester

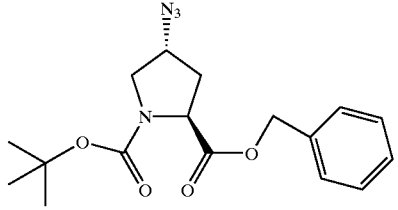

A solution of the compound of step 1 above (9.0 g, 26.5 mmol) and sodium azide (7.36 g, 113 mmol) in dimethylformamide (270 mL) was heated at 75° C. for 2 days. Water (100 mL) was added and the reaction mixture was extracted with ethyl acetate (3×100 mL). The combined organic layers were washed with water (3×50 mL), dried (sodium sulfate), filtered and concentrated. The oil was purified by flash chromatography using ethyl acetate/hexane 1:1 to give the title compound (8.59 g, 24.8 mmol, 94%).

Step 3

N-tert-butoxycarbonyl-trans-4-(N-fluorenylmethyloxycarbonyl_amino)-L-proline

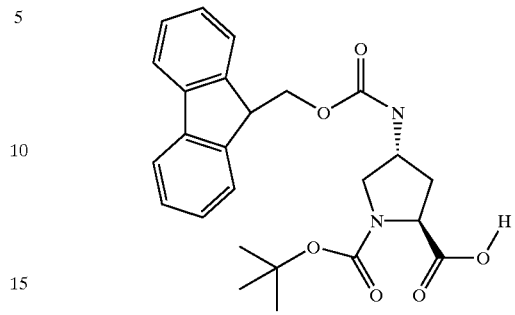

A mixture of the compound of step 2 above (8.59 g, 24.8 mmol) and 10% palladium on carbon (900 mg) in ethanol (500 mL) was hydrogenated at 50 psi for 14 h using a Parr hydrogenation apparatus. The mixture was filtered, concentrated, dissolved in methanol (60 mL), refiltered and concentrated to give a colorless oil. The oil was dissolved in water (53 mL) containing sodium carbonate (5.31 g, 50.1 mmol) and a solution of fluorenylmethyl succinyl carbonate (8.37 g, 29.8 mmol) in dioxane (60 mL) was added over 40 min. The reaction mixture was stirred at room temperature for 17 h, then concentrated to remove the dioxane and diluted with water (200 mL). The solution was washed with ether (3×100 mL). The pH of the aqueous solution was adjusted to 2 by the addition of citric acid (caution! foaming!) and water (100 mL). The mixture was extracted with dichloromethane (400 mL, 100 mL, 100 mL) and the combined organic layers were dried (sodium sulfate), filtered and concentrated to give the title compound.

N-α-t-butoxycarbonyl-4-trans-(N-fluorenylmethyloxvcarbonyl aminomethyl)-L-proline (Boc-Pro(4t-MeNHFmoc)-OH) (Steps 1–4 Below):

Step 1

N-α-t-butoxycarbonyl cis-4-hydroxy-L-proline Benzyl Ester

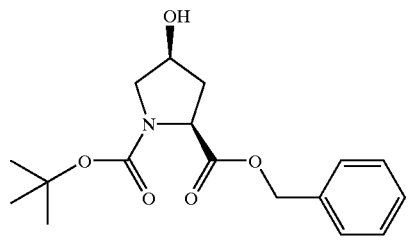

To a mixture of cis-hydroxy-L-proline (5 g, 38.1 mmol) in benzene (45 mL) and benzyl alcohol (45 mL) was added p-toluenesulfonic acid monohydrate (7.6 g, 40.0 mmol). The reaction mixture was heated at 125° C. for 20 h while water (2 ml) was removed using a Dean-Stark trap. The solution was filtered while still hot, and then ether (150 ml) was added. The solution was allowed to cool for three h at room temperature, then three h at 4° C. The resulting solid was collected, washed with ether (100 mL) and dried in vacuo for 1 h to give 13.5 grams of white solid. The solid was dissolved in dioxane (40 mL) and diisopropylethylamine (7.6 mL), and then di-tert-butyl-dicarbonate (10 g, 45.8 mmol) was added over 5 min while using an ice bath to maintain a constant reaction temperature. After 10 h at room temperature the reaction mixture was poured into cold water (200 mL) and extracted with ethyl acetate (3×200 mL). The combined organic layers were washed with water (3×100 mL) and saturated aqueous sodium chloride (50 mL), dried (sodium sulfate), filtered and concentrated. The crude product was purified by flash chromatography using 40–60% ethyl acetate in hexanes to give the title compound (10.04 g, 31.24 mmol, 82%).

Step 2

N-α-t-butoxycarbonyl cis-4-mesyloxy-L-proline Benzyl Ester

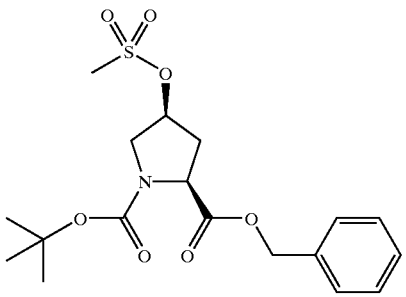

To a solution of the compound of step 2 above (8.45 g, 26.3 mmol) in pyridine (65 mL) at 0° C., was added methanesulfonyl chloride (3.4 mL, 44 mmol) dropwise over 7 min. The reaction mixture was allowed to warm to room temperature over 2 h, then stirred overnight. A solution of 10% water in pyridine (20 mL) was added over 15 min and the reaction mixture was concentrated. The residue was dissolved in water and extracted with ethyl acetate (2×200 mL). The combined organic layers were washed with water (2×50 mL) saturated aqueous sodium bicarbonate (50 mL) and saturated aqueous sodium chloride (50 mL), dried (sodium sulfate), filtered and concentrated. The resulting residue was dissolved in toluene (100 mL) and concentrated to remove traces of pyridine. The residue was dried in vacuo for 30 min to afford the title compound (10.7 g, 102%), then used in the next step without purification.

Step 3

N-α-t-butoxycarbonyl-trans-4-(R)-cyano-L-proline Benzyl Ester:

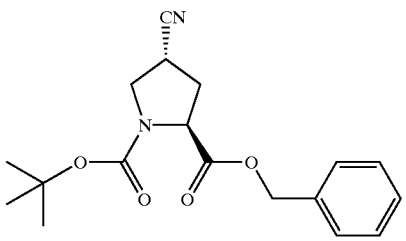

A solution of the compound of Step 3 above (10.7 g, 26.3 mmol) and tetrabutylammonium cyanide (15.0 g, 56 mmol) in dimethylformamide (100 mL) was heated in an oil bath at 55° C. for 28 h. After cooling, water (150 mL) was added and the mixture was extracted with ethyl acetate (3×200 mL). The combined organic layers were washed with water (3×100 mL) and saturated aqueous sodium chloride (100 mL), dried (sodium sulfate), filtered and concentrated. The resulting residue was purified by flash chromatography (1:1 ether/hexanes) and then recrystallized from ethyl acetate/hexanes to provide the title compound (2.40 g, 7.26 mmol, 28%).

Step 4

N-α-t-butoxycarbonyl-4-trans-(N-fluorenylmethyloxycarbonyl aminomethyl)-L-proline:

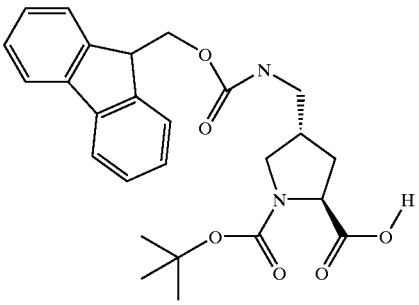

A mixture the compound of Step 3 above (2.31 g, 7 mmol), water (10 mL), methanol (85 mL) and 10% palladium on carbon (700 mg) was hydrogenated at 50 psi for 11 h using a Parr hydrogenation apparatus. The mixture was filtered and concentrated. Water (15 mL) and sodium carbonate (1.5 g, 14.2 mmol) was added to the residue. A solution of fluorenylmethyl succinyl carbonate (2.36 g, 7.0 mmol) in dioxane (17 mL) was added over 5 min and stirring was continued for 28 h at room temperature. The reaction was concentrated in vacuo to a 15 mL volume, and water (100 mL) was added. The solution was washed with ether (3×75 mL). The pH of the aqueous solution was adjusted to 2 by the addition of citric acid (approx. 20 g, caution! foaming!) and water (100 mL). The mixture was extracted with dichloromethane (4×100 mL), and the combined organic layers were dried (sodium sulfate), filtered and concentrated. The crude product contained a major impurity which necessitated a three step purification. The crude product was dissolved in dichloromethane (50 mL) and trifluoroacetic acid (50 mL) and stirred for 5 h before being concentrated. The residue was purified by preparatory reverse-phase HPLC. The pure 4-(N-fluorenylmethyloxycarbonyl aminomethyl)proline trifluoroacetate salt (1.887 g, 3.93 mmol) was dissolved in dioxane (10 mL), acetonitrile (20 mL) and diisopropylethylamine (1.4 mL, 8 mmol). To the reaction mixture was added a solution of di-tert-butyidicarbonate (1.1 g, 5 mmol) in dioxane (5 mL). After stirring for 18 h, the pH of the solution was adjusted to 2 by the addition of citric acid (caution: foaming!) and water (100 mL). The mixture was extracted with ethyl acetate (3×150 mL) and the combined organic layers were washed with saturated aqueous sodium chloride (100 mL), dried (sodium sulfate), filtered and concentrated. The crude product was dissolved in saturated aqueous sodium bicarbonate(100 mL) and washed with ether (3×75 mL). The pH of the aqueous layer was adjusted to 3 by the addition of citric acid, then extracted with dichloromethane (4×100 mL). The combined organic layers were dried (sodium sulfate), filtered and concentrated to the title compound (1.373 g, 2.94 mmol, 42%).

Procedure to Synthesize Inventive Compounds:

Procedure A:

Coupling reaction: To the resin suspended in DMF (10–15 mL/gram resin) was added Fmoc-amino acid (1 eq), HOBt (1 eq), TBTU (1 eq) and DIEA (1 eq). The mixture was let to react for 4–48 hours. The reactants were drained and the resin was washed successively with dimethylformamide, dichloromethane, methanol, dichloromethane and diethylether (use 10–15 mL solvent/gram resin). The resin was then dried in vacuo.

Procedure B:

Coupling reaction: To the resin suspended in N-methylpyrrolidine (NMP) (10–15 mL/gram resin) was added Fmoc-amino acid (2 eq), HOAt (2 eq), HATU (2 eq)

and diisopropylethylamine (4 eq). The mixture was let to react for 4–48 hours. The reactants were drained and the resin was washed successively with dimethylformamide, dichloromethane, methanol, dichloromethane and diethylether (use 10–15 mL solvent/gram resin). The resin was then dried in vacuo.

Procedure C:

Fmoc deprotection: The Fmoc-protected resin was treated with 20% piperidine in dimethylformamide (10 mL reagent/g resin) for 30 minutes. The reagents were drained and the resin was washed successively with dimethylformamide, dichloromethane, methanol, dichloromethane and diethyl ether (10 mL solvent/gram resin).

Procedure D:

Boc deprotection: The Boc-protected resin was treated with a 1:1 mixture of dichloromethane and trifluoroacetic acid for 20–60 minutes (10 mL solvent/gram resin). The reagents were drained and the resin was washed successively with dichloromethane, dimethylformamide, 5% diisopropylethylamine in dimethylformamide, dimethylformamide, dichloromethane and dimethylformamide (10 mL solvent/gram resin).

Procedure E:

Acetylation with acetic anhydride: The resin was suspended in dimethylformamide. The acetylating reagent, prepared by adding 5 mmol (0.47 mL) acetic anhydride and 5 mmol (0.70 mL) triethylamine to 15 mL Dimethylformamide, was added to the resin and the resin was agitated for 30 minutes. The resin was washed successively with dimethylformamide, dichloromethane, methanol, dichloromethane and diethyl ether (10 mL solvent/gram resin).

Procedure F:

Semicarbazone hydrolysis: The resin was suspended in the cleavage cocktail (10 mL/g resin) consisting of trifluoroacetic acid: pyruvic acid: dichloromethane: water 9:2:2:1 for 2 hours. The reactants were drained and the procedure was repeated three more times. The resin was washed successively with dichloromethane, water and dichloromethane and dried under vacuum.

Procedure G:

HF cleavage: The dried peptide-nVal(CO)-G-O-PAM resin (50 mg) was placed in an HF vessel containing a small stir bar. Anisole (10% of total volume) was added as a scavenger. In the presence of glutamic acid and cysteine amino acids, thioanisole (10%) and 1,2-ethanedithiol (0.2%) were also added. The HF vessel was then hooked up to the HF apparatus (from Immuno Dynamics, Incorporated) and the system was flushed with nitrogen for five minutes. It was then cooled down to −70° C. with a dry ice/isopropanol bath. After 20 minutes, HF was distilled to the desired volume (10 mL HF/g resin). The reaction was let to proceed for one and a half hour at 0° C. Work up consisted of removing all the HF using nitrogen. Dichloromethane was then added to the resin and the mixture was stirred for five minutes. This was followed by the addition of 20% acetic acid in water (4 mL). After stirring for 20 minutes, the resin was filtered using a fritted funnel and the dichloromethane was removed under reduced pressure. Hexane was added to the remaining residue and the mixture was agitated, and the layers separated (this was repeated twice to remove scavengers). Meanwhile, the resin was soaked in 1 mL methanol. The aqueous layer (20% HOAC) was added back to the resin and the mixture was agitated for five minutes and then filtered. The methanol was removed under reduced pressure and the aqueous layer was lyophilized. The peptide was then dissolved in 10–25% methanol (containing 0.1% trifluoroacetic acid) and purified by reverse phase HPLC.

Procedure H:

HF pyridine cleavage: To dried peptide-nVal(CO)-G-O-PAM resin (50 mg) in a HDPE 20 mL scintillation vial containing a ½ inch football stir bar was added thioanisole (100 μL) using a pipetman. A commercially available solution of 70% HF/Pyridine (1 mL) was added. The vial was immediately sealed tight with a polypropylene lined cap and placed in an ice bath with gentle stirring. After stirring in a 0° C. bath for one hour, the bath was removed and the mixture was stirred at room temperature for one hour. During the two hour cleavage process, the vial was inspected periodically and if necessary the resin which built up on the sides of the flask was dispersed back into the HF solution. The vial was cooled back to 0° C. and its cap was carefully removed. The vial were then cooled to −15° C. using a salt/ice bath. A 10 mL B-D syringe body equipped with a 23 gauge needle was held above the vial. To this syringe body was added methoxytrimethylsilane (2 mL) using a repetitive autopipette. After the syringe body dripped empty, additional portions of methoxytrimethylsilane (2×2 mL, 3 mL, (9 mL total)) were added until the HF was neutralized. The vial was stirred for 5 minutes and then removed from the bath and stirred for 20 min. The vial was loaded in the speed vac and concentrated. Methylene chloride (5 mL) was added and the resin was stirred for 10 minutes and filtered into a 16×100 mm test tube using a 5 mL disposable column. The methylene chloride filtrate was concentrated. The resin was additionally washed with 20% AcOH in water (2×mL) and diethyl ether (2 mL) into the before mentioned test tube. The mixture was agitated to dissolve the oil. The ether layer was then removed and the aqueous layer was lyophilized. The peptide was then dissolved in 10–25% methanol (containing 0.1% trifluoroacetic acid) and purified by reverse phase HPLC.

EXAMPLE I

Solid Phase Synthesis of Ac-EEVVP-nV(CO)-G-OH (SEQ ID NO: 1)

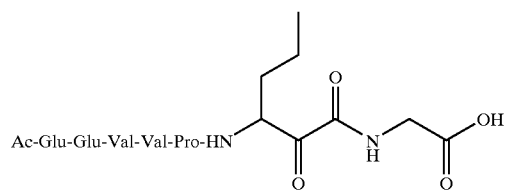

Step I. Synthesis of H-nVal(dpsc)-Gly-PAM Resin

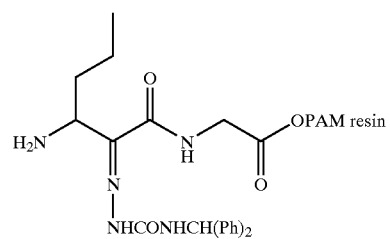

a) Preparation of N-α-t-butoxycarbonyl-norvalinol

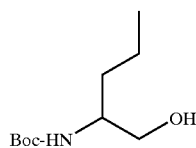

To a solution of N-α-t-butoxycarbonyl-norvaline (25.0 g, 0.115 mol) in tetrahydrofuran (461 mL), cooled to 0° C., was added borane/tetrahydrofuran complex (461 mL of a 1.0M solution in THF) dropwise. After 1 h at 0° C., the solution was warmed to room temperature over a period of 1.5 h. TLC indicated that the reaction was complete. Methanol was added to quench the reaction. The solution was concentrated to yield the title compound (22.56 g, 96%) as a foamy syrup. TLC of the products indicated satisfactory purity. $R_f$=0.34 (40% ethyl acetate/hexanes).

b) Preparation of N-α-t-butoxycarbonyl-norvaline hydroxy t-butyl Amide

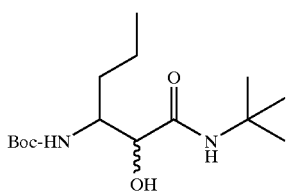

Part I:

To a solution of the compound of step Ia (7.77 g, 38 mmol), in anhydrous dimethylsulfoxide (153 mL) and toluene (153 mL) was added EDC (73.32 g, 382 mmol). After the solution was cooled to 0° C., dichloroacetic acid (15.8 mL, 191 mmol) was added dropwise. After addition was complete, the reaction was stirred for 15 min. The solution was allowed to warm to room temperature over a period of 2 h. The reaction mixture was concentrated to remove the toluene, then dissolved in ethyl acetate. The solution was washed successively with 1N sodium bisulfate, saturated sodium bicarbonate and brine, dried over sodium sulfate, then concentrated to afford crude N-α-t-butoxycarbonyl-norvalinal which was used directly in the next step. $R_f$=0.84 (40% ethyl acetate/hexanes).

Part II:

To a solution of the crude N-α-t-butoxycarbonyl-norvalinal in dichloromethane (153 mL) was added t-butyl isocyanide (5.19 mL, 46 mmol) and 2,4,6-collidine (20.2 mL, 153mmol). After the solution was cooled to 0° C., trifluoroacetic acid (7.64 mL, 76mmol) was added dropwise. After stirring for 1 h, the solution was stirred at room temperature for 3 days while allowing the solvent from the reaction mixture in an uncovered vessel to evaporate under ambient conditions. The reaction mixture was concentrated to remove the toluene, then dissolved in ethyl acetate. The solution was washed successively with 1 N sodium bisulfate, saturated sodium bicarbonate and brine, dried over sodium sulfate, then concentrated. The residue was purified by flash silica gel chromatography eluting with 10–40% ethyl acetate/hexanes to afford 8.12 g of the title compound (70% yield) as a yellow syrup. $R_f$=0.44 (40% ethyl acetate/hexanes).

c) Preparation of Ethyl 3-(N-t-butoxycarbonyl)amino-2-hydroxy-hexanoate

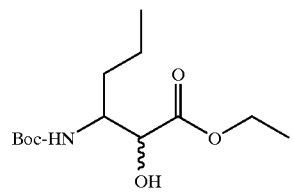

The compound of step Ib above (22.7 g, 75 mmol) was refluxed in 6N HCl (480 mL) for 4h. The reaction mixture was allowed to cool to room temperature, then washed with dichloromethane (3×100 mL). The aqueous layerwas concentrated to dryness. The residue was triturated with toluene/n-heptane (3×), dried in vacuo to give crude 3-amino-2-hydroxy-hexanoic acid. The crude 3-amino-2-hydroxy-hexanoic acid was dissolved in hydrogen chloride saturated ethanol (40 mL). After 4 h, the solution was concentrated under reduced pressure. The residue was triturated with n-heptane (3×), then dried in vacuo to give crude ethyl 3-amino-2-hydroxy-hexanoate. To the crude ethyl 3-amino-2-hydroxy-hexanoate in water (150 mL) was added potassium carbonate (37.32 g, 270mmol). After dissolution was complete, dioxane was added (150 mL), followed by di-t-butyldicarbonate (17.7 g, 81.0 mmol). The reaction mixture was allowed to stir overnight, then concentrated under reduced pressure to remove the dioxane. The solution was extracted with ether (3×), then acidified to pH 2–3 with 1N sodium bisulfate. The solution was extracted with ethyl acetate (3×200 mL), dried over sodium sulfate, and the solvent was removed in vacuo to give 13.21 g of the title compound in 71% yield.

d) Preparation of Ethyl N-α-t-butoxycarbonyl-norvalyl Carboxylate Diphenylmethylsemicarbazone (Part I–Part III Below)

Part I: Synthesis of 1-t-Butoxycarbonyl-semicarbazid-4-yl Diphenylmethane

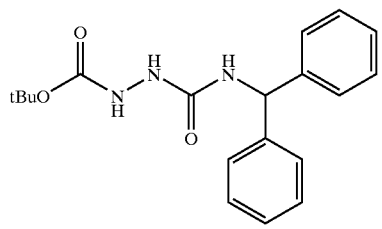

A solution of carbonyidiimidazole (16.2 g, 0.10 mole) in 225 mL of dimethylformamide was prepared at room temperature and allowed to stir under nitrogen. A solution of t-butyl carbazate (13.2 g, 0.100 mol) in 225 mL DMF was then added dropwise overa 30 min. period. Diphenylmethylamine (18.3 g, 0.10 mol) was added next over a 30 min. period. The reaction was allowed to stir at room temperature under nitrogen for one hour. Water (10 mL) was added and the mixture was concentrated to about 150 mL under reduced pressure. This solution was poured into 500 mL water and extracted with 400 mL of ethyl acetate. The ethylacetate phase was extracted two times each with 75 mL 1N HCl, H₂O, saturated sodium bicarbonate solution and sodium chloride, and dried with magnesium sulfate. The mixture was filtered and the solution was concentrated to give 29.5 g (85% yield) of a white foam. This material could be purified by recrystallization from ethyl acetate/hexane, but was pure enough to use directly in the next step: mp 142–143° C. ¹H NMR (CDCl₃) d 1.45 (s, 9H), 6.10 (dd, 2H), 6.42 (S, 1H), 6.67 (bs, 1H), 7.21–7.31 (m, 10H). Anal: Calcd. for C₁₉H₂₃N₃O₃: C, 66.84; H, 6.79; N, 12.31. Found: C, 66.46; H, 6.75; N; 12.90.

Part II): Synthesis of Diphenylmethyl Semicarbazide (dpsc) Trifluoroacetate Salt

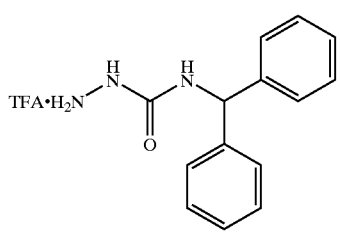

A solution of the product obtained in part I (above) (3.43 g, 10 mmol) in 12.5 mL of dichloromethane was treated with 12.5 mL of trifluoroacetic acid at room temperature and allowed to stir for 30 min. The solution was added dropwise to 75 mL of ether and the resulting precipitate (2.7 g, 80%) was filtered on a glass funnel. mp 182–184° C. ¹H NMR (CD₃OD) d 6.05 (s, 1H), 7.21–7.35 (m, 10H). ¹³C NMR (CD₃OD) d 57.6, 118.3 (q, CF₃), 126.7, 127.9, 141.6, 156.9, 160.9 (q, CF₃CO₂H).

Part III): Preparation of Ethyl N-α-t-butoxycarbonyl-norvalyl Carboxylate Diphenylmethylsemicarbazone To a cooled (0° C.) solution of the compound of step Ic above (13.21 g, 48 mmol) and EDC (92.1 g, 0.48 mol) in dimethylsulfoxide (20 mL) and toluene (20 mL), was added dichloroacetic acid (20.6 mL, 0.24 mol) dropwise. The reaction mixture was stirred for 15 min, then allowed to warm to room temperature over a 2 h period. The reaction mixture was concentrated under reduced pressure, then diluted with ethyl acetate, and washed successively with 1N sodium bisulfate, saturated sodium bicarbonate and brine. The organic layer was dried over sodium sulfate, and the solvent was removed in vacuo to afford crude ethyl N-α-t-butoxycarbonyl-norvalyl carboxylate. Ethyl N-α-t-butoxycarbonyl-norvalyl carboxylate was dissolved in ethanol (180 mL), and water (60 mL), diphenylmethylsemicarbazide (obtained in part II above) (34.12 g, 96mmol) and sodium acetate (4.73 g, 57.6mmol) was added. The reaction mixture was refluxed overnight, then allowed to cool to room temperature. The reaction mixture was concentrated under reduced solvent, then diluted with ethyl acetate. The organic layer was washed successively with 1N sodium bisulfate, saturated sodium bicarbonate and brine, dried over sodium sulfate, and the solvent was removed in vacuo. The residue was chromatographed over flash silica gel using 20–30% ethyl acetate/hexanes as eluent to afford 4.02 g of the title compound in 17% yield as a white powder. $R_f$=0.60 (40% ethyl acetate/hexanes).

e) Preparation of N-α-t-butoxycarbonyl-norvalyl Carboxylic Acid Diphenylmethylsemicarbazone (Boc-nVal(dpsc)-OH)

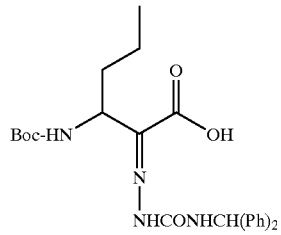

To the compound of step Id above (4.02 g, 8.1 mmol) in ethanol (40.5 mL) was slowly added 1N lithium hydroxide (64.8 mL, 64.8 mmol). After 3 h, Dowex 50WX8-400 ion exchange resin was added until the pH of the solution reached 4, and the mixture was stirred for 5 min. The mixture was filtered, washed with methanol, and concentrated. The solution was diluted with water, washed with ether. The aqueous solution was concentrated in vacuo. The resulting solid was triturated with toluene, then dried in vacuo to yield 1.44 g of the title compound (38%) as a white solid.

HPLC: $R_t$=16.2 and 17.7 minutes in a 30% to 90% acetonitrile gradient in 0.1% aqueous TFA buffer on a 4.6×250 mm, 5 mM particle, 100 Å pore, C18 column at a 1.0 mL/min flow rate.

f) Synthesis of H-nVal(dpsc)-Gly-PAM Resin

The commercially available Boc-Gly-PAM resin (5 g, 3.35 mmol) was deprotected according to Procedure D in a 250 mL fritted solid phase reaction vessel equipped with a nitrogen inlet. It was then coupled to Boc-nVal(dpsc)-OH (step Ie above) (2.81 g, 6 mmol)according to Procedure A. The resin was then subjected to Boc deprotection according to procedure D.

Step II. Synthesis of Fmoc-Pro-nVal(dpsc)-Gly-PAM rRsin

The resin obtained in step 1 (3.5 g, 1.80 mmol) was reacted with Fmoc-Pro-OH (4.5 mmol, 1.52 g) according to Procedure A. After 18 hours, qualitative ninhydrin analysis showed colorless beads and solution indicating a high yield of coupling.

Step III. Synthesis of Fmoc-Val-Pro-nVal(dpsc)-Gly-PAM Resin (SEQ ID NO: 2)

The compound of step II above (100 mg) was transferred to a fritted polypropylene tube and was deprotected according to Procedure C. A ninhydrin assay on a small aliquot gave dark blue resin and solution, indicating a high yield for the deprotection. The resin was resuspended in DMF (1 mL) and coupled to Fmoc-Val-OH (51 mg, 0.15 mmol) according to Procedure A. A small aliquot was taken for qualitative ninhydrin analysis which showed colorless beads and a dark red solution indicating a high yield of coupling.

Step IV. Synthesis of Fmoc-Val-Val-Pro-nVal(dpsc)-Gly-PAM Resin (SEQ ID NO: 3)

The compound of the previous step (100 mg) was deprotected according to Procedure C. A ninhydrin assay on a small aliquot gave dark blue resin and solution showing a high yield for the deprotection. The resin was resuspended in DMF (1 mL) and was coupled to Fmoc-Val-OH (51 mg, 0.15 mmol), according to Procedure A for 20 hours. A small aliquot was taken for qualitative ninhydrin analysis which showed colorless beads and solution indicating a high yield of coupling.

Step V. Synthesis of Fmoc-Glu(OtBu)-Val-Val-Pro-nVal(dpsc)-Gly-PAM Resin (SEQ ID NO: 4)

The compound of the previous step (100 mg) was deprotected according to Procedure C. A ninhydrin assay on a small aliquot gave dark blue resin and solution showing a high yield for the deprotection. The resin was resuspended in DMF (1 mL) and was coupled to Fmoc-Glu(OtBu)-OH (64 mg, 0.15 mmol), according to Procedure A for 5 hours. A small aliquot was taken for qualitative ninhydrin analysis which showed colorless beads and solution indicating a high yield of coupling.

Step VI. Synthesis of Fmoc-Glu(OtBu)-Glu(OtBu)-Val-Val-Pro-nVal(dpsc)-Gly-PAM Resin (SEQ ID NO: 5)

The compound of the previous step (100 mg) was deprotected according to Procedure C. A ninhydrin assay on a small aliquot gave dark blue resin and solution showing a high yield for the deprotection. The resin was resuspended in DMF (1 ml) and was coupled to Fmoc-Glu(OtBu)-OH (64 mg, 0.15 mmol), according to Procedure A for 5 hours. A small aliquot was taken for qualitative ninhydrin analysis which showed colorless beads and solution indicating a high yield of coupling.

Step VII. Synthesis of Ac-Glu(OtBu)-Glu(OtBu)-Val-Val-Pro-nVal(dpsc)-Gly-PAM Resin (SEQ ID NO: 6)

The compound of the previous step (100 mg) was deprotected according to Procedure C and acylated according to Procedure E. The resin was vacuum dried and a small aliquot was taken for qualitative ninhydrin analysis which showed colorless beads and solution indicating a high yield of coupling.

Step VIII. Synthesis of Ac-Glu(OtBu)-Glu(OtBu)-Val-Val-Pro-nVal-(CO)-Gly-PAM Resin (SEQ ID NO: 7)

The compound of the previous step (100 mg) was subjected to semicarbazone hydrolysis Procedure F.

Step IX. Synthesis of Ac-Glu-Glu-Val-Val-Pro-nVal-(CO)-Gly-OH (SEQ ID NO: 8)

The resin of the previous step (100 mg) was subjected to HF cleavage condition (Procedure G) to yield the desired crude product. The material was purified by HPLC using a 2.2×25 cm reverse phase column, containing a C-18 resin comprised of 10 micron size gel particles with a 300 angstrom pore size, eluting with a gradient using 5–25% acetonitrile in water. Analytical HPLC using a 4.6×250 mm reverse phase column, containing a C-18 resin comprised of 5 micron size gel particles with a 300 angstrom pore size, eluting with 5–25% acetonitrile (containing 0.1% trifluoro acetic acid) showed one peak at 17.5 minutes. Low resolution mass spectrum confirmed the desired mass (MH$^+$798.5).

Table of Compounds Synthesized According to Example I

| COMPOUND NAME | SYNTHESIS |
|---|---|
| Ac-EEVVP-nV-(CO)-G-OH (SEQ ID NO: 9) | example I |
| Ac-EEVV-Sar-nV-(CO)-G-OH (SEQ ID NO: 10) | step II: used Fmoc-Sar-OH |
| Ac-EEVV-Aze-nV-(CO)-G-OH (SEQ ID NO: 11) | step II: used Fmoc-azetidine-OH |
| Ac-EEV-G(Chx)-P-nV-(CO)-G-OH (SEQ ID NO: 12) | step III: used Fmoc-Gly(CHx)-OH |
| Ac-EEVFP-nV-(CO)-G-OH (SEQ ID NO: 13) | step III: used Fmoc-Phe-OH |
| Ac-EEVIP-nV-(CO)-G-OH (SEQ ID NO: 14) | step III: used Fmoc-Ile-OH |
| Ac-EEVV-dlPip-nV-(CO)-G-OH (SEQ ID NO: 15) | step II: used Boc-d,l-pipecolic acid |
| Ac-EEVV-Tiq-nV-(CO)-G-OH (SEQ ID NO: 16) | step II: used Fmoc-Tiq-OH |
| Ac-EEVV-C(Me)-nV-(CO)-G-OH (SEQ ID NO: 17) | step II: used Fmoc-Cys(Me)-OH |
| Ac-EEVV-C(O2,Me)-nV-(CO)-G-OH (SEQ ID NO: 18) | step II: used Fmoc-Cys(O2,Me)-OH |
| Ac-EEVV-C(2-AcOH)-nV-(CO)-G-OH (SEQ ID NO: 19) | step II: used Fmoc-Cys(2-AcOtBu)-OH |
| Ac-EEVV-M(O2)-nV-(CO)-G-OH (SEQ ID NO: 20) | step II: used Fmoc-Met(O2)-OH |
| Ac-EEVV-P(4t-Bn)-nV-(CO)-G-OH (SEQ ID NO: 21) | step II: used Boc-Pro(4t-Bn)-OH |
| Ac-EEVV-P(4t-Bn(4-OMe))-nV-(CO)-G-OH (SEQ ID NO: 22) | step II: used Boc-Pro(4t-Bn(4-OMe))-OH |
| Ac-EEVV-P(4t-allyl)-nV-(CO)-G-OH (SEQ ID NO: 23) | step II: used Boc-Pro(4t-allyl)-OH |
| Ac-EEVVD-nV-(CO)-G-OH (SEQ ID NO: 24) | step II: used Fmoc-Asp(OtBu)-OH |
| Ac-EEVVE-nV-(CO)-G-OH (SEQ ID NO: 25) | step II: used Boc-Glu(OtBu)-OH |
| Ac-EEVVF-nV-(CO)-G-OH (SEQ ID NO: 26) | step II: used Fmoc-Phe-OH |
| Ac-EEVV-P(4t-AcOH)-nV-(CO)-G-OH (SEQ ID NO: 27) | step II: used Boc-Pro(4t-AcOBn)-OH |
| Ac-EESVP-nV-(CO)-G-OH (SEQ ID NO: 28) | step IV: used Fmoc-Ser(tBu)-OH |
| Ac-EAVVP-nV-(CO)-G-OH (SEQ ID NO: 29) | Step V: used Fmoc-Ala-OH |
| Ac-EEHVP-nV-(CO)-G-OH (SEQ ID NO: 30) | step IV: used Fmoc-His(Trt)-OH |
| Ac-EENVP-nV-(CO)-G-OH (SEQ ID NO: 31) | step IV: used Fmoc-Asn(Trt)-OH |
| Ac-EEVV-P(4t-Ph)-nV-(CO)-G-OH (SEQ ID NO: 32) | step II: used Boc-Pro(4t-Ph)-OH |
| Ac-EEVV-P(3t-Me)-nV-(CO)-G-OH (SEQ ID NO: 33) | step II: used Boc-Pro(3t-Me)-OH |
| Ac-EE-Orn-VP-nV-(CO)-G-OH (SEQ ID NO: 34) | step IV: used Fmoc-Orn(Boc)-OH |
| Ac-EdEVVP-nV-(CO)-G-OH (SEQ ID NO: 35) | step V: used Fmoc-dGlu(OtBu)-OH |

-continued

| COMPOUND NAME | SYNTHESIS |
|---|---|
| Ac-EE-(s,s)alloT-VP-nV-(CO)-G-OH (SEQ ID NO: 36) | step IV: used Fmoc-(s,s)allo-Thr-OH |
| Ac-EE-Dif-VP-nV-(CO)-G-OH (SEQ ID NO: 37) | step III: used Fmoc-Dif-OH |
| Ac-EE-daba-VP-nV-(CO)-G-OH (SEQ ID NO: 38) | step III: used Fmoc-*Daba(Boc)-OH |
| Ac-EEDVP-nV-(CO)-G-OH (SEQ ID NO: 39) | step IV: used Fmoc-Asp(OtBu)-OH |
| Ac-EEEVP-nV-(CO)-G-OH (SEQ ID NO: 40) | step IV: used Fmoc-Glu(OtBu)-OH |
| Ac-EETVP-nV-(CO)-G-OH (SEQ ID NO: 41) | step IV: used Fmoc-Thr(tBu)-OH |
| Ac-AEVVP-nV-(CO)-G-OH (SEQ ID NO: 42) | step VI: used Fmoc-Ala-OH |
| Ac-EELVP-nV-(CO)-G-OH (SEQ ID NO: 43) | step IV: used Fmoc-Leu-OH |

*Note: Daba denotes diaminobutyric acid

Example II

Solution Phase Synthesis of Ac-EEVVP-nV-(CO)-G-allylAm (SEQ ID NO: 44)

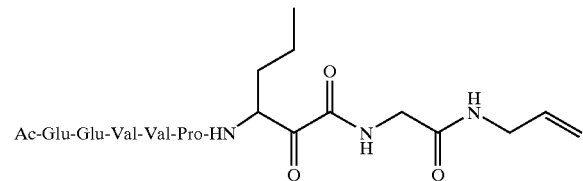

Step I. Synthesis of Boc-nVal(CHOH)-Gly-OEt

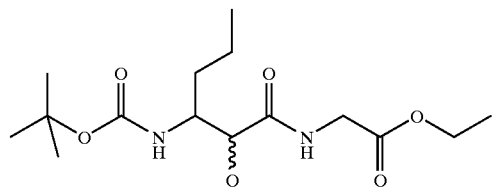

Trifluoroacetic acid (4.15 mL, 41.54 mmol) was added dropwise to a cooled solution (0° C.) of Boc-nVal-aldehyde (4.18 g, 20.77 mmol) (obtained in example 1, step Ib(part I)), ethylisocyanoacetate (2.72 mL, 24.93 mmol), and pyridine (6.72 mL, 83.09 mmol) in dichloromethane (83 mL). After two hours, the reaction was brought to room temperature and stirred uncapped for 48 hours. The reaction mixture was concentrated and dissolved in ethylacetate (80 mL). It was then extracted three times each with 10 mL portions of 1N sodium bisulfate, saturated sodium bicarbonate and brine. The organic layer was dried and concentrated and the remaining residue was subjected to purification using flash column chromatography in 1:4 ethylacetate: hexane followed by 2:3 ethylacetate: hexane. The desired fractions were pulled and concentrated to a yellowish flake (24.5 g, 78.6%). Thin layer chromatography in 2:3 ethylacetate: hexane showed one spot with an Rf of 0.16. Low resolution mass spectrum confirmed the desired mass (M+Na$^+$489).

Step II. Synthesis of HCl.H-nVal(CHOH)-Gly-OEt

The product obtained in step I above (1.12 g, 3.38 mmol) was treated for one hour with 10 mL saturated solution of anhydrous HCl in ethanol. It was then concentrated and triturated with n-heptane to a solid (0.9 g, 99.2%).

Step III. Synthesis of Ac-Glu(OtBu)-Glu(OtBu)-Val-Val-Pro-OH (SEQ ID NO:45) (steps a-f below)

a) Synthesis of Fmoc-Val-Pro-2ClTrt Resin

In a 1 L solid phase reaction vessel equipped with a nitrogen inlet, 25 g of Pro-2ClTrt resin (200–400 mesh, 0.64 mmol/g substitution) was suspended in dimethylformamide (213 mL). Fmoc-Val-OH (1.5 g, 32 mmol) was coupled for four hours according to Procedure A. A small aliquot was taken for calorimetric ninhydrin analysis which showed a 99.5% coupling efficiency in the production of the title compound.

b) Synthesis of Fmoc-Val-Val-Pro-2ClTrt Resin

The resin from the previous step (0.53 mmol/g) was deprotected according to Procedure C. It was then coupled to Fmoc-Val-OH (10.85 g, 32 mmol) according to Procedure A with 99.5% efficiency.

c) Synthesis of Fmoc-Glu(OtBu)-Val-Val-Pro-2ClTrt Resin (SEQ ID NO: 46)

The resin from the previous step (0.504 mmol/g) was deprotected according to Procedure C. It was then coupled to Fmoc-Glu(OtBu)-OH (13.63 g, 32 mmol) according to Procedure A with 99.4% efficiency.

d) Synthesis of Fmoc-Glu(OtBu)-Glu(OtBu)-Val-Val-Pro-2ClTrt Resin (SEQ ID NO: 47)

The resin from the previous step (0.461 mmol/g) was deprotected according to Procedure C. It was then coupled to Fmoc-Glu(OtBu)-OH (13.63 g, 32 mmol) according to procedure A with 99.2% efficiency to yield the titled compound.

e) Synthesis of Ac-Glu(OtBu)-Glu(OtBu)-Val-Val-Pro-2ClTrt Resin (SEQ ID NO: 48)

The resin from the previous step (0.42 mmol/g) was deprotected according to procedure C. The N-terminus was then capped according to Procedure D to yield the desired compound in 99.7% efficiency.

f) Synthesis of Ac-Glu(OtBu)-Glu(OtBu)-Val-Val-Pro-OH (SEQ ID NO: 49)

The resin from the previous step was transferred to a 1 L plastic bottle and cleaved in the presence of 525 ml solution of acetic acid: trifluoroethanol: dichloromethane (1:1:3) with vigorous shaking for two hours. The resin was filtered using a fritted funnel and washed 3×50 mL with dichloromethane. The brownish red filtrate was concentrated to an oil which was then treated three times with 50 ml of a 1:1 mixture of dichloromethane: n-heptane. The crude off-white powder (13 g) was then dissolved in minimum amount of methanol and purified by HPLC using a 2.2×25 cm reverse phase column, containing a C-18 resin comprised of 10 micron size gel particles with a 300 angstrom pore size, eluting with a gradient ranging from 15–55% acetonitrile in water. The pure fractions were pulled and concentrated to a fluffy, white product (7.5 g, 65%). Analytical HPLC using a 4.6×250 mm reverse phase column, containing a C-18 resin comprised of 5 micron size gel particles with a 300 angstrom pore size ran at 5–50% acetonitrile (containing 0.1% trifluoroacetic acid) showed one peak with the retention time of 20.5 min. Low resolution mass spectrum confirmed the desired mass (MH$^+$726.5).

Step IV. Synthesis of Ac-Glu(OtBu)-Glu(OtBu)-Val-Val-Pro-nVal(CHOH)-Gly-OEt (SEQ ID NO: 50)

The compound of step III above (Ac-Glu(OtBu)-Glu (OtBu)-Val-Val-Pro-OH) (0.72 g, 1 mmol) was coupled to the compound of step II above (HCl.H-nVal(CHOH)-Gly-OEt) (0.27 g, 1 mmol) using HOAt (0.204 g, 1.5 mmol), HATU (0.418 g, 1.1 mmol) and diisopropylethylamine (0.87 mL, 5 mmol) in DMF at room temperature. After 18 hours, the reaction mixture was concentrated. The remaining residue was picked up in ethylacetate and washed three times each with 10 mL portions of 1N sodium bisulfate, saturated sodium bicarbonate and brine. It was then dried over sodium sulfate and concentrated to a crusty yellowish product which was taken to the next step without further purification (0.98 g). Analytical HPLC using a 4.6×250 mm reverse phase column, containing a C-18 resin comprised of 5 micron size gel particles with a 300 angstrom pore size, eluting with 5–50% acetonitrile (containing 0.1% trifluoroacetic acid) showed a 2:1 ratio of diastereomers with retention times of 21 minutes and 21.5 minutes, respectively.

Step V. Synthesis of Ac-Glu(OtBu)-Glu(OtBu)-Val-Val-Pro-nVal(CHOH)-Gly-OH (SEQ ID NO: 51)

To the compound obtained in step IV above (0.94 g, 1 mmol) in ethanol (15 mL) was added 1N lithium hydroxide (4 mL, 4 mmol) and the reaction was stirred at room temperature for two hours. The reaction was stopped by the addition of enough Dowex ion exchange resin (50×8–400) to obtain an acidic solution, pH ~3. After stirring for 15 minutes, the reaction mixture was filtered and concentrated. The crude product was subjected to HPLC purification using a 5.5×30 cm reverse phase column, containing a C-18 resin comprised of 5 micron size gel particles with a 300 angstrom pore size, eluting with a 30 minute gradient using 5–30% acetonitrile in water. The desired fractions were pulled and concentrated to a white solid (238 mg, 26%).

Step VI. Synthesis of Ac-Glu(OtBu)-Glu(OtBu)-Val-Val-Pro-nVal(CHOH)-Gly-allylamide (SEQ ID NO: 52)

The compound of step V above (129 mg, 0.14 mmol) was coupled to allylamine (13□l, 0.17 mmol) in the presence of HOBt (58.5 mg, 0.38 mmol), EDC (54.3 mg, 0.28 mmol) and diisopropylethylamine (124□□l, 0.71 mmol) in dimethylformamide (10 ml). After 18 hours, the reaction mixture was concentrated and the remaining residue was picked-up in ethylacetate and washed three times each with 5 mL portions of 1N sodium bisulfate, saturated sodium bicarbonate and brine. After drying over sodium sulfate, the organic layer was concentrated to give a white precipitate which was taken to the next step without further purification (115 mg, 85%). Analytical HPLC using a 4.6×250 mm reverse phase column, containing a C-18 resin comprised of 5 micron size gel particles with a 300 angstrom pore size, eluting with 5–50% acetonitrile (containing 0.1% trifluoroacetic acid) showed two diastereomeric peaks with retention times of 15.9 and 16.5 minutes, respectively. Low resolution mass spectrum confirmed the desired mass (M+Na$^+$973.5).

Step VII. Synthesis of Ac-Glu(OtBu)-Glu(OtBu)-Val-Val-Pro-nVal(CO)-Gly-allylamide (SEQ ID NO: 53)

Under a stream of nitrogen gas, the product of step VI above (115.2 mg, 0.12 mmol) was dissolved in dimethylsulfoxide (5 mL) and toluene (5 mL). Water soluble carbodiimide (EDC, 232.2 mg, 1.21 mmol) was then added in one batch. The reaction mixture was cooled to 0° C. and dichloroacetic acid (52 □, 0.60 mmol) was added dropwise. Stirring at 0° C. continued for 15 minutes. The ice bath was removed and the reaction continued for two hours at room temperature. The toluene was removed under reduced pressure. The remaining solution was diluted with ethylacetate and washed three times each with 5 mL portions of 1N sodium bisulfate, saturated sodium bicarbonate and brine. It was then concentrated to a yellowish foam (85.5 mg, 74.4%).

Step VIII. Synthesis of Ac-Glu-Glu-Val-Val-Pro-nVal(CO)-Gly-allylamide (SEQ ID NO: 54)

The product of step VII above (0.86 g, 0.91 mmol) was treated with a 1:1 mixture of dichloromethane: trifluoroacetic acid (20 ml) for one hour. The reaction mixture was then concentrated and the remaining residue was purified using a 2.2×25 cm reverse phase HPLC column, containing a C-18 resin comprised of 10 micron size gel particles with a 300 angstrom pore size, eluting with a 30 minutes gradient using 10–25% acetonitrile in water. The purified fractions were pulled and lyophilized to a white powder (21.5 mg, 28.5%). Analytical HPLC using a 4.6×250 mm reverse phase column, containing a C-18 resin comprised of 5 micron size gel particles with a 300 angstrom pore size, eluting with 5–75% acetonitrile (containing 0.1% trifluoroacetic acid) showed one peak at 9.5 minutes. Low resolution mass spectrum confirmed the desired mass (MH$^+$ 837.5).

Table of Compounds Synthesized According to Example II

| COMPOUND NAME | SYNTHESIS |
| --- | --- |
| Ac-EEVVP-nV-(CO)-G-allylAm (SEQ ID NO: 55) | example II |
| Ac-EEVVP-nV-(CO)-G-2PhEtAm (SEQ ID NO: 56) | step VI: used phenethylamine |
| Ac-EEVVP-nV-(CO)-G-PropAm (SEQ ID NO: 57) | step VI: used propylamine |
| Ac-EEVVP-nV-(CO)-G-propynylAm (SEQ ID NO: 58) | step VI: used propynylamine |
| Ac-EEVVP-nV-(CO)-G-iPrAm (SEQ ID NO: 59) | step VI: used isopropylamine |

Example III

Solution Phase Synthesis of Ac-EEVVP-nV-(CO)-G (Oallyl) (SEQ ID NO: 60)

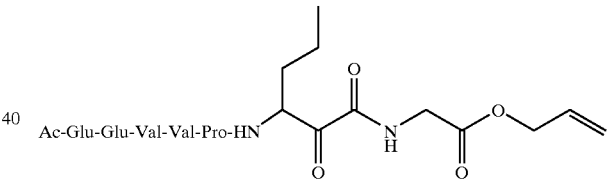

Step I. Synthesis of Fmoc-nVal-Gly-Oallyl (steps a–c Below)

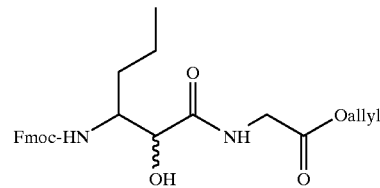

a) Synthesis of Allyl Isocyanoacetate a1) Ethyl isocyanoacetate (96.6 mL, 0.88 mol) was added dropwise to a chilled solution of ethanol (1.5 L) and potassium hydroxide (59.52 g, 1.0 mol). The reaction was slowly warmed to room temperature. After two hours, the precipitated product was filtered on a glass funnel and washed with several portions of chilled ethanol. The potassium salt of isocyanoacetic acid thus obtained was dried in vacuo to a golden-brown solid (99.92 g, 91.8%).

a2) To the product of step a1 (99.92 g, 0.81 mol) dissolved in acetonitrile (810 mL) was added allyl bromide (92 mL, 1.05 mol). After refluxing for four hours, a dark brown solution was obtained. The reaction mixture was concentrated and the remaining residue was picked-up in ether (1.5 L) and washed three times with water (500 ml). The organic layer was dried and concentrated to a dark brown syrup. The crude was purified by vacuum distillation at 7 mm Hg (98° C.) to a clear oil (78.92 g, 77.7%). NMR δ ppm (CDCl$_3$): 5.9 (m, 1 H), 5.3 (m, 2H), 4.7 (d, 2H), 4.25 (s, 2H).

b) Synthesis of 9-fluorenylmethoxycarbonyl-norvalinal (Steps b1–b3 Below)

b1) Synthesis of 9-fluorenylmethoxycarbonyl-norvaline Methyl Ester:

To a chilled solution of Fmoc-norvaline (25 g, 73.75 mmol) in anhydrous methanol (469 mL) was added thionyl chloride (53.76 mL, 0.74 mol) over one hour. Thin layer chromatography in ethylacetate taken an hour later confirmed the completion of the reaction ($R_f$=0.85). The reaction mixture was concentrated and the remaining residue was picked-up in ethylacetate. The organic layer was washed with three 200 ml portions of saturated sodium bicarbonate followed by brine. The organic layer was dried and concentrated to afford the title product as a white solid (26.03 g) in quantitative yield. NMR δ ppm (CD$_3$OD): 7.7 (m, 2H), 7.6 (m, 2H), 7.4 (m, 2H), 7.3 (m, 2H), 4.3 (m, 2H), 4.1 (m, 2H), 3.7 (s, 3H), 1.7 (m, 1H), 1.6 (m,1H), 1.4 (m, 2H), 0.95 (t, 3H).

b2) Synthesis of 9-fluorenylmethoxycarbonyl-norvalinol:

To the product of step b1 (26.03 g, 73.75 mmol) in tetrahydrofuran (123 mL) and methanol (246 mL) was added calcium chloride (16.37 g, 147.49 mmol). The reaction mixture was cooled to 0° C. and sodium borohydride (11.16 g, 0.3 mol) was added in several batches. Methanol (500 mL) was added to the thick paste obtained and the reaction was stirred at room temperature for 90 minutes. Thin layer chromatography in 2:3 ethylacetate: hexane confirmed the completion of the reaction ($R_f$=0.25). The reaction was quenched with the slow addition of 100 mL water at 0° C. The methanol was removed under reduced pressure and the remaining aqueous phase was diluted with ethylacetate (500 mL). The organic layer was washed three times each with 500 ml portions of water, saturated sodium bicarbonate and brine. The organic layer was dried over sodium sulfate and concentrated to a white solid (21.70 g, 90.5%). NMR δ ppm (CD$_3$OD): 7.8 (m, 2H), 7.7 (m, 2H), 7.4 (m, 2H), 7.3 (m, 2H), 4.3–4.5 (m, 2H), 4.2 (m, 1H), 3.6 (s, 1H), 3.5 (s, 2H), 1.5 (m, 1H), 1.3–1.4 (m, 3H), 0.99 (m, 3H).

b3) Synthesis of 9-fluorenylmethoxycarbonyl-norvalinal:

To the product of step b2 (21.70 g, 66.77 mmol) in dichloromethane (668 mL) was added triethylamine (37.23 mL, 267.08 mmol) and the solution was cooled to 0 C. A suspension of pyridine sulfur trioxide complex (42.51 g, 267.08 mmol) in dimethylsulfoxide (96 mL) was added to the chilled solution. After one hour, thin layer chromatography in 2:3 ethylacetate: hexane confirmed the completion of the reaction. The dichloromethane was removed under reduced pressure and the remaining residue was picked-up in ethylacetate and washed with several 50 mL portions of water, 1N saturated sodium bisulfate, saturated sodium bicarbonate and brine. The organic layer was concentrated to yield a white solid. Theoretical yield (21.57 g) was assumed and the reaction was taken to the next step without further purification.

c) Synthesis of Fmoc-nVal(CHOH)-Gly-Oallyl

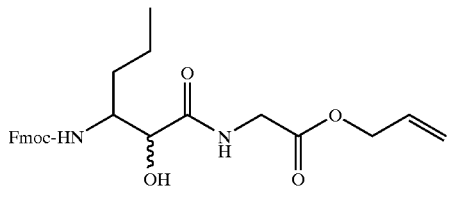

To a solution of 9-fluorenylmethoxycarbonyl-norvalinal obtained from step b3 (5.47 g, 16.90 mmol) in dichloromethane (170 mL) was added allyl isocyanoacetate (step I a2 above) (2.46 mL, 20.28 mmol) and pyridine (5.47 mL, 67.61 mmol). The reaction mixture was cooled to 0° C. and trifluoroacetic acid (3.38 mL, 33.80 mmol) was added dropwise. The reaction was stirred at 0 C for 1 h, and then at room temperature for 48 hours. Thin layer chromatography taken in ethylacetate confirmed the completion of the reaction. The reaction mixture was concentrated and subjected to flash column chromatography using a gradient composed of 20:80 ethylacetate: hexane to 70:30 ethylacetate: hexane. Fractions containing the desired product were pooled and concentrated to a white foam (6.88 g, 87.3%). TLC in 50:50 ethylacetate showed one spot ($R_f$=0.37). NMR δ ppm (CD$_3$OD): 7.8 (m, 2H), 7.65 (m, 2H), 7.4 (m, 2H), 7.3 (m, 2H), 5.9 (m, 1H), 5.1–5.4 (m, 2H), 4.55–4.65 (m, 2H), 4.3–4.4 (m, 2H), 4.15–4.25 (m, 1H), 4.01 (s, 1H), 3.9–4.0 (m, 3H), 1.5–1.6 (m, 2H), 1.35–1.45 (m, 3H), 0.9 (m, 3H).

Step II. Synthesis of H-nVal(CHOH)-Gly-Oallyl

To Fmoc-nVal(CHOH)-Gly-Oallyl (300 mg, 0.64 mmol) (obtained in step Ic above) dissolved in tetrahydrofuran (5.8 mL) was added diethylamine (0.64 mL) and the resulting solution was stirred at room temperature for two hours. The reaction mixture was concentrated and the remaining solid was triturated with a 1:4 ether: hexane mixture. The product was collected on a glass funnel and washed several times with a 1:1 ether: hexane mixture (93.7 mg, 57%). Low resolution mass spectrum confirmed the desired mass (MH$^+$ 245.0).

Step III. Synthesis of Ac-Glu(OtBu)-Glu(OtBu)-Val-Val-Pro-nVal(CHOH)-Gly-Oallyl (SEQ ID NO: 61)

The product obtained from step II above (28.2 mg, 0.11 mmol) was coupled to Ac-Glu(OtBu)-Glu(OtBu)-Val-Val-Pro-OH (example II, step III) (84 mg, 0.11 mmol) in the presence of HOAt (23.6 mg, 0.17 mmol), HATU (48.4 mg, 0.13 mmol), diisopropylethylamine (100.8 μl, 0.58 mmol) in dimethylformamide (20 mL) for 4 hours at room temperature. The DMF was removed under reduced pressure and the remaining residue was picked up in ethylacetate and washed with 1N sodium bisulfate, saturated sodium bicarbonate and brine. After drying over sodium sulfate, the organic layer was concentrated to give a white solid (100.3 mg, 91%) which was taken to the next step without further purification. Low resolution mass spectrum confirmed the desired mass (M+Na$^+$974.5).

Step IV. Synthesis of Ac-Glu(OtBu)-Glu(OtBu)-Val-Val-Pro-nVal(CO)-Gly-Oallyl (SEQ ID NO: 62)

Under a stream of nitrogen gas, the product of the previous step (51.5 mg, 0.054 mmol) was dissolved in dimethylsulfoxide (1.2 mL) and toluene (1.2 mL). Water soluble carbodiimide (EDC, 103.8 mg, 0.54 mmol) was then added in one batch. The reaction mixture was cooled to 0° C. and dichloroacetic acid (22.3 □l, 0.27 mmol) was added dropwise. Stirring at 0° C. continued for 15 minutes. The ice bath was removed and the reaction was slowly brought to room temperature. The reaction was stopped after 90 minutes. The toluene was removed under reduced pressure. The reaction was diluted with ethylacetate and washed with 1N sodium bisulfate, saturated sodium bicarbonate and brine. It was then concentrated to a yellowish foam (40.4 mg, 79%) and taken to the next step without further purification.

Step V. Synthesis of Ac-Glu-Glu-Val-Val-Pro-nVal(CO)-Gly-Oallyl (SEQ ID NO: 63)

The product of the previous step (40.4 mg, 0.042 mmol) was treated with a 1:1 mixture of dichloromethane: trifluoroacetic acid (4 mL) for two hours. The reaction mixture was then concentrated and purified on a 1×25 cm reverse phase HPLC column, containing a C-18 resin comprised of 10 micron size gel particles with a 300 angstrom pore size, eluting with a 30 minute gradient using 10–30% acetonitrile in water. The desired fractions were pulled and concentrated to a white powder (8.5 mg, 24%). Analytical HPLC using a 4.6×250 mm reverse phase column, containing a C-18 resin comprised of 5 micron size gel particles with a 300 angstrom pore size, ran at 5–50% acetonitrile (containing 0.1% trifluoroacetic acid) showed one peak at 15 minutes. Low resolution mass spectrum confirmed the desired mass (MH+ 838.0).

Table: Compounds Synthesized According to Example III

| COMPOUND NAME | SYNTHESIS |
|---|---|
| Ac-EEVVPnV-(CO)-G-Oallyl (SEQ ID NO: 64) | example III |
| Ac-EEVVP-nL-(CO)-G-Oallyl (SEQ ID NO: 65) | step I(b1): used Fmoc-nLeu-OH |
| Ac-EEVVP-V-(CO)-G-Oallyl (SEQ ID NO: 66) | step I(b1): used Fmoc-Val-OH |
| Ac-EEVVPL-(CO)-G-Oallyl (SEQ ID NO: 67) | step I(b1): used Fmoc-Leu-OH |
| Ac-EEVVP-G(propynyl)-(CO)-G-Oallyl (SEQ ID NO: 68) | step I(b1): used Fmoc-Gly(propynyl)-OH |
| Ac-EEVVPnV-(CO)-G-OEt (SEQ ID NO: 69) | step Ic: used ethyl isocyanoacetate |
| Ac-EEVVP-G(allyl)-(CO)-G-Oallyl (SEQ ID NO: 70) | step I(b1): used Fmoc-Gly(allyl)-OH |
| Ac-EEVVG-L-(CO)-G-Oallyl (SEQ ID NO: 71) | step I(b1): used Fmoc-Leu-OH, example II, step IIIa: used Gly-2ClTrt-resin |
| Ac-EEVVPnV-(CO)-G-OtBu (SEQ ID NO: 72) | step Ic: used t-butyl isocyanoacetate |
| Ac-EEVVP-G(allyl)-(CO)-G-OEt (SEQ ID NO: 73) | step Ic: used ethyl isocyanoacetate, step I(b1): used Fmoc-Gly(allyl)-OH |
| Ac-EEVVP-C(Me)-(CO)-G-OMe (SEQ ID NO: 74) | step Ic: used methyl isocyanoacetate, step I(b1): used Boc-Cys(Me)-OH |

Example IV

Solid Phase Synthesis of Ac-EEVV-G(N-Bu(4NH2, 4-CO2H))-nV-(CO)-G-OH (SEQ ID NO: 75)

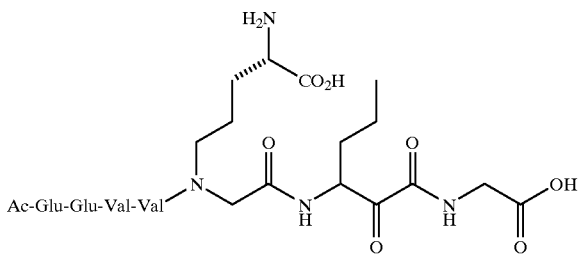

Step I. Synthesis of bromoacetyl-nVal(dpsc)-Gly-PAM Resin

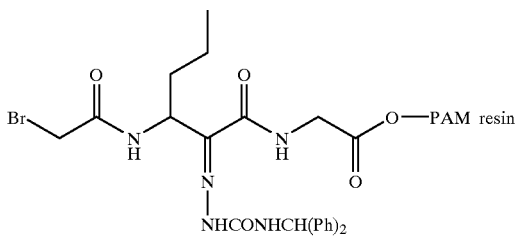

In a solid phase vessel, bromoacetic acid (1.29 g, 9.27 mmol) was coupled to the resin obtained in example I (step If) (1.5 g, 0.77 mmol) in the presence of diisopropylcarbodiimide (1.27 g, 10.04 mmol) and dimethylformamide (10 mL) for five hours. The reagents were filtered and the reaction was repeated once more for 18 hours, at which time qualitative ninhydrin test showed colorless beads and solution indicating that the reaction had gone to completion. All reagents were drained and the resin was washed thoroughly with 15 mL portions of dimethylformamide, methanol and dichloromethane.

Step II. Synthesis of Gly(N-Bu(4NH-Boc,4-COOtBu)-nVal(dpsc)-Gly-PAM Resin

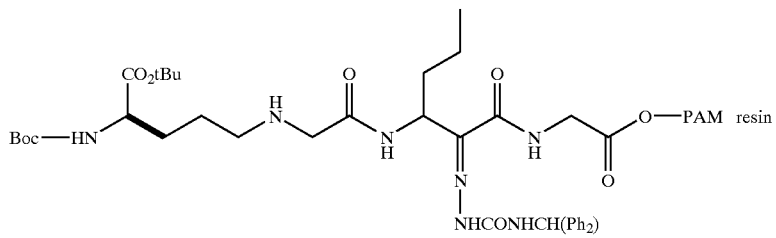

The product of the previous step (0.12 g, 0.06 mmol) was treated with Boc-Orn-OtBu.AcOH (0.86 g, 2.47 mmol) in the presence of diisopropylethylamine (0.05 mL, 0.31 mmol) and dimethylsulfoxide (1.2 mL) for 18 hours. The reagents were drained and the procedure was repeated for 5 hours using fresh reagents. All reagents were drained and the resin was washed thoroughly with 2 mL portions of dimethylformamide, methanol and dichloromethane.

Step III. Synthesis of Ac-Glu-Glu-Val-Val-Gly(N-Bu (4NH2,4-COOH)-nVal(CO)-Gly-OH (SEQ ID NO: 76)

The following steps were carried out sequentially:

a) Fmoc-Val-OH (0.04 g, 0.10 mmol) was double coupled to the product of step II above (0.12 g, 0.05 mmol) according to Procedure B.
b) The resin was deprotected according to Procedure C and coupled to Fmoc-Val-OH (0.04 g, 0.10 mmol) according to Procedure B.
c) The resin was deprotected according to Procedure C and coupled to Fmoc-Glu(OtBu)-OH (0.04 g, 0.10 mmol) according to Procedure B.
d) The resin was deprotected according to Procedure C and coupled to Fmoc-Glu(OtBu)-OH (0.04 g, 0.10 mmol) according to Procedure B.
e) The resin was deprotected according to Procedure C and acylated at the N-terminus according to Procedure E.
f) The semicarbazone group of the product obtained in step e was hydrolyzed according to Procedure F, and the product was subjected to HF cleavage according to Procedure G. The crude material was subjected to HPLC purification using a 1×25 cm reverse phase column, containing a C-18 resin comprised of 10 micron size gel particles with a 300 angstrom pore size, eluting with a 30 minute gradient using 10–40% acetonitrile in water. Analytical HPLC using a 4.6×250 mm reverse phase column, containing a C-18 resin comprised of 5 micron size gel particles with a 300 angstrom pore size, eluting with 5–75% acetonitrile (containing 0.1% trifluoroacetic acid) showed one peak at 8 minutes. Low resolution mass spectrum confirmed the presence of the desired product (MH+ 873.5).

Table of Compounds Synthesized According to Example IV

| COMPOUND NAME | SYNTHESIS |
|---|---|
| Ac-EEVV-G(N-Bu(4NH2,4-CO2H))-nV-(CO)-G-OH (SEQ ID NO: 77) | example IV |
| AC-EEVV-G(N-Et(CO2H))-nV-(CO)-G-OH (SEQ ID NO: 78) | step II: used □-Ala(OtBu).HCl |
| Ac-EEVV-G(N-EtPh(3,4diOMe))-nV-(CO)-G-OH (SEQ ID NO: 79) | step II: used 3,4-dimethoxyphenethylamine |
| Ac-EEVV-G(N-Pe(5-NH2,5-CO2H))-nV-(CO)-G-OH (SEQ ID NO: 80) | step II: used CBz-Lys(OBzl).benzene sulfonate |

Example V

Solid Phase Synthesis of Ac-EEVV-G(N-Et(NHBz))-nV-(CO)-G-OH (SEQ ID NO: 81)

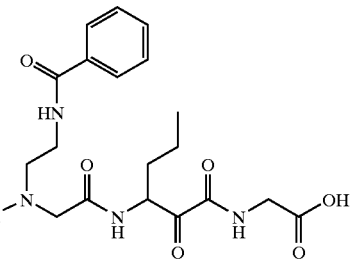

Step I. Synthesis of Gly(N-Et(NH-Boc))-nVal(dpsc)-Gly-PAM Resin

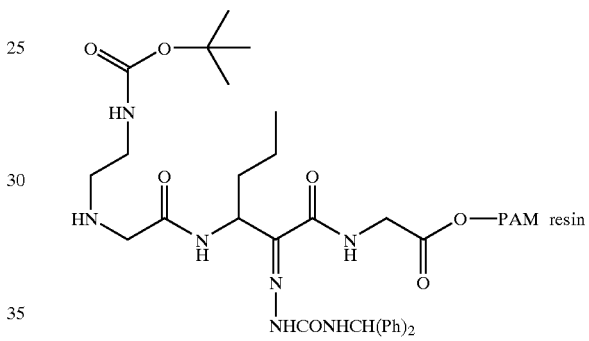

The resin obtained in example IV (step I) (0.24 g, 0.12 mmol) was treated with t-butyl N-(2-aminoethyl)-carbamate (0.78 mL, 4.94 mmol) in the presence of diisopropylethylamine (0.11 mL, 0.62 mmol) and dimethylsulfoxide (2.4 mL) for 18 hours. The reagents were drained and the procedure was repeated for 5 hours using fresh reagents. All reagents were drained and the resin was washed thoroughly with 2 mL portions of dimethylformamide, methanol and dichloromethane.

Step II. Synthesis of Fmoc-Val-Gly(N-Et(NH-Boc))-nVal (dpsc)-Gly-PAM Resin (SEQ ID NO: 82)

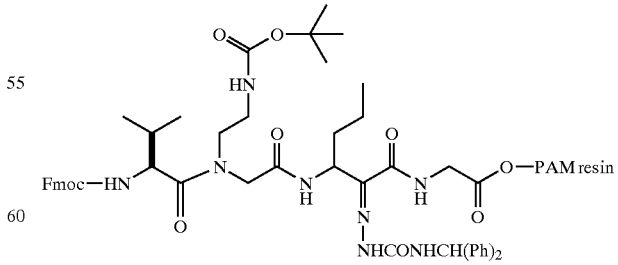

Fmoc-Val-OH (0.07 g, 0.21 mmol) was double coupled to the product of step I above (0.24 g, 0.10 mmol) according to Procedure B.

157

Step III. Synthesis of Fmoc-Val-Gly(N-Et(NHBz))-nVal (dpsc)-Gly-PAM Resin (SEQ ID NO: 83)

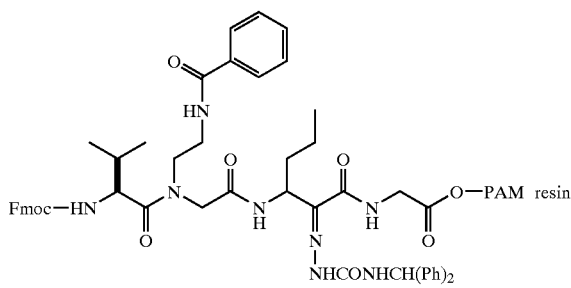

The product obtained from step II above (0.12 g, 0.06 mmol) was treated with a 1:1 mixture of trifluoroacetic acid: dichloromethane according to Procedure D. The free amine generated was then capped with the addition of benzoyl chloride (0.02 mL, 0.19 mmol) in the presence of diisopropylethylamine (0.06 mL, 0.37 mmol) in N-methylpyrrolidine (1.24 mL).

Step IV. Synthesis of Ac-Glu-Glu-Val-Val-Gly(N-Et (NHBz))-nVal(CO)-Gly-OH (SEQ ID NO: 84)

The following steps were carried out sequentially:

a) The resin obtained in step III above was deprotected according to Procedure C and coupled to Fmoc-Val-OH (0.04 g, 0.10 mmol) according to Procedure B.
b) The resin obtained in the previous step was deprotected according to Procedure C and coupled to Fmoc-Glu (OtBu)-OH (0.04 g, 0.10 mmol) according to Procedure B.
c) The resin obtained in the previous step was deprotected according to Procedure C and coupled to Fmoc-Glu (OtBu)-OH (0.04 g, 0.10 mmol) according to Procedure B.
d) The resin obtained in the previous step (0.12 g) was deprotected according to Procedure C and acylated at the N-terminus according to Procedure E.
e) The semicarbazone group of the product obtained in step d was hydrolyzed according to procedure F, and the product was subjected to HF cleavage according to procedure G. Analytical HPLC using a 4.6×250 mm reverse phase column, containing a C-18 resin comprised of 5 micron size gel particles with a 300 angstrom pore size, ran at 5–50% acetonitrile (containing 0.1% trifluoroacetic acid) showed one peak at 14 minutes. Low resolution mass spectrum confirmed the presence of the desired product (MH+ 905.5).

Table of Compounds Synthesized According to Example V

| COMPOUND NAME | SYNTHESIS |
|---|---|
| Ac-EEVV-G(N-Et(NHBz))-nV-(CO)-G-OH (SEQ ID NO: 84) | example V |
| Ac-EEVV-G(N-Et(NHBzl(3-OPh)))-nV-(CO)-G-OH (SEQ ID NO: 85) | step III: used 3-phenoxybenzoic acid as capping group |
| Ac-EEVV-G(N-Prop(NHBz))-nV-(CO)-G-OH (SEQ ID NO: 86) | step I: used t-butyl N-(2-aminopropyl)-carbamate |

158

Example VI

Solid Phase Synthesis of Ac-EEVVP-nV(CO)-Am (SEQ ID NO: 87)

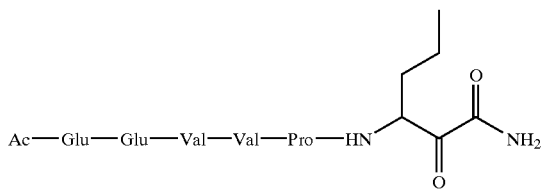

Step I. Formation of HOBt Ammonium Salt

Ammonium hydroxide (0.5 mL) was added dropwise to a slurry of HOBt (2 g, 13.07 mmol) in water (5 mL). The mixture was stirred at room temperature until a clear solution was obtained. The product was precipitated by the slow addition of acetone (50 mL). It was then filtered on a glass funnel and washed thoroughly with cold acetone (white powder, 2.23 g, 78%; mp 177–181° C.).

Step II. Synthesis of HCl.H-nVal-(CHOH)-CONH2

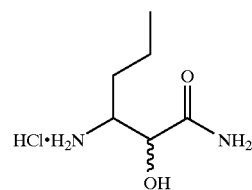

Boc-nVal-(CHOH)-COOH (295 mg, 1.19 mmol) (example V, step II) was reacted with the product of the previous step (362 mg, 2.38 mmol) in the presence of EDC (342 mg, 1.78 mmol) in dimethylformamide (10 mL) at room temperature for 18 hours. The reaction mixture was concentrated and the remaining residue was picked up in ethylacetate (5 mL) and washed three times each with 5 mL portions of 1N sodium bisulfate, saturated sodium bicarbonate and brine. The organic layer was dried over sodium sulfate and concentrated to a white solid (170 mg, 58%). After drying in vacuo, the product was treated with 5N anhydrous HCl in ethylacetate (5 mL) for 1 hour and concentrated (120 mg, 94%).

Step III. Synthesis of Ac-Glu(OtBu)-Glu(OtBu)-Val-Val-Pro-nVal-(CHOH)-CONH2 (SEQ ID NO: 88)

The product obtained from step II above (19 mg, 0.103 mmol) was coupled to Ac-Glu(OtBu)-Glu(OtBu)-Val-Val-Pro-OH (example II, step IIIf) (50 mg, 0.069 mmol) in the presence of HOAt (14.1 mg, 0.103 mmol), HATu (28.8 mg, 0.076 mmol), diisopropylethylamine (60 µl, 0.345 mmol) in dimethylformamide (10 mL) for 4 hours at room temperature. The DMF was removed under reduced pressure and the remaining residue was picked up in ethylacetate and washed with 1N sodium bisulfate, saturated sodium bicarbonate and brine. After drying over sodium sulfate it was concentrated to give a white solid (40 mg, 68%) which was taken to the next step without further purification. Low resolution mass spectrum confirmed the desired mass (M+Na+ 876.5).

Step IV. Synthesis of Ac-Glu(OtBu)-Glu(OtBu)-Val-Val-Pro-nVal-(CO)-CONH2 (SEQ ID NO: 89)

Under a stream of nitrogen gas, the product of the previous step (40 mg, 0.047 mmol) was dissolved in dimethylsulfoxide (4 mL) and toluene (4 mL). Water soluble carbodiimide (EDC, 89.8 mg, 0.47 mmol) was then added in one batch. The reaction mixture was cooled to 0° C. and dichloroacetic acid (20 □l, 0.23 mmol) was added dropwise. Stirring at 0° C. continued for 15 minutes. The ice bath was removed and the reaction was slowly brought to room temperature. The reaction was stopped after 90 minutes. The toluene was removed under reduced pressure. The reaction was diluted with ethylacetate and washed with 1N sodium bisulfate, saturated sodium bicarbonate and brine. It was then concentrated to a yellowish foam (40 mg, 53%) and taken to the next step without further purification. Low resolution mass spectrum confirmed the desired mass (M+Na+ 852.5).

Step V. Synthesis of Ac-Glu-Glu-Val-Val-Pro-nVal-(CO)-CONH2 (SEQ ID NO: 90)

The product of the previous step (39.9 mg, 0.047 mmol) was treated with a 1:1 mixture of dichloromethane: trifluoroacetic acid (10 mL) for two hours. The reaction mixture was concentrated and the remaining residue was subjected to HPLC purification using a 1×25 cm reverse phase column, containing a C-18 resin comprised of 10 micron size gel particles with a 300 angstrom pore size, eluting with a 30 minute gradient using 5–25% acetonitrile in water. The purified fractions were pulled and lyophilized to a white powder (3.6 mg, 10%). Low resolution mass spectrum confirmed the desired mass (MH+ 740.0).

Table of Compounds Synthesized According to Example VI

| COMPOUND NAME | SYNTHESIS |
|---|---|
| Ac-EEVVP-nV-(CO)-Am (SEQ ID NO: 91) | example VI |

Example VII
Solid Phase Synthesis of Ac-EEVV-P(4t-MeNHBzl (3-OPh))-nV-(CO)-G-OH (SEQ ID NO: 92)

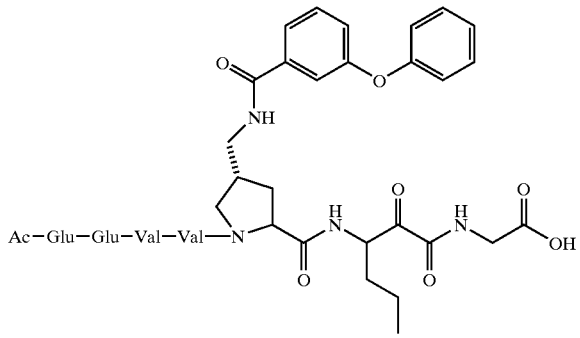

Step I. Synthesis of H-Pro(4t-MeNHFmoc)-nVal-(dpsc)-Gly-PAM Resin

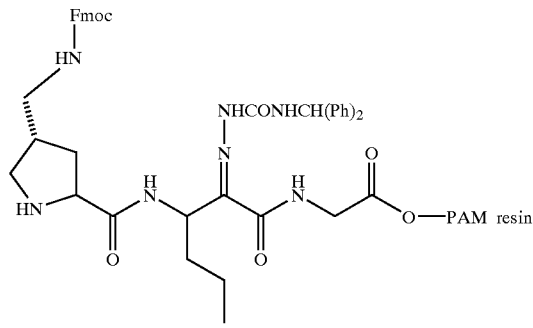

The resin obtained from example I (step I) (0.70 g, 0.36 mmol) was coupled with Boc-Pro(4t-MeNHFmoc)-OH according to procedure B for 18 hours, with 99.98% efficiency. The resin was then subjected to deprotection according to procedure D to obtain the title product.

Step II. Synthesis of Ac-Glu(OtBu)-Glu(OtBu)-Val-Val-Pro(4t-MeNHFmoc)-nVal-(dpsc)-Gly-PAM Resin (SEQ ID No: 93)

The resin obtained from the previous step (0.7 g, 0.29 mmol) was double coupled to Ac-Glu(OtBu)-Glu(OtBu)-Val-Val-OH (0.45 g, 0.72 mmol) (obtained similar to example II (step III) starting from H-Val-2ClTrt-resin) according to procedure B.

Step III. Synthesis of Ac-Glu(OtBu)-Glu(OtBu)-Val-Val-Pro(4t-MeNH2)-nVal-(dpsc)-Gly-PAM Resin (SEQ ID No: 94)

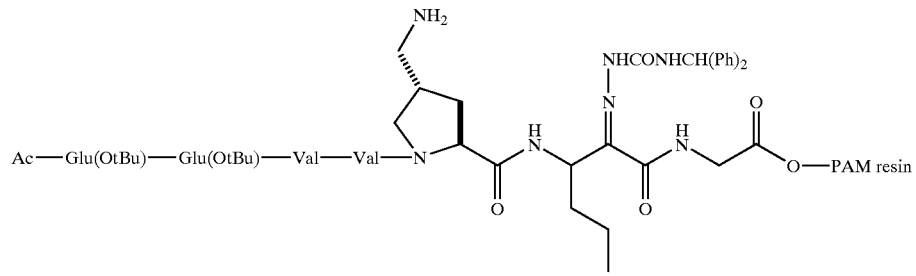

The Fmoc side chain protecting group of the product obtained from the previous step was removed according to procedure C to afford the title compound.

Step IV. Synthesis of Ac-Glu(OtBu)-Glu(OtBu)-Val-Val-Pro (4t-MeNHBzl(3-OPh))-nVal-(dpsc)-Gly-PAM Resin (SEQ ID No: 95)

The resin obtained from the previous step (0.15 g, 0.05 mmol) was coupled to 3-phenoxy benzoic acid (0.02 g, 0.10 mmol) according to procedure B with 99.97% efficiency.

Step V. Synthesis of Ac-Glu-Glu-Val-Val-Pro(4t-MeNHBzl (3-OPh))-nVal-(CO)-Gly-OH (SEQ ID No: 96)

The resin obtained from the previous step was subjected to semicarbazone hydrolysis according to procedure F, followed by HF cleavage according to procedure H to yield the crude product. The material was subjected to HPLC purification using a 1×25 cm reverse phase column, containing a C-18 resin comprised of 10 micron size gel particles with a 300 angstrom pore size, eluting with a 30 minute gradient ranging from 10–35% acetonitrile in water. Analytical HPLC using a 4.6×250 mm reverse phase column, containing a C-18 resin comprised of 5 micron size gel particles with a 300 angstrom pore size, eluting with 5–75% acetonitrile (containing 0.1% trifluoroacetic acid) showed one peak at 14.5 minutes. Low resolution mass spectrum confirmed the presence of the desired product (MH$^+$ 1049.5).

Table of Compounds Synthesized According to Example VII

| COMPOUND NAME | SYNTHESIS |
| --- | --- |
| Ac-EEVV-P(4t-MeNHBzl(3-OPh))-nV-(CO)-G-OH (SEQ ID NO: 92) | example VII |
| Ac-EEVV-P(4t-MeNHCO2Ph)-nV-(CO)-G-OH (SEQ ID NO: 97) | step IV: used phenyl chloroformate, DIEA, NMP |
| Ac-EEVV-P(4t-MeNHCOPh)-nV-(CO)-G-OH (SEQ ID NO: 98) | step IV: used benzoyl chloride, DIEA, NMP |
| Ac-EEVV-P(4t-MeNH-Fmoc)-nV-(CO)-G-OH (SEQ ID NO: 99) | omitted steps III and IV |
| Ac-EEVV-P(4t-MeNHSO2Ph)-nV-(CO)-G-OH (SEQ ID NO: 100) | step IV: used benzenesulfonyl chloride, 2,4,6-collidine, NMP |
| Ac-EEVV-P(4t-MeUreaPh)-nV-(CO)-G-OH (SEQ ID NO: 101) | step IV: used phenyl isocyanate, DIEA, NMP |
| Ac-EEVV-P(4t-NH-Fmoc)-nV-(CO)-G-OH (SEQ ID NO: 102) | step I: used Boc-Pro(4t-NH-Fmoc)-OH |

Example VIII

Solid Phase Synthesis of Ac-EEVV-P(4t-NHBZl)-nV-(CO)-G-OH (SEQ ID No: 103)

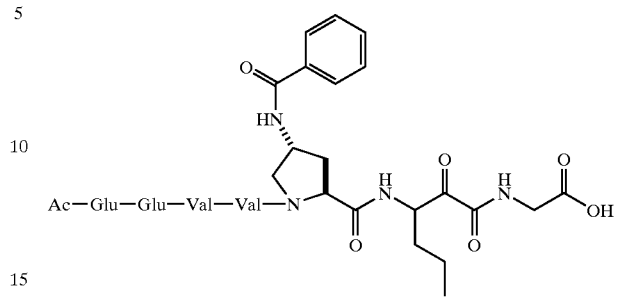

Step I. Synthesis of Boc-Pro(4t-NH2)-nVal-(dpsc)-Gly-PAM Resin

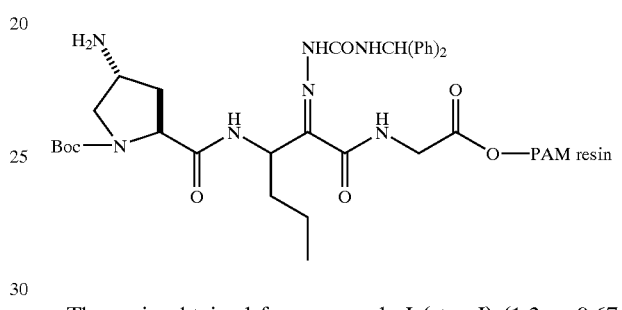

The resin obtained from example I (step I) (1.3 g, 0.67 mmol) was coupled with Boc-Pro(4t-NHFmoc)-OH (0.61 g, 1.34 mmol) according to procedure B for 18 hours, at which time qualitative ninhydrin test confirmed completion of the reaction. The resin was then subjected to deprotection according to Procedure C to obtain the title product.

Step II. Synthesis of Boc-Pro(4t-NHBzl)-nVal-(dpsc)-Gly-PAM Resin

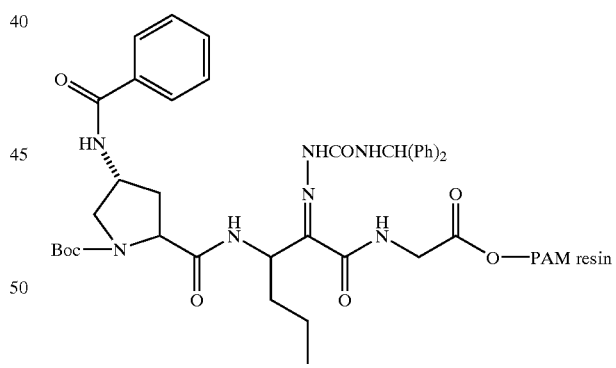

The resin obtained from the previous step (0.13 g, 0.05 mmol) was transferred to a fritted polypropylene tube and was suspended in N-methylpyrrolidine (1.5 mL). It was then capped with benzoyl chloride (0.02 mL, 0.16 mmol) in the presence of diisopropylethylamine (0.05 mL, 0.32 mmol) for four hours to yield the title product.

Step III. Synthesis of Fmoc-Val-Pro(4t-NHBzl)-nVal-(dpsc)-Gly-PAM Resin (SEQ ID No: 104)

The compound of the previous step (100 mg, 0.05 mmol) was deprotected according to Procedure D. A ninhydrin assay on a small aliquot gave dark blue resin and solution showing a high yield for the deprotection. The resin was resuspended in N-methylpyrrolidine (1.47 mL) and coupled to Fmoc-Val-OH (0.03 g, 0.10 mmol) according to Procedure B. A small aliquot was taken for qualitative ninhydrin analysis which showed colorless beads and a dark red solution indicating a high yield of coupling.

Step IV. Synthesis of Fmoc-Val-Val-Pro(4t-NHBzl)-nVal-(dpsc)-Gly-PAM Resin (SEQ ID No: 105)

The compound of the previous step (100 mg) was deprotected according to Procedure D. A ninhydrin assay on a small aliquot gave dark blue resin and solution showing a high yield for the deprotection. The resin was resuspended in N-methylpyrrolidine (1.47 mL) and was coupled to Fmoc-Val-OH (0.03, 0.10 mmol) as in step III.

Step V. Synthesis of Fmoc-Glu(OtBu)-Val-Val-Pro(4t-NHBzl)-nVal-(dpsc)-Gly-PAM Resin (SEQ ID No: 106)

The compound of the previous step (100 mg, 0.03 mmol) was deprotected according to Procedure D. A ninhydrin assay on a small aliquot gave dark blue resin and solution showing a high yield for the deprotection. The resin was resuspended in N-methylpyrrolidine (1.47 mL) and was coupled to Fmoc-Glu(OtBu)-OH (0.04 g, 0.10 mmol), according to Procedure B for 5 hours. A small aliquot was taken for qualitative ninhydrin analysis which showed colorless beads and solution indicating a high yield of coupling.

Step VI. Synthesis of Fmoc-Glu(OtBu)-Glu(OtBu)-Val-Val-Pro(4t-NHBzl)-nVal-(dpsc)-Gly-PAM Resin (SEQ ID No: 107)

The compound of the previous step (100 mg) was deprotected according to Procedure D and coupled to Fmoc-Glu(OtBu)-OH (0.04 g, 0.10 mmol) in the same manner.

Step VII. Synthesis of Ac-Glu-Glu-Val-Val-Pro(4t-NHBzl)-nVal-(CO)-Gly-OH (SEQ ID No: 108)

The compound of previous step (100 mg) was deprotected according to Procedure C and acylated according to Procedure E. The resin was vacuum dried and a small aliquot was taken for qualitative ninhydrin analysis which showed colorless beads and solution indicating a high yield of coupling. The resin was then subjected to semicarbazone hydrolysis followed by HF cleavage reactions according to Procedures F and H, respectively. The crude product was subjected to HPLC purification using a 1×25 cm reverse phase column, containing a C-18 resin comprised of 10 micron size gel particles with a 300 angstrom pore size, eluting with a 30 minute gradient using 10–40% acetonitrile in water. Analytical HPLC using a 4.6×250 mm reverse phase column, containing a C-18 resin comprised of 5 micron size gel particles with a 300 angstrom pore size, ran at 5–50% acetonitrile (containing 0.1% trifluoroacetic acid) showed one peak at 13 minutes. Low resolution mass spectrum confirmed the presence of the desired product (MH+ 917.5).

Table of Compounds Synthesized According to Example VIII

| COMPOUND NAME | SYNTHESIS |
|---|---|
| Ac-EEVV-P(4t-NHBzl)-nV-(CO)-G-OH (SEQ ID NO: 103) | example VIII |
| Ac-EEVV-P(4t-NHBzl(4-OMe))-nV-(CO)-G-OH (SEQ ID NO: 109) | step II: used 4-methoxybenzoyl chloride, DIEA, NMP |
| Ac-EEVV-P(4t-NHBzl(4-OPh))-nV-(CO)-G-OH (SEQ ID NO: 110) | step II: used 4-phenoxybenzoic acid |
| Ac-EEVV-P(4t-NHBzl(3-OPh))-nV-(CO)-G-OH (SEQ ID NO: 111) | step II: used 3-phenoxybenzoic acid |
| Ac-EEVV-P(4t-NHBzl(3,4-OMeO))-nV-(CO)-G-OH (SEQ ID NO: 112) | step II: used piperonyloyl chloride, DIEA, NMP |
| Ac-EEVV-P(4t-NHBzl(4F))-nV-(CO)-G-OH (SEQ ID NO: 113) | step II: used 4-fluorobenzoyl chloride, DIEA, NMP |
| Ac-EEVV-P(4t-NHiBoc)-nV-(CO)-G-OH (SEQ ID NO: 114) | step II: used isobutyl chloroformate, DIEA, NMP |
| Ac-EEVV-P(4t-NHSO2Ph)-nV-(CO)-G-OH (SEQ ID NO: 115) | step II: used benzene sulfonyl chloride, 2,4,6-collidine, NMP |
| Ac-EEVV-P(4t-NHSO2Ph(4-OMe))-nV-(CO)-G-OH (SEQ ID NO: 116) | step II: used 4-methoxybenzene sulfonyl chloride, 2,4,6-collidine, NMP |
| Ac-EEVV-P(4t-UreaPh)-nV-(CO)-G-OH (SEQ ID NO: 117) | step II: used phenyl isocyanate, DIEA, NMP |
| Ac-EEVV-P(4t-UreaPh(4-OMe))-nV-(CO)-G-OH (SEQ ID NO: 118) | step II: used 4-methoxyphenyl isocyanate, DIEA, NMP |

Example IX

Solution Phase Synthesis of Ac-EEVVP-nV-(CO)-OH (SEQ ID No: 119)

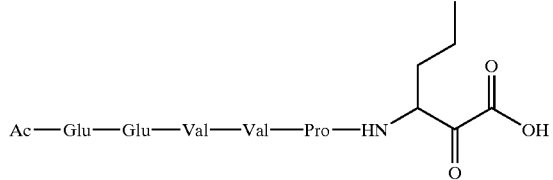

Step I. Synthesis of Ethyl (R,S)-2-hydroxy-3-amino Hexanoate Hydrochloride

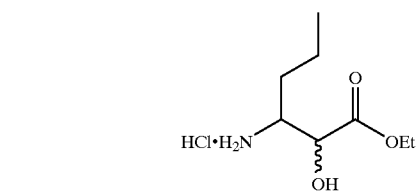

The product obtained in example I (step Ib) (1.99 g, 6.59 mmol) was refluxed in 6N HCl (42 mL) for four hours. After cooling to room temperature, the reaction mixture was extracted with dichloromethane (3×30 mL) and the aqueous layer was concentrated to dryness (1.65 g crude). Some of the resulting product (0.88 g, 4.8 mmol) was stirred in 20 mL saturated solution of anhydrous HCl in ethanol for 90 minutes. The mixture was concentrated to a white solid (0.95 g, 93%).

Step II. Synthesis of Ac-Glu(OtBu)-Glu(OtBu)-Val-Val-Pro-nVal(CHOH)-OEt (SEQ ID No: 120)

The product obtained from the previous step (88 mg, 0.41 mmol) was coupled to Ac-Glu(OtBu)-Glu(OtBu)-Val-Val-Pro-OH (example II, step IIIf) (200 mg, 0.26 mmol) in the presence of HOAt (56.3 mg, 0.41 mmol), HATu (115.3 mg, 0.30 mmol), diisopropylethylamine (240 I, 1.37 mmol) in dimethylformamide (10 mL) for 18 hours at room temperature. The DMF was removed under reduced pressure and the remaining residue was subjected to HPLC purification using a 2.2×25 cm reverse phase column, containing a C-18 resin comprised of 10 micron size gel particles with a 300 angstrom pore size, eluting with a 30 minute gradient ranging from 15–50% acetonitrile in water. The desired fractions were pulled and concentrated to a solid (67 mg, 27.5%). Analytical HPLC using a 4.6×250 mm reverse phase column, containing a C-18 resin comprised of 5 micron size gel particles with a 300 angstrom pore size, eluting with 5–50% acetonitrile (containing 0.1% trifluoroacetic acid) showed one peak at 23.5 minutes. Low resolution mass spectrum confirmed the desired mass (MH+ 883.5).

Step III. Synthesis of Ac-Glu(OtBu)-Glu(OtBu)-Val-Val-Pro-nVal(CHOH)-Carboxylic Acid (SEQ ID No: 121)

To the product obtained in the previous step (67 mg, 0.076 mmol) dissolved in ethanol (3.8 mL) was added 1N lithium hydroxide (304 I, 0.304 mmol) and the reaction was stirred at room temperature for 90 minutes. The reaction was stopped by the addition of enough Dowex ion exchange resin (50×8-400) to obtain an acidic solution, pH ~3. After stirring for 15 minutes, the reaction mixture was filtered and concentrated to a white solid (53.4 mg, 82.2%).

Step IV. Synthesis of Ac-Glu-Glu-Val-Val-Pro-nVal (CHOH)-Carboxylic Acid (SEQ ID No: 122)

The product obtained in the previous step (53.1 mg) stirred in a 1:1 mixture of trifluoroacetic acid: dichloromethane (1 0 mL) for 90 minutes. The reaction mixture was concentrated to a yellowish solid (50 mg) which was taken to the next step without further purification.

Step V. Synthesis of Ac-Glu-Glu-Val-Val-Pro-nVal(CO)-Carboxylic Acid (SEQ ID No: 123)

The product obtained in the previous step (55.7 mg, 0.075 mmol) was dissolved in dichloromethane (8 mL) and dimethylsulfoxide (2 mL). Triethylamine (125.5 □l, 0.901 mmol) followed by pyridine sulfur trioxide (1 43.4 mg, 0.901 mmol) were added and the reaction was stirred at room temperature for two hours. Dichloromethane was removed under reduced pressure and the remaining residue was diluted with methanol (containing 0.1% TFA) and purified on a reverse phase HPLC column (1×25 cm) containing a C-18 resin comprised of 10 micron size gel particles with a 300 angstrom pore size, eluting with a 30 minute gradient using 5–15% acetonitrile in water. The desired fractions were pulled and concentrated to an oil (15.2 mg, 27.4%). Analytical HPLC using a 4.6×250 mm reverse phase column, containing a C-18 resin comprised of 5 micron size gel particles with a 300 angstrom pore size, ran at 5–50% acetonitrile (containing 0.1% trifluoroacetic acid) showed one peak at 11 minutes. Low resolution mass spectrum confirmed the desired mass (MH+ 741.0).

Table of Compound Synthesized According to Example IX

| | |
|---|---|
| Ac-EEVVP-nV-(CO)-OH (SEQ ID NO: 124) | example IX |

Assay for HCV Protease Inhibitory Activity:

Spectrophotometric Assay:

Spectrophotometric assay for the HCV serine protease was performed on the inventive compounds by following the procedure described by R. Zhang et al, *Analytical Biochemistry*, 270 (1999) 268–275, the disclosure of which is incorporated herein by reference. The assay based on the proteolysis of chromogenic ester substrates is suitable for the continuous monitoring of HCV NS3 protease activity. The substrates were derived from the P side of the NS5A-NS5B junction sequence (Ac-DTEDVVX(Nva)(SEQ ID No: 125), where X=A or P) whose C-terminal carboxyl groups were esterified with one of four different chromophoric alcohols (3- or 4-nitrophenol, 7-hydroxy-4-methyl-coumarin, or 4-phenylazophenol). Presented below are the synthesis, characterization and application of these novel spectrophotometric ester substrates to high throughput screening and detailed kinetic evaluation of HCV NS3 protease inhibitors.

Materials and Methods:

Materials: Chemical reagents for assay related buffers were obtained from Sigma Chemical Company (St. Louis, Mo.). Reagents for peptide synthesis were from Aldrich Chemicals, Novabiochem (San Diego, Calif.), Applied Biosystems (Foster City, Calif.) and Perseptive Biosystems (Framingham, Mass.). Peptides were synthesized manually or on an automated ABI model 431A synthesizer (from Applied Biosystems). UV/VIS Spectrometer model LAMBDA 12 was from Perkin Elmer (Norwalk, Conn.) and 96-well UV plates were obtained from Corning (Corning, N.Y.). The prewarming block was from USA Scientific (Ocala, Fla.) and the 96-well plate vortexer was from Labline Instruments (Melrose Park, Ill.). A Spectramax Plus microtiter plate reader with monochrometer was obtained from Molecular Devices (Sunnyvale, Calif.).

Enzyme Preparation:

Recombinant heterodimeric HCV NS3/NS4A protease (strain 1a) was prepared by using the procedures published previously (D. L. Sali et al, *Biochemistry*, 37 (1998) 3392–3401). Protein concentrations were determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) was exchanged for the assay buffer (25 mM MOPS pH 6.5, 300 mM NaCl, 10% glycerol, 0.05% lauryl maltoside, 5 $\mu$M EDTA and 5 $\mu$M DTT) utilizing a Biorad Bio-Spin P-6 prepacked column.

Substrate Synthesis and Purification:

The synthesis of the substrates was done as reported by R. Zhang et al, (ibid.) and was initiated by anchoring Fmoc-Nva-OH to 2-chlorotrityl chloride resin using a standard protocol (K. Barlos et al, *Int J. Pept. Protein Res.*, 37 (1991), 513–520). The peptides were subsequently assembled, using Fmoc chemistry, either manually or on an automatic ABI model 431 peptide synthesizer. The N-acetylated and fully protected peptide fragments were cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash was evaporated azeotropically (or repeatedly extracted by aqueous $Na_2CO_3$ solution) to remove the acid used in cleavage. The DCM phase was dried over $Na_2SO_4$ and evaporated.

The ester substrates were assembled using standard acid-alcohol coupling procedures (K. Holmber et al, *Acta Chem. Scand.*, B33 (1979) 410–412). Peptide fragments were dissolved in anhydrous pyridine (30–60 mg/ml) to which 10 molar equivalents of chromophore and a catalytic amount (0.1 eq.) of paratoluenesulfonic acid (PTSA) were added. Dicyclohexylcarbodiimide (DCC, 3 eq.) was added to initiate the coupling reactions. Product formation was monitored by HPLC and found to be complete following 12–72 hour reaction at room temperature. Pyridine solvent was evaporated under vacuum and further removed by azeotropic evaporation with toluene. The peptide ester was deprotected with 95% TFA in DCM for two hours and extracted three times with anhydrous ethyl ether to remove excess chromophore. The deprotected substrate was purified by reversed phase HPLC on a C3 or C8 column with a 30% to 60% acetonitrile gradient (using six column volumes). The overall yield following HPLC purification was approximately 20–30%. The molecular mass was confirmed by electrospray ionization mass spectroscopy. The substrates were stored in dry powder form under desiccation.

Spectra of Substrates and Products:

Spectra of substrates and the corresponding chromophore products were obtained in the pH 6.5 assay buffer. Extinction coefficients were determined at the optimal off-peak wavelength in 1-cm cuvettes (340 nm for 3-Np and HMC, 370 nm for PAP and 400 nm for 4-Np) using multiple dilutions. The optimal off-peak wavelength was defined as that wavelength yielding the maximum fractional difference in absorbance between substrate and product (product OD—substrate OD)/substrate OD).

Protease Assay:

HCV protease assays were performed at 30° C. using a 200 μl reaction mix in a 96-well microtiter plate. Assay buffer conditions (25 mM MOPS pH 6.5, 300 mM NaCl, 10% glycerol, 0.05% lauryl maltoside, 5 μM EDTA and 5 μM DTT) were optimized for the NS3/NS4A heterodimer (D. L. Sali et al, ibid.)). Typically, 150 μl mixtures of buffer, substrate and inhibitor were placed in wells (final concentration of DMSO 4% v/v) and allowed to preincubate at 30° C. for approximately 3 minutes. Fifty μls of prewarmed protease (12 nM, 30° C.) in assay buffer, was then used to initiate the reaction (final volume 200 μl).The plates were monitored over the length of the assay (60 minutes) for change in absorbance at the appropriate wavelength (340 nm for 3-Np and HMC, 370 nm for PAP, and 400 nm for 4-Np) using a Spectromax Plus microtiter plate reader equipped with a monochrometer (acceptable results can be obtained with plate readers that utilize cutoff filters). Proteolytic cleavage of the ester linkage between the Nva and the chromophore was monitored at the appropriate wavelength against a no enzyme blank as a control for non-enzymatic hydrolysis. The evaluation of substrate kinetic parameters was performed over a 30-fold substrate concentration range (~6–200 μM). Initial velocities were determined using linear regression and kinetic constants were obtained by fitting the data to the Michaelis-Menten equation using non-linear regression analysis (Mac Curve Fit 1.1, K. Raner). Turnover numbers ($k_{cat}$) were calculated assuming the enzyme was fully active.

Evaluation of Inhibitors and Inactivators:

The inhibition constants ($K_i$) for the competitive inhibitors Ac-D-(D-Gla)-L-I-(Cha)-C-OH (27), Ac-DTEDVVA(Nva)-OH (SEQ ID No: 127) and Ac-DTEDVVP(Nva)-OH (SEQ ID No: 128) were determined experimentally at fixed concentrations of enzyme and substrate by plotting $v_o/v_i$ vs. inhibitor concentration ($[I]_o$) according to the rearranged Michaelis-Menten equation for competitive inhibition kinetics: $v_o/v_i = 1 + [I]_o/(K_i(1+[S]_o/K_m))$, where $v_o$ is the uninhibited initial velocity, $v_i$ is the initial velocity in the presence of inhibitor at any given inhibitor concentration ($[I]_o$) and $[S]_o$ is the substrate concentration used. The resulting data were fitted using linear regression and the resulting slope, $1/(K_i(1+[S]_o/K_m))$, was used to calculate the $K_i^*$ value.

The obtained $K_i^*$ values for the various compounds of the present invention are given in the Tables wherein the compounds have been arranged in the order of ranges of $K_i^*$ values. From these test results, it would be apparent to the skilled artisan that the compounds of the invention have excellent utility as NS3-serine protease inhibitors.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

TABLE 3

| STRUCTURE | NAME | Ki* Range |
|---|---|---|
| 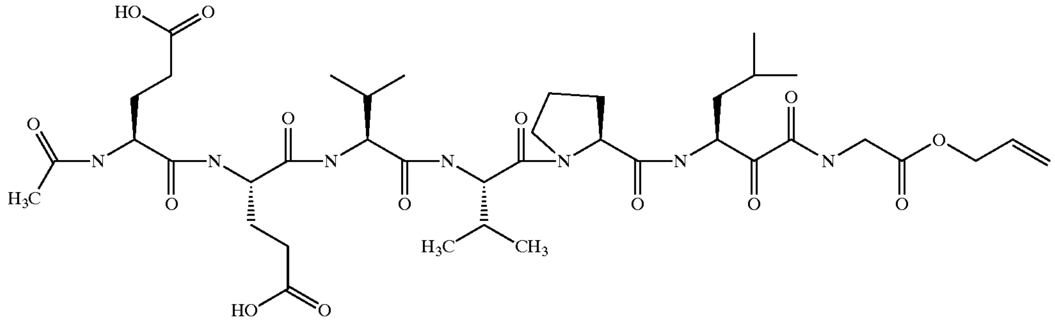 | Ac-EEVVP-L-(CO)-G-Oallyl (SEQ ID NO: 67) | |
| 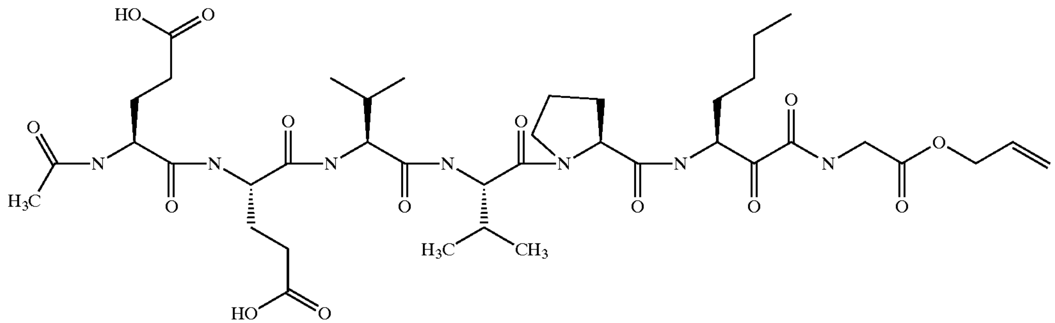 | Ac-EEVVP-nL-(CO)-G-Oallyl (SEQ ID NO: 65) | a |
| 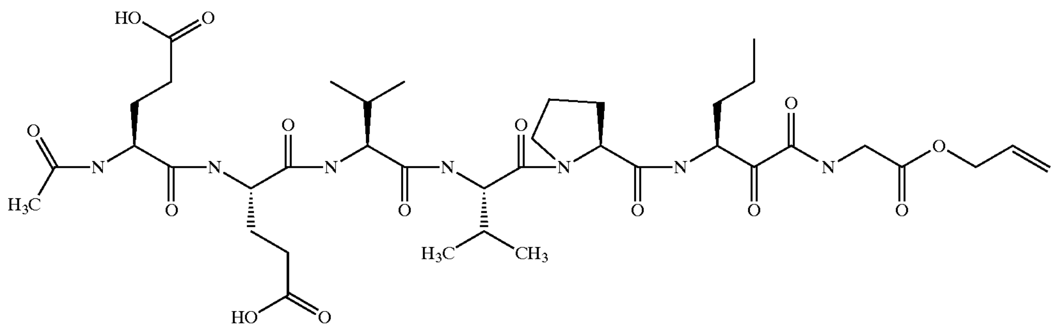 | Ac-EEVVP-nV-(CO)-G-Oallyl (SEQ ID NO: 64) | a |

TABLE 3-continued

| STRUCTURE | NAME | Ki* Range |
|---|---|---|
| 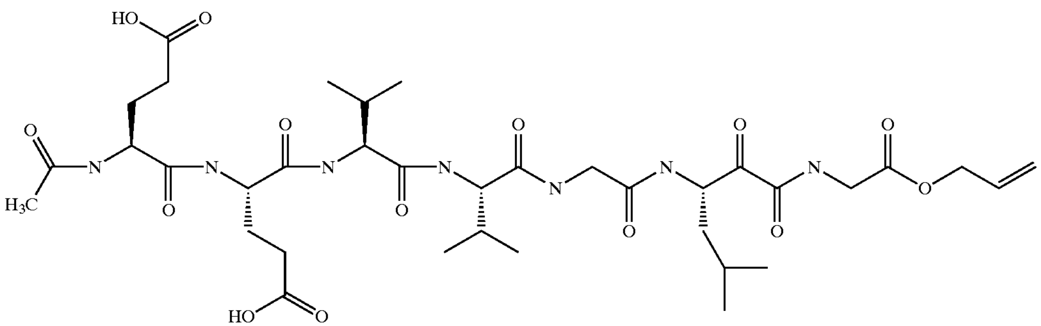 | Ac-EEVVG-L-(CO)-G-Oallyl (SEQ ID NO: 71) | b |
| 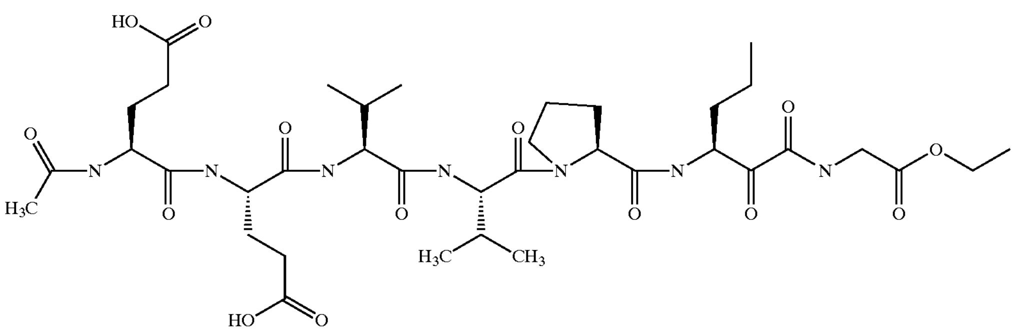 | Ac-EEVVP-nV-(CO)-G-OEt (SEQ ID NO: 69) | c |
| 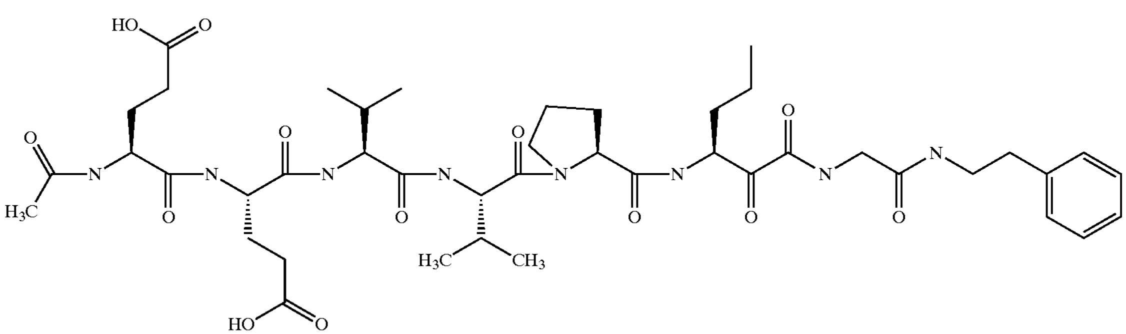 | Ac-EEVVP-nV-(CO)-G-2PhEtAm (SEQ ID NO: 56) | c |

TABLE 3-continued

| STRUCTURE | NAME | Ki* Range |
|---|---|---|
| 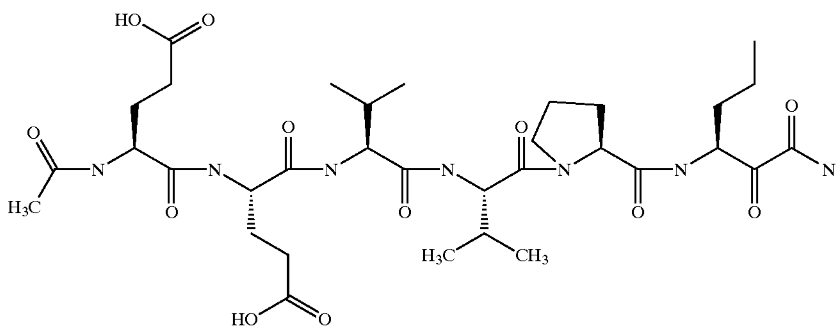 | Ac-EEVVP-nV-(CO)-Am (SEQ ID NO: 91) | b |
| 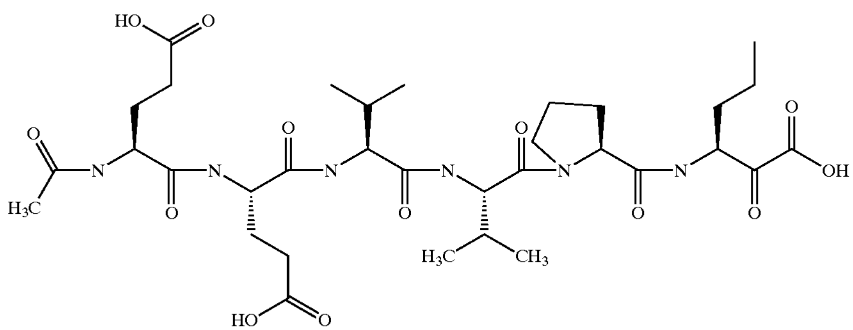 | Ac-EEVVP-nV-(CO)-OH (SEQ ID NO: 119) | c |
| 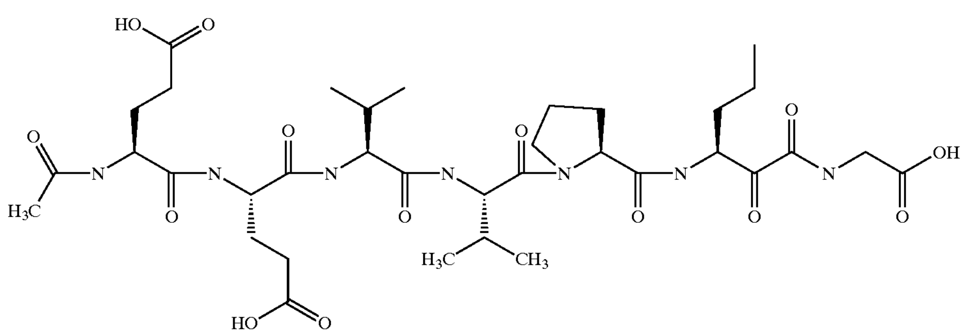 | Ac-EEVVP-nV-(CO)-G-OH (SEQ ID NO: 9) | a |

TABLE 3-continued

| STRUCTURE | NAME | Ki* Range |
|---|---|---|
| 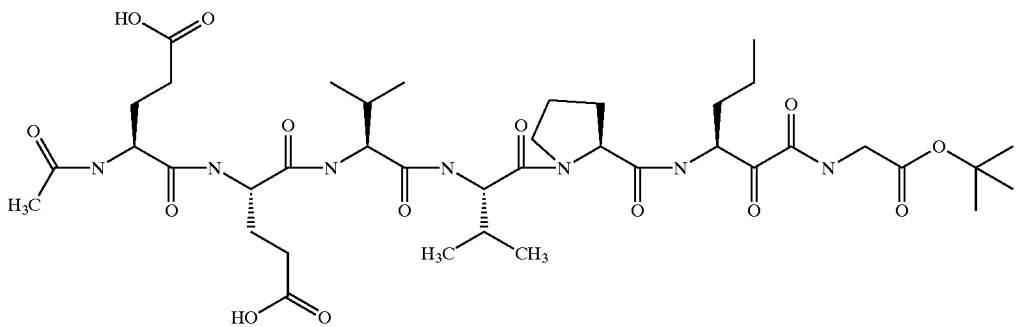 | Ac-EEVVP-nV-(CO)-G-OtBu (SEQ ID NO: 72) | b |
| 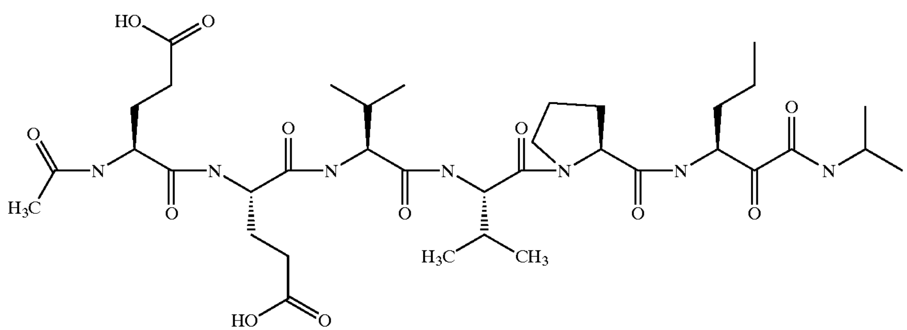 | Ac-EEVVP-nV-(CO)-iPrAm (SEQ ID NO: 129) | c |
| 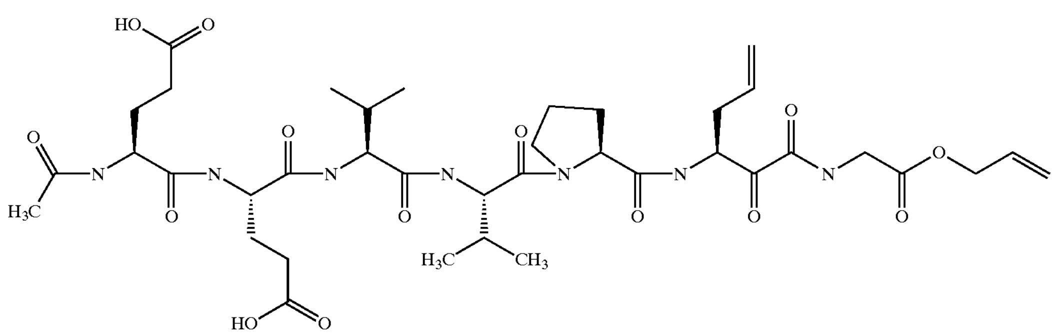 | Ac-EEVVP-G(allyl)-(CO)-G-Oallyl (SEQ ID NO: 70) | b |

TABLE 3-continued

| STRUCTURE | NAME | Ki* Range |
|---|---|---|
| (structure) | Ac-EEVVP-G(allyl)-(CO)-G-OEt (SEQ ID NO: 73) | b |
| (structure) | Ac-EEVVP-nV-(CO)-G-allylAm (SEQ ID NO: 44) | b |
| (structure) | Ac-EEVVP-nV-(CO)-G-propynylamide (SEQ ID NO: 58) | c |

TABLE 3-continued

| STRUCTURE | NAME | Ki* Range |
|---|---|---|
| 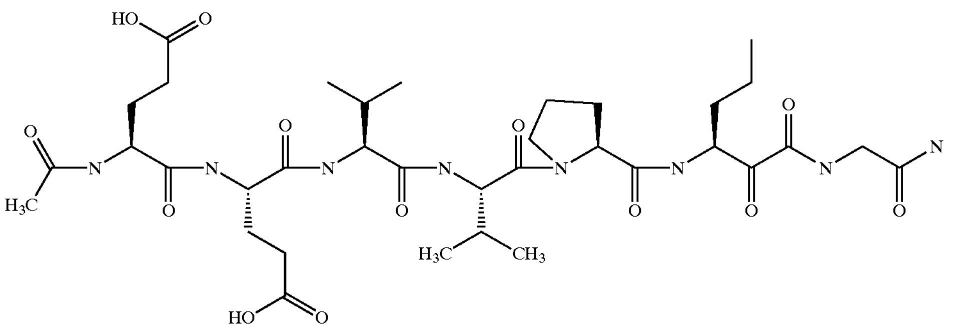 | Ac-EEVVP-nV-(CO)-G-Am (SEQ ID NO: 130) | c |
| 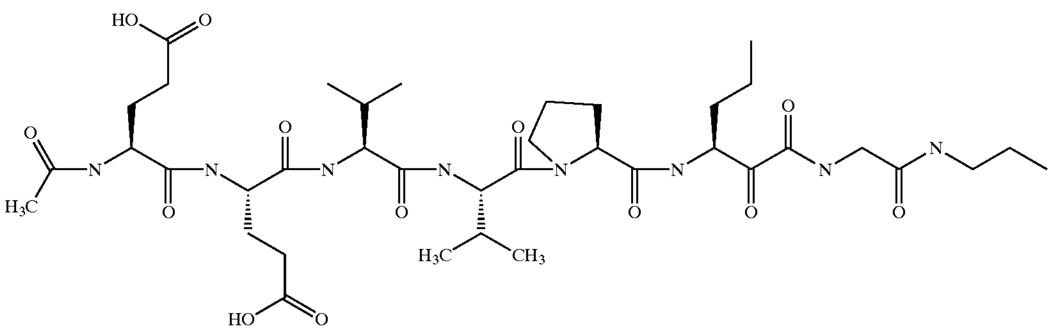 | Ac-EEVVP-nV-(CO)-G-Propylamide (SEQ ID NO: 57) | c |
| 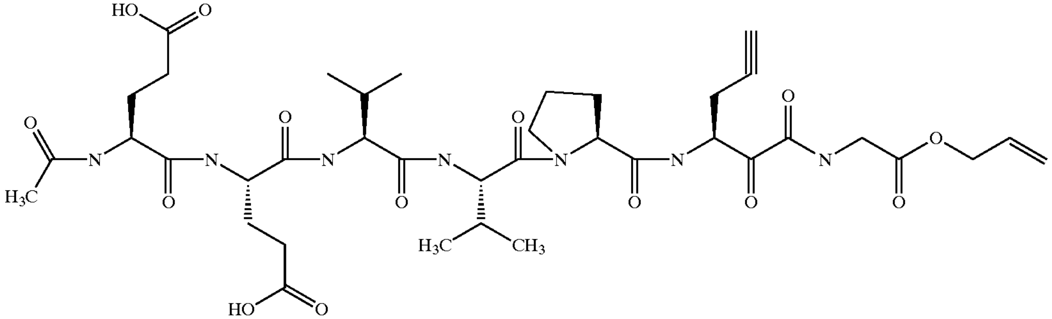 | Ac-EEVVP-G(propynyl)-(CO)-G-Oallyl (SEQ ID NO: 68) | b |

TABLE 3-continued

| STRUCTURE | NAME | Ki* Range |
|---|---|---|
| 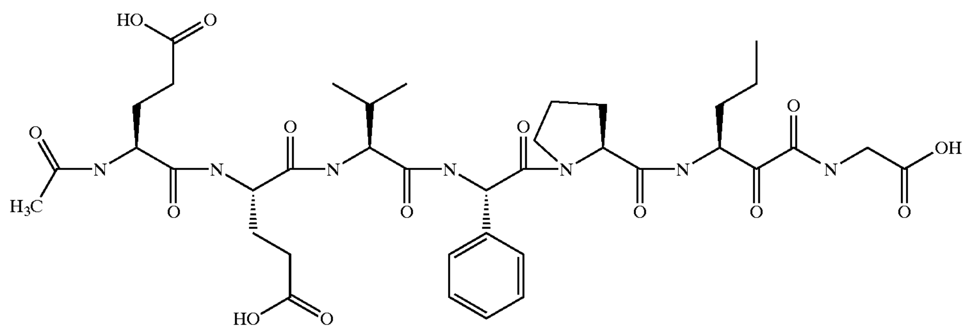 | Ac-EEV-G(Ph)-P-nV-(CO)-G-OH (SEQ ID NO: 131) | b |
| 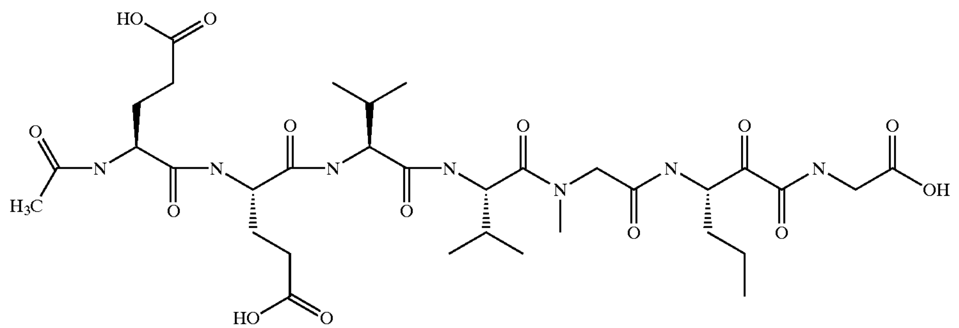 | Ac-EEVV-Sar-nV-(CO)-G-OH (SEQ ID NO: 10) | b |
| | Ac-EEVV-Aze-nV-(CO)-G-OH (S TABLE 3-continued

| STRUCTURE | NAME | Ki* Range |
|---|---|---|
| 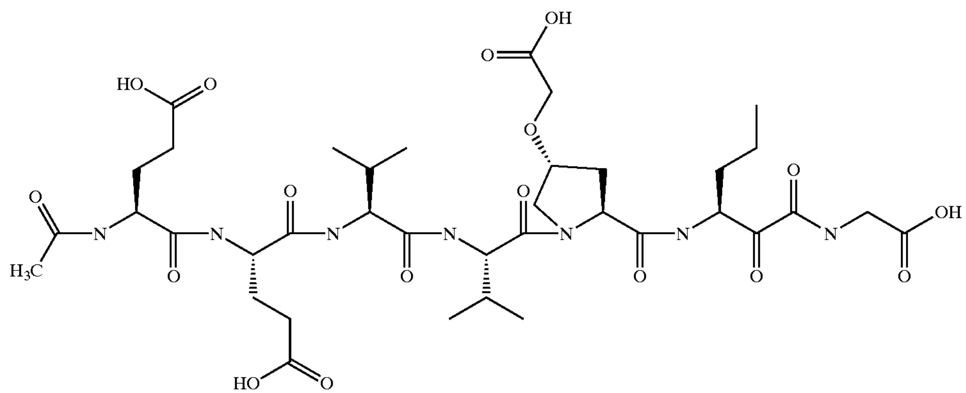 | Ac-EEVV-P(4t-O-2AcOH)-nV-(CO)-G-OH (SEQ ID NO: 132) | a |
| | Ac-EEV-G(Chx)-P-nV-(CO)-G-OH (SEQ ID N TABLE 3-continued

| STRUCTURE | NAME | Ki* Range |
|---|---|---|
| 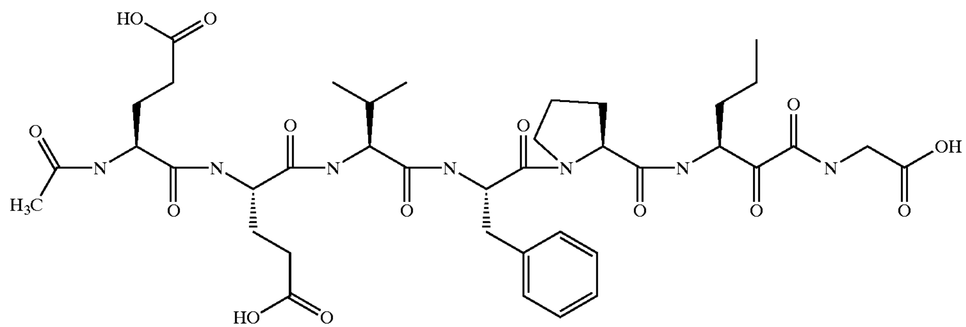 | Ac-EEVFP-nV-(CO)-G-OH (SEQ ID NO: 13) | b |
| 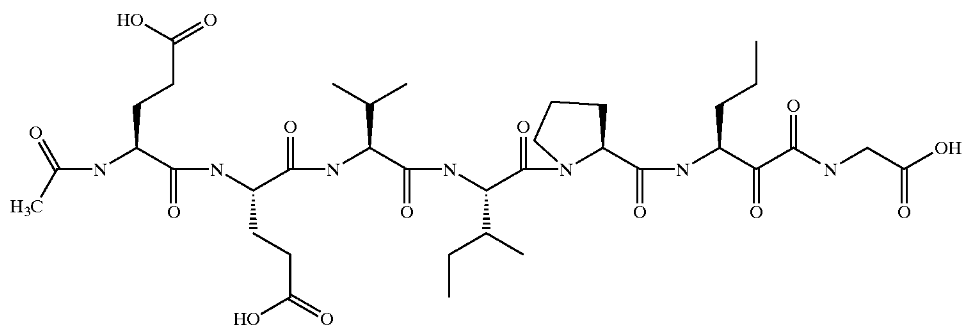 | Ac-EEVIP-nV-(CO)-G-OH (SEQ ID NO: 14) | a |
| 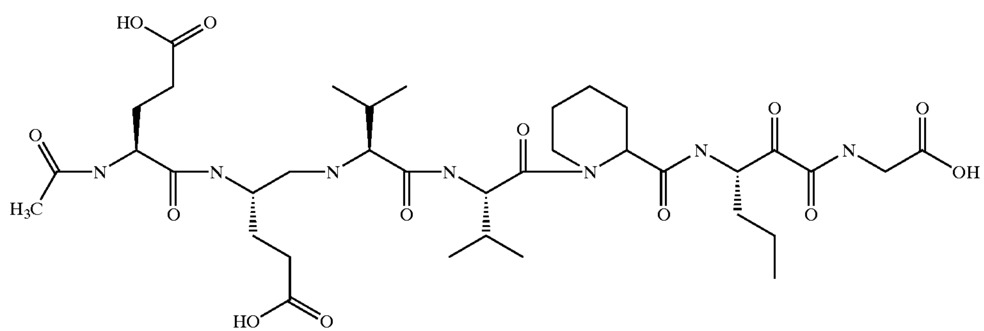 | Ac-EEVV-dlPip-nV-(CO)-G-OH (SEQ ID NO: 15) | a |

TABLE 3-continued

| STRUCTURE | NAME | Ki* Range |
|---|---|---|
| 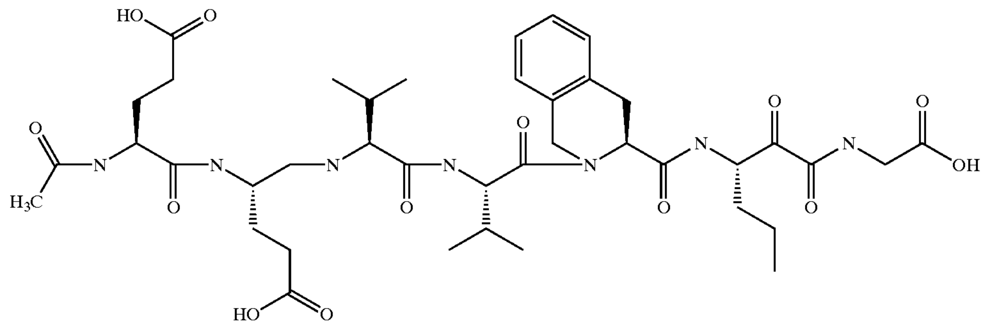 | Ac-EEVV-Tiq-nV-(CO)-G-OH (SEQ ID NO: 16) | a |
| 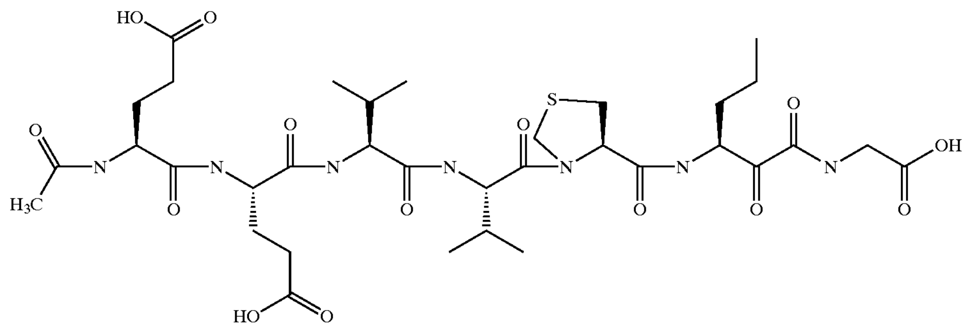 | Ac-EEVV-thioP-nV-(CO)-G-OH (SEQ ID NO: 133) | a |
| 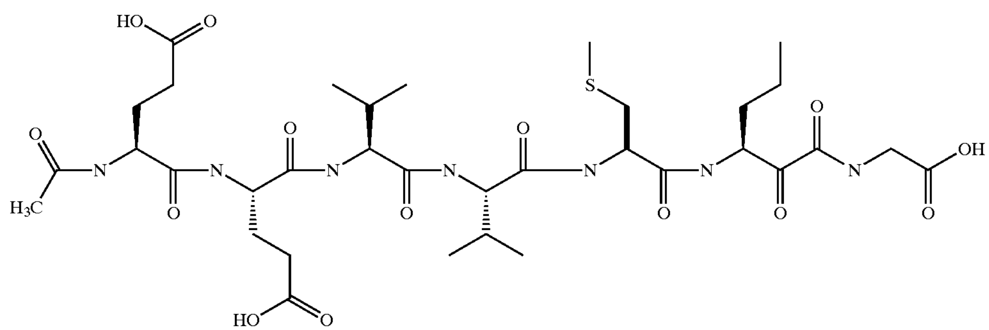 | Ac-EEVV-C(Me)-nV-(CO)-G-OH (SEQ ID NO: 17) | a |

TABLE 3-continued

| STRUCTURE | NAME | Ki* Range |
|---|---|---|
| 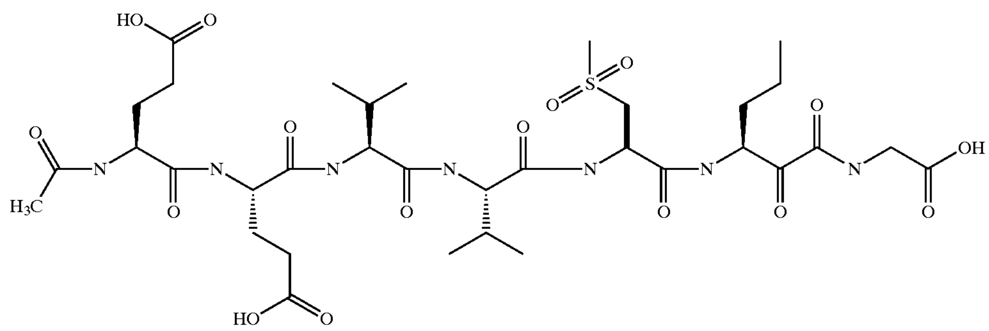 | Ac-EEVV-C(O2,Me)-nV-(CO)-G-OH (SEQ ID NO: 18) | a |
| 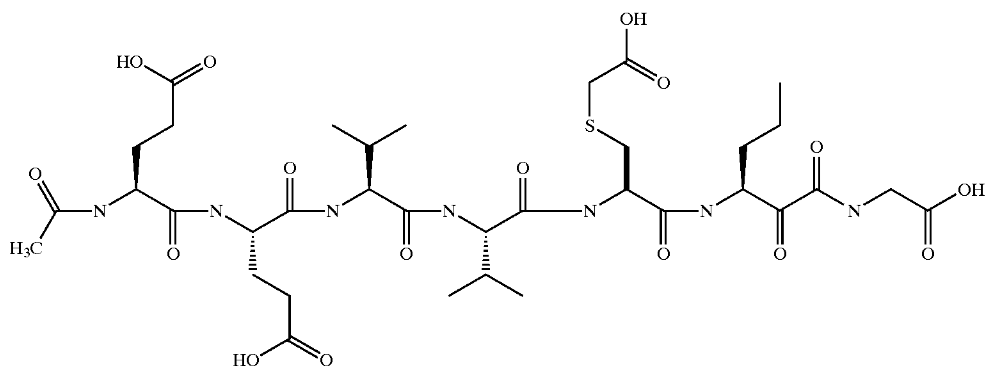 | Ac-EEVV-C(2-AcOH)-nV-(CO)-G-OH (SEQ ID NO: 19) | a |
| 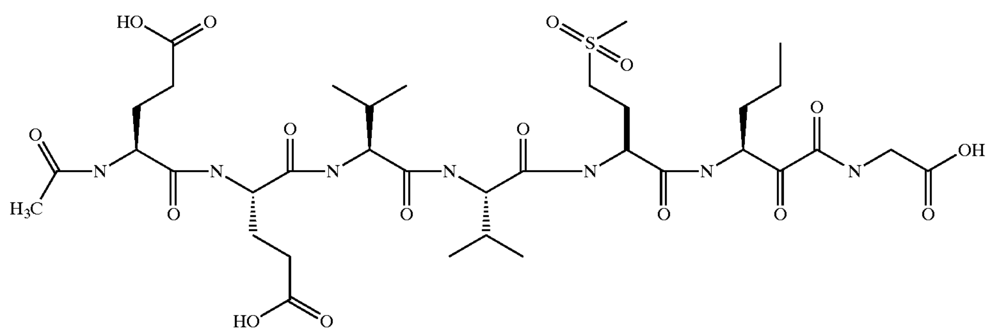 | Ac-EEVV-M(O2)-nV-(CO)-G-OH (SEQ ID NO: 20) | b |

TABLE 3-continued

| STRUCTURE | NAME | Ki* Range |
|---|---|---|
| 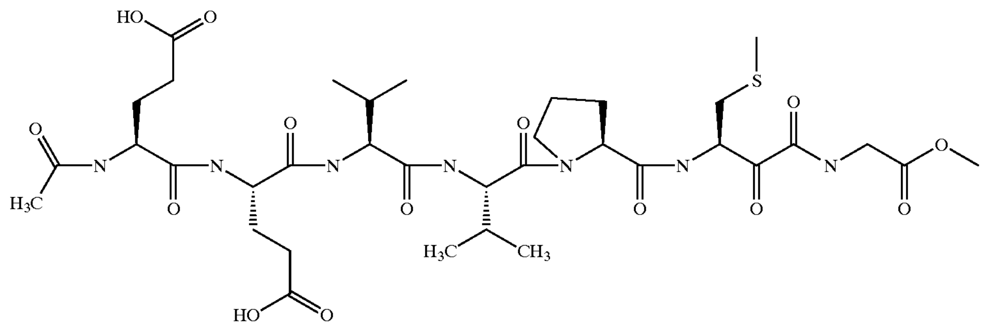 | Ac-EEVVP-C(Me)-(CO)-G-OMe (SEQ ID NO: 74) | c |
| | Ac-EEVV-P(4l-MeNHCO2Ph)-nV-(CO)-G-OH (SEQ ID NO: 97) | a |

TABLE 3-continued

| STRUCTURE | NAME | Ki* Range |
|---|---|---|
| 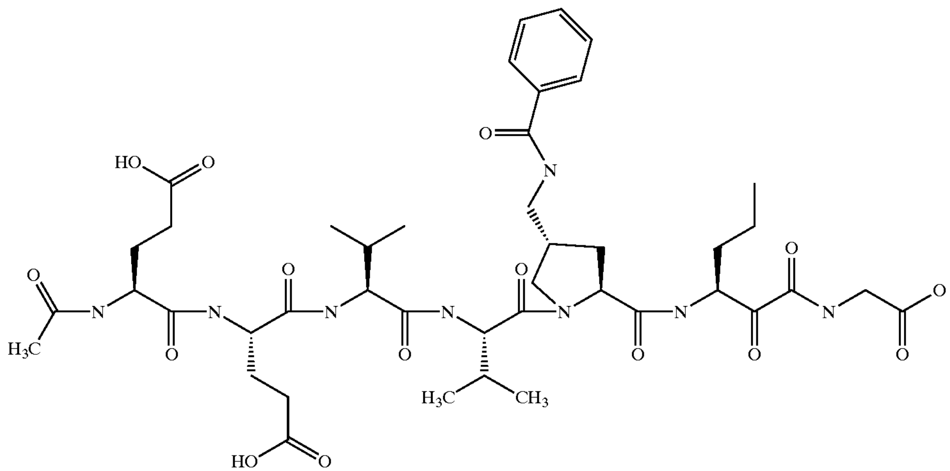 | Ac-EEVV-P(4t-MeNHCOPh)-nV-(CO)-G-OH (SEQ ID NO: 98) | a |
| 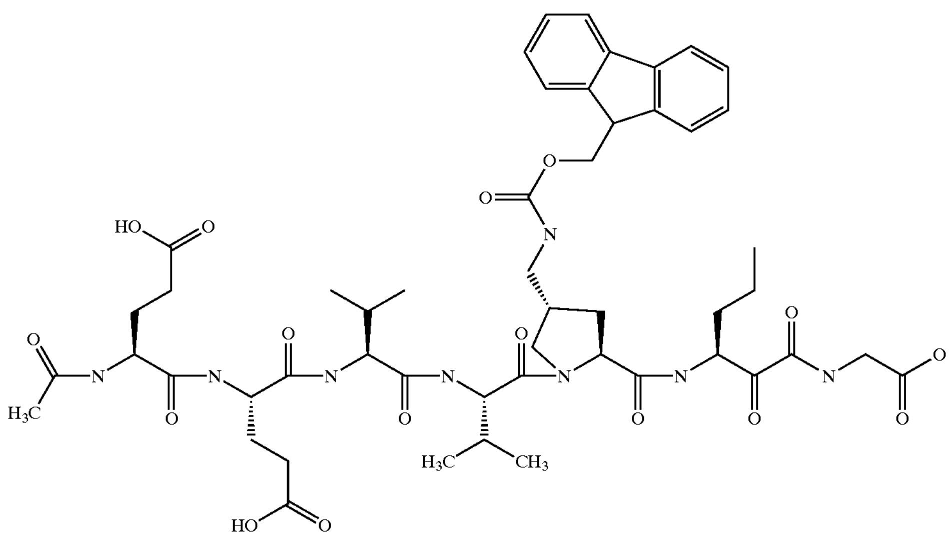 | Ac-EEVV-P(4t-MeNH-Fmoc)-nV-(CO)-G-OH (SEQ ID NO: 99) | a |

TABLE 3-continued

| STRUCTURE | NAME | Ki* Range |
|---|---|---|
| 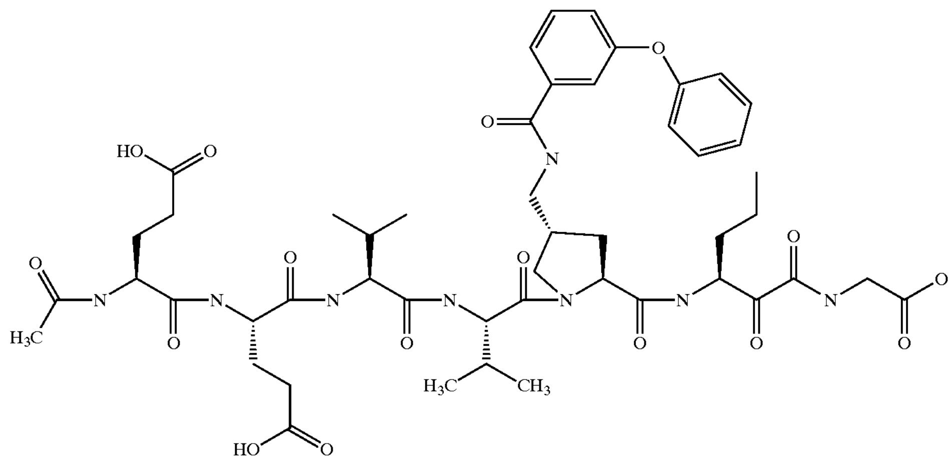 | Ac-EEVV-P(4t-MeNHBzl(3-OPh))-nV-(CO)-G-OH (SEQ ID NO: 92) | a |
| 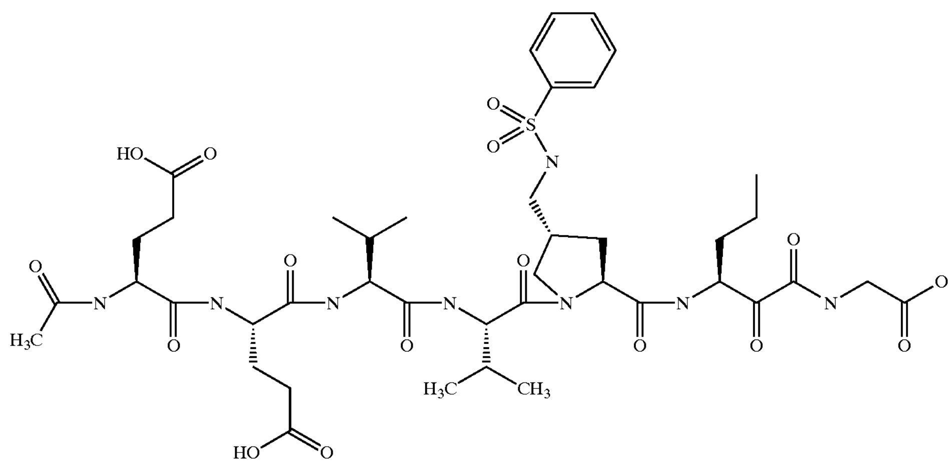 | Ac-EEVV-P(4t-MeNHSO2Ph)-nV-(CO)-G-OH (SEQ ID NO: 100) | a |

TABLE 3-continued
| STRUCTURE | NAME | Ki* Range |
|---|---|---|
| 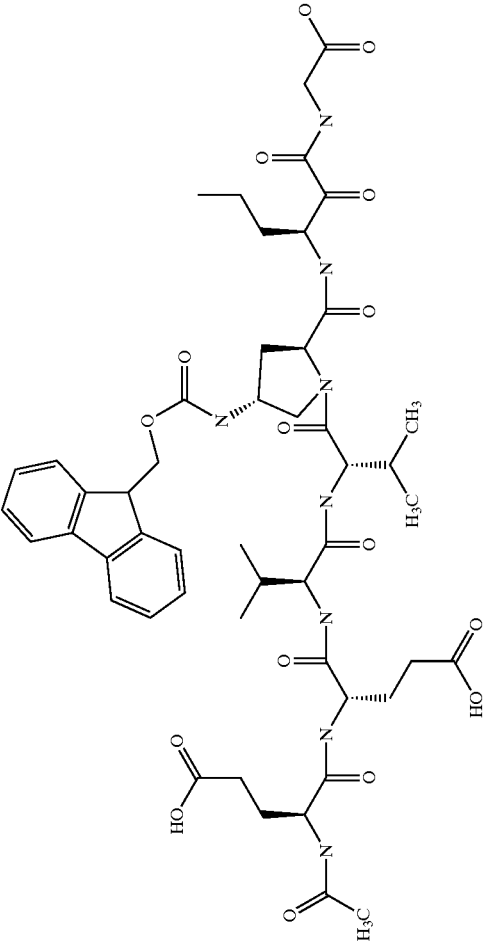 | Ac-EEVV-P(4t-NH-Fmoc)-nV-(CO)-G-OH (SEQ ID NO: 102) | a |
| 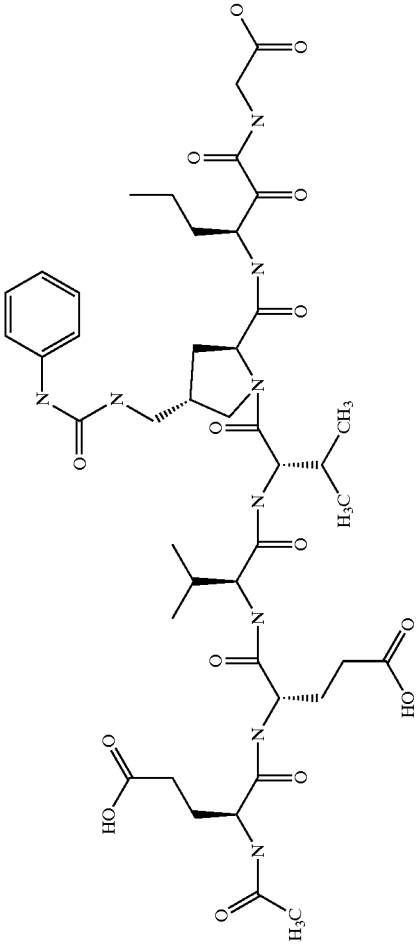 | Ac-EEVV-P(4t-MeUreaPh)-nV-(CO)-G-OH (SEQ ID NO: 101) | a |

TABLE 3-continued

| STRUCTURE | NAME | Ki* Range |
|---|---|---|
| 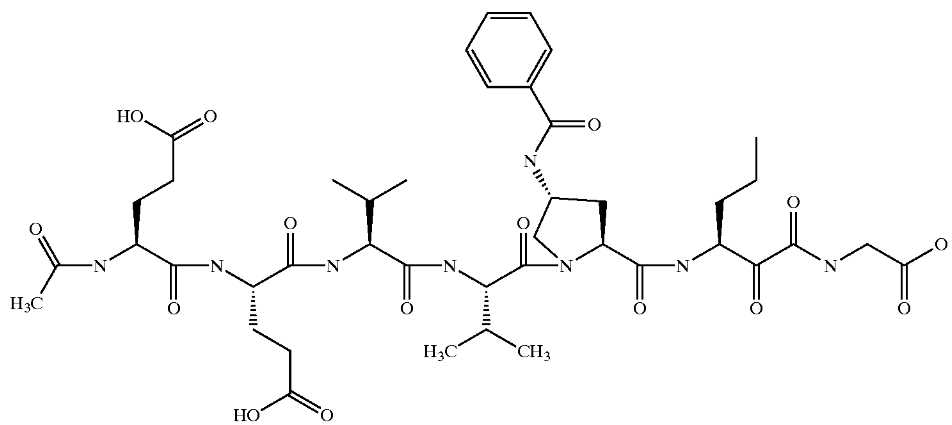 | Ac-EEVV-P(4t-NHBzl)-nV-(CO)-G-OH (SEQ ID NO: 103) | a |
| 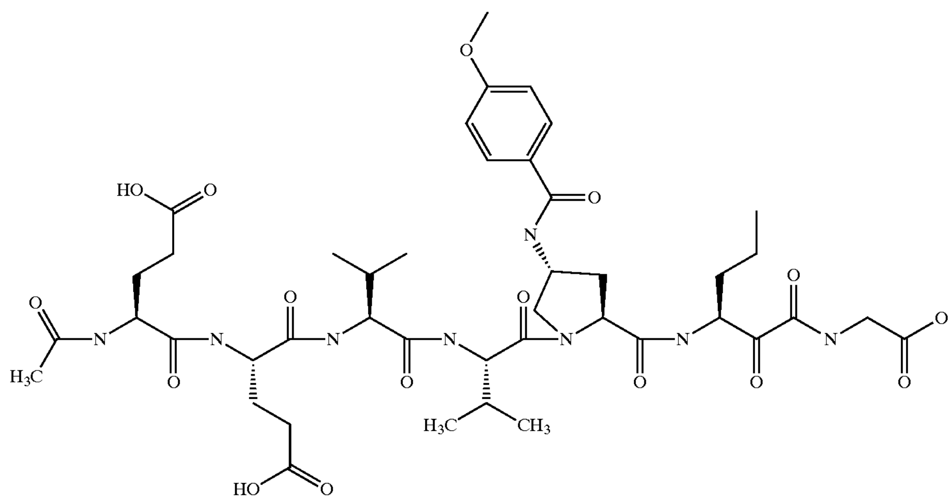 | Ac-EEVV-P(4t-NHBzl(4-OMe))-nV-(CO)-G-OH (SEQ ID NO: 109) | a |

TABLE 3-continued

| STRUCTURE | NAME | Ki* Range |
|---|---|---|
| 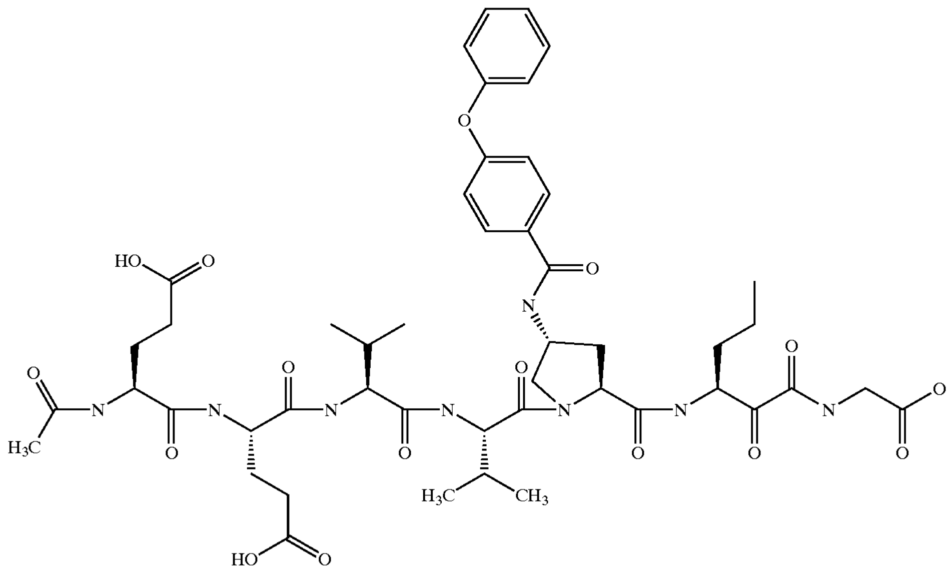 | Ac-EEVV-P(4t-NHBzl(4-OPh))-nV-(CO)-G-OH (SEQ ID NO: 110) | a |

TABLE 3-continued

| STRUCTURE | NAME | Ki* Range |
|---|---|---|
| 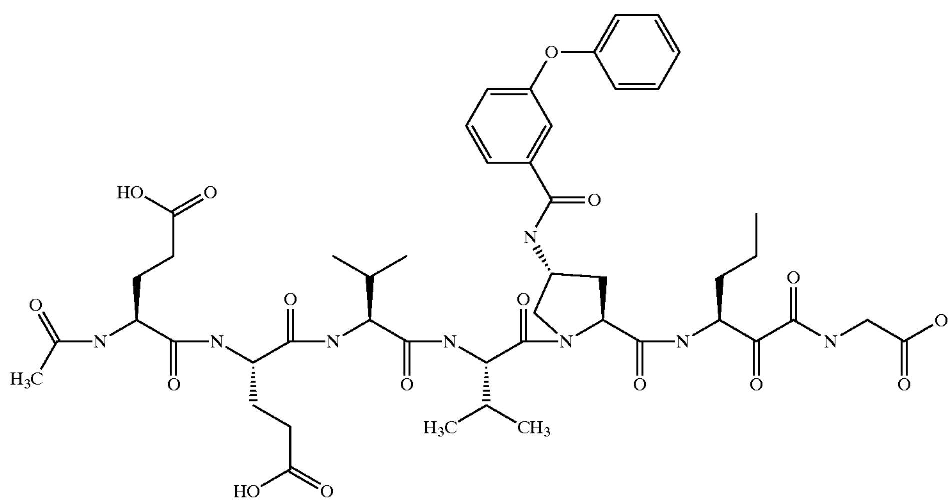 | Ac-EEVV-P(4t-NHBzl(3-OPh))-nV-(CO)-G-OH (SEQ ID NO: 111) | a |
| 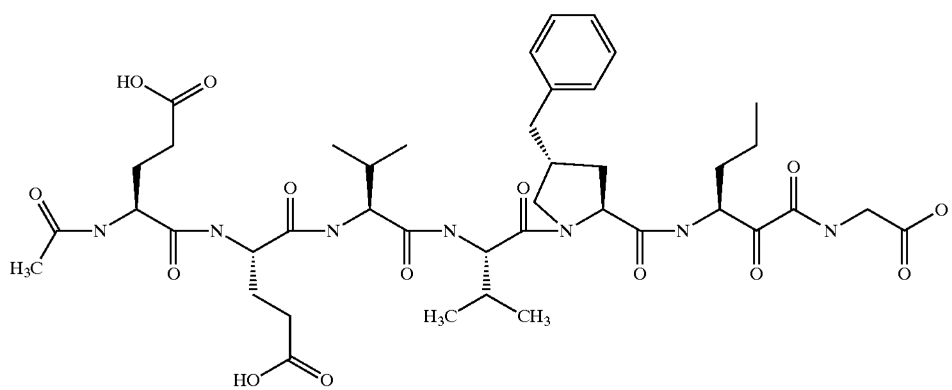 | Ac-EEVV-P(4t-Bn)-nV-(CO)-G-OH (SEQ ID NO: 21) | a |

TABLE 3-continued

| STRUCTURE | NAME | Ki* Range |
|---|---|---|
| 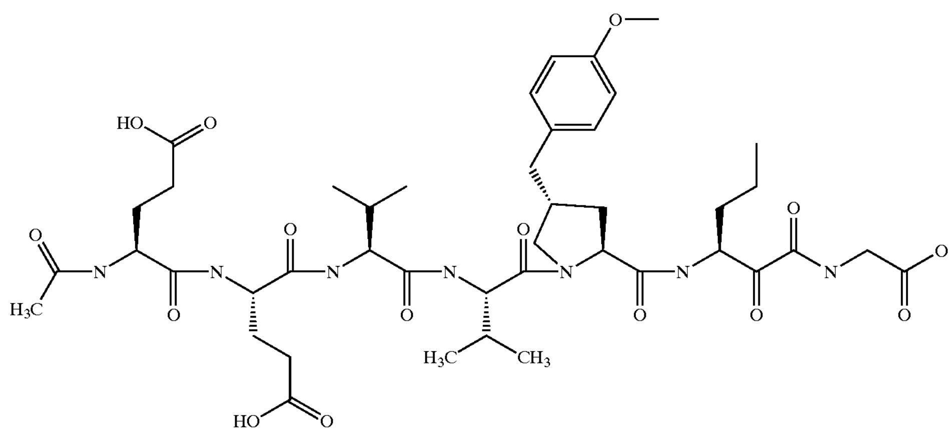 | Ac-EEVV-P(4t-Bn(4-OMe))-nV-(CO)-G-OH (SEQ ID NO: 22) | a |
| 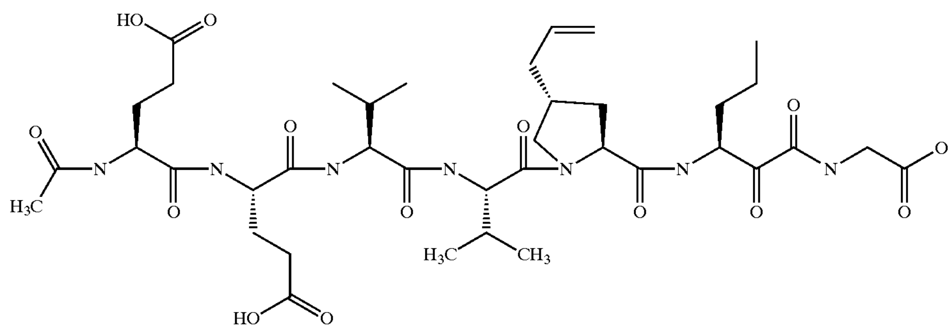 | Ac-EEVV-P(4t-allyl)-nV-(CO)-G-OH (SEQ ID NO: 23) | a |

TABLE 3-continued

| STRUCTURE | NAME | Ki* Range |
|---|---|---|
| 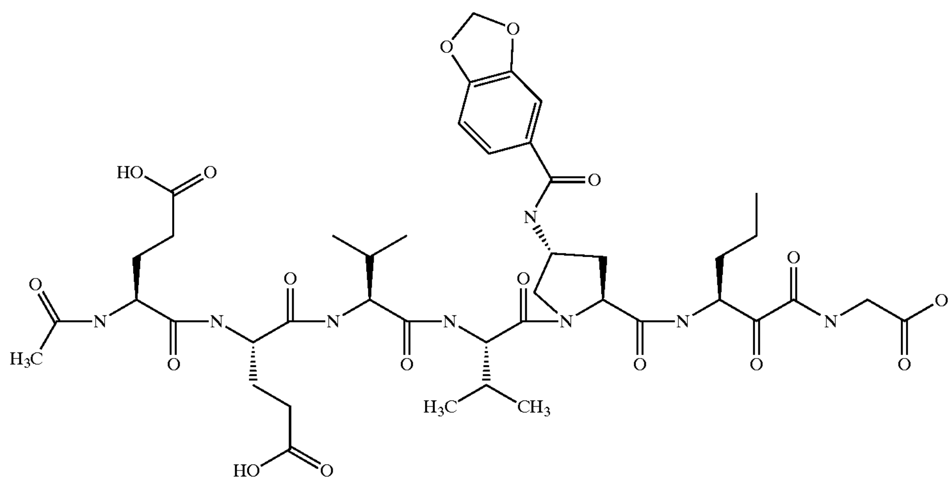 | Ac-EEVV-P(4t-NHBzl)3,4-OMeO))-nV-(CO)-G-OH (SEQ ID NO: 112) | a |
| 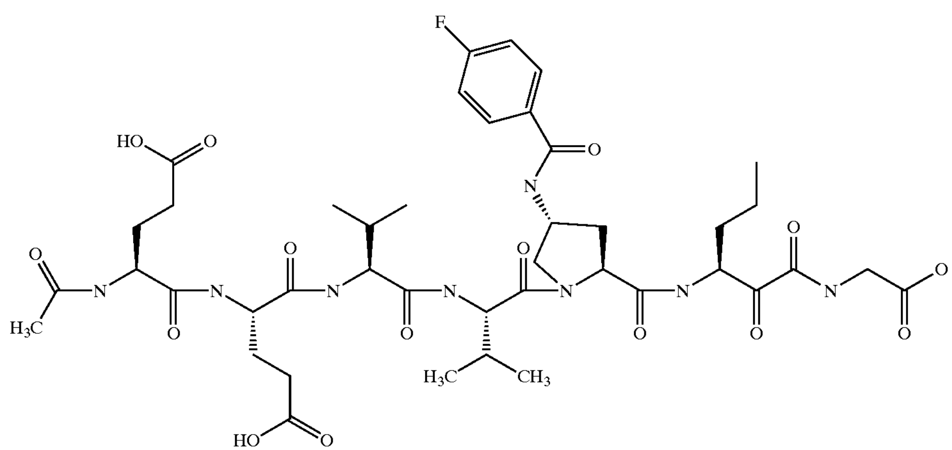 | Ac-EEVV-P(4t-NHBzl(4F))-nV-(CO)-G-OH (SEQ ID NO: 113) | a |

TABLE 3-continued

| STRUCTURE | NAME | Ki* Range |
|---|---|---|
| 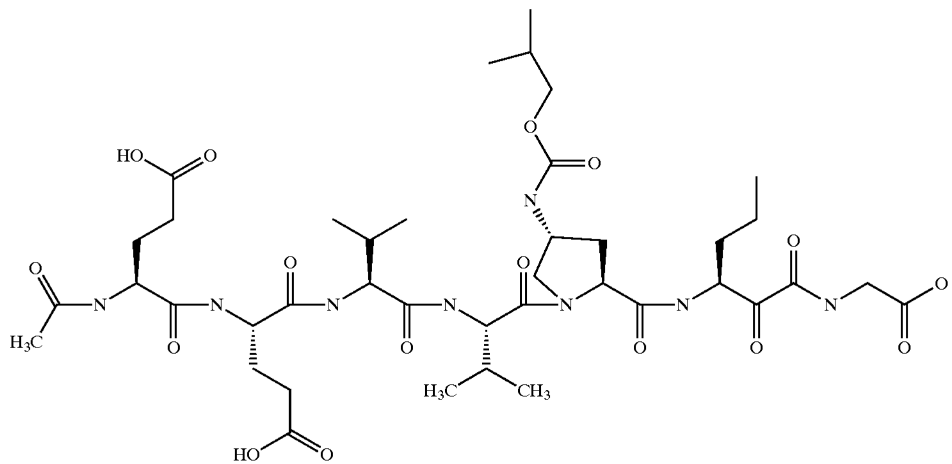 | Ac-EEVV-P(4t-NHiBoc)-nV-(CO)-G-OH (SEQ ID NO: 114) | a |
| 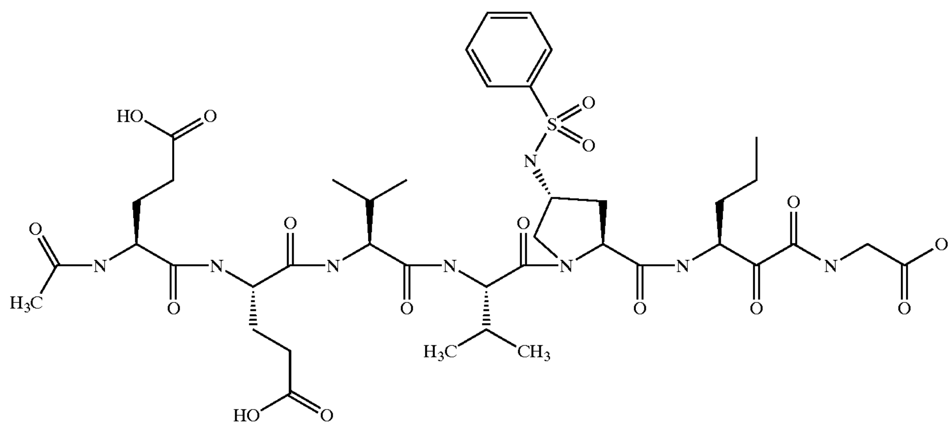 | Ac-EEVV-P(4t-NHSO2Ph)-nV-(CO)-G-OH (SEQ ID NO: 115) | a |

TABLE 3-continued

| STRUCTURE | NAME | Ki* Range |
|---|---|---|
| 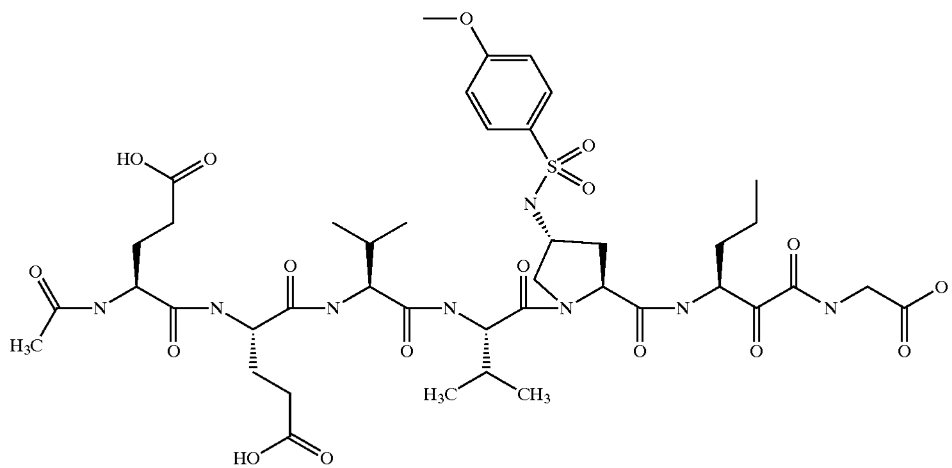 | Ac-EEVV-P(4t-NHSO2Ph(4-OMe))-nV-(CO)-G-OH (SEQ ID NO: 116) | a |
| 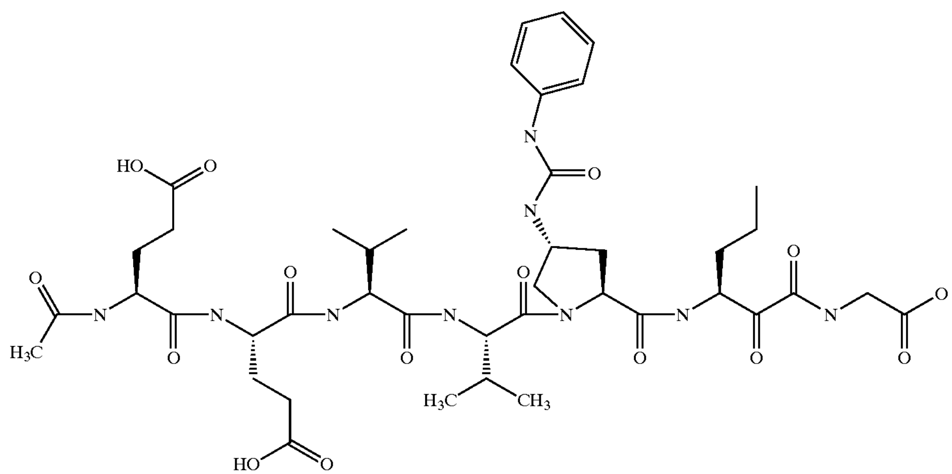 | Ac-EEVV-P(4t-UreaPh)-nV-(CO)-G-OH (SEQ ID NO: 117) | a |

TABLE 3-continued

| STRUCTURE | NAME | Ki* Range |
|---|---|---|
| 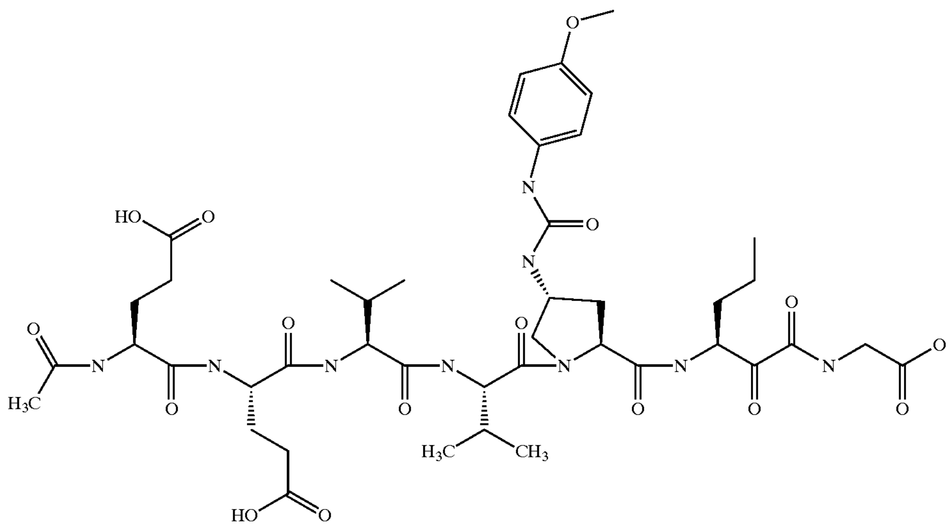 | Ac-EEVV-P(4t-UreaPh(4-OMe))-nV-(CO)-G-OH (SEQ ID NO: 118) | a |
| 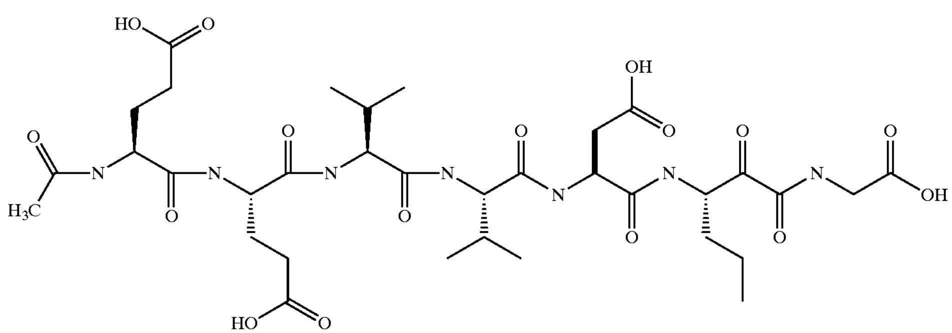 | Ac-EEVVD-nV-(CO)-G-OH (SEQ ID NO: 24) | b |

TABLE 3-continued

| STRUCTURE | NAME | Ki* Range |
|---|---|---|
| 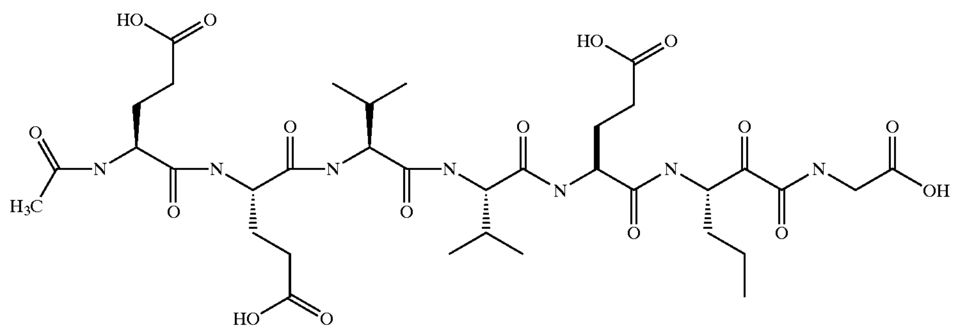 | Ac-EEVVE-nV-(CO)-G-OH (SEQ ID NO: 25) | a |
| 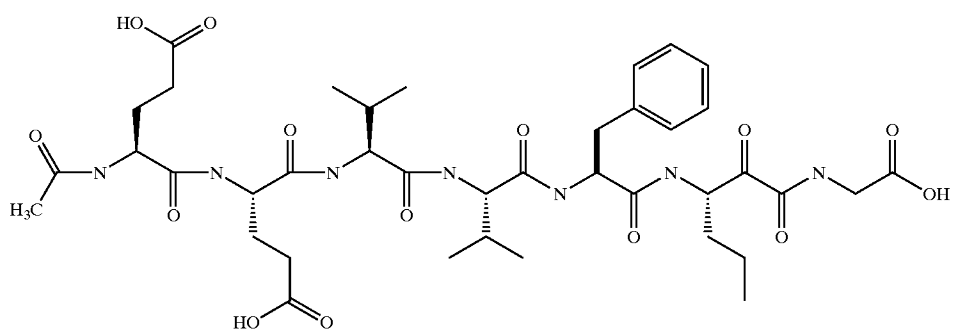 | Ac-EEVVF-nV-(CO)-G-OH (SEQ ID NO: 26) | a |
| 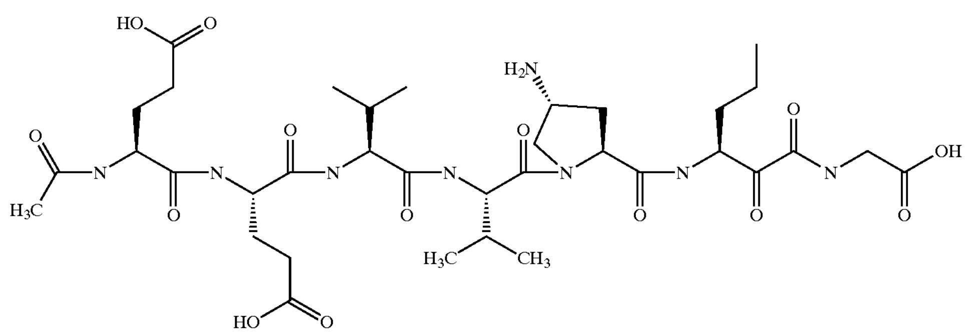 | Ac-EEVV-P(4t-NH2)-nV-(CO)-G-OH (SEQ ID NO: 134) | b |

TABLE 3-continued

| STRUCTURE | NAME | Ki* Range |
|---|---|---|
| 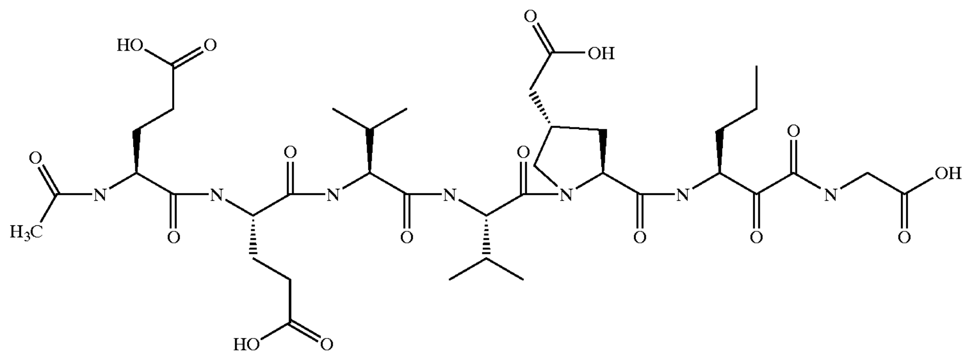 | Ac-EEVV-P(4t-AcOH)-nV-(CO)-G-OH (SEQ ID NO: 27) | a |
| 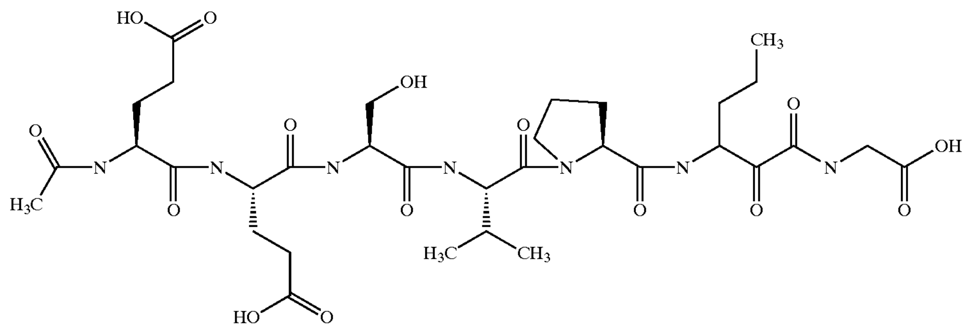 | Ac-EESVP-nV-(CO)-G-OH (SEQ ID NO: 28) | b |
| 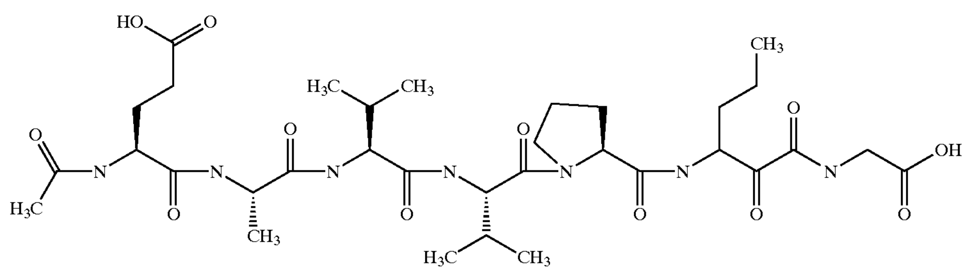 | Ac-EAVVP-nV-(CO)-G-OH (SEQ ID NO: 29) | a |

TABLE 3-continued

| STRUCTURE | NAME | Ki* Range |
|---|---|---|
| 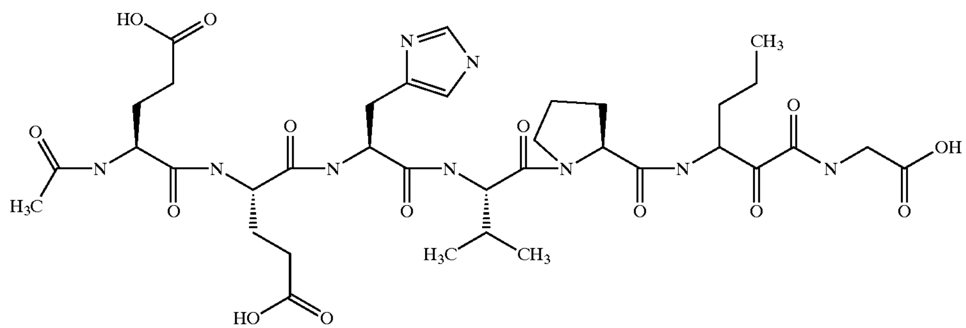 | Ac-EEHVP-nV-(CO)-G-OH (SEQ ID NO: 30) | b |
| 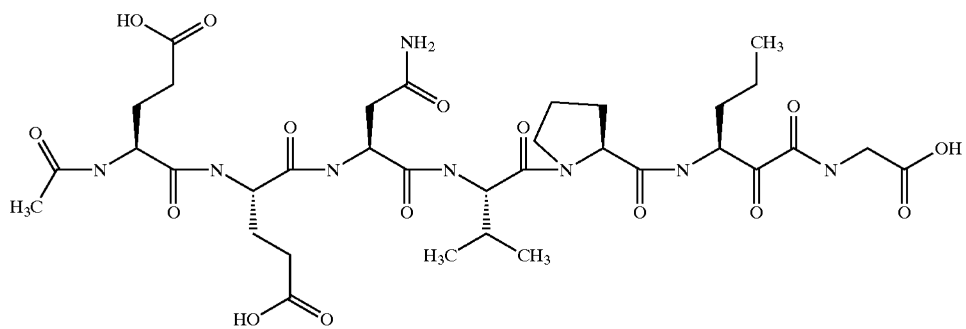 | Ac-EENVP-nV-(CO)-G-OH (SEQ ID NO: 31) | b |
| 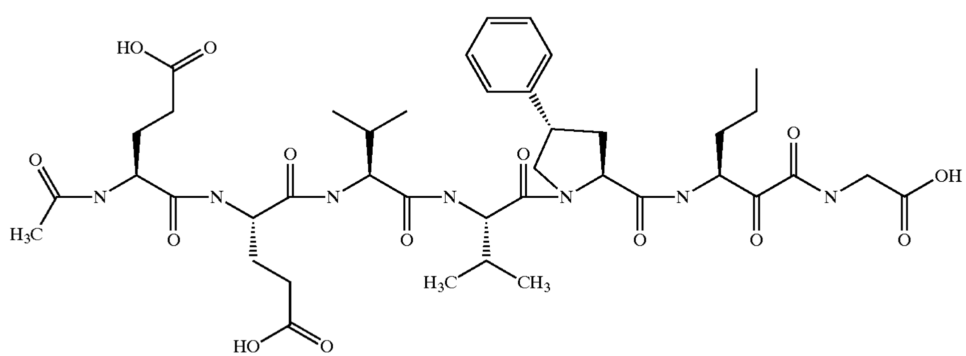 | Ac-EEVV-P(4t-Ph)-nV-(CO)-G-OH (SEQ ID NO: 32) | a |

TABLE 3-continued

| STRUCTURE | NAME | Ki* Range |
|---|---|---|
| 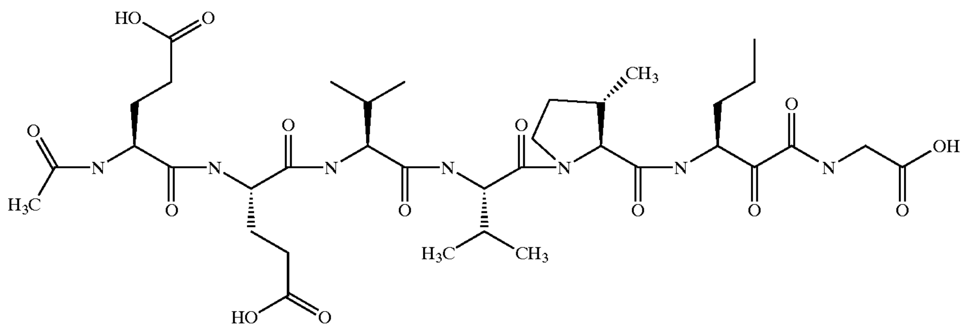 | Ac-EEVV-P(3t-Me)-nV-(CO)-G-OH (SEQ ID NO: 33) | a |
| 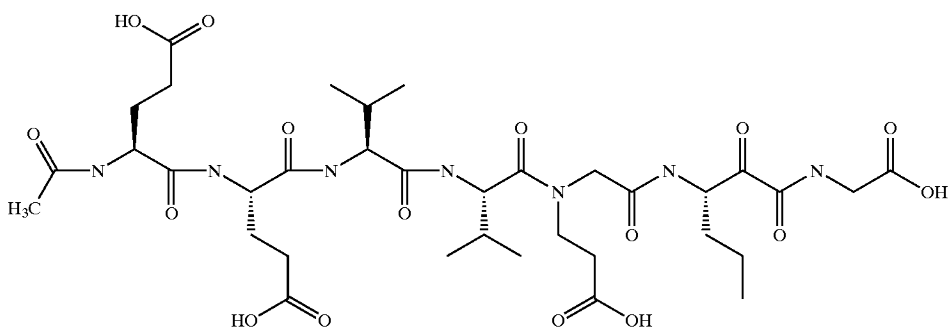 | Ac-EEVV-G(N-Et(CO2H))-nV-(CO)-G-OH (SEQ ID NO: 78) | a |

TABLE 3-continued
| STRUCTURE | NAME | Ki* Range |
|---|---|---|
| 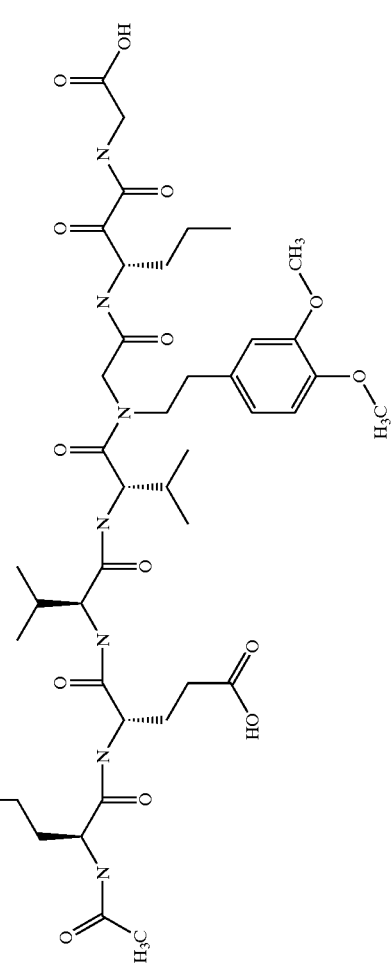 | Ac-EEVV-G(N-EtPh(3,4diOMe))-nV-(CO)-G-OH (SEQ ID NO: 79) | b |
| 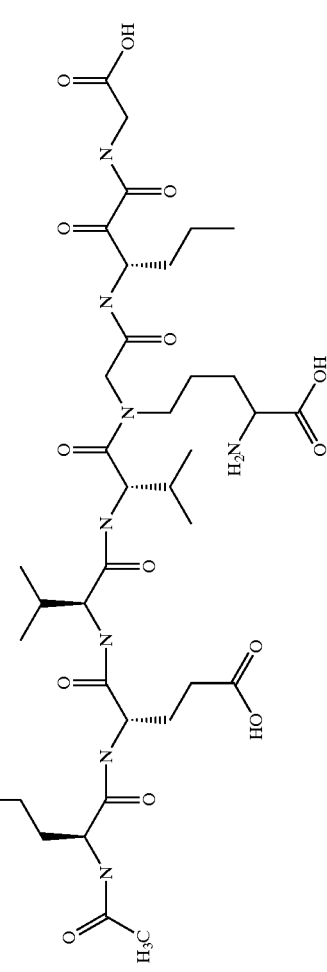 | Ac-EEVV-G(N-Bu(4NH2,4-CO2H)-nV-(CO)-G-OH (SEQ ID NO: 75) | a |

TABLE 3-continued

| STRUCTURE | NAME | Ki* Range |
|---|---|---|
| 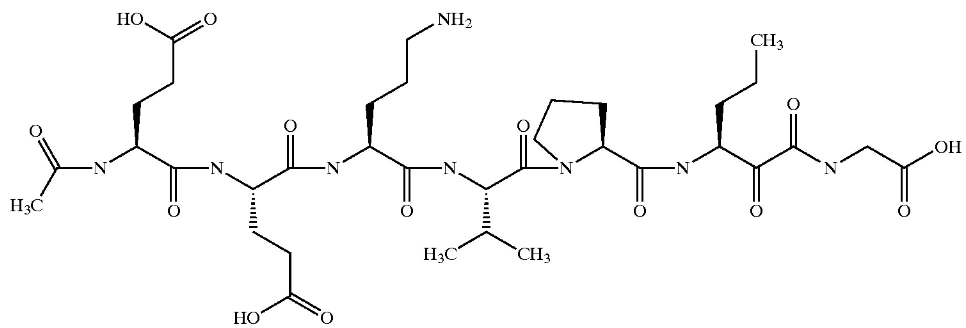 | Ac-EE-Orn-VP-nV-(CO)-G-OH (SEQ ID NO: 34) | b |
| 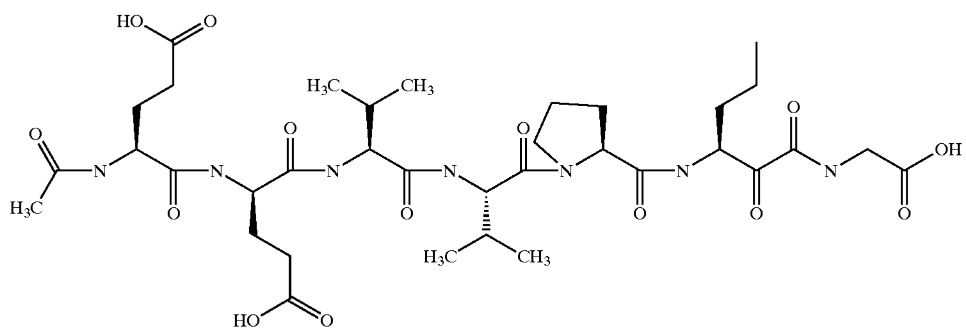 | Ac-EdEVVP-nV-(CO)-G-OH (SEQ ID NO: 35) | a |
| 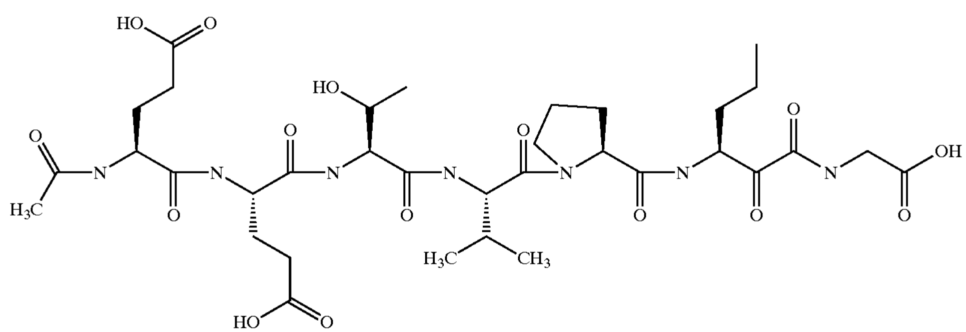 | Ac-EE-(s,s)alloT-VP-nV-(CO)-G-OH (SEQ ID NO: 36) | a |

TABLE 3-continued

| STRUCTURE | NAME | Ki* Range |
|---|---|---|
| 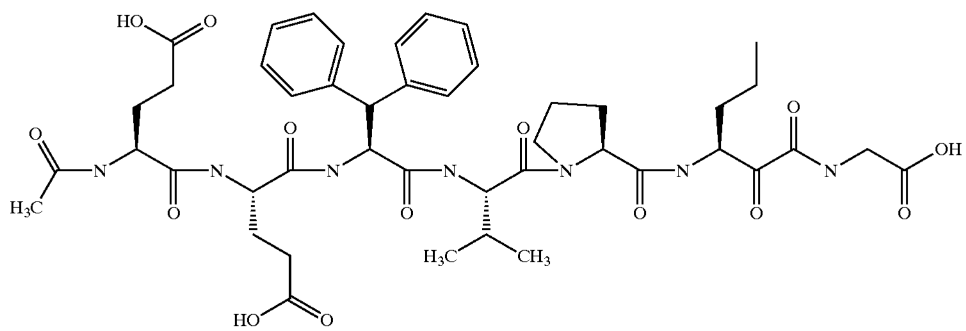 | Ac-EE-Dif-VP-nV-(CO)-G-OH (SEQ ID NO: 37) | a |
| 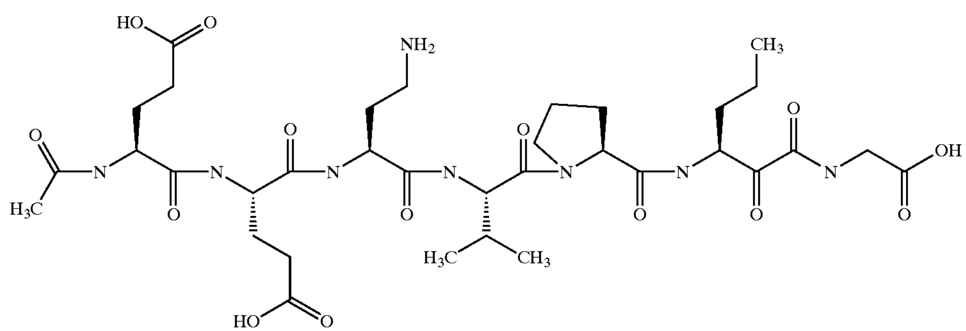 | Ac-EE-daba-VP-nV-(CO)-G-OH (SEQ ID NO: 38) | b |
| 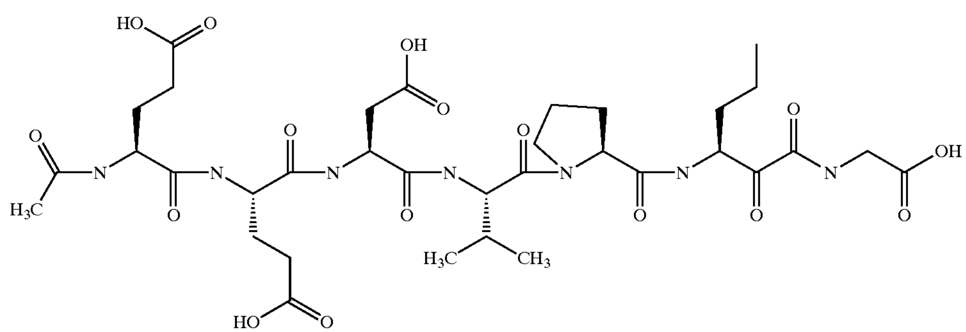 | Ac-EEDVP-nV-(CO)-G-OH (SEQ ID NO: 39) | c |

TABLE 3-continued

| STRUCTURE | NAME | Ki* Range |
|---|---|---|
| 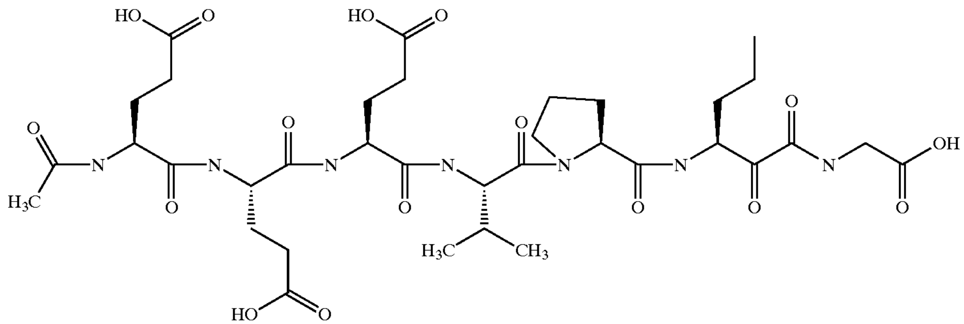 | Ac-EEEVP-nV-(CO)-G-OH (SEQ ID NO: 40) | b |
| 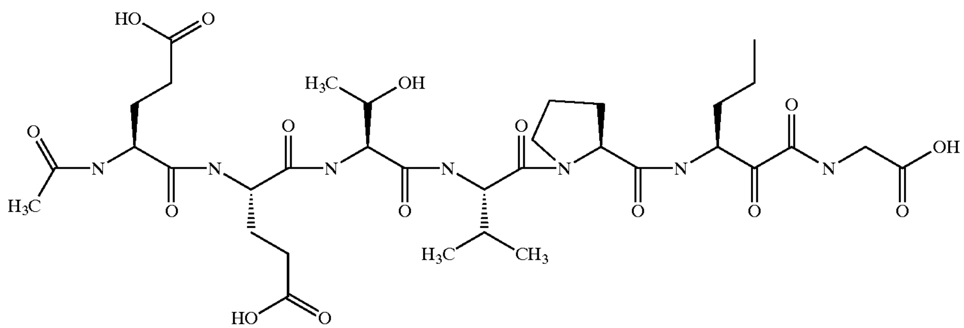 | Ac-EETVP-nV-(CO)-G-OH (SEQ ID NO: 41) | b |
| 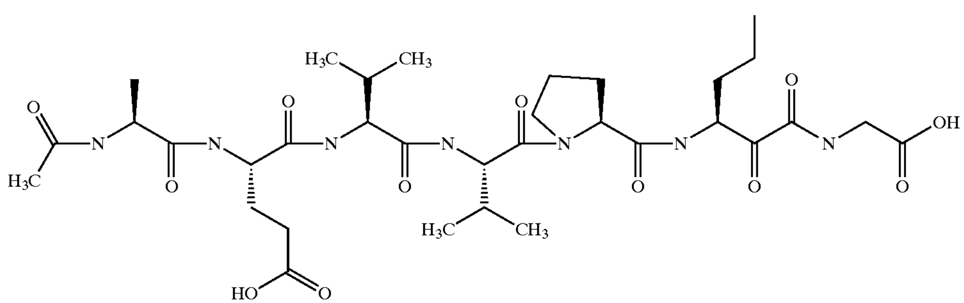 | Ac-AEVVP-nV-(CO)-G-OH (SEQ ID NO: 42) | b |

TABLE 3-continued

| STRUCTURE | NAME | Ki* Range |
|---|---|---|
| 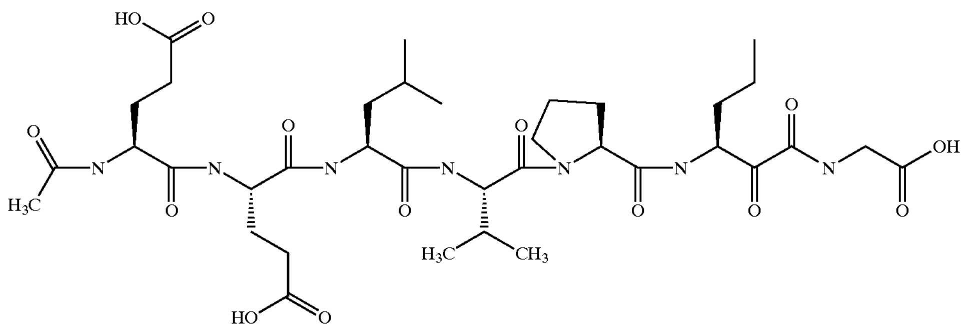 | Ac-EELVP-nV-(CO)-G-OH (SEQ ID NO: 43) | a |
| 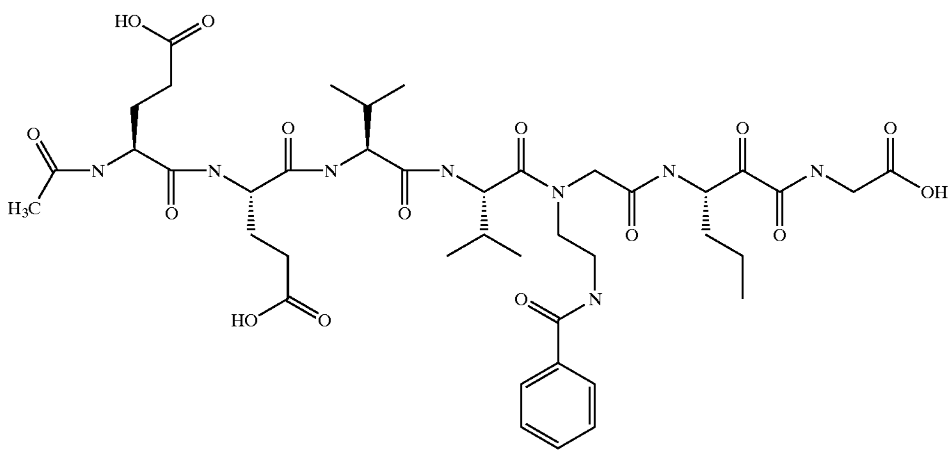 | Ac-EEVV-G(N-Et(NHBz))-nV-(CO)-G-OH (SEQ ID NO: 81) | b |

TABLE 3-continued

| STRUCTURE | NAME | Ki* Range |
|---|---|---|
| | Ac-EEVV-G(N-Et(NHBzl(3-OPh))-nV-(CO)-G-OH (SEQ ID NO: 85) | a |
| | Ac-EEVV-G(N-Prop(NHBz))-nV-(CO)-G-OH (SEQ ID NO:

TABLE 3-continued
| STRUCTURE | NAME | Ki* Range |
|---|---|---|
| 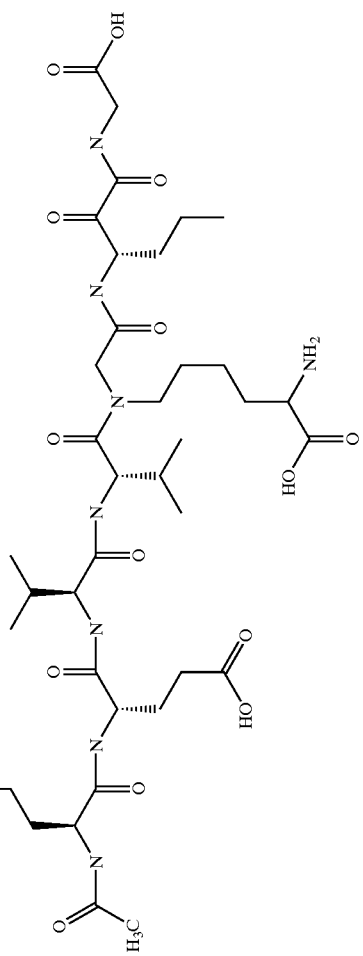 | Ac-EEVV-G(N-Pe(5-NH2,5-CO2H))-nV-(CO)-G-OH (SEQ ID NO: 80) | a |
| 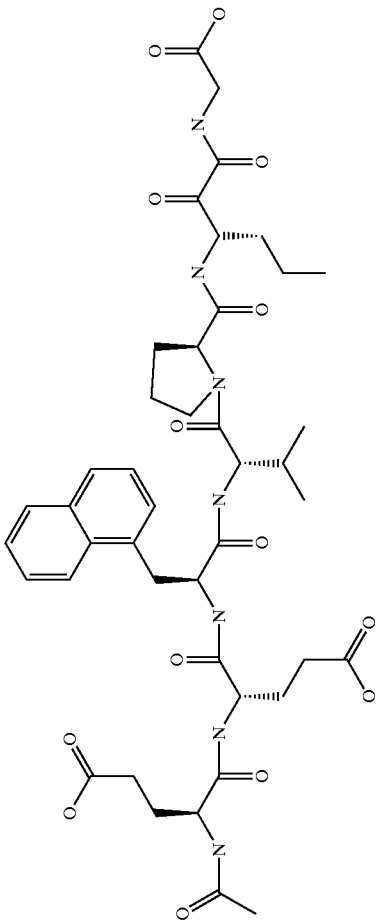 | Ac-EEA(1-Np)VP-nV-(CO)-G-OH (SEQ ID NO: 135) | b |

TABLE 3-continued

| STRUCTURE | NAME | Ki* Range |
|---|---|---|
| 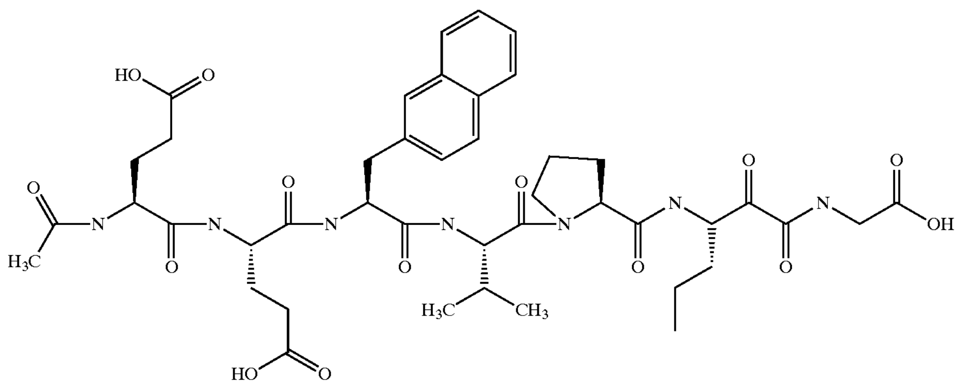 | Ac-EEA(2-Np)VP-nV-(CO)-G-OH (SEQ ID NO: 136) | b |
| 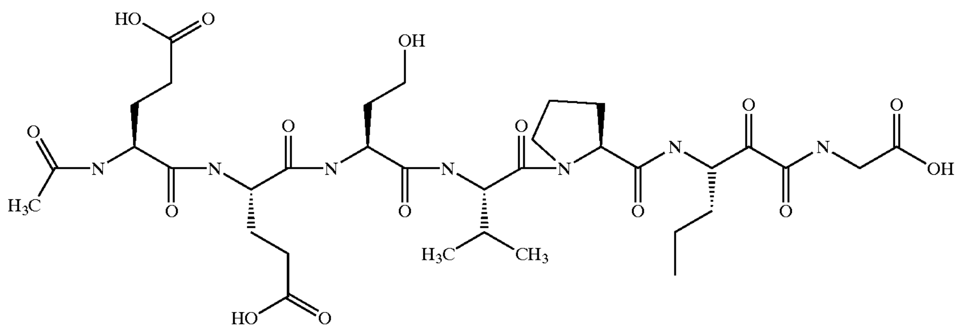 | Ac-EEhSVP-nV-(CO)-G-OH (SEQ ID NO: 28) | c |

TABLE 3-continued

| STRUCTURE | NAME | Ki* Range |
|---|---|---|
| 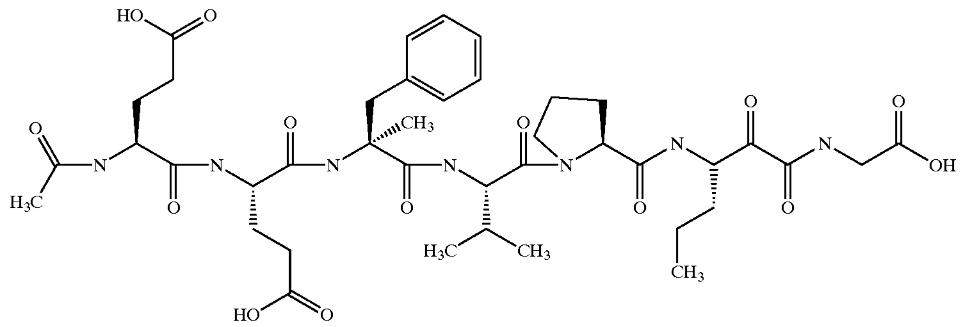 | Ac-EEF(alpha-Me)VP-nV-(CO)-G-OH (SEQ ID NO: 137) | c |
| 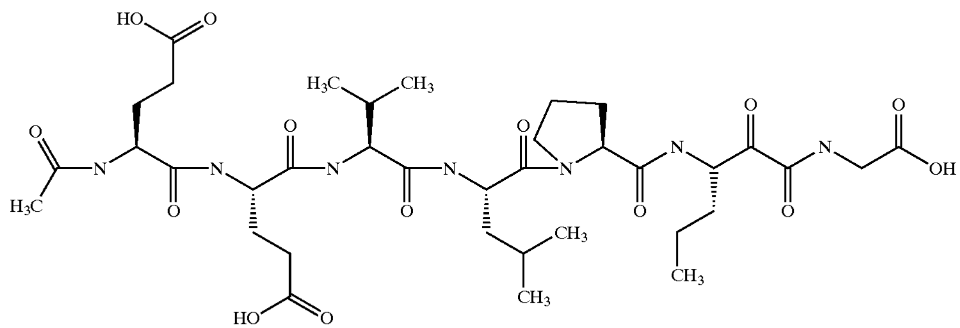 | Ac-EEVLP-nV-(CO)-G-OH (SEQ ID NO: 138) | b |
| 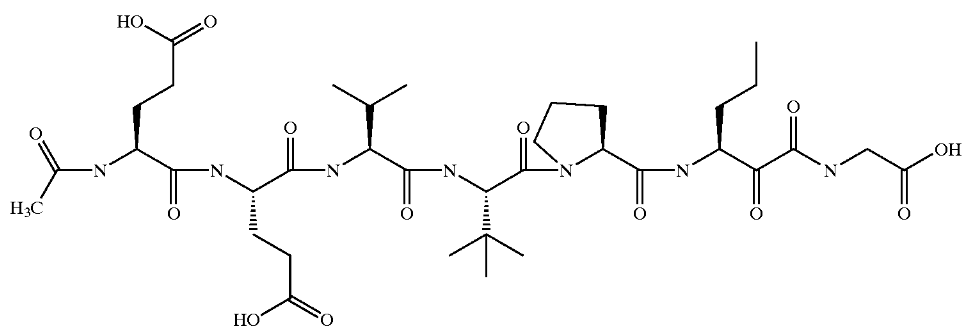 | Ac-EEVG(t-Bu)P-nV-(CO)-G-OH (SEQ ID NO: 139) | a |

TABLE 3-continued

| STRUCTURE | NAME | Ki* Range |
|---|---|---|
| 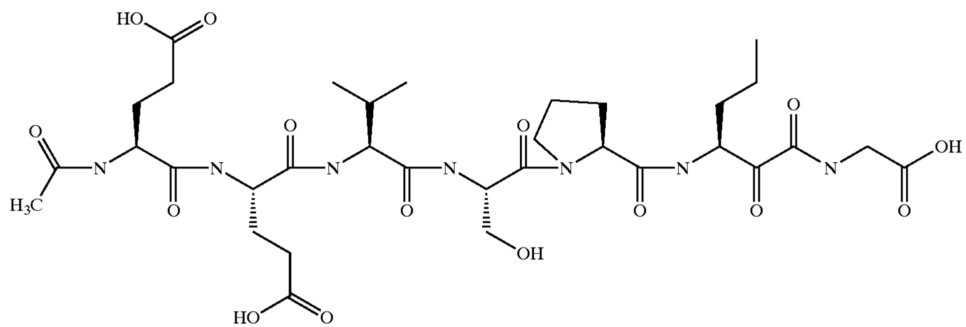 | Ac-EEVSP-nV-(CO)-G-OH (SEQ ID NO: 140) | c |
| 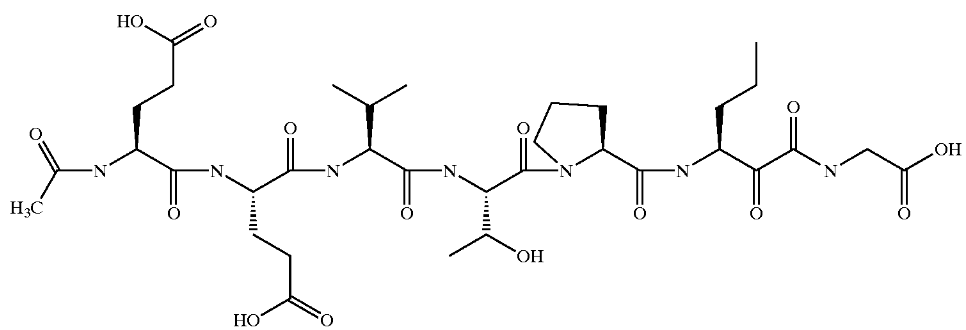 | Ac-EEVTP-nV-(CO)-G-OH (SEQ ID NO: 141) | c |
| 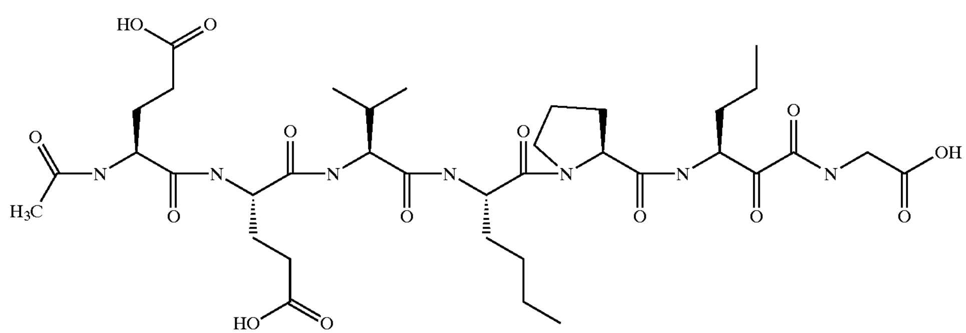 | Ac-EEV-nL-P-nV-(CO)-G-OH (SEQ ID NO: 142) | b |

TABLE 3-continued

| STRUCTURE | NAME | Ki* Range |
|---|---|---|
| 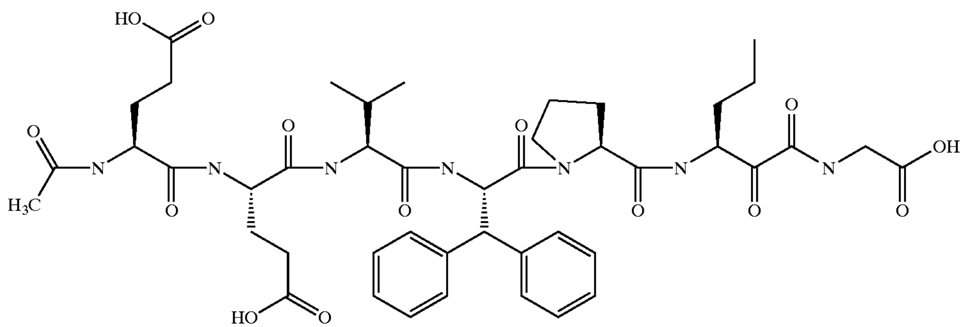 | Ac-EEVDifP-nV-(CO)-G-OH (SEQ ID NO: 143) | b |
| 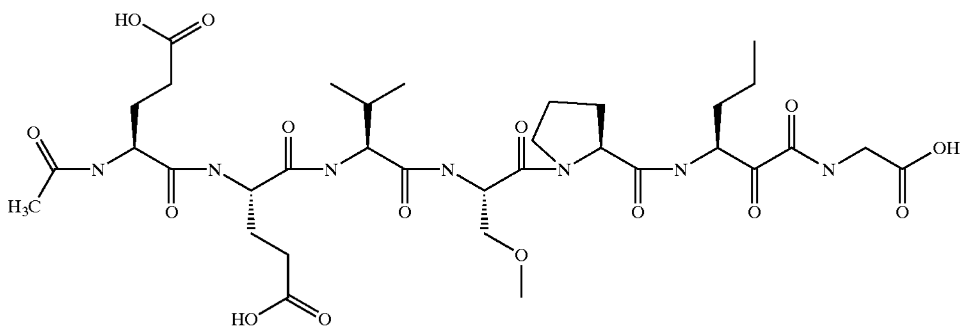 | Ac-EEVS(Me)P-nV-(CO)-G-OH (SEQ ID NO: 144) | c |
| 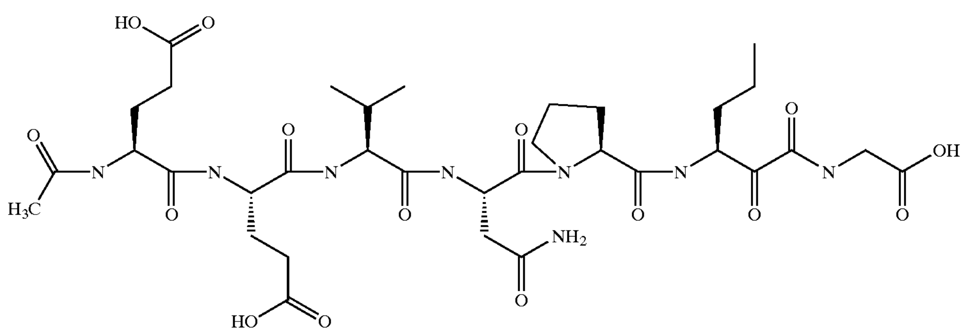 | Ac-EEVNP-nV-(CO)-G-OH (SEQ ID NO: 145) | c |

TABLE 3-continued

| STRUCTURE | NAME | Ki* Range |
|---|---|---|
| 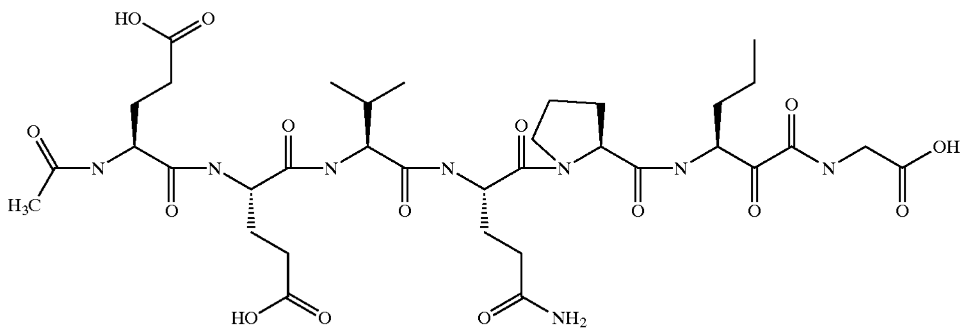 | Ac-EEVQP-nV-(CO)-G-OH (SEQ ID NO: 146) | c |
| 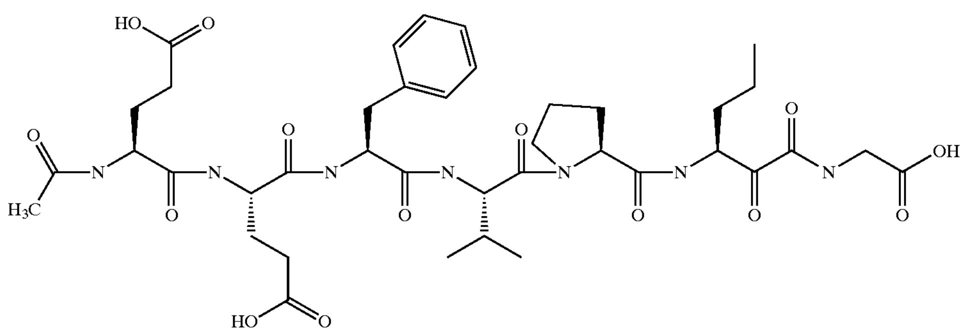 | Ac-EEFVP-nV-(CO)-G-OH (SEQ ID NO: 147) | b |
| 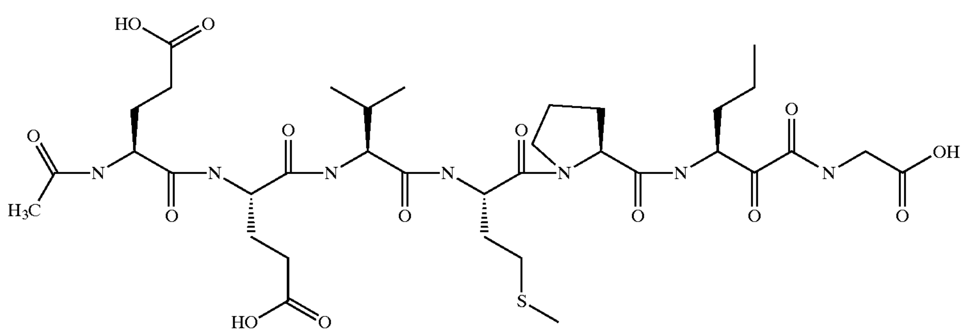 | Ac-EEVMP-nV-(CO)-G-OH (SEQ ID NO: 148) | b |

TABLE 3-continued

| STRUCTURE | NAME | Ki* Range |
|---|---|---|
| (structure) | Ac-EEVCP-nV-(CO)-G-OH (SEQ ID NO: 149) | b |

What is claimed is:

1. A compound exhibiting HCV protease inhibitory activity, including enantiomers, stereoisomers, rotamers and tautomers of said compound, and pharmaceutically acceptable salts or solvates of said compound, said compound being selected from the group of compounds with structures listed below:

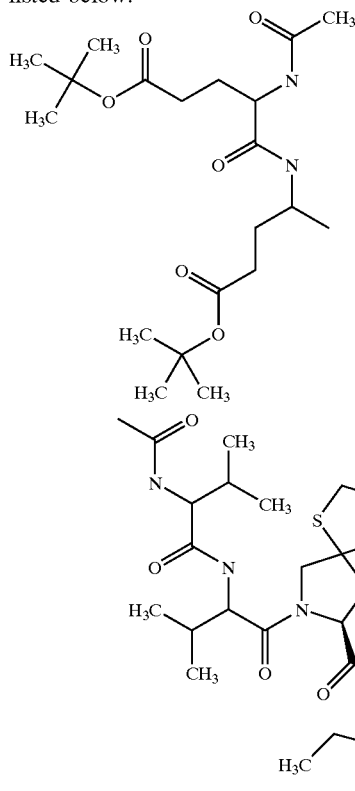

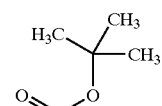

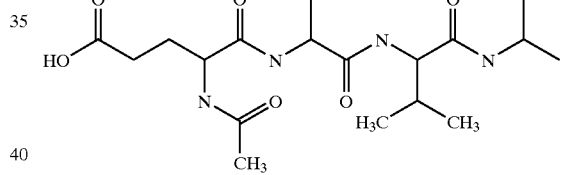

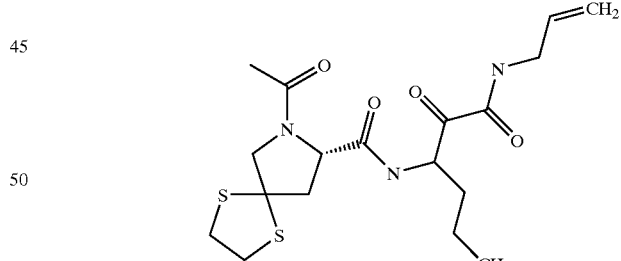

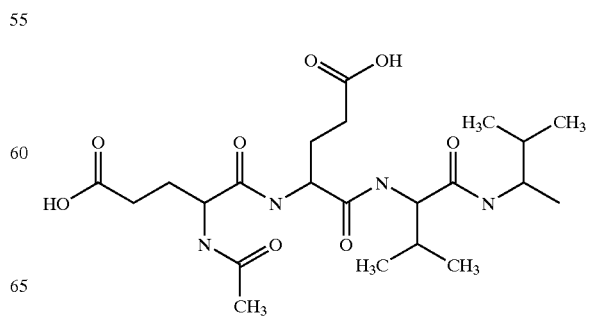

343
-continued
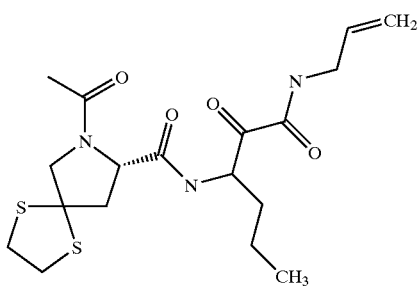
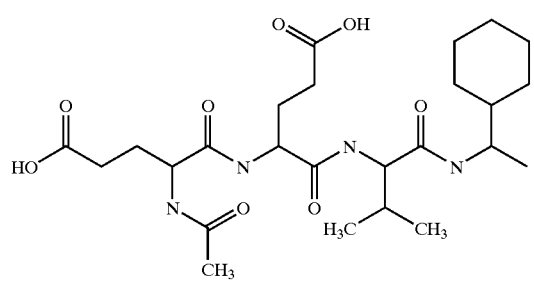
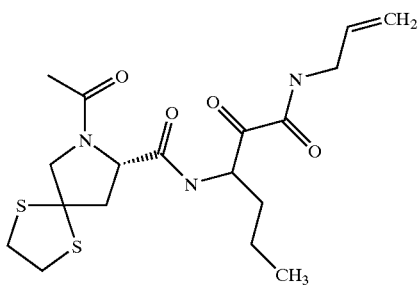
344
-continued
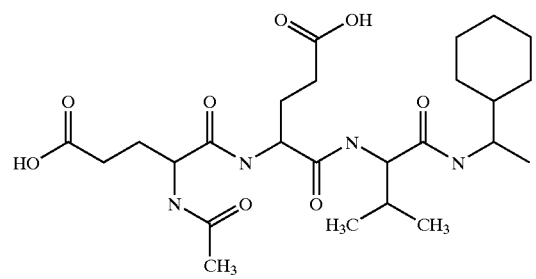
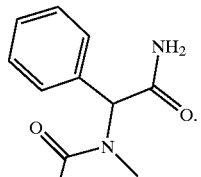
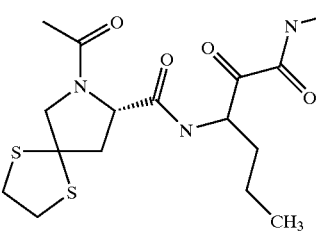
* * * * *

UNITED STATES PATENT AND TRADEMARK OFFICE
CERTIFICATE OF CORRECTION

PATENT NO.       : 6,800,434 B2
APPLICATION NO.  : 09/909062
DATED            : October 5, 2004
INVENTOR(S)      : Anil K. Saksena et al.

It is certified that error appears in the above-identified patent and that said Letters Patent is hereby corrected as shown below:

Column 14, line 38, insert --HCV continuous assay Ki* range:--.
Column 48, line 66, "start ing" should read --starting--.
Columns 83-84, compound from Example No. 32 should read -- 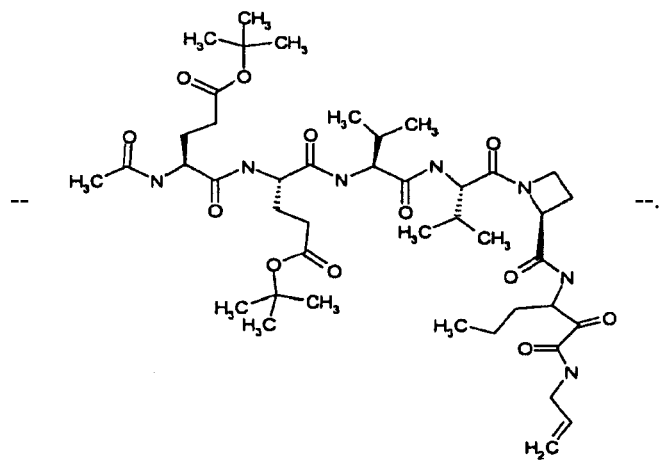 --.

Column 138, line 17, after "mixture" insert --of--.
Column 140, line 17, "were" should read --was--.
Column 142, line 15, "layerwas" should read --layer was--.
Column 142, line 64, "overa" should read --over a--.
Column 144, line 50, "rRsin" should read --resin--.
Column 149, line 31, delete "13☐l" and insert --13µl--.
Column 149, line 33, delete "124☐☐l" and insert --124µl--.
Column 149, line 55, delete "52☐l" and insert --52µl--.
Column 152, line 64, delete "22.3☐l" and insert --22.3µl--.

UNITED STATES PATENT AND TRADEMARK OFFICE
CERTIFICATE OF CORRECTION

PATENT NO. : 6,800,434 B2
APPLICATION NO. : 09/909062
DATED : October 5, 2004
INVENTOR(S) : Anil K. Saksena et al.

It is certified that error appears in the above-identified patent and that said Letters Patent is hereby corrected as shown below:

Column 153, line 21, "Table: Compounds Synthesized According to" should be deleted.
Column 153, line 23, insert --Table: Compounds synthesized according to-- before "Example III.".
Column 155, line 60, delete "☐" and insert --$\beta$--.
Column 159, line 9, delete "20☐l" and insert --20µl--.
Column 165, line 34, delete "125.5☐l" and insert --125.5µl--.

Signed and Sealed this

Twenty-third Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 6,800,434 B2  Page 1 of 1
APPLICATION NO. : 09/909062
DATED : October 5, 2004
INVENTOR(S) : Saksena et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (0) days Delete the phrase "by 0" and insert --by 50 days--

Signed and Sealed this

Seventeenth Day of February, 2009

JOHN DOLL
*Acting Director of the United States Patent and Trademark Office*

SEQUENCE LISTING

<160> NUMBER OF SEQ ID NOS: 149

<210> SEQ ID NO 1
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)

<400> SEQUENCE: 1

Glu Glu Val Val Pro Xaa Gly
1               5

<210> SEQ ID NO 2
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Fmoc-Val
<220> FEATURE:
<221> NAME/KEY: MISC_FEATURE
<222> LOCATION: (3)..(3)
<223> OTHER INFORMATION: norvaline-diphenylmethyl semicarbazide (dpsc)
<220> FEATURE:
<221> NAME/KEY: MISC_FEATURE
<222> LOCATION: (4)..(4)
<223> OTHER INFORMATION: Gly-PAM resin

<400> SEQUENCE: 2

Xaa Pro Xaa Xaa
1

<210> SEQ ID NO 3
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Fmoc-Val
<220> FEATURE:
<221> NAME/KEY: MISC_FEATURE
<222> LOCATION: (4)..(4)
<223> OTHER INFORMATION: norvaline-diphenylmethyl semicarbazide (dpsc)
<220> FEATURE:
<221> NAME/KEY: MISC_FEATURE
<222> LOCATION: (5)..(5)
<223> OTHER INFORMATION: Gly-PAM resin

<400> SEQUENCE: 3

Xaa Val Pro Xaa Xaa
1               5

<210> SEQ ID NO 4
<211> LENGTH: 6
<212> TYPE: PRT

```
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Fmoc-Glu(OtBu)
<220> FEATURE:
<221> NAME/KEY: MISC_FEATURE
<222> LOCATION: (5)..(5)
<223> OTHER INFORMATION: norvaline-diphenylmethyl semicarbazide (dpsc)
<220> FEATURE:
<221> NAME/KEY: MISC_FEATURE
<222> LOCATION: (6)..(6)
<223> OTHER INFORMATION: Gly-PAM resin

<400> SEQUENCE: 4

Xaa Val Val Pro Xaa Xaa
1               5

<210> SEQ ID NO 5
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Fmoc-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (6)..(6)
<223> OTHER INFORMATION: norvaline-diphenylmethyl semicarbazide (dpsc)
<220> FEATURE:
<221> NAME/KEY: MISC_FEATURE
<222> LOCATION: (7)..(7)
<223> OTHER INFORMATION: Gly-PAM resin

<400> SEQUENCE: 5

Xaa Xaa Val Val Pro Xaa Xaa
1               5

<210> SEQ ID NO 6
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (6)..(6)
<223> OTHER INFORMATION: norvaline-diphenylmethyl semicarbazide (dpsc)
<220> FEATURE:
<221> NAME/KEY: MISC_FEATURE
<222> LOCATION: (7)..(7)
<223> OTHER INFORMATION: Gly-PAM resin

<400> SEQUENCE: 6

Xaa Xaa Val Val Pro Xaa Xaa
1               5
```

```
<210> SEQ ID NO 7
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (6)..(6)
<223> OTHER INFORMATION: norvaline-C(=O)
<220> FEATURE:
<221> NAME/KEY: MISC_FEATURE
<222> LOCATION: (7)..(7)
<223> OTHER INFORMATION: Gly-PAM resin

<400> SEQUENCE: 7

Xaa Xaa Val Val Pro Xaa Xaa
1               5

<210> SEQ ID NO 8
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu
<220> FEATURE:
<221> NAME/KEY: MISC_FEATURE
<222> LOCATION: (6)..(6)
<223> OTHER INFORMATION: norvaline-C(=O)

<400> SEQUENCE: 8

Xaa Glu Val Val Pro Xaa Gly
1               5

<210> SEQ ID NO 9
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)

<400> SEQUENCE: 9

Glu Glu Val Val Pro Xaa Gly
1               5

<210> SEQ ID NO 10
<211> LENGTH: 7
<212> TYPE: PRT
<213> ORGANISM: Artificial Sequence
<220> FEATURE:
<223> OTHER INFORMATION: synthetic peptide
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: sar.
<220> FEATURE:
<221> NAME/KEY: MISC_FEATURE
<222> LOCATION: (6)..(6)
<223> OTHER INFORMATION: norvaline-C(=O)

<400> SEQUENCE: 10

Glu Glu Val Val Xaa Xaa Gly
1               5

<210> SEQ ID NO 11
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Aze
<220> FEATURE:
<221> NAME/KEY: MISC_FEATURE
<222> LOCATION: (6)..(6)
<223> OTHER INFORMATION: norvaline-C(=O)

<400> SEQUENCE: 11

Glu Glu Val Val Xaa Xaa Gly
1               5

<210> SEQ ID NO 12
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: G (Chx)
<220> FEATURE:
<221> NAME/KEY: MISC_FEATURE
<222> LOCATION: (6)..(6)
<223> OTHER INFORMATION: norvaline-C(=O)

<400> SEQUENCE: 12

Glu Glu Val Xaa Pro Xaa Gly
1               5

<210> SEQ ID NO 13
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MISC_FEATURE
<222> LOCATION: (6)..(6)
<223> OTHER INFORMATION: norvaline-C(=O)

<400> SEQUENCE: 13

Glu Glu Val Phe Pro Xaa Gly
1               5

<210> SEQ ID NO 14
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)

<400> SEQUENCE: 14

Glu Glu Val Ile Pro Xaa Gly
1               5

<210> SEQ ID NO 15
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: dl-pip-norvaline-C-(=O)

<400> SEQUENCE: 15

Glu Glu Val Val Xaa Gly
1               5

<210> SEQ ID NO 16
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Tiq-norvaline-C(=O)

<400> SEQUENCE: 16

Glu Glu Val Val Xaa Gly
1               5

<210> SEQ ID NO 17
<211> LENGTH: 7
<212> TYPE: PRT
<213> ORGANISM: Artificial Sequence
<220> FEATURE:
<223> OTHER INFORMATION: synthetic peptide
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Cys (Me)
<220> FEATURE:
<221> NAME/KEY: MISC_FEATURE
<222> LOCATION: (6)..(6)
<223> OTHER INFORMATION: norvaline-C(=O)

<400> SEQUENCE: 17

Glu Glu Val Val Xaa Xaa Gly
1               5

<210> SEQ ID NO 18
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Cysteine (O2, Met)
<220> FEATURE:
<221> NAME/KEY: MISC_FEATURE
<222> LOCATION: (6)..(6)
<223> OTHER INFORMATION: norvaline-C(=O)

<400> SEQUENCE: 18

Glu Glu Val Val Xaa Xaa Gly
1               5

<210> SEQ ID NO 19
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Cys (2-AcOH)
<220> FEATURE:
<221> NAME/KEY: MISC_FEATURE
<222> LOCATION: (6)..(6)
<223> OTHER INFORMATION: norvaline-C(=O)

<400> SEQUENCE: 19

Glu Glu Val Val Xaa Xaa Gly
1               5

<210> SEQ ID NO 20
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MISC_FEATURE
<222> LOCATION: (5)..(5)
<223> OTHER INFORMATION: Met (O2)
<220> FEATURE:
<221> NAME/KEY: MISC_FEATURE
<222> LOCATION: (6)..(6)
<223> OTHER INFORMATION: norvaline-(C=O)

<400> SEQUENCE: 20

Glu Glu Val Val Xaa Xaa Gly
1               5

<210> SEQ ID NO 21
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro (4t-Bn)
<220> FEATURE:
<221> NAME/KEY: MISC_FEATURE
<222> LOCATION: (6)..(6)
<223> OTHER INFORMATION: norvaline-C(=O)

<400> SEQUENCE: 21

Glu Glu Val Val Xaa Xaa Gly
1               5

<210> SEQ ID NO 22
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Pro (4t-Bn(4-OMe))
<220> FEATURE:
<221> NAME/KEY: MISC_FEATURE
<222> LOCATION: (6)..(6)
<223> OTHER INFORMATION: norvaline-C(=O)
<220> FEATURE:
<221> NAME/KEY: MOD_RES
<222> LOCATION: (1)..(1)
<223> OTHER INFORMATION: ACETYLATION

<400> SEQUENCE: 22

Glu Glu Val Val Xaa Xaa Gly
1               5

<210> SEQ ID NO 23
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro (4t-allyl)
```

```
<220> FEATURE:
<221> NAME/KEY: MISC_FEATURE
<222> LOCATION: (6)..(6)
<223> OTHER INFORMATION: norvaline-C(=O)

<400> SEQUENCE: 23

Glu Glu Val Val Xaa Xaa Gly
1               5

<210> SEQ ID NO 24
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)

<400> SEQUENCE: 24

Glu Glu Val Val Asp Xaa Gly
1               5

<210> SEQ ID NO 25
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)

<400> SEQUENCE: 25

Glu Glu Val Val Glu Xaa Gly
1               5

<210> SEQ ID NO 26
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)

<400> SEQUENCE: 26

Glu Glu Val Val Phe Xaa Gly
1               5

<210> SEQ ID NO 27
<211> LENGTH: 7
<212> TYPE: PRT
<213> ORGANISM: Artificial Sequence
<220> FEATURE:
```

```
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro-(4t-AcOH)
<220> FEATURE:
<221> NAME/KEY: MISC_FEATURE
<222> LOCATION: (6)..(6)
<223> OTHER INFORMATION: norvaline-C(=O)

<400> SEQUENCE: 27

Glu Glu Val Val Xaa Xaa Gly
1               5

<210> SEQ ID NO 28
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (6)..(6)
<223> OTHER INFORMATION: norvaline-C(=O)
<220> FEATURE:
<221> NAME/KEY: MOD_RES
<222> LOCATION: (1)..(1)
<223> OTHER INFORMATION: ACETYLATION

<400> SEQUENCE: 28

Glu Glu Ser Val Pro Xaa Gly
1               5

<210> SEQ ID NO 29
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)

<400> SEQUENCE: 29

Glu Ala Val Val Pro Xaa Gly
1               5

<210> SEQ ID NO 30
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)

<400> SEQUENCE: 30
```

```
Glu Glu His Val Pro Xaa Gly
1               5

<210> SEQ ID NO 31
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)

<400> SEQUENCE: 31

Glu Glu Asn Val Pro Xaa Gly
1               5

<210> SEQ ID NO 32
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro (4t-Ph)
<220> FEATURE:
<221> NAME/KEY: MISC_FEATURE
<222> LOCATION: (6)..(6)
<223> OTHER INFORMATION: norvaline-C(=O)

<400> SEQUENCE: 32

Glu Glu Val Val Xaa Xaa Gly
1               5

<210> SEQ ID NO 33
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro (3t-Me)
<220> FEATURE:
<221> NAME/KEY: MISC_FEATURE
<222> LOCATION: (6)..(6)
<223> OTHER INFORMATION: norvaline-C(=O)

<400> SEQUENCE: 33

Glu Glu Val Val Xaa Xaa Gly
1               5

<210> SEQ ID NO 34
<211> LENGTH: 7
<212> TYPE: PRT
<213> ORGANISM: Artificial Sequence
```

```
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Orn.
<220> FEATURE:
<221> NAME/KEY: MISC_FEATURE
<222> LOCATION: (6)..(6)
<223> OTHER INFORMATION: norvaline-C(=O)

<400> SEQUENCE: 34

Glu Glu Xaa Val Pro Xaa Gly
1               5

<210> SEQ ID NO 35
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: D-Glu
<220> FEATURE:
<221> NAME/KEY: MISC_FEATURE
<222> LOCATION: (6)..(6)
<223> OTHER INFORMATION: norvaline-C(=O)

<400> SEQUENCE: 35

Glu Xaa Val Val Pro Xaa Gly
1               5

<210> SEQ ID NO 36
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: (s,s)allo-Thr
<220> FEATURE:
<221> NAME/KEY: MISC_FEATURE
<222> LOCATION: (6)..(6)
<223> OTHER INFORMATION: norvaline-C(=O)

<400> SEQUENCE: 36

Glu Glu Xaa Val Pro Xaa Gly
1               5

<210> SEQ ID NO 37
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Dif
<220> FEATURE:
<221> NAME/KEY: MISC_FEATURE
<222> LOCATION: (6)..(6)
<223> OTHER INFORMATION: norvaline-C(=O)

<400> SEQUENCE: 37

Glu Glu Xaa Val Pro Xaa Gly
1               5

<210> SEQ ID NO 38
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: diaminobutyric acid
<220> FEATURE:
<221> NAME/KEY: MISC_FEATURE
<222> LOCATION: (6)..(6)
<223> OTHER INFORMATION: norvaline-C(=O)

<400> SEQUENCE: 38

Glu Glu Xaa Val Pro Xaa Gly
1               5

<210> SEQ ID NO 39
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)

<400> SEQUENCE: 39

Glu Glu Asp Val Pro Xaa Gly
1               5

<210> SEQ ID NO 40
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)

<400> SEQUENCE: 40
```

```
Glu Glu Glu Val Pro Xaa Gly
1               5

<210> SEQ ID NO 41
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)

<400> SEQUENCE: 41

Glu Glu Thr Val Pro Xaa Gly
1               5

<210> SEQ ID NO 42
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)

<400> SEQUENCE: 42

Ala Glu Val Val Pro Xaa Gly
1               5

<210> SEQ ID NO 43
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)

<400> SEQUENCE: 43

Glu Glu Leu Val Pro Xaa Gly
1               5

<210> SEQ ID NO 44
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MISC_FEATURE
<222> LOCATION: (6)..(6)
<223> OTHER INFORMATION: norvaline-C(=O)
<220> FEATURE:
<221> NAME/KEY: MISC_FEATURE
<222> LOCATION: (7)..(7)
<223> OTHER INFORMATION: Gly-AllylAm

<400> SEQUENCE: 44

Glu Glu Val Val Pro Xaa Xaa
1               5

<210> SEQ ID NO 45
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Glu (OtBu)
<220> FEATURE:
<221> NAME/KEY: MISC_FEATURE
<222> LOCATION: (2)..(2)
<223> OTHER INFORMATION: Glu (OtBu)

<400> SEQUENCE: 45

Xaa Xaa Val Val Pro
1               5

<210> SEQ ID NO 46
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Fmoc-Glu(OtBu)
<220> FEATURE:
<221> NAME/KEY: MISC_FEATURE
<222> LOCATION: (4)..(4)
<223> OTHER INFORMATION: Pro-2ClTrt resin

<400> SEQUENCE: 46

Xaa Val Val Xaa
1

<210> SEQ ID NO 47
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Fmoc-Glu(OtBu)
<220> FEATURE:
<221> NAME/KEY: MISC_FEATURE
<222> LOCATION: (5)..(5)
<223> OTHER INFORMATION: Pro-2ClTrt resin
<220> FEATURE:
<221> NAME/KEY: MISC_FEATURE
<222> LOCATION: (2)..(2)
<223> OTHER INFORMATION: Glu(OtBu)
```

-continued

```
<400> SEQUENCE: 47

Xaa Xaa Val Val Xaa
1               5

<210> SEQ ID NO 48
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu(OtBu)
<220> FEATURE:
<221> NAME/KEY: MISC_FEATURE
<222> LOCATION: (5)..(5)
<223> OTHER INFORMATION: Pro-2ClTrt resin
<220> FEATURE:
<221> NAME/KEY: MISC_FEATURE
<222> LOCATION: (2)..(2)
<223> OTHER INFORMATION: Glu(OtBu)

<400> SEQUENCE: 48

Xaa Xaa Val Val Xaa
1               5

<210> SEQ ID NO 49
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu(OtBu)
<220> FEATURE:
<221> NAME/KEY: MISC_FEATURE
<222> LOCATION: (2)..(2)
<223> OTHER INFORMATION: Glu(OtBu)

<400> SEQUENCE: 49

Xaa Xaa Val Val Pro
1               5

<210> SEQ ID NO 50
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (6)..(6)
<223> OTHER INFORMATION: norvaline-(CHOH)
<220> FEATURE:
<221> NAME/KEY: MISC_FEATURE
<222> LOCATION: (7)..(7)
<223> OTHER INFORMATION: Gly-OEt

<400> SEQUENCE: 50

Xaa Xaa Val Val Pro Xaa Xaa
1               5
```

```
<210> SEQ ID NO 51
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (6)..(6)
<223> OTHER INFORMATION: norvaline-(CHOH)

<400> SEQUENCE: 51

Xaa Xaa Val Val Pro Xaa Gly
1               5

<210> SEQ ID NO 52
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (6)..(6)
<223> OTHER INFORMATION: norvaline-(CHOH)
<220> FEATURE:
<221> NAME/KEY: MISC_FEATURE
<222> LOCATION: (7)..(7)
<223> OTHER INFORMATION: Gly-allylamide

<400> SEQUENCE: 52

Xaa Xaa Val Val Pro Xaa Xaa
1               5

<210> SEQ ID NO 53
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (6)..(6)
<223> OTHER INFORMATION: norvaline-C(=O)
<220> FEATURE:
<221> NAME/KEY: MISC_FEATURE
<222> LOCATION: (7)..(7)
<223> OTHER INFORMATION: Gly-allylamide
```

```
<400> SEQUENCE: 53

Xaa Xaa Val Val Pro Xaa Xaa
1               5

<210> SEQ ID NO 54
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu
<220> FEATURE:
<221> NAME/KEY: MISC_FEATURE
<222> LOCATION: (6)..(6)
<223> OTHER INFORMATION: norvaline-C(=O)
<220> FEATURE:
<221> NAME/KEY: MISC_FEATURE
<222> LOCATION: (7)..(7)
<223> OTHER INFORMATION: Gly-allylamide

<400> SEQUENCE: 54

Xaa Glu Val Val Pro Xaa Xaa
1               5

<210> SEQ ID NO 55
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)
<220> FEATURE:
<221> NAME/KEY: MISC_FEATURE
<222> LOCATION: (7)..(7)
<223> OTHER INFORMATION: Gly-allylAm

<400> SEQUENCE: 55

Glu Glu Val Val Pro Xaa Xaa
1               5

<210> SEQ ID NO 56
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)
<220> FEATURE:
<221> NAME/KEY: MISC_FEATURE
<222> LOCATION: (7)..(7)
<223> OTHER INFORMATION: Gly-2PhEtAm

<400> SEQUENCE: 56

Glu Glu Val Val Pro Xaa Xaa
1               5
```

```
<210> SEQ ID NO 57
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)
<220> FEATURE:
<221> NAME/KEY: MISC_FEATURE
<222> LOCATION: (7)..(7)
<223> OTHER INFORMATION: Gly-PropAm

<400> SEQUENCE: 57

Glu Glu Val Val Pro Xaa Xaa
1               5

<210> SEQ ID NO 58
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)
<220> FEATURE:
<221> NAME/KEY: MISC_FEATURE
<222> LOCATION: (7)..(7)
<223> OTHER INFORMATION: Gly-propynylAm

<400> SEQUENCE: 58

Glu Glu Val Val Pro Xaa Xaa
1               5

<210> SEQ ID NO 59
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)
<220> FEATURE:
<221> NAME/KEY: MISC_FEATURE
<222> LOCATION: (7)..(7)
<223> OTHER INFORMATION: Gly-iPrAm

<400> SEQUENCE: 59

Glu Glu Val Val Pro Xaa Xaa
1               5

<210> SEQ ID NO 60
<211> LENGTH: 7
```

```
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)
<220> FEATURE:
<221> NAME/KEY: MISC_FEATURE
<222> LOCATION: (7)..(7)
<223> OTHER INFORMATION: Gly (OAllyl)

<400> SEQUENCE: 60

Glu Glu Val Val Pro Xaa Xaa
 1               5

<210> SEQ ID NO 61
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (6)..(6)
<223> OTHER INFORMATION: norvaline-(CHOH)
<220> FEATURE:
<221> NAME/KEY: MISC_FEATURE
<222> LOCATION: (7)..(7)
<223> OTHER INFORMATION: Gly-(OAllyl)

<400> SEQUENCE: 61

Xaa Xaa Val Val Pro Xaa Xaa
 1               5

<210> SEQ ID NO 62
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (6)..(6)
<223> OTHER INFORMATION: norvaline-C(=O)
<220> FEATURE:
<221> NAME/KEY: MISC_FEATURE
<222> LOCATION: (7)..(7)
<223> OTHER INFORMATION: Gly-(OAllyl)

<400> SEQUENCE: 62

Xaa Xaa Val Val Pro Xaa Xaa
 1               5
```

```
<210> SEQ ID NO 63
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)
<220> FEATURE:
<221> NAME/KEY: MISC_FEATURE
<222> LOCATION: (7)..(7)
<223> OTHER INFORMATION: Gly-(OAllyl)

<400> SEQUENCE: 63

Glu Glu Val Val Pro Xaa Xaa
1               5

<210> SEQ ID NO 64
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)
<220> FEATURE:
<221> NAME/KEY: MISC_FEATURE
<222> LOCATION: (7)..(7)
<223> OTHER INFORMATION: Gly-(OAllyl)

<400> SEQUENCE: 64

Glu Glu Val Val Pro Xaa Xaa
1               5

<210> SEQ ID NO 65
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norleucine-C(=O)
<220> FEATURE:
<221> NAME/KEY: MISC_FEATURE
<222> LOCATION: (7)..(7)
<223> OTHER INFORMATION: Gly-(OAllyl)

<400> SEQUENCE: 65

Glu Glu Val Val Pro Xaa Xaa
1               5

<210> SEQ ID NO 66
<211> LENGTH: 7
```

```
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: Valine-C(=O)
<220> FEATURE:
<221> NAME/KEY: MISC_FEATURE
<222> LOCATION: (7)..(7)
<223> OTHER INFORMATION: Gly-(OAllyl)

<400> SEQUENCE: 66

Glu Glu Val Val Pro Xaa Xaa
1               5

<210> SEQ ID NO 67
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: Leucine-C(=O)
<220> FEATURE:
<221> NAME/KEY: MISC_FEATURE
<222> LOCATION: (7)..(7)
<223> OTHER INFORMATION: Gly-(OAllyl)

<400> SEQUENCE: 67

Glu Glu Val Val Pro Xaa Xaa
1               5

<210> SEQ ID NO 68
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: Gly-(Propynyl)-C(=O)
<220> FEATURE:
<221> NAME/KEY: MISC_FEATURE
<222> LOCATION: (7)..(7)
<223> OTHER INFORMATION: Gly-(OAllyl)

<400> SEQUENCE: 68

Glu Glu Val Val Pro Xaa Xaa
1               5

<210> SEQ ID NO 69
<211> LENGTH: 7
<212> TYPE: PRT
<213> ORGANISM: Artificial Sequence
<220> FEATURE:
<223> OTHER INFORMATION: synthetic peptide
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-C(=O)
<220> FEATURE:
<221> NAME/KEY: MISC_FEATURE
<222> LOCATION: (7)..(7)
<223> OTHER INFORMATION: Gly-OEt

<400> SEQUENCE: 69

Glu Glu Val Val Pro Xaa Xaa
1               5

<210> SEQ ID NO 70
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: Gly-(allyl)-C(=O)
<220> FEATURE:
<221> NAME/KEY: MISC_FEATURE
<222> LOCATION: (7)..(7)
<223> OTHER INFORMATION: Gly-(OAllyl)

<400> SEQUENCE: 70

Glu Glu Val Val Pro Xaa Xaa
1               5

<210> SEQ ID NO 71
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: Leucine-C(=O)
<220> FEATURE:
<221> NAME/KEY: MISC_FEATURE
<222> LOCATION: (7)..(7)
<223> OTHER INFORMATION: Gly-(OAllyl)

<400> SEQUENCE: 71

Glu Glu Val Val Gly Xaa Xaa
1               5

<210> SEQ ID NO 72
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MISC_FEATURE
<222> LOCATION: (6)..(6)
<223> OTHER INFORMATION: norvaline-C(=O)
<220> FEATURE:
<221> NAME/KEY: MISC_FEATURE
<222> LOCATION: (7)..(7)
<223> OTHER INFORMATION: Gly-(OtBu)

<400> SEQUENCE: 72

Glu Glu Val Val Pro Xaa Xaa
1               5

<210> SEQ ID NO 73
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: Gly(Allyl)-C(=O)
<220> FEATURE:
<221> NAME/KEY: MISC_FEATURE
<222> LOCATION: (7)..(7)
<223> OTHER INFORMATION: Gly-(OEt)

<400> SEQUENCE: 73

Glu Glu Val Val Pro Xaa Xaa
1               5

<210> SEQ ID NO 74
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: Cys(Me)-C(=O)
<220> FEATURE:
<221> NAME/KEY: MISC_FEATURE
<222> LOCATION: (7)..(7)
<223> OTHER INFORMATION: Gly-OMe

<400> SEQUENCE: 74

Glu Glu Val Val Pro Xaa Xaa
1               5

<210> SEQ ID NO 75
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Gly (N-Bu(4NH2, 4-CO2H))
```

```
<220> FEATURE:
<221> NAME/KEY: MISC_FEATURE
<222> LOCATION: (6)..(6)
<223> OTHER INFORMATION: norvaline-C(=O)

<400> SEQUENCE: 75

Glu Glu Val Val Xaa Xaa Gly
1               5

<210> SEQ ID NO 76
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Gly (N-Bu(4NH2, 4-COOH))
<220> FEATURE:
<221> NAME/KEY: MISC_FEATURE
<222> LOCATION: (6)..(6)
<223> OTHER INFORMATION: norvaline-C(=O)

<400> SEQUENCE: 76

Glu Glu Val Val Xaa Xaa Gly
1               5

<210> SEQ ID NO 77
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Gly(N-Bu(4NH2, 4-COOH))
<220> FEATURE:
<221> NAME/KEY: MISC_FEATURE
<222> LOCATION: (6)..(6)
<223> OTHER INFORMATION: norvaline-C(=O)

<400> SEQUENCE: 77

Glu Glu Val Val Xaa Xaa Gly
1               5

<210> SEQ ID NO 78
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Gly(N-Et(CO2H))
<220> FEATURE:
<221> NAME/KEY: MISC_FEATURE
<222> LOCATION: (6)..(6)
<223> OTHER INFORMATION: norvaline-C(=O)
```

```
<400> SEQUENCE: 78

Glu Glu Val Val Xaa Xaa Gly
1               5

<210> SEQ ID NO 79
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Gly(N-EtPh(3,4 diOMe))
<220> FEATURE:
<221> NAME/KEY: MISC_FEATURE
<222> LOCATION: (6)..(6)
<223> OTHER INFORMATION: norvaline-C(=O)

<400> SEQUENCE: 79

Glu Glu Val Val Xaa Xaa Gly
1               5

<210> SEQ ID NO 80
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Gly(N-Pe(5-NH2,5-CO2H))
<220> FEATURE:
<221> NAME/KEY: MISC_FEATURE
<222> LOCATION: (6)..(6)
<223> OTHER INFORMATION: norvaline-C(=O)

<400> SEQUENCE: 80

Glu Glu Val Val Xaa Xaa Gly
1               5

<210> SEQ ID NO 81
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Gly(N-Et(NHBz))
<220> FEATURE:
<221> NAME/KEY: MISC_FEATURE
<222> LOCATION: (6)..(6)
<223> OTHER INFORMATION: norvaline-C(=O)

<400> SEQUENCE: 81

Glu Glu Val Val Xaa Xaa Gly
```

-continued

<210> SEQ ID NO 82
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Fmoc-Val
<220> FEATURE:
<221> NAME/KEY: MISC_FEATURE
<222> LOCATION: (2)..(2)
<223> OTHER INFORMATION: Gly(N-Et(NH-Boc))
<220> FEATURE:
<221> NAME/KEY: MISC_FEATURE
<222> LOCATION: (3)..(3)
<223> OTHER INFORMATION: norvaline-(dspc)
<220> FEATURE:
<221> NAME/KEY: MISC_FEATURE
<222> LOCATION: (4)..(4)
<223> OTHER INFORMATION: Gly-PAM resin

<400> SEQUENCE: 82

Xaa Xaa Xaa Xaa
1

<210> SEQ ID NO 83
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Fmoc-Val
<220> FEATURE:
<221> NAME/KEY: MISC_FEATURE
<222> LOCATION: (2)..(2)
<223> OTHER INFORMATION: Gly(N-Et(NHBz))
<220> FEATURE:
<221> NAME/KEY: MISC_FEATURE
<222> LOCATION: (3)..(3)
<223> OTHER INFORMATION: norvaline-(dspc)
<220> FEATURE:
<221> NAME/KEY: MISC_FEATURE
<222> LOCATION: (4)..(4)
<223> OTHER INFORMATION: Gly-PAM resin

<400> SEQUENCE: 83

Xaa Xaa Xaa Xaa
1

<210> SEQ ID NO 84
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Gly(N-Et(NHBz))
<220> FEATURE:
<221> NAME/KEY: MISC_FEATURE
<222> LOCATION: (6)..(6)
<223> OTHER INFORMATION: norvaline-(C=O)

```
<400> SEQUENCE: 84

Glu Glu Val Val Xaa Xaa Gly
1               5

<210> SEQ ID NO 85
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Gly(N-Et(NHBzl(3-OPh)))
<220> FEATURE:
<221> NAME/KEY: MISC_FEATURE
<222> LOCATION: (6)..(6)
<223> OTHER INFORMATION: norvaline-(C=O)

<400> SEQUENCE: 85

Glu Glu Val Val Xaa Xaa Gly
1               5

<210> SEQ ID NO 86
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Gly(N-Prop(NHBz))
<220> FEATURE:
<221> NAME/KEY: MISC_FEATURE
<222> LOCATION: (6)..(6)
<223> OTHER INFORMATION: norvaline-(C=O)

<400> SEQUENCE: 86

Glu Glu Val Val Xaa Xaa Gly
1               5

<210> SEQ ID NO 87
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION
<220> FEATURE:
<221> NAME/KEY: MISC_FEATURE
<222> LOCATION: (6)..(6)
<223> OTHER INFORMATION: norvaline-(C=O)

<400> SEQUENCE: 87

Glu Glu Val Val Pro Xaa
```

-continued

```
1               5

<210> SEQ ID NO 88
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (6)..(6)
<223> OTHER INFORMATION: norvaline-(CHOH)-CONH2

<400> SEQUENCE: 88

Xaa Xaa Val Val Pro Xaa
1               5

<210> SEQ ID NO 89
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (6)..(6)
<223> OTHER INFORMATION: norvaline-(C=O)-CONH2

<400> SEQUENCE: 89

Xaa Xaa Val Val Pro Xaa
1               5

<210> SEQ ID NO 90
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-(C=O)-CONH2

<400> SEQUENCE: 90

Glu Glu Val Val Pro Xaa
1               5

<210> SEQ ID NO 91
<211> LENGTH: 6
<212> TYPE: PRT
<213> ORGANISM: Artificial Sequence
<220> FEATURE:
```

```
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-(C=O)-Am

<400> SEQUENCE: 91

Glu Glu Val Val Pro Xaa
1               5

<210> SEQ ID NO 92
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-MeNHBzl(3-OPh))
<220> FEATURE:
<221> NAME/KEY: MISC_FEATURE
<222> LOCATION: (6)..(6)
<223> OTHER INFORMATION: norvaline-(C=O)

<400> SEQUENCE: 92

Glu Glu Val Val Xaa Xaa Gly
1               5

<210> SEQ ID NO 93
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (5)..(5)
<223> OTHER INFORMATION: Pro(4t-MeNHFmoc)
<220> FEATURE:
<221> NAME/KEY: MISC_FEATURE
<222> LOCATION: (6)..(6)
<223> OTHER INFORMATION: norvaline-(dpsc)
<220> FEATURE:
<221> NAME/KEY: MISC_FEATURE
<222> LOCATION: (7)..(7)
<223> OTHER INFORMATION: Gly-PAM resin

<400> SEQUENCE: 93

Xaa Xaa Val Val Xaa Xaa Xaa
1               5

<210> SEQ ID NO 94
<211> LENGTH: 7
<212> TYPE: PRT
<213> ORGANISM: Artificial Sequence
<220> FEATURE:
```

```
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (5)..(5)
<223> OTHER INFORMATION: Pro(4t-MeNH2)
<220> FEATURE:
<221> NAME/KEY: MISC_FEATURE
<222> LOCATION: (6)..(6)
<223> OTHER INFORMATION: norvaline-(dspc)
<220> FEATURE:
<221> NAME/KEY: MISC_FEATURE
<222> LOCATION: (7)..(7)
<223> OTHER INFORMATION: Gly-PAM resin

<400> SEQUENCE: 94

Xaa Xaa Val Val Xaa Xaa Xaa
1               5

<210> SEQ ID NO 95
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (5)..(5)
<223> OTHER INFORMATION: Pro(4t-MeNHBzl(3-OPh))
<220> FEATURE:
<221> NAME/KEY: MISC_FEATURE
<222> LOCATION: (6)..(6)
<223> OTHER INFORMATION: norvaline-(dspc)
<220> FEATURE:
<221> NAME/KEY: MISC_FEATURE
<222> LOCATION: (7)..(7)
<223> OTHER INFORMATION: Gly-PAM resin

<400> SEQUENCE: 95

Xaa Xaa Val Val Xaa Xaa Xaa
1               5

<210> SEQ ID NO 96
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-MeNHBzl(3-OPh))
<220> FEATURE:
<221> NAME/KEY: MISC_FEATURE
<222> LOCATION: (6)..(6)
<223> OTHER INFORMATION: norvaline-(C=O)
```

```
<400> SEQUENCE: 96

Glu Glu Val Val Xaa Xaa Gly
1               5

<210> SEQ ID NO 97
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-MeNHCO2Ph)
<220> FEATURE:
<221> NAME/KEY: MISC_FEATURE
<222> LOCATION: (6)..(6)
<223> OTHER INFORMATION: norvaline-(C=O)

<400> SEQUENCE: 97

Glu Glu Val Val Xaa Xaa Gly
1               5

<210> SEQ ID NO 98
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-MeNHCOPh)
<220> FEATURE:
<221> NAME/KEY: MISC_FEATURE
<222> LOCATION: (6)..(6)
<223> OTHER INFORMATION: norvaline-(C=O)

<400> SEQUENCE: 98

Glu Glu Val Val Xaa Xaa Gly
1               5

<210> SEQ ID NO 99
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-MeNH-Fmoc)
<220> FEATURE:
<221> NAME/KEY: MISC_FEATURE
<222> LOCATION: (6)..(6)
<223> OTHER INFORMATION: norvaline-(C=O)

<400> SEQUENCE: 99

Glu Glu Val Val Xaa Xaa Gly
```

```
<210> SEQ ID NO 100
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-MeNHSO2Ph)
<220> FEATURE:
<221> NAME/KEY: MISC_FEATURE
<222> LOCATION: (6)..(6)
<223> OTHER INFORMATION: norvaline-(C=O)

<400> SEQUENCE: 100

Glu Glu Val Val Xaa Xaa Gly
1               5

<210> SEQ ID NO 101
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-MeUreaPh)
<220> FEATURE:
<221> NAME/KEY: MISC_FEATURE
<222> LOCATION: (6)..(6)
<223> OTHER INFORMATION: norvaline-(C=O)

<400> SEQUENCE: 101

Glu Glu Val Val Xaa Xaa Gly
1               5

<210> SEQ ID NO 102
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-NH-Fmoc)
<220> FEATURE:
<221> NAME/KEY: MISC_FEATURE
<222> LOCATION: (6)..(6)
<223> OTHER INFORMATION: norvaline-(C=O)

<400> SEQUENCE: 102

Glu Glu Val Val Xaa Xaa Gly
1               5

<210> SEQ ID NO 103
```

```
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-NHBzl)
<220> FEATURE:
<221> NAME/KEY: MISC_FEATURE
<222> LOCATION: (6)..(6)
<223> OTHER INFORMATION: norvaline-(C=O)

<400> SEQUENCE: 103

Glu Glu Val Val Xaa Xaa Gly
1               5

<210> SEQ ID NO 104
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Fmoc-Val
<220> FEATURE:
<221> NAME/KEY: MISC_FEATURE
<222> LOCATION: (2)..(2)
<223> OTHER INFORMATION: Pro(4t-NHBzl)
<220> FEATURE:
<221> NAME/KEY: MISC_FEATURE
<222> LOCATION: (3)..(3)
<223> OTHER INFORMATION: norvaline-(dpsc)
<220> FEATURE:
<221> NAME/KEY: MISC_FEATURE
<222> LOCATION: (4)..(4)
<223> OTHER INFORMATION: Gly-PAM resin

<400> SEQUENCE: 104

Xaa Xaa Xaa Xaa
1

<210> SEQ ID NO 105
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Fmoc-Val
<220> FEATURE:
<221> NAME/KEY: MISC_FEATURE
<222> LOCATION: (3)..(3)
<223> OTHER INFORMATION: Pro(4t-NHBzl)
<220> FEATURE:
<221> NAME/KEY: MISC_FEATURE
<222> LOCATION: (4)..(4)
<223> OTHER INFORMATION: norvaline-(dpsc)
<220> FEATURE:
<221> NAME/KEY: MISC_FEATURE
<222> LOCATION: (5)..(5)
<223> OTHER INFORMATION: Gly-PAM resin

<400> SEQUENCE: 105

Xaa Val Xaa Xaa Xaa
```

<210> SEQ ID NO 106
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Fmoc-Glu(OtBu)
<220> FEATURE:
<221> NAME/KEY: MISC_FEATURE
<222> LOCATION: (4)..(4)
<223> OTHER INFORMATION: Pro(4t-NHBzl)
<220> FEATURE:
<221> NAME/KEY: MISC_FEATURE
<222> LOCATION: (5)..(5)
<223> OTHER INFORMATION: norvaline-(dpsc)
<220> FEATURE:
<221> NAME/KEY: MISC_FEATURE
<222> LOCATION: (6)..(6)
<223> OTHER INFORMATION: Gly-PAM resin

<400> SEQUENCE: 106

Xaa Val Val Xaa Xaa Xaa
1               5

<210> SEQ ID NO 107
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Fmoc-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (5)..(5)
<223> OTHER INFORMATION: Pro(4t-NHBzl)
<220> FEATURE:
<221> NAME/KEY: MISC_FEATURE
<222> LOCATION: (6)..(6)
<223> OTHER INFORMATION: norvaline-(dpsc)
<220> FEATURE:
<221> NAME/KEY: MISC_FEATURE
<222> LOCATION: (7)..(7)
<223> OTHER INFORMATION: Gly-PAM resin

<400> SEQUENCE: 107

Xaa Xaa Val Val Xaa Xaa Xaa
1               5

<210> SEQ ID NO 108
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-NHBzl)

```
<220> FEATURE:
<221> NAME/KEY: MISC_FEATURE
<222> LOCATION: (6)..(6)
<223> OTHER INFORMATION: norvaline-(C=O)

<400> SEQUENCE: 108

Glu Glu Val Val Xaa Xaa Gly
1               5

<210> SEQ ID NO 109
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-NHBzl(4-OMe))
<220> FEATURE:
<221> NAME/KEY: MISC_FEATURE
<222> LOCATION: (6)..(6)
<223> OTHER INFORMATION: norvaline-(C=O)

<400> SEQUENCE: 109

Glu Glu Val Val Xaa Xaa Gly
1               5

<210> SEQ ID NO 110
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-NHBzl(4-OPh))
<220> FEATURE:
<221> NAME/KEY: MISC_FEATURE
<222> LOCATION: (6)..(6)
<223> OTHER INFORMATION: norvaline-(C=O)

<400> SEQUENCE: 110

Glu Glu Val Val Xaa Xaa Gly
1               5

<210> SEQ ID NO 111
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-NHBzl(3-OPh))
<220> FEATURE:
<221> NAME/KEY: MISC_FEATURE
<222> LOCATION: (6)..(6)
<223> OTHER INFORMATION: norvaline-(C=O)
```

-continued

<400> SEQUENCE: 111

Glu Glu Val Val Xaa Xaa Gly
1               5

<210> SEQ ID NO 112
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-NHBzl(3,4-OMeO))
<220> FEATURE:
<221> NAME/KEY: MISC_FEATURE
<222> LOCATION: (6)..(6)
<223> OTHER INFORMATION: norvaline-(C=O)

<400> SEQUENCE: 112

Glu Glu Val Val Xaa Xaa Gly
1               5

<210> SEQ ID NO 113
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-NHBzl(4F))
<220> FEATURE:
<221> NAME/KEY: MISC_FEATURE
<222> LOCATION: (6)..(6)
<223> OTHER INFORMATION: norvaline-(C=O)

<400> SEQUENCE: 113

Glu Glu Val Val Xaa Xaa Gly
1               5

<210> SEQ ID NO 114
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-NHiBoc)
<220> FEATURE:
<221> NAME/KEY: MISC_FEATURE
<222> LOCATION: (6)..(6)
<223> OTHER INFORMATION: norvaline-(C=O)

<400> SEQUENCE: 114

Glu Glu Val Val Xaa Xaa Gly

```
1               5

<210> SEQ ID NO 115
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-NHSO2Ph)
<220> FEATURE:
<221> NAME/KEY: MISC_FEATURE
<222> LOCATION: (6)..(6)
<223> OTHER INFORMATION: norvaline-(C=O)

<400> SEQUENCE: 115

Glu Glu Val Val Xaa Xaa Gly
1               5

<210> SEQ ID NO 116
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-NHSO2Ph(4-OMe))
<220> FEATURE:
<221> NAME/KEY: MISC_FEATURE
<222> LOCATION: (6)..(6)
<223> OTHER INFORMATION: norvaline-(C=O)

<400> SEQUENCE: 116

Glu Glu Val Val Xaa Xaa Gly
1               5

<210> SEQ ID NO 117
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-UreaPh)
<220> FEATURE:
<221> NAME/KEY: MISC_FEATURE
<222> LOCATION: (6)..(6)
<223> OTHER INFORMATION: norvaline-(C=O)

<400> SEQUENCE: 117

Glu Glu Val Val Xaa Xaa Gly
1               5

<210> SEQ ID NO 118
```

```
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-UreaPh(4-OMe))
<220> FEATURE:
<221> NAME/KEY: MISC_FEATURE
<222> LOCATION: (6)..(6)
<223> OTHER INFORMATION: norvaline-(C=O)

<400> SEQUENCE: 118

Glu Glu Val Val Xaa Xaa Gly
1               5

<210> SEQ ID NO 119
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-(C=O)

<400> SEQUENCE: 119

Glu Glu Val Val Pro Xaa
1               5

<210> SEQ ID NO 120
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetyl-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (6)..(6)
<223> OTHER INFORMATION: norvaline-(CHOH)-OEt

<400> SEQUENCE: 120

Xaa Xaa Val Val Pro Xaa
1               5

<210> SEQ ID NO 121
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
```

```
<223> OTHER INFORMATION: acetyl-Glu(OtBu)
<220> FEATURE:
<221> NAME/KEY: MISC_FEATURE
<222> LOCATION: (2)..(2)
<223> OTHER INFORMATION: Glu(OtBu)
<220> FEATURE:
<221> NAME/KEY: MISC_FEATURE
<222> LOCATION: (6)..(6)
<223> OTHER INFORMATION: norvaline-(CHOH)-carboxylic acid

<400> SEQUENCE: 121

Xaa Xaa Val Val Pro Xaa
1               5

<210> SEQ ID NO 122
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-(CHOH)-carboxylic acid

<400> SEQUENCE: 122

Glu Glu Val Val Pro Xaa
1               5

<210> SEQ ID NO 123
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-(C=O)-carboxylic acid

<400> SEQUENCE: 123

Glu Glu Val Val Pro Xaa
1               5

<210> SEQ ID NO 124
<211> LENGTH: 6
<212> TYPE: PRT
<213> ORGANISM: Artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-(C=O)-OH

<400> SEQUENCE: 124

Glu Glu Val Val Pro Xaa
1               5
```

```
<210> SEQ ID NO 125
<211> LENGTH: 8
<212> TYPE: PRT
<213> ORGANISM: Artificial Sequence
<220> FEATURE:
<223> OTHER INFORMATION: NS5A-NS5B junction sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (7)..(7)
<223> OTHER INFORMATION: alanine or proline
<220> FEATURE:
<221> NAME/KEY: MISC_FEATURE
<222> LOCATION: (8)..(8)
<223> OTHER INFORMATION: norvaline

<400> SEQUENCE: 125

Asp Thr Glu Asp Val Val Xaa Xaa
1               5

<210> SEQ ID NO 126
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: D-Gla
<220> FEATURE:
<221> NAME/KEY: MISC_FEATURE
<222> LOCATION: (4)..(4)
<223> OTHER INFORMATION: I-(Cha)

<400> SEQUENCE: 126

Asp Xaa Leu Xaa Cys
1               5

<210> SEQ ID NO 127
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (8)..(8)
<223> OTHER INFORMATION: norvaline

<400> SEQUENCE: 127

Asp Thr Glu Asp Val Val Ala Xaa
1               5

<210> SEQ ID NO 128
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MISC_FEATURE
<222> LOCATION: (8)..(8)
<223> OTHER INFORMATION: norvaline

<400> SEQUENCE: 128

Asp Thr Glu Asp Val Val Pro Xaa
1               5

<210> SEQ ID NO 129
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-(C=O)-iPrAm

<400> SEQUENCE: 129

Glu Glu Val Val Pro Xaa
1               5

<210> SEQ ID NO 130
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: AMIDATION
<220> FEATURE:
<221> NAME/KEY: MISC_FEATURE
<222> LOCATION: (6)..(6)
<223> OTHER INFORMATION: norvaline-(C=O)

<400> SEQUENCE: 130

Glu Glu Val Val Pro Xaa Gly
1               5

<210> SEQ ID NO 131
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Gly(Ph)
<220> FEATURE:
<221> NAME/KEY: MISC_FEATURE
<222> LOCATION: (6)..(6)
<223> OTHER INFORMATION: norvaline-(C=O)

<400> SEQUENCE: 131
```

```
Glu Glu Val Xaa Pro Xaa Gly
1               5

<210> SEQ ID NO 132
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro(4t-O-2AcOH)
<220> FEATURE:
<221> NAME/KEY: MISC_FEATURE
<222> LOCATION: (6)..(6)
<223> OTHER INFORMATION: norvaline-(C=O)

<400> SEQUENCE: 132

Glu Glu Val Val Xaa Xaa Gly
1               5

<210> SEQ ID NO 133
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: thio-Pro
<220> FEATURE:
<221> NAME/KEY: MISC_FEATURE
<222> LOCATION: (6)..(6)
<223> OTHER INFORMATION: norvaline-(C=O)

<400> SEQUENCE: 133

Glu Glu Val Val Xaa Xaa Gly
1               5

<210> SEQ ID NO 134
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (5)..(5)
<223> OTHER INFORMATION: Pro-(4t-NH2)
<220> FEATURE:
<221> NAME/KEY: MISC_FEATURE
<222> LOCATION: (6)..(6)
<223> OTHER INFORMATION: norvaline-(C=O)

<400> SEQUENCE: 134

Glu Glu Val Val Xaa Xaa Gly
1               5
```

```
<210> SEQ ID NO 135
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Ala(1-Np)
<220> FEATURE:
<221> NAME/KEY: MISC_FEATURE
<222> LOCATION: (6)..(6)
<223> OTHER INFORMATION: norvaline-(C=O)

<400> SEQUENCE: 135

Glu Glu Xaa Val Pro Xaa Gly
1               5

<210> SEQ ID NO 136
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Ala(2-Np)
<220> FEATURE:
<221> NAME/KEY: MISC_FEATURE
<222> LOCATION: (6)..(6)
<223> OTHER INFORMATION: norvaline-(C=O)

<400> SEQUENCE: 136

Glu Glu Xaa Val Pro Xaa Gly
1               5

<210> SEQ ID NO 137
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Phe(alpha-Me)
<220> FEATURE:
<221> NAME/KEY: MISC_FEATURE
<222> LOCATION: (6)..(6)
<223> OTHER INFORMATION: norvaline-(C=O)

<400> SEQUENCE: 137

Glu Glu Xaa Val Pro Xaa Gly
1               5

<210> SEQ ID NO 138
<211> LENGTH: 7
<212> TYPE: PRT
```

```
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-(C=O)

<400> SEQUENCE: 138

Glu Glu Val Leu Pro Xaa Gly
1               5

<210> SEQ ID NO 139
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Gly(t-Bu)
<220> FEATURE:
<221> NAME/KEY: MISC_FEATURE
<222> LOCATION: (6)..(6)
<223> OTHER INFORMATION: norvaline-(C=O)

<400> SEQUENCE: 139

Glu Glu Val Xaa Pro Xaa Gly
1               5

<210> SEQ ID NO 140
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-(C=O)

<400> SEQUENCE: 140

Glu Glu Val Ser Pro Xaa Gly
1               5

<210> SEQ ID NO 141
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-(C=O)
```

```
<400> SEQUENCE: 141

Glu Glu Val Thr Pro Xaa Gly
1               5

<210> SEQ ID NO 142
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: norleucine
<220> FEATURE:
<221> NAME/KEY: MISC_FEATURE
<222> LOCATION: (6)..(6)
<223> OTHER INFORMATION: norvaline-(C=O)

<400> SEQUENCE: 142

Glu Glu Val Xaa Pro Xaa Gly
1               5

<210> SEQ ID NO 143
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Dif
<220> FEATURE:
<221> NAME/KEY: MISC_FEATURE
<222> LOCATION: (6)..(6)
<223> OTHER INFORMATION: norvaline-(C=O)

<400> SEQUENCE: 143

Glu Glu Val Xaa Pro Xaa Gly
1               5

<210> SEQ ID NO 144
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Ser(Me)
<220> FEATURE:
<221> NAME/KEY: MISC_FEATURE
<222> LOCATION: (6)..(6)
<223> OTHER INFORMATION: norvaline-(C=O)

<400> SEQUENCE: 144

Glu Glu Val Xaa Pro Xaa Gly
1               5
```

<210> SEQ ID NO 145
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-(C=O)

<400> SEQUENCE: 145

Glu Glu Val Asn Pro Xaa Gly
1               5

<210> SEQ ID NO 146
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-(C=O)

<400> SEQUENCE: 146

Glu Glu Val Gln Pro Xaa Gly
1               5

<210> SEQ ID NO 147
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-(C=O)

<400> SEQUENCE: 147

Glu Glu Phe Val Pro Xaa Gly
1               5

<210> SEQ ID NO 148
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-(C=O)

```
<400> SEQUENCE: 148

Glu Glu Val Met Pro Xaa Gly
1               5

<210> SEQ ID NO 149
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: norvaline-(C=O)

<400> SEQUENCE: 149

Glu Glu Val Cys Pro Xaa Gly
1               5
```